United States Patent
Bourke, Jr. et al.

(10) Patent No.: US 12,076,579 B2
(45) Date of Patent: Sep. 3, 2024

(54) ENERGY AUGMENTATION STRUCTURES IN ADHESIVE BONDING COMPOSITIONS

(71) Applicant: IMMUNOLIGHT, LLC, Detroit, MI (US)

(72) Inventors: Frederic A. Bourke, Jr., Detroit, MI (US); Harold Walder, Detroit, MI (US); Zakaryae Fathi, Detroit, MI (US); Wayne F. Beyer, Detroit, MI (US); Ronald A. Rudder, Bristow, VA (US); Joseph H. Simmons, Detroit, MI (US)

(73) Assignee: IMMUNOLIGHT, LLC, Detroit, MI (US)

( * ) Notice: Subject to any disclaimer, the term of this patent is extended or adjusted under 35 U.S.C. 154(b) by 212 days.

(21) Appl. No.: 17/433,768

(22) PCT Filed: Feb. 27, 2020

(86) PCT No.: PCT/US2020/020036
§ 371 (c)(1),
(2) Date: Aug. 25, 2021

(87) PCT Pub. No.: WO2020/180587
PCT Pub. Date: Sep. 10, 2020

(65) Prior Publication Data
US 2022/0148997 A1 May 12, 2022

Related U.S. Application Data

(60) Provisional application No. 62/955,533, filed on Dec. 31, 2019, provisional application No. 62/946,648, (Continued)

(51) Int. Cl.
*A61N 5/06* (2006.01)
*A61K 35/12* (2015.01)
(Continued)

(52) U.S. Cl.
CPC ............ *A61N 5/0625* (2013.01); *A61K 35/12* (2013.01); *A61K 41/00* (2013.01);
(Continued)

(58) Field of Classification Search
CPC ............. H01L 31/06; H01L 31/035281; H01L 24/29; H01L 24/83; H01L 31/054;
(Continued)

(56) References Cited

U.S. PATENT DOCUMENTS 7,538,641 B2   5/2009   Puente Baliarda et al.
8,376,013 B2   2/2013   Bourke
(Continued)

FOREIGN PATENT DOCUMENTS

EP   1 917 556 B1   5/2008
EP   2 028 225 A1   2/2009
(Continued)

OTHER PUBLICATIONS

International Search Report and Written Opinion dated Jun. 2, 2020 in PCT/US2020/020036 filed Feb. 27, 2020, 2 pages.
(Continued)

*Primary Examiner* — Mouloucoulaye Inoussa
(74) *Attorney, Agent, or Firm* — TUCKER ELLIS, L.L.P.; J. Derek Mason

(57) ABSTRACT

An emission enhancement structure having at least one energy augmentation structure; and an energy converter capable of receiving energy from an energy source, converting the energy and emitting therefrom a light of a different energy than the received energy. The energy converter is disposed in a vicinity of the at least one energy augmentation structure such that the emitted light is emitted with an intensity larger than if the converter were remote from the at least one energy augmentation structure. Also described are various uses for the energy emitters, energy augmentation
(Continued)

structures and energy collectors in a wide array of fields, including various adhesives applications.

279 Claims, 112 Drawing Sheets

Related U.S. Application Data filed on Dec. 11, 2019, provisional application No. 62/897,677, filed on Sep. 9, 2019, provisional application No. 62/855,508, filed on May 31, 2019, provisional application No. 62/813,390, filed on Mar. 4, 2019.

(51) Int. Cl.

| | | |
|---|---|---|
| A61K 41/00 | (2020.01) | |
| A61N 5/067 | (2006.01) | |
| C09J 133/08 | (2006.01) | |
| C09K 11/02 | (2006.01) | |
| C09K 11/59 | (2006.01) | |
| C09K 11/76 | (2006.01) | |
| C09K 11/77 | (2006.01) | |
| C12N 15/01 | (2006.01) | |
| F21K 2/00 | (2006.01) | |
| F21S 11/00 | (2006.01) | |
| F21V 9/40 | (2018.01) | |
| H01J 45/00 | (2006.01) | |
| H01L 23/00 | (2006.01) | |
| H01L 31/0352 | (2006.01) | |
| H01L 31/054 | (2014.01) | |
| H01L 31/055 | (2014.01) | |
| H01L 31/06 | (2012.01) | |

(52) U.S. Cl.
CPC ........ *A61K 41/0057* (2013.01); *A61N 5/0601* (2013.01); *A61N 5/062* (2013.01); *A61N 5/067* (2021.08); *C09J 133/08* (2013.01); *C09K 11/025* (2013.01); *C09K 11/595* (2013.01); *C09K 11/76* (2013.01); *C09K 11/7701* (2013.01); *C09K 11/7792* (2013.01); *C12N 15/01* (2013.01); *F21K 2/00* (2013.01); *F21S 11/007* (2013.01); *F21V 9/40* (2018.02); *H01J 45/00* (2013.01); *H01L 24/29* (2013.01); *H01L 24/83* (2013.01); *H01L 31/035281* (2013.01); *H01L 31/054* (2014.12); *H01L 31/06* (2013.01); *A61N 2005/0661* (2013.01); *A61N 2005/0662* (2013.01); *A61N 2005/0663* (2013.01); *H01L 31/055* (2013.01); *H01L 2224/2919* (2013.01); *H01L 2224/29393* (2013.01); *H01L 2224/8322* (2013.01); *H01L 2224/83855* (2013.01)

(58) Field of Classification Search
CPC ......... H01L 22/12; H01L 24/48; H01L 25/50; H01L 2224/2939; H01L 2224/2957; H01L 2224/83851; H01L 2224/83874; H01L 2224/2919; H01L 2224/83885; H01L 2224/29393; H01L 2224/29565; H01L 2224/83948; H01L 2224/83855; H01L 2224/83986; H01L 2224/2732; H01L 2224/74; H01L 2224/29561; H01L 2224/7598; H01L 2224/83048; H01L 2224/29082; H01L 2224/32225; H01L 2224/8322; H01L 2224/294; H01L 2224/29499; H01L 2224/75252; A23L 3/26; A23L 5/30; A23L 2/50; C09K 11/595; C09K 11/7741; C09K 11/7701; C09K 11/7792; C09K 11/76; C09K 11/025; C09K 11/02; C09K 11/7769; A61N 5/062; A61N 5/0601; A61N 5/10; A61N 5/067; A61N 5/0625; A61N 5/06; A61N 2005/0662; A61N 2005/0661; A61N 2005/0663; A61K 35/12; A61K 41/00; A61K 41/0057; G02F 1/354; G02F 1/355; G02F 1/353; C09J 11/04; C09J 5/00; C09J 9/00; C09J 11/02; C09J 11/06; C09J 133/08; C09J 9/02; C09J 2301/416; A61P 37/00; C12N 15/01; F21S 11/007; F21V 9/40; Y02P 10/25; G02B 6/4239; B01L 3/502707; B22F 12/22; B22F 2003/1042; B32B 38/0008; B32B 3/266; B32B 2260/046; B32B 2260/023; A61B 17/0057; C08K 2201/001

USPC .................................................. 257/E23.116
See application file for complete search history.

(56) References Cited

U.S. PATENT DOCUMENTS

| | | |
|---|---|---|
| 8,389,958 B2 | 3/2013 | Vo-Dinh |
| 8,618,509 B2 | 12/2013 | Vo-Dinh |
| 8,658,086 B2 | 2/2014 | Bourke |
| 8,927,615 B2 | 1/2015 | Bourke |
| 9,004,131 B2 | 4/2015 | Bourke |
| 9,005,406 B2 | 4/2015 | Bourke |
| 9,023,249 B2 | 5/2015 | Fathi |
| 9,174,190 B2 | 11/2015 | Bourke |
| 9,232,618 B2 | 1/2016 | Bourke |
| 9,278,331 B2 | 3/2016 | Bourke |
| 9,488,916 B2 | 11/2016 | Bourke |
| 9,526,914 B2 | 12/2016 | Vo-Dinh |
| 9,579,523 B2 | 2/2017 | Bourke |
| 9,630,022 B2 | 4/2017 | Bourke |
| 9,649,832 B2 | 5/2017 | Fathi |
| 9,662,389 B2 | 5/2017 | Vo-Dinh |
| 9,676,918 B2 | 6/2017 | Fathi |
| 9,701,102 B2 | 7/2017 | Fathi |
| 9,715,159 B1 | 7/2017 | Akselrod et al. |
| 9,907,976 B2 | 3/2018 | Bourke |
| 9,937,695 B2 | 4/2018 | Fathi |
| 10,026,711 B2 | 7/2018 | Fathi |
| 10,029,117 B2 | 7/2018 | Bourke |
| 10,074,627 B2 | 9/2018 | Fathi |
| 10,080,275 B2 | 9/2018 | Bourke |
| 10,087,343 B2 | 10/2018 | Fathi |
| 10,093,784 B2 | 10/2018 | Fathi |
| 10,201,796 B2 | 2/2019 | Bourke |
| 10,213,763 B2 | 2/2019 | Bourke |
| 10,283,476 B2 | 5/2019 | Fathi |
| 10,363,541 B2 | 7/2019 | Bourke |
| 10,410,991 B2 | 9/2019 | Fathi |
| 10,494,500 B2 | 12/2019 | Fathi |
| 10,575,541 B2 | 3/2020 | Bourke |
| 10,593,642 B2 | 3/2020 | Fathi |
| 10,682,624 B2 | 6/2020 | Bourke |
| 10,717,062 B2 | 7/2020 | Bourke |
| 10,734,353 B2 | 8/2020 | Fathi |
| 10,748,868 B2 | 8/2020 | Fathi |
| 10,847,666 B2 | 11/2020 | Bourke |
| 10,874,123 B2 | 12/2020 | Bourke |
| 10,899,907 B2 | 1/2021 | Fathi |
| 10,974,493 B2 | 4/2021 | Fathi |
| 11,173,467 B2 | 11/2021 | Bourke |
| 11,270,973 B2 | 3/2022 | Fathi |
| 11,278,861 B2 | 3/2022 | Bourke |
| 11,345,833 B2 | 5/2022 | Fathi |
| 11,476,222 B2 | 10/2022 | Fathi |
| 11,589,432 B2 | 2/2023 | Bourke |
| 11,648,750 B2 | 5/2023 | Fathi |
| 11,678,682 B2 | 6/2023 | Bourke |
| 2004/0233512 A1 | 11/2004 | Fujioka |

(56) References Cited

U.S. PATENT DOCUMENTS

| | | |
|---|---|---|
| 2008/0057000 A1 | 3/2008 | Loveridge |
| 2008/0248001 A1 | 10/2008 | Bourke |
| 2009/0159510 A1 | 6/2009 | Haushalter |
| 2009/0314333 A1 | 12/2009 | Shepard |
| 2010/0188171 A1 | 7/2010 | Mohajer-Iravani et al. |
| 2010/0261263 A1 | 10/2010 | Vo-Dinh et al. |
| 2011/0126889 A1 | 6/2011 | Bourke, Jr. et al. |
| 2012/0089180 A1* | 4/2012 | Fathi ............... H01L 24/32 257/E23.116 |
| 2013/0171060 A1 | 7/2013 | Vo-Dinh |
| 2014/0269806 A1 | 9/2014 | Bora et al. |
| 2014/0323946 A1 | 10/2014 | Bourke, Jr. et al. |
| 2015/0014022 A1 | 1/2015 | Young |
| 2015/0246521 A1* | 9/2015 | Fathi ............... C09J 9/02 522/182 |
| 2016/0027949 A1 | 1/2016 | Cooke |
| 2017/0154866 A1 | 6/2017 | Fathi et al. |
| 2017/0162537 A1* | 6/2017 | Fathi ............. B32B 38/0008 |
| 2017/0167977 A1 | 6/2017 | Rivera |
| 2017/0239489 A1 | 8/2017 | Bourke, Jr. et al. |
| 2018/0269174 A1* | 9/2018 | Fathi ............... B32B 5/12 |
| 2018/0271121 A1 | 9/2018 | Bourke, Jr. et al. |
| 2018/0317307 A1 | 11/2018 | Bourke, Jr. et al. |
| 2018/0358327 A1* | 12/2018 | Fathi ............... A61L 24/06 |
| 2019/0157234 A1* | 5/2019 | Fathi ............... B32B 5/18 |
| 2020/0323711 A1 | 10/2020 | Bourke |
| 2020/0357943 A1 | 11/2020 | Rotschild |
| 2021/0035945 A1* | 2/2021 | Heinrich ............. H01L 24/27 |
| 2021/0353954 A1 | 11/2021 | Bourke |
| 2022/0146076 A1* | 5/2022 | Bourke, Jr. ........ G02F 1/354 |
| 2022/0148997 A1 | 5/2022 | Bourke |
| 2022/0181292 A1 | 6/2022 | Fathi |
| 2022/0275914 A1 | 9/2022 | Bourke |
| 2022/0315809 A1 | 10/2022 | Bourke |
| 2023/0191747 A1 | 6/2023 | Fathi |

FOREIGN PATENT DOCUMENTS

| | | |
|---|---|---|
| KR | 10-1928757 | 1/2014 |
| WO | WO 99/11727 | 3/1999 |
| WO | WO 2010/107720 A2 | 9/2010 |

OTHER PUBLICATIONS

P. Jung, et al., "Progress in Superconducting Metamaterials", Superconductor Science and Technology, 27, 2014, 13pp.

P. Cai, et al., "Synthesis and Realization of Novel Ultra-Wideband Bandpass Filters using 3/4 Wavelength Parallel-Coupled Line Resonators", Proceedings of Asia-Pacific Microwave Conference, 2006, 4pp.

Search Report dated Mar. 14, 2023, in European Patent Application No. 20766537.3.

Search Report dated Mar. 24, 2023, in European Patent Application No. 20766868.2.

Search Report dated Feb. 17, 2023, in European Patent Application No. 20765906.1.

Search Report dated Feb. 21, 2023, in European Patent Application No. 20767183.5.

K. Watanabe, et al., "A Microstrip UWB Bandpass Filter Using a Stub-Loaded Dual-Mode Ring Resonator and a Step Impedance Two-Mode Resonator", Microwave Conference, 2008, 4pp. XP031636965.

L. Snehalatha, et al., "A Compact Half-Wave Folded Waveguide Resonator for Dual-Band Applications", National Conference on Recent Advances in Electronics & Computer Engineering, 2015, 4pp., XP032923138.

Supplementary European Search Report dated Mar. 27, 2023 in European Patent Application No. 20765910.3.

* cited by examiner

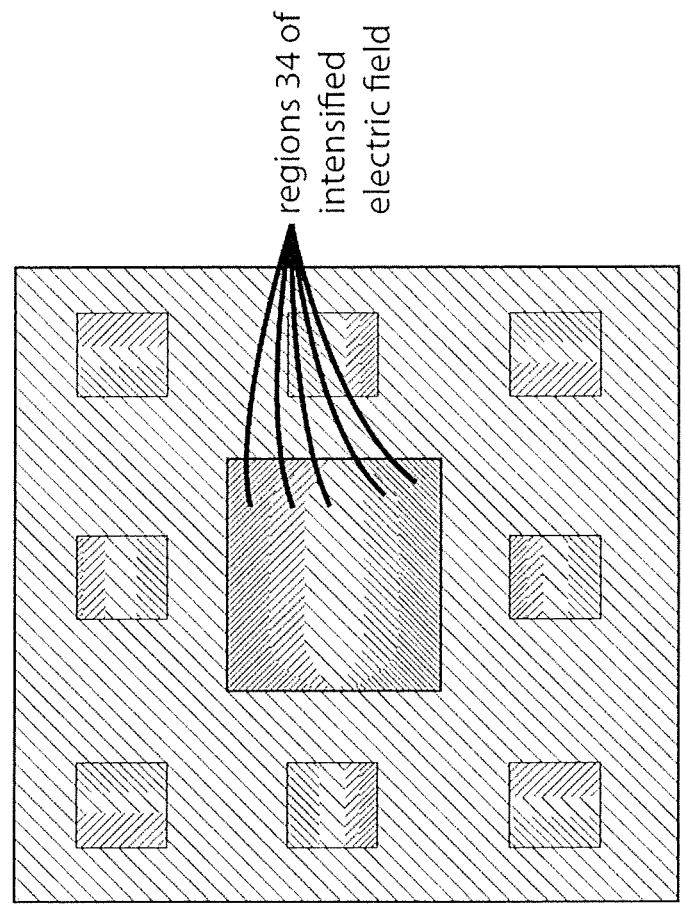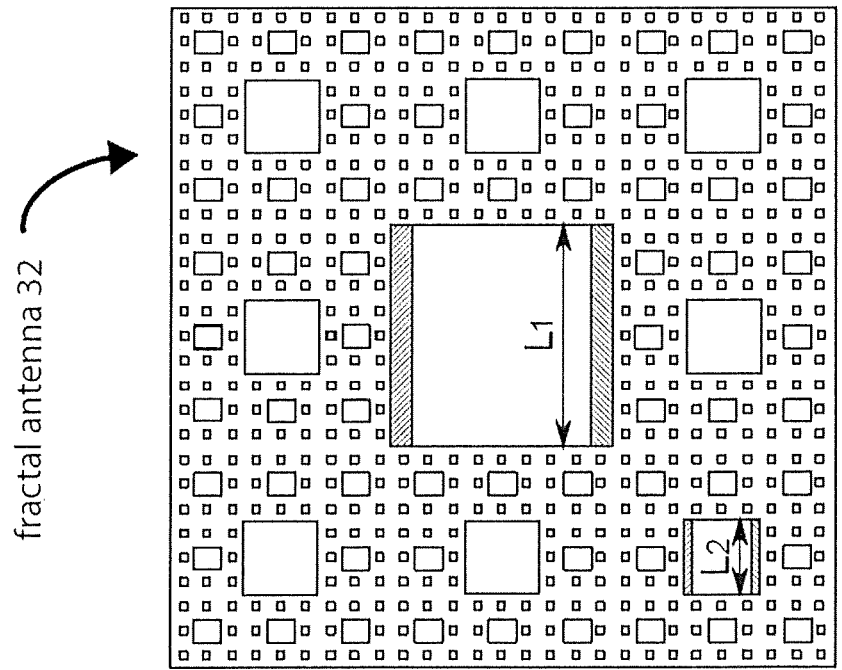
Figure 13

PLASMONICS-ACTIVE METAL STRUCTURES

METAL NANOPARTICLE

DIELECTRIC NANOPARTICLE CORE COVERED WITH METAL NANOCAP

- ▨ METAL 1 (e.g. Au,Ag)
- ▨ METAL 2 (e.g. Au,Ag)
- ▨ MATERIAL CONTAINING PA
- ▥ PROTECTIVE COATING

SPHERICAL METAL NANOSHELL COVERING UCn SPHEROID CORE

OBLATE METAL NANO-SHELL COVERING UCn SPHEROID CORE

METAL NANOPARTICLE CORE COVERED WITH UCn NANOSHELL

METAL NANOSHELL WITH CUm CORE AND PROTECTIVE COATING LAYER

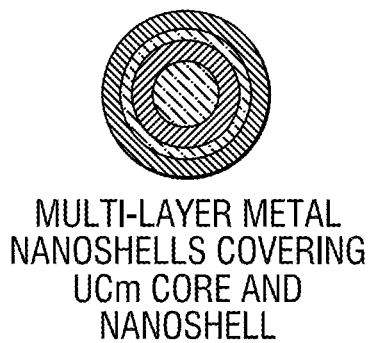

MULTI-LAYER METAL NANOSHELLS COVERING UCm CORE AND NANOSHELL

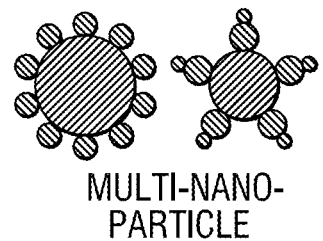

MULTI-NANO-PARTICLE

METAL NANOCUBE AND TRIANGLE

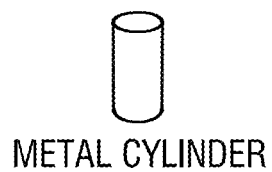

METAL CYLINDER

*FIG. 28C*

LaOBr:Tm3+ coated with Silica was measured during the course of the present invention to emit in the UVB, UVA and the Visible.

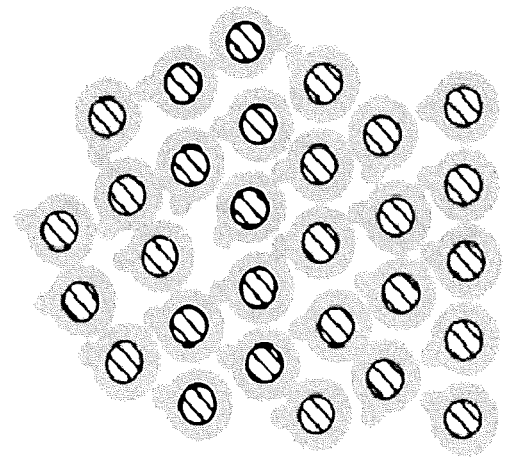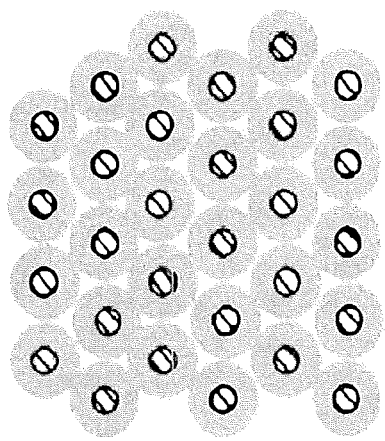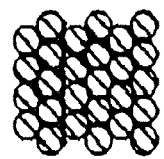
Figure 39

Figure 43B — The silica carrier particle decorated with nano-size particles

Figure 43A — The silica carrier particle of 2 microns in size

Dispensing of 2 adhesive beads through a coaxial needle

Special Dispensing syringe with 2 coaxial containers

Dispensing of 2 adhesive beads

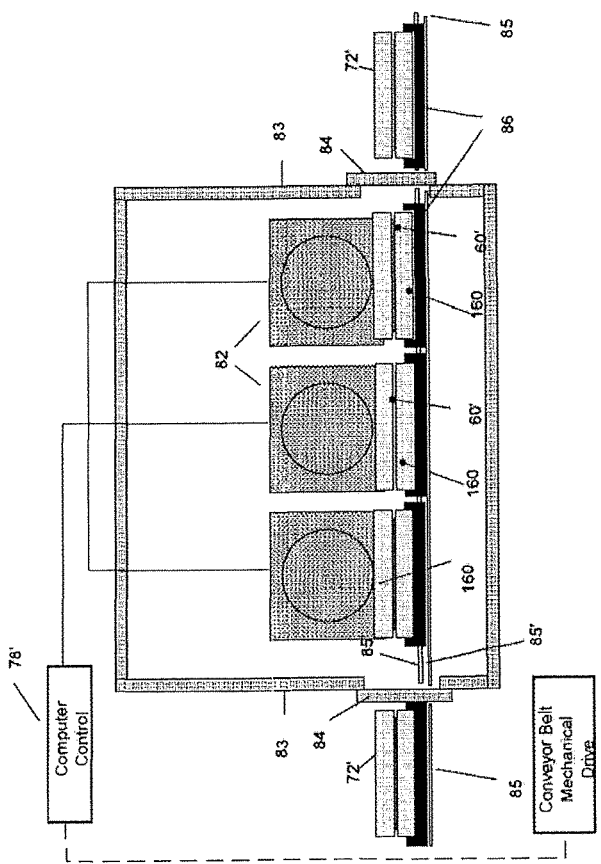
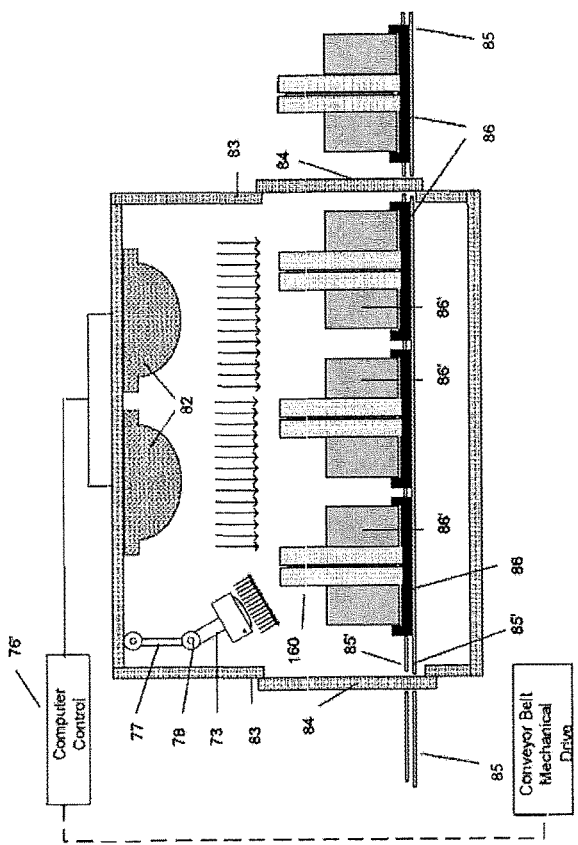
Figure 69B
Figure 69A
The assemblies 160 are oriented in the same direction as the X-ray propagation (in the horizontal plane)
The assemblies 160 are oriented in the same direction as the X-ray propagation in the vertical plane)

Top view of the Wafer Bonding Tool

Cross section view of the Wafer Bonding Tool assemblies 160 interfacing with the conveyor going through a tunnel that stops leakage of X-ray radiation Different Perspective of the assemblies 160 interfacing with the conveyor Contactless chamber design that stops X-ray radiation leakage.

Contactless chambers that stops X-ray radiation leakage to enable wafer processing in a clean room.

A robotic arm can dispense and place metallic components on composite panel 80.

An adhesively bonded metallic fasteners to a composite panel

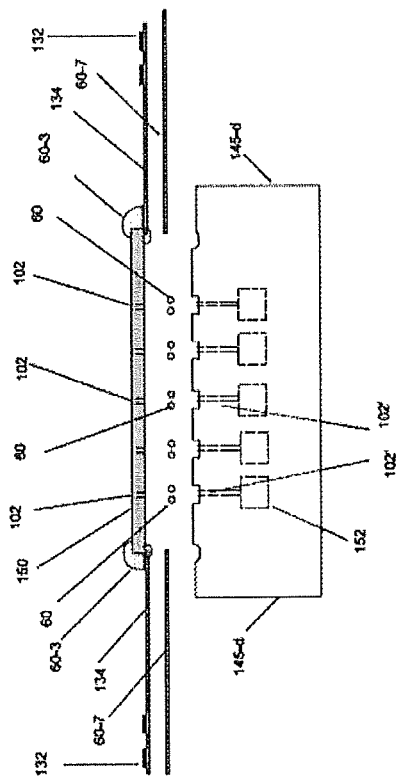
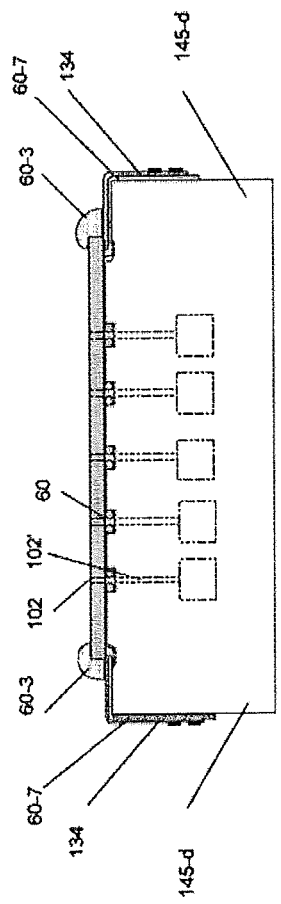
Figure 87A
Figure 87B

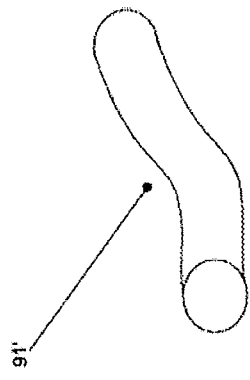
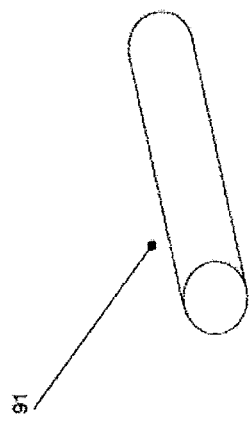
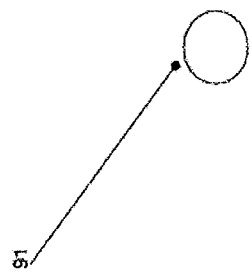
Figure 88A
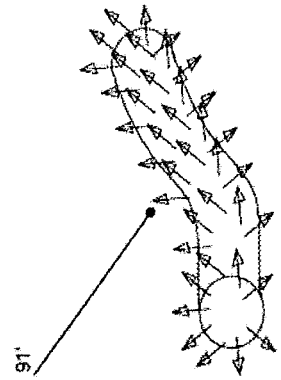
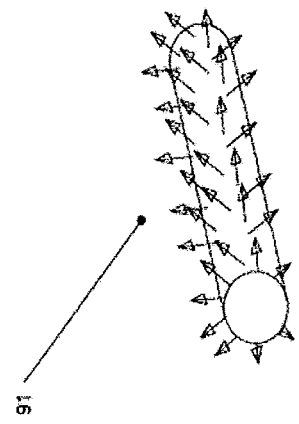
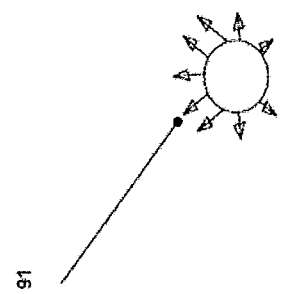
Figure 88B

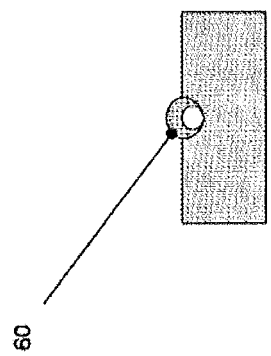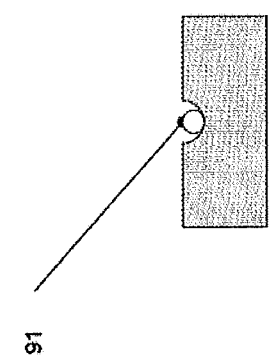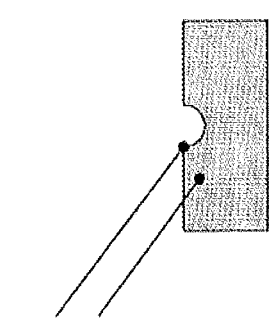
Figure 89A
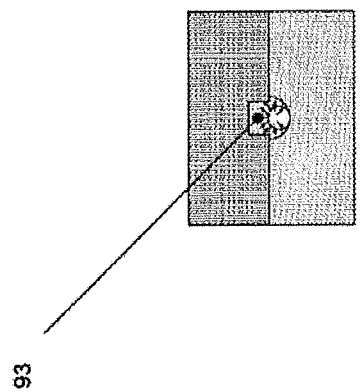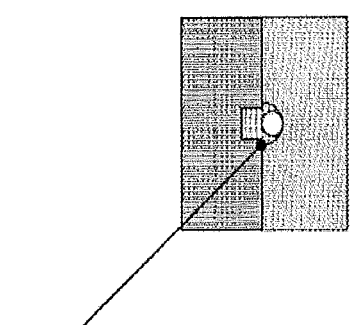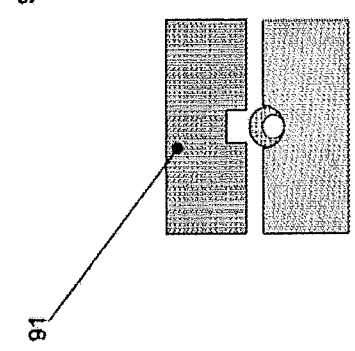
Figure 89B Phosphor without a coating and with a coating
A number of powders can be individually coated when ball milling is used

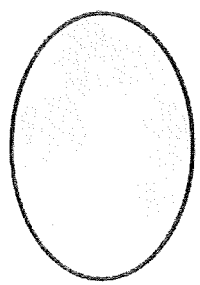 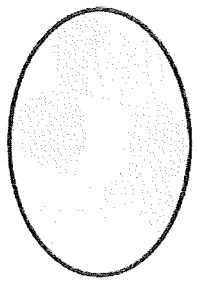
An aggregate of a mix of phosphor particles with a PMMA coating
An aggregate of a mix of phosphor particles with a PMMA coating containing a peroxide chemistry
Figure 102D

*The conformable film that is phosphor loaded can accommodate stretching and maintaining its shape across complex interfaces.*

ENERGY AUGMENTATION STRUCTURES IN ADHESIVE BONDING COMPOSITIONS

CROSS REFERENCE TO RELATED APPLICATIONS

This application is a 371 of international PCT application PCT/US2020/020036, filed Feb. 27, 2020. This application is related to, and claims priority to, provisional application U.S. Ser. No. 62/955,533, filed Dec. 31, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/946,648, filed Dec. 11, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/897,677, filed Sep. 9, 2019, entitled ENERGY AUGMENTATION STRUCTURE; ENERGY COLLECTOR CONTAINING THE SAME; AND EMISSION ENHANCEMENTS UTILIZING AT LEAST ONE ENERGY AUGMENTATION STRUCTURE, the entire disclosure of which is incorporated herein by reference. This application is related to, and claims priority to, provisional application U.S. Ser. No. 62/855,508, filed May 31, 2019, entitled ENERGY AUGMENTATION STRUCTURE; ENERGY COLLECTOR CONTAINING THE SAME; AND COLOR ENHANCEMENT UTILIZING AT LEAST ONE ENERGY AUGMENTATION STRUCTURE, the entire disclosure of which is hereby incorporated by reference. This application is related to, and claims priority to, provisional application U.S. Ser. No. 62/813,390, filed Mar. 4, 2019, entitled COLOR ENHANCEMENT UTILIZING AT LEAST ONE ENERGY AUGMENTATION STRUCTURE, the entire disclosure of which is hereby incorporated by reference. This application is related to U.S. application Ser. No. 16/599,732, filed Oct. 11, 2019, pending, which claims priority to provisional application U.S. Ser. No. 62/745,057, filed Oct. 12, 2018, the entire contents of each of which are hereby incorporated by reference. This application is related to U.S. Ser. No. 13/204,355 filed Aug. 5, 2011, the entire disclosures of which are hereby incorporated by reference. This application is related to U.S. provisional patent application 61/371,549, filed Aug. 6, 2010. This application is related to U.S. provisional patent application 61/161,328, filed Mar. 18, 2009 and to U.S. provisional patent application 61/259,940, filed Nov. 10, 2009, the entire disclosures of which are hereby incorporated by reference. This application is related to U.S. Ser. No. 12/725,108, the entire disclosures of which are hereby incorporated by reference.

This application is related to Provisional Application Ser. Nos. 60/954,263; filed Aug. 6, 2007, and 61/030,437, filed Feb. 21, 2008, and U.S. application Ser. No. 12/059,484, filed Mar. 31, 2008, the contents of which are hereby incorporated herein by reference. This application is also related to U.S. application Ser. No. 11/935,655, filed Nov. 6, 2007; and Provisional Application Ser. Nos. 61/042,561, filed Apr. 4, 2008; 61/035,559, filed Mar. 11, 2008, and 61/080,140, filed Jul. 11, 2008; the entire contents of which are hereby incorporated herein by reference. This application is related to U.S. patent application Ser. No. 12/401,478 filed Mar. 10, 2009, the entire contents of which are hereby incorporated herein by reference. This application is related to U.S. patent application Ser. No. 11/935,655, filed Nov. 6, 2007, and Ser. No. 12/059,484, filed Mar. 31, 2008; U.S. patent application Ser. No. 12/389,946, filed Feb. 20, 2009; U.S. patent application Ser. No. 12/417,779, filed Apr. 3, 2009; the entire disclosures of which are hereby incorporated by reference.

BACKGROUND OF THE INVENTION

Field of the Invention

The invention relates to methods, systems, and devices for energy augmentation, with and without an energy modulation agent/energy conversion agent present, and uses particularly for generating or enhancing photon or electron emission and/or for enhancing light or photon collection.

Discussion of the Background

Presently, light (i.e., electromagnetic radiation from the radio frequency through the visible to the X-ray wavelength range) is used in a number of industrial, communication, electronic, and pharmaceutical processes. Light in the infrared and visible range is typically generated from an electrical energy source which for example either heats a material to extremely high temperatures where black body emission occurs (as in an incandescent lamp). Light in the visible and ultraviolet range is typically generated by heating a gas to an electrical discharge where transitions from one electronic state of the gas atom or molecule occur with the emission of light. There are also semiconductor based light sources (as in light emitting diodes and semiconducting lasers) where electrons/holes in a material recombine to produce light emission.

Visible light is defined as the electromagnetic radiation with wavelengths between 380 nm and 750 nm. In general, electromagnetic radiation including light is generated by the acceleration and deceleration or changes in movement (vibration) of electrically charged to particles, such as parts of molecules (or adjacent atoms) with high thermal energy, or electrons in atoms (or molecules).

For reference purposes, infra-red (IR) radiation just beyond the red end of the visible region; and, ultra-violet (UV) radiation has a shorter wavelength than violet light. The UNI portion of the spectrum is divided into three regions: UVA (315-400 nm), UVB (280-315 nm) and UVC (100-280 nm).

Industrial lamps used in lighting applications cover the visible range of wavelengths for proper white perception. Thermal sources like heated filaments can be made of different type conductors, including NV-filaments, halogen-protected NV-filaments, and electrically induced high temperature plasmas (arc lamps).

The power (energy emitted per second) of a radiant source is frequently expressed in watts (W), but light can also be expressed in lumens (lm) to account for the varying sensitivity of the eye to different wavelengths of light. The derived relevant units are the radiance (luminance) of a source in $W/m^2$ ($lm/m^2$) in a certain direction per steradian (unit of solid angle) and the irradiance (illuminance) of a surface in $W/m^2$ ($lm/m^2$ or lux).

With the development of ultraviolet sources, ultraviolet radiation is being increasingly utilized for industrial, chemical, and pharmaceutical purposes. For example, UV light is known to sterilize media and is known to drive a number of photo-activated chemical processes such as the cross-linking of polymers in adhesives or coatings. Typically, ultraviolet sources use gas discharge lamps to generate emitted light in the ultraviolet range. The emitted light is then optically filtered to remove many of not all of the non-ultraviolet frequencies. Ultraviolet light can also be produced in semiconductor phosphors from the excitation of these phosphors from high energy sources such as, for example, X-ray irradiation.

With the development of infrared radiation sources, infrared radiation is being increasingly utilized for communications and signaling purposes. Typically, infrared sources use broad spectrum light sources referred to as glowbars to generate a broad spectrum of light centered in the infrared range or use lasers to emit very specific infrared wavelengths. For the broad band sources, the emitted light is optically filtered to remove many, if not all, of the non-infrared frequencies.

It is generally desirable to have devices, materials, and capabilities to convert light from one frequency range to another. Down conversion has been one way to convert higher energy light to lower energy, as used in the phosphors noted above. Up conversion has also been shown where lower energy light is converted to higher energy light. Typically, this process is a multi-photon absorption process where two or more photons are used to promote an excited electronic state in a host medium which in turn radiates at a wavelength of light that has a higher energy than the energy of the incident light which promoted the multi-photon absorption process. Both down conversion and up conversion have been studied and documented in the past.

Indeed, workers have studied the phenomenon of photoluminescence and fluorescence, which is the ability of certain solids to emit light when driven or charged by an external energy source. Many well-known phosphors and fluorescors are triggered by high-energy electrons or photons and emit photons of lower energy. It has been recognized that certain infrared phosphors can convert infrared light to light in the visible range (violet through red).

The properties of light such as its radiance is particularly important in reading or display applications where the human eye has to perceive and discern temporary images or permanent images (as for example shown by road and highway signs) formed with visible light. Televisions, computer monitors, displays, and signs use a cathode ray technology (CRT) technology where high energy electrons impinge on phosphors that emit visible light. Televisions, computer monitors, displays, and signs more recently have used liquid crystal display or plasma display technology to generate visible images discernable to the human eye.

In these and other reading or display applications, attempts have been made to develop displays with relatively high contrast images while minimizing the amount of broadband light emitted or reflected from a display, which may detract from the contrast of the image displayed.

In general, the up conversion and the down conversion discussed above have been used in a number of fields to in effect convert an incident wavelength of light to a different wavelength. In one example, high energy photons such as X-rays are converted by absorption in phosphors of the x-ray energy, and luminescence from the phosphors in the ultraviolet, visible, and/or near infrared spectrum has been used for driving photoactive reactions. In other examples, infrared or near infrared light has been up converted by absorption in phosphors of the infrared or near infrared light, and luminescence from the phosphors in the visible and/or ultraviolet spectrum. In other examples, light within the visible region can be down converted or up converted (depending on the phosphors chosen) to a different band within the visible wavelengths. This shifting (energy conversion) can be for color enhancement and can be used in solar cells to convert one part of the solar spectrum to another part more favorable for a photovoltaic device to generate power.

In many of these prior applications, metallic structures have been placed on the phosphors or in a vicinity of the phosphors to generate a plasmonics effect which essentially is an amplification of the local field very nearby the outside of the metallic structures. Plasmonic effects can enhance coupling of incident light into the phosphors and/or enhance the reactivity of the converted light tons nearby receptor. While the plasmons in the metal can propagate along the metal, the plasmons decay evanescently in the z direction normal to the metal/dielectric interface with 1/e decay length of the order of half the wavelength (~200 nm for wavelengths in the visible range).

In some prior applications, photonic band gap structures have been used. In a photonics band gap structure, the materials thereof consist or photonic crystals (PhCs) are materials with a periodic dielectric profile, which can prevent light of certain frequencies or wavelengths from propagating in one, two or any number of directions within the materials. In this way, light not suitable or detrimental to a process can be rejected while light more suitable for a process can be confined within the photonic band gap structure or better confined within the photovoltaic converter.

In the field of solar cells, the addition of plasmonics, photonics band gap, and up and down conversion is known in the literature. Additionally, antireflection coatings and concentrators are well known in the literature.

The problem with the plasmonics effect is that, as noted above, the plasmons and the electric field enhancement decays rapidly with distance away from the metal structure meaning that the effect is only useful for a small volume of interaction.

The problem with antireflection coatings is that, although sun light is not scattered away as much as if there were no coatings, the light transmitted is still predominantly that of wavelengths that are not optimum for power generation.

The problem with concentrators is that, besides concentrating light which can be converted to power, a concentrator also concentrates light which does not generate power, which in general makes for waste heat.

While photonic band gap structures can serve to reflect or confine light, they have no effective way to gain power from the discarded light.

Adhesives are well known and are used for a wide variety of applications. One particularly important application domain is in the field of manufacturing and assembly, where thermoset adhesives are used to bond one material to another material. Commercially available materials are formulated to meet various requirements, and in addition to the monomer(s) may contain particulate fillers such as metal, oxides, or dielectric powders, as well as various additives to control thermal conductivity, viscosity and other properties. The is adhesive materials are typically dispensed as a thixotropic fluid in precise locations, and after all the parts are placed, the entire assembly is heated to a temperature necessary to polymerize the monomers or crosslink resins. The adhesion of two objects is done by adding the adhesive material at the interface of two objects to be bonded. The potential elimination of the addition of a third layer (the adhesive in this case) would be of great benefits. The tool used to dispense an adhesive is eliminated and the step required to cure the adhesive under heat is also rendered obsolete which saves overall cycle time.

As modern assembly methods evolve and more process steps are streamlined for a more efficient and more vertically integrated process, the steps needed to maximize assembly tool utilization, the permissible thermal budget and process cycle time during assembly continue to decrease. Faster manufacturing and higher yields are always of great benefit to the manufacturers.

The clear limitation of conventional photoinitiators is the need to have direct line-of sight access to a suitable light source. The clear limitation of conventional thermally activated adhesive is the inherent poor thermal conductivity of the materials to be bonded which results in a long process time. The direct welding of two interfaces would be highly desirable. A further disadvantage of thermal activation of adhesives is the potential thermal expansion mismatch when bonding unlike materials to one another may occur especially if the heating heats the bulk of the two materials above their glass transition temperatures, which thereafter cool and contract at different rates, thus increasing stress at the interface.

Furthermore, the assemblies used for various commercial products are relatively small. While electron beam can deliver a desirable source of radiation, the electron beam is not compact and is more applicable to large form factors (such is the case of a wide web process for example). Meanwhile, X-Ray energy can be delivered through a more compact set of equipment and can be integrated in various tools for more efficient tool utilization.

In one embodiment, the present invention provides materials and methods for polymer curing, particularly adhesive curing and bonding, and more particularly to methods for using energy conversion and photoinitiator chemistries in applications where access to an external light source is not available and/or where bonding without a coefficient of thermal expansion mismatch is desirable. These materials and methods can be used with or without the energy augmentation structures described herein and with or without the energy conversion materials and devices described herein. With the energy augmentators present, this invention can generate local regions of intense electric fields to enhance light emission from the energy converters in proximity to those local regions, locally generating or enhancing light emission or localized internal heating within the medium to be cured. The internally generated light would activate the photoinitiator chemistries or generate free radicals inside the adhesive medium. The microdomains of internally generated heat would activate thermosetting polymers and adhesives, while maintaining an overall lower bulk temperature for the curing of the polymers/adhesives.

One particularly important application domain is in the field of microelectronics assembly, where thermoset adhesives are used to bond bare die to substrate, establish conductive contacts, and perform various roles in packaging and sealing structures such as glob-top and die-underfill structures. Commercially available materials are formulated to meet various requirements, and in addition to the monomer(s) may contain particulate fillers zs such as metal, oxides, or dielectric powders, as well as various additives to control thermal conductivity, viscosity and other properties. The materials are typically dispensed as a thixotropic fluid in precise locations, and after all the parts are placed, the entire assembly is heated to a temperature necessary to polymerize the monomers or crosslink resins.

As modern electronic components evolve to smaller sizes, and integrated circuits include ever-smaller features such as ultra-shallow junctions, the permissible thermal budget during assembly continues to decrease. New memory device technologies, for example, incorporate phase-change materials that are temperature sensitive and may need to be assembled using low-temperature processing. Similarly, polymer composites used for dental restorations must be cured without subjecting the patient to high curing temperatures. To address these issues, many photo-curing polymer systems have been developed. In general, these systems employ at least one photoinitiator, which, when exposed to UV light, releases chemical energy to form free radicals or cations to initiate the reaction of the monomers at substantially ambient temperatures.

The clear limitation of conventional photoinitiators is the need to have direct line-of-sight access to a suitable light source. This prevents the use of conventional materials for advanced processes such as multilayer stacks of individual silicon dies, because there is no way to get the UV light into the interior of the stack.

Furthermore, the conventional UV curable adhesives cure from the outside surface of an adhesive bead to the inside of the adhesive bead; and, in most cases curing is accompanied by the formation of a skin. In the present invention curing is more controllable and can proceed across the entire volume of the adhesive bead.

SUMMARY OF THE INVENTION

In one embodiment, there is provided an energy augmentation structure capable of capturing one or more wavelengths of electromagnetic energy, and augmenting the one or more wavelengths of electromagnetic energy in at least one property.

In one embodiment, the energy augmentation structure may be one or more of an electromagnetic resonator structure, a folded resonator structure, and a fractal structure having a region of an intensified electromagnetic field within the structure.

In a further embodiment, there is provided an energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

In one embodiment, the energy converter noted above is disposed with an energy augmentation structure comprising one or more of an electromagnetic resonator structure, a folded resonator structure, and a fractal structure, any of which having a region of an intensified electromagnetic field within the resonating structures.

In one embodiment, the energy converter noted above includes one or more luminescing materials. As described herein, there are uses of the energy augmentation structure and/or energy collector embodiments which enhance bioluminescence, chemo-luminescence, photoluminescence, fluorescence, and mechano-luminescence.

In one embodiment, the energy converter noted above includes for the one or more luminescent materials phosphorescent materials, fluorescent materials, electroluminescent materials, chemo-luminescent materials, bioluminescent materials, and mechano-luminescent materials used in conjunction with or not in conjunction with the energy augmentation structure noted above. When used in conjunction with the energy augmentation structure noted above, the emitted electromagnetic energy from the luminescent material is emitted with at least one augmented property compared to if the energy converter (e.g., the luminescent material) were remote from the at least one energy augmentation structure.

In one embodiment, the energy converter noted above includes for the one or more luminescing materials phosphorescent materials, fluorescent materials, electroluminescent materials, chemo-luminescent materials, bioluminescent materials, and mechano-luminescent materials used in conjunction with or not in conjunction with the energy augmentation structure noted above and which emit one of ultra-violet, visible, near infrared, and infrared light. In this embodiment, UV-emitting electroluminescent materials or mechano-luminescent devices and materials can be used. In this embodiment, UV-emitting bioluminescent materials can be used.

In one embodiment, there is provided a color enhancement structure having a) an energy collector comprising at least one energy augmentation structure, and b) an energy converter capable of converting a second wavelength of light into and emitting therefrom a third wavelength of light shifted in wavelength from the second wavelength of light. In one embodiment, the energy converter is disposed in a vicinity of the at least one energy augmentation structure such that the light shifted in wavelength is emitted with an intensity larger than if the converter were remote from the at least one energy augmentation structure.

In additional embodiments, there are provided uses of the energy augmentation structure and energy collector embodiments in adhesives/resins and other end uses.

In another embodiment, the above noted distributed energy collector can deliver light to different positions within an artificial medium for adhesive curing of the artificial medium.

In one embodiment, the above noted energy augmentation structure can be used alone to promote thermocuring of adhesives that are heated in a vicinity of the region of the intensified electromagnetic field.

In one embodiment, the above noted energy augmentation structure can be used in conjunction with the energy converters to promote curing of adhesives either in a vicinity of the region of the intensified electromagnetic field or outside of the energy augmentation structure by enhanced emissions from the energy converters because of their presence in the vicinity of the region of the intensified electromagnetic field. In the above two embodiments, excitation of the energy augmentation structure by an infrared laser generates the region of the intensified electromagnetic field. In the embodiment with energy converters, x-ray excitation or other high energy source (electrons, protons, gamma, or beta particles) can be used to stimulate luminescence from the energy converters for photocuring.

In one embodiment, the above noted energy augmentation structure can be used alone to promote localized heating in a vicinity of the region of the intensified electromagnetic field.

In another embodiment, there are provided uses of the energy augmentation structure and/or energy converters inside plasma (light-emitting) capsules to promote generation and maintenance of plasma state ions which light.

In another embodiment, there are provided uses of the energy augmentation structure and/or energy converters to enhance electron emission from surfaces in a vicinity of the energy augmentation structure.

In one embodiment, the energy converter noted above includes one or more electron emitting materials. The electron emitting materials may be photon-induced materials which photo-eject an electron under exposure to UV light. The electron emitting materials may be thermally heated materials which emit electrons from heated surfaces of the emitting materials.

In one embodiment, the energy converter noted above includes for the one or more electron emitting materials nanoscale field emission tips. When used in conjunction with the energy augmentation structure noted above, the emitted electron flux from the electron emitting materials is higher compared to if the energy converter (e.g., the nanoscale field emission tips) were remote from the at least one energy augmentation structure.

One object of the present invention is to provide polymer formulations (i.e. monomers, photoinitiators, and energy converters) with or without the energy augmentators that can be cured by indirect photoinitiation, i.e. in the absence of line-of-sight access to the external energy source.

A further object of the present invention is to provide an adhesive composition that may be cured at ambient temperature.

Another object of the present invention is to provide a flowable adhesive composition with or without the energy augmentators containing a photoinitiator and an energy converter, preferably a downconverter such as a phosphor or scintillator material (or a combination of a phosphor and a scintillator material).

Another object of the present invention is to provide a flexible (but conformal) sheet adhesive material with or without the energy augmentators capable of being polymerized by selected ionizing radiation.

Another object of the present invention is to provide a method for adhesive bonding with or without the energy augmentators at ambient temperature, as well as a method of adhesive bonding suitable for bonding silicon dies or wafers in a stack at ambient temperature, along with a wide variety of other end uses.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 13 is a diagram showing a fractal antenna segment where the straight-line sides of the metal pads have locally intensified electric field;

FIG. 16 is a diagram showing a paired three-dimensional fractal structure with an intensified electric field in between;

FIG. 28C is a schematic illustrating various plasmonics-active converter structures of the invention;

FIG. 39 provides a representation of the effects of a large coating thickness or coating shape on packing factor of a phosphor.

FIGS. 69A-C provide representations of different embodiments of the method of the present invention whereby the workpiece being irradiated is oriented in different ways with respect to the radiation source.

FIGS. 87A and 87B provide representations of use of an embodiment of the present invention in connecting an active device to a fluidic reservoir.

FIGS. 88A and 88B provide representations of leaky optical fiber elements that can be used for curing in the present invention FIGS. 89A and 89B provide representations of an embodiment of the present invention using leaky optical fiber elements.

FIG. 102D is a schematic depicting an aggregate of different phosphors with and without a coating of PMMA.

DETAILED DESCRIPTION OF THE INVENTION

Figure 1:
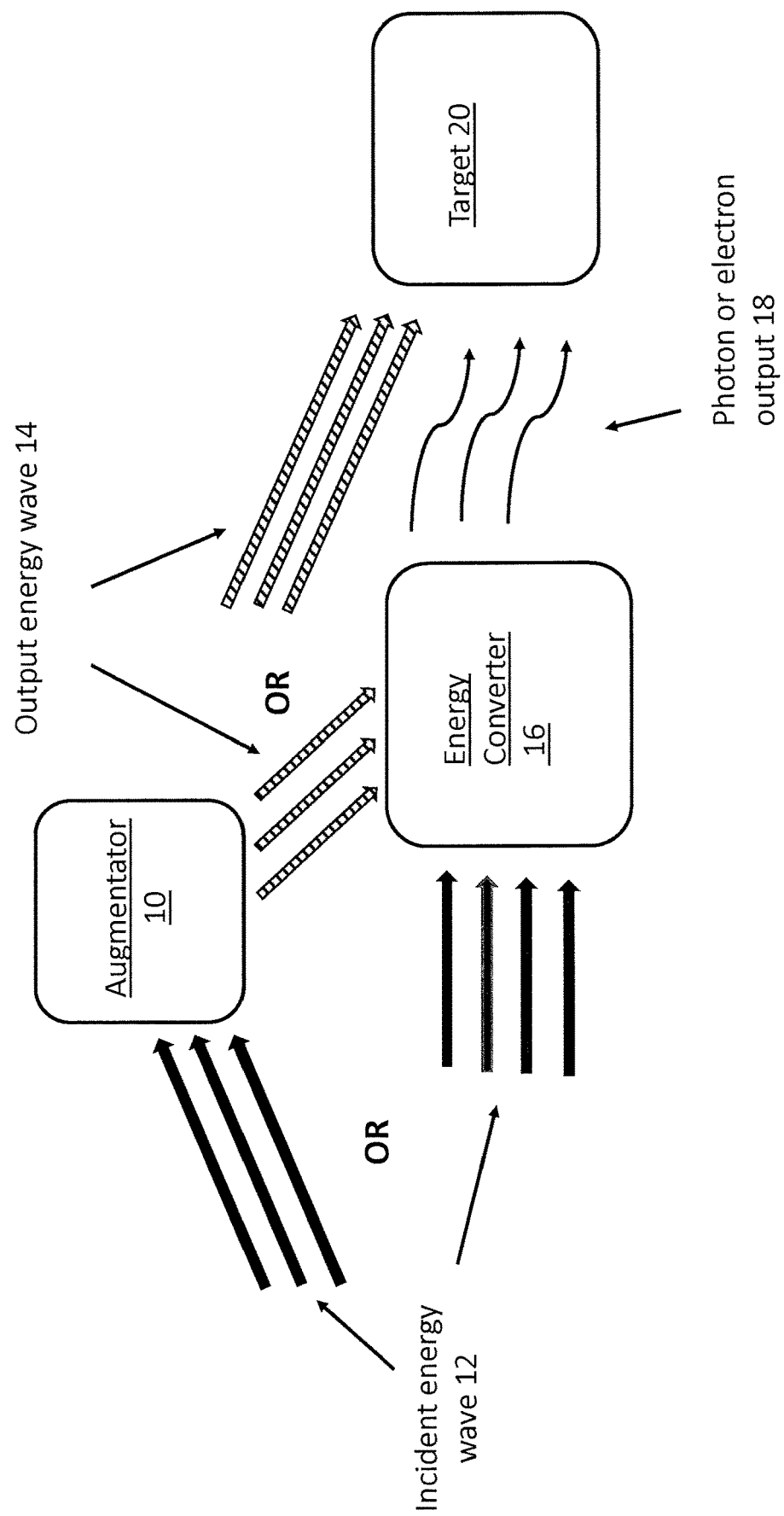
FIG. 1 is a schematic depicting an energy augmentator system of the invention with optional inclusion of an energy converter.

Reference will now be made in detail to a number of embodiments of the invention, examples of which are illustrated in the accompanying drawings, in which like reference characters refer to corresponding elements.

As noted above, energy converters such up conversion materials and down conversion materials have been used in a number of fields in effect to convert an incident wavelength of light to a different wavelength. Metallic structures have been placed on the phosphors or in a vicinity of the phosphors to generate a plasmonics effect which essentially is an amplification of the local field very nearby the outside of the metallic structures. In some applications, to photonic band gap structures have been used in solar cell applications to prevent light of certain frequencies or wavelengths from propagating in one, two or any number of directions within the materials. Additionally, antireflection coatings and concentrators are well known in the literature.

The present inventors recognized that the shortcomings of these structures could be addressed by use of the energy augmentation structures described herein used separately or in conjunction with energy converters.

A. Energy Augmentation Structures

In the present invention, the term "energy augmentation" means effecting some change in one or more wavelengths of electromagnetic energy in at least one property, including, but not limited to, intensity, power, associated electrical field, associated magnetic field, wave amplitude, photonic flux, magnetic flux, phase, coherence, propagation direction, etc. The structure performing the energy augmentation can be termed an "energy augmentation structure" or an "energy augmentator". These terms are used interchangeably herein. Preferably the energy augmentation structure is a non-plasmonic structure (a structure that does not exhibit plasmonic properties).

The energy augmentator can take any desired form so long as it can perform the necessary function of augmenting the energy applied to it, causing a change in one or more wavelengths of electromagnetic energy in at least one property as noted above. Examples of such energy augmentators include, but are not limited to, at least one non-plasmonic member selected from the group consisting of resonators, fractal antennas, electrical grid patterns, antennas, cavities, etalons, nanoparticles, microparticles, nanostructures, and microstructures, just to name a few.

In one embodiment, as shown schematically in FIG. 1, an energy augmentator 10 is provided that is capable of receiving or capturing one or more wavelengths of electromagnetic energy representing an incident energy wave 12. Having received or captured the incident energy wave 12, the energy augmentator 10 is capable of augmenting the one or more wavelengths of received or captured energy wave flux 12 in at least one property. As shown in FIG. 1, in one embodiment, energy augmentator 10 then outputs an energy wave 14 with the at least one property augmented, with the augmented energy wave 14 incident on target 20. Details of the augmentation are described below.

In another embodiment, the output (augmented) energy wave 14 (i.e., one or more output wavelengths of electromagnetic energy) can be incident on an energy converter 16 (such as the up conversion materials and down conversion materials noted above). The energy converter 16 can output photons or electrons 18 which can be directed to target 20. In these embodiments, target 20 may receive the photons or electrons 18 or the output augmented energy wave 14 simultaneously or separately.

In one embodiment, the energy augmentator 10 may be one or more of an electromagnetic resonator structure, a folded resonator structure, and a fractal structure having a region of an intensified electromagnetic field within those structures.

Figure 2:
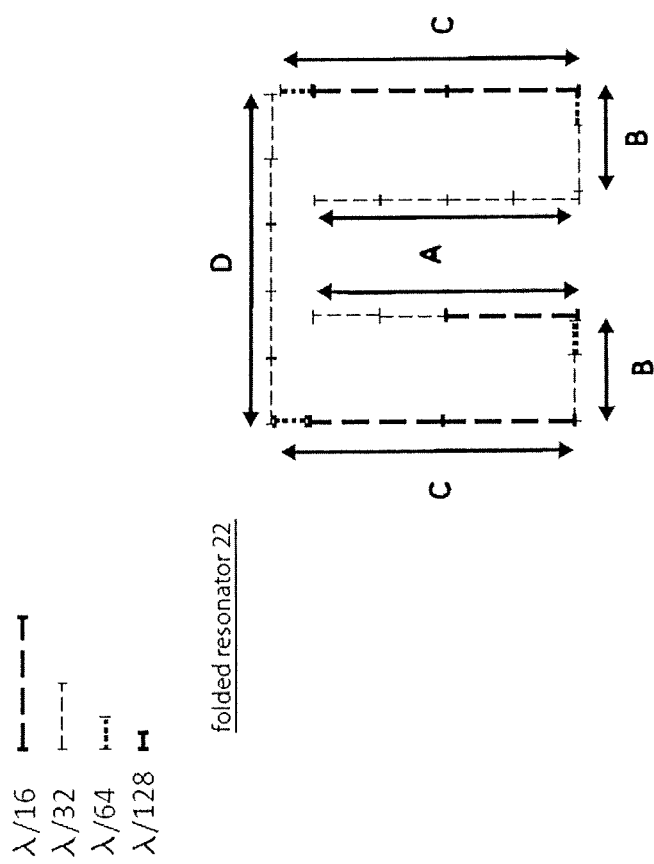
FIG. 2 is a schematic depicting a folded resonator as an illustrative energy augmentation structure of the invention.

FIG. 2 below is a diagram depicting a folded resonator structure 22 of this invention.

The resonator in one embodiment of the present invention is a ¾λ metal structure bent, as shown in FIG. 2 having a "folded" structure making for opposing electrodes between which an intense electric field is developed. Exemplary characteristics of the "folded structure" antenna are listed in the following table:

TABLE 1

| Antenna Side | Wavelength (nm) | | | | | | | | | | |
|---|---|---|---|---|---|---|---|---|---|---|---|
| | 1400 | 1300 | 1200 | 1100 | 1000 | 900 | 800 | 700 | 600 | 500 | 400 |
| A | 175.0 | 162.5 | 150.0 | 137.5 | 125.0 | 112.5 | 100.0 | 87.5 | 75.0 | 62.5 | 50.0 |
| B | 65.6 | 60.9 | 56.3 | 51.6 | 45.9 | 42.2 | 37.5 | 32.8 | 28.1 | 23.4 | 18.8 |
| C | 195.9 | 152.8 | 168.8 | 154.7 | 140.6 | 126.6 | 112.5 | 98.4 | 84.4 | 70.3 | 56.3 |
| D | 218.8 | 203.1 | 187.5 | 171.9 | 156.3 | 140.6 | 125.0 | 109.4 | 93.8 | 78.1 | 62.5 |
| Total | 1093.8 | 1015.6 | 937.5 | 859.4 | 782.3 | 703.2 | 625.0 | 546.9 | 458.8 | 390.6 | 312.5 |
| ¾ lambda | 1050 | 975 | 900 | 825 | 750 | 675 | 600 | 525 | 450 | 375 | 300 |

The calculations of a theoretical ¾λ and the slightly oversized antenna to account for all the bending corners involved in making the antenna would result in this structure having a size between the theoretical 0.75*λ and the upper oversized limit 0.78*λ.

While the resonators shown in most of the drawings could be characterized as having a rectangular-shape loop connecting the opposing antenna sections or electrodes together, the invention is not so limited, Other "loop" shapes could be used, so long as the opposing electrodes are parallel and coplanar with one another, with the loop forming an electrical path having a length of ½ λ, with the opposing electrodes having a length of ⅛ λ each, thereby making the ¾ λ resonator.

Figure 3:
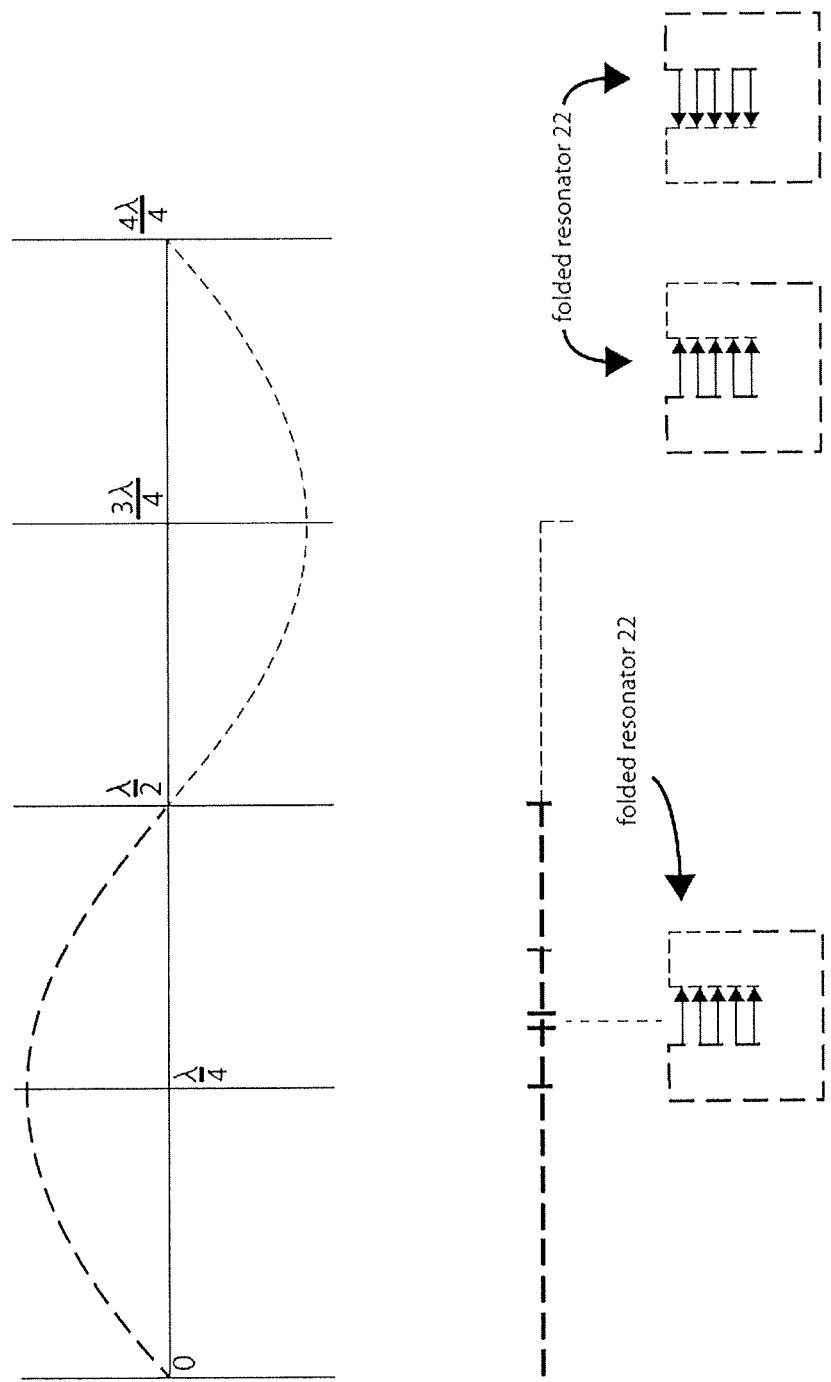
FIG. 3 is a diagram depicting the basic concepts underlying one of the energy augmentation structures of this invention.

FIG. 3 is a diagram depicting the basic concepts underlying one of the energy augmentation structures of this invention. In the depiction in FIG. 3 is a sinusoidal wave representing for example an instantaneous waveform of a light wave (an incident energy flux 12). The depiction shows the length of ¾ of the wavelength λ, and how in one embodiment a ¾ λ resonator is constructed with the open ends of the resonator "folded" together to form in this embodiment a ¾ λ folded resonator 22, As shown in FIG. 3, the folded ends form a region of an intensified, amplified electric field denoted by the horizontally directed arrows between the opposing open ends. When light nominally of a wavelength λ (or harmonics thereof 2λ, 3λ, 4λ, etc.) is incident on the folded antenna structure, a fraction-a of the light will be coupled into this structure establishing the amplified electric field. Since the light from sun comes continuously and at different rotational polarizations, subsequent light waves will continue to "pump" the electric fields in the resonant structure until some "loss" mechanism caps the strength of the electric fields. For resonators made of low loss materials, high Q-factors are obtained which, in this case, could mean that the electric field strength between the opposing electrodes may be for example 100 to 1000 times the peak amplitude of the electric field vector of the incident waveform.

Figure 4:
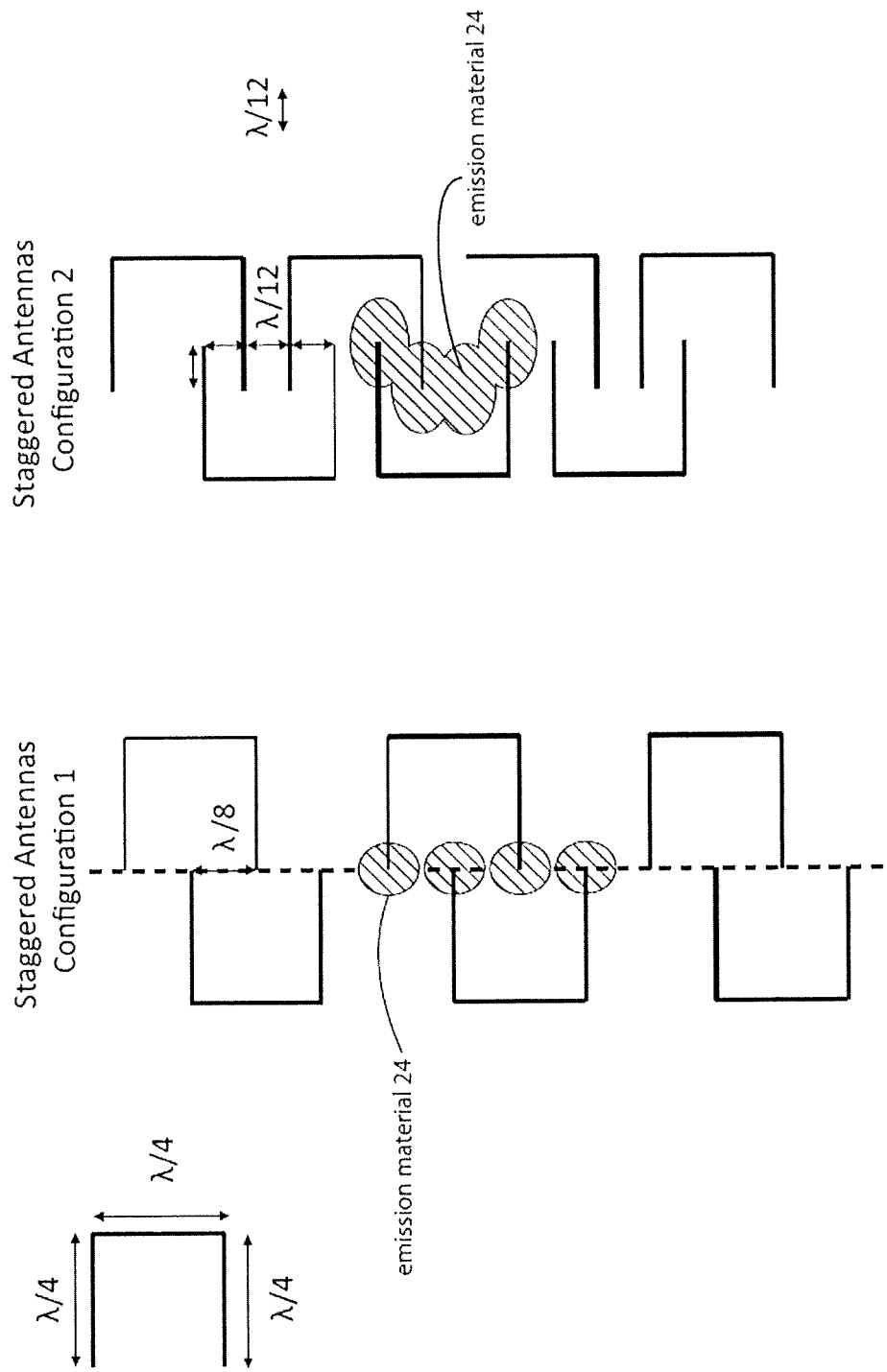
FIG. 4 is a schematic depicting a staggered antenna configuration as an illustrative energy augmentation structure of the invention.

In another embodiment, a resonating antenna could have the configuration below shown in FIG. 4. Here, the ¾ λ structures oppose and are interdigitated together without a "folded" structure. In the depiction in FIG. 4, the horizontal stubs are ¼ λ long, the vertical extending connectors are ¼ long, and the vertical spacing between the horizontal stubs and the extend of interdigitation varies as shown between configuration 1 and configuration 2. In one embodiment of the invention, an energy converter, a light or electron emitting material, or a color emitting or color converter material (i.e., emissive material 24) is placed inside or around the region of an intensified electric field, as shown in FIG. 4.

Figure 5:
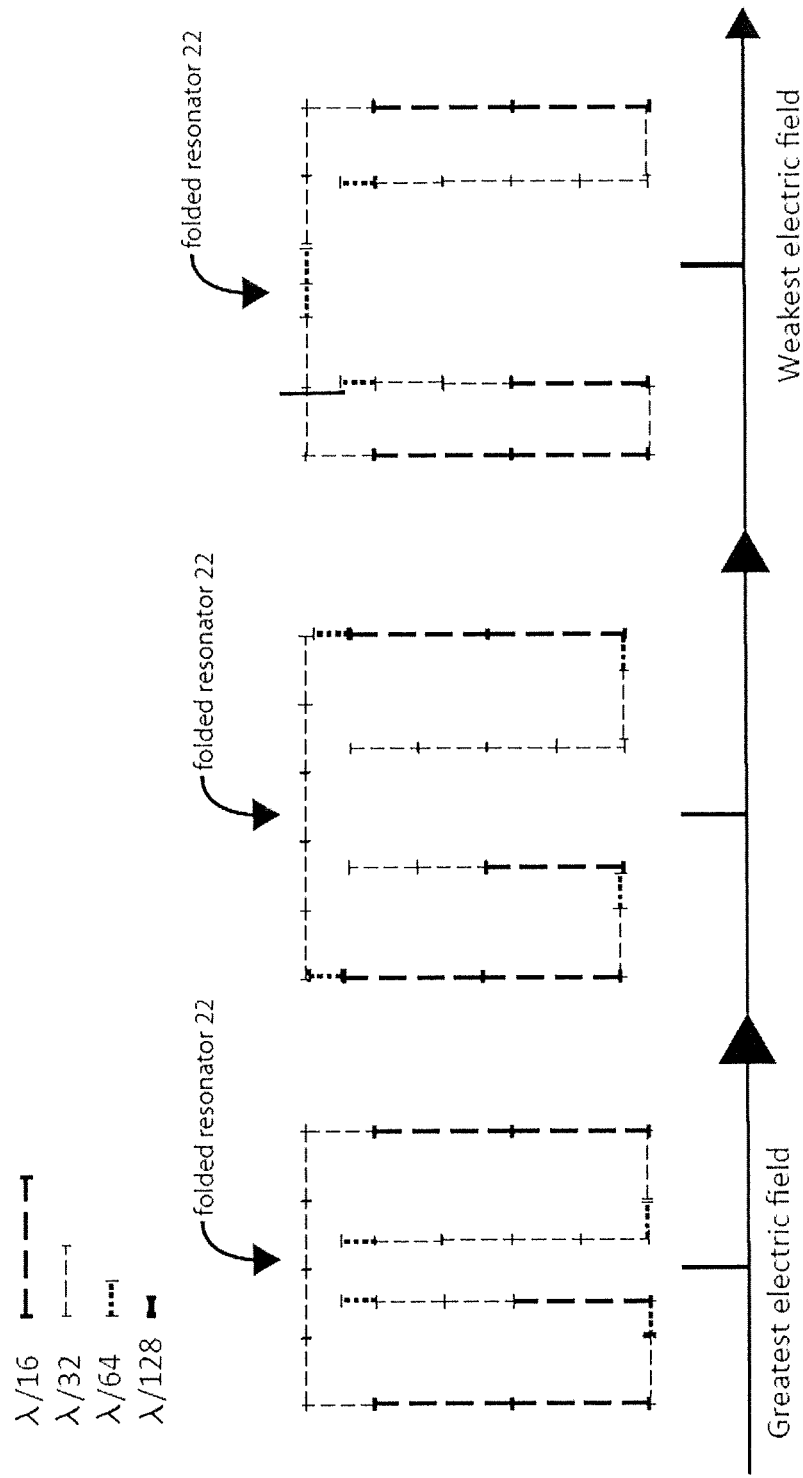
FIG. 5 is a schematic depicting the effect of electrode spacing in the folded resonator of the invention.

FIG. 5 shows that different ¾ λ folded resonators can be made having different distances between the opposing electrodes and thus different electric field strengths. In this way, the folded resonators of the invention can be adjusted such that the strength of the electric field between the opposing electrodes does not exceed the dielectric strength of any material in between. Exceeding the dielectric strength of any material in between could result in destruction of that material as intense current (e.g., a micro-arc) would flow during any time that the dielectric strength was exceeded, thus breaking the material down. As shown, here the opposing sides need not have an exact length of ⅛ λ.

In one embodiment of the invention, an energy converter, a light or electron emitting material, or a color emitting or color converter material (i.e., an emissive material) 24 is placed inside or around the regions of intensified electric field near/between the opposing electrodes. In one embodiment of the invention, the color emitting or color converter material may itself be absorbing a color light such as for example blue light and emitting lower energy, down-shifted red light. In this case, a red phosphor could be the color emitting or color converter material.

While the ¾ λ folded resonator in one embodiment could be designed to resonate at blue light (λ=420 to 440 nm), the resonator is preferably designed to resonate from light at a different frequency than the blue light that is being absorbed by the red phosphor. In one embodiment, for color enhancement for objects under solar light, the ¾ λ folded resonator could be designed to be driven by infrared light from the solar spectrum (e.g. λ=700 to 1000 nm) to generate the intensified electric field, and the red phosphor disposed in the region of intensified electric field would have a brighter red emission than if the intensified electric field were not present.

Figure 6:
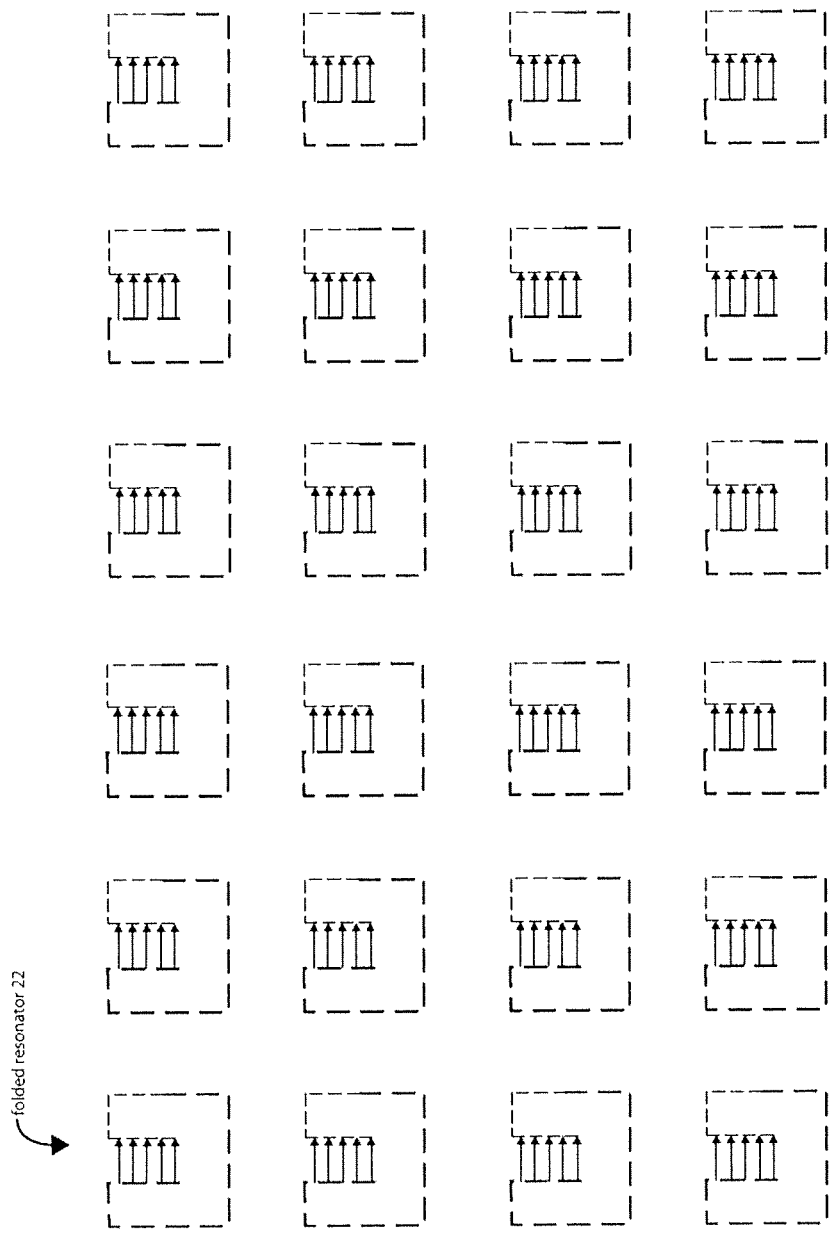
FIG. 6 is a diagram showing a pattern of ¾ λ folded resonators distributed in space.

FIG. 6 is diagram showing a pattern of ¾ λ folded resonators 22 distributed in space. As to be discussed in more detail later, there are numerous ways to distribute the ¾ λ folded resonators. The present invention is not limited to the regular, uniformly spaced and sized resonators shown in FIG. 6. There is no requirement that the distribution be regular, uniformly spaced, uniformly sized, or uniformly oriented. Differently sized, spaced, and oriented resonators may provide better utilization of the full spectrum of the sun or any other light source incident on the object.

Figure 7A:
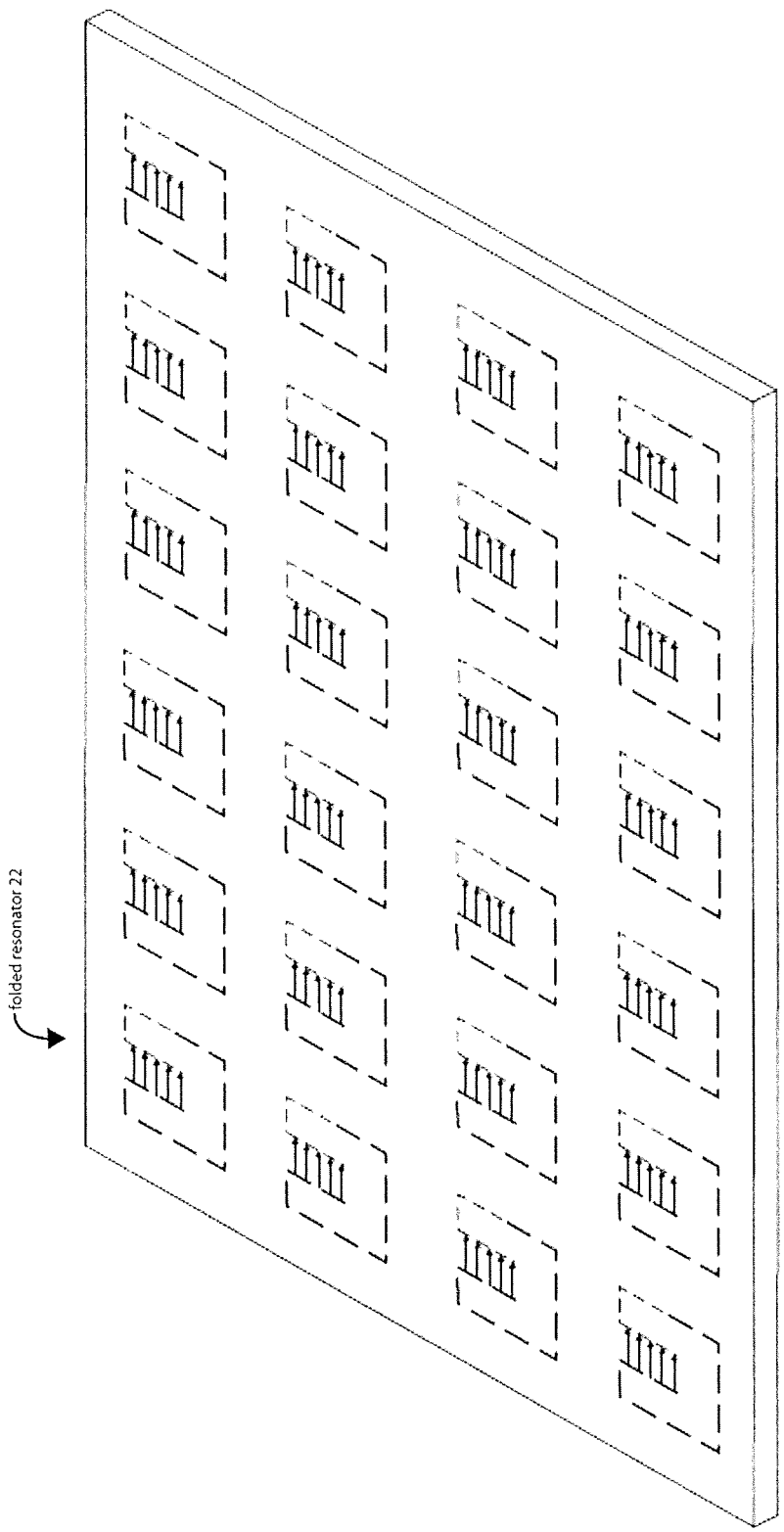
FIGS. 7A-7C is a diagram showing a pattern of ¾ λ folded resonators distributed in a plane or otherwise along a surface of an object.

FIG. 7 is diagram showing a pattern of ¾ λ folded resonators 22 distributed in a plane or otherwise along a surface of an object. In one embodiment, this pattern could be formed by lithographic or stamping processes onto a planar surface such as a glass plate or onto a curved sheet type product. In one embodiment, the glass plate could itself be a phosphorescent plate or could have sections of different phosphorescent material deposited in a pattern that would align/match the respective positions of the opposing electrodes on each resonator. In one embodiment, the sheet product could be a laminate type of product applied to for example a nominally white object. Upon solar irradiation, the infrared part of the solar spectrum (normally only heating the surface) would generate the intensified electric field regions. In those regions, down converting phosphors converting deep blue and ultraviolet light to visible light would convert the deep blue and ultraviolet light of the solar spectrum to visible light, and the intensified electric field would enhance greater visible light emission.

Figure 7B:
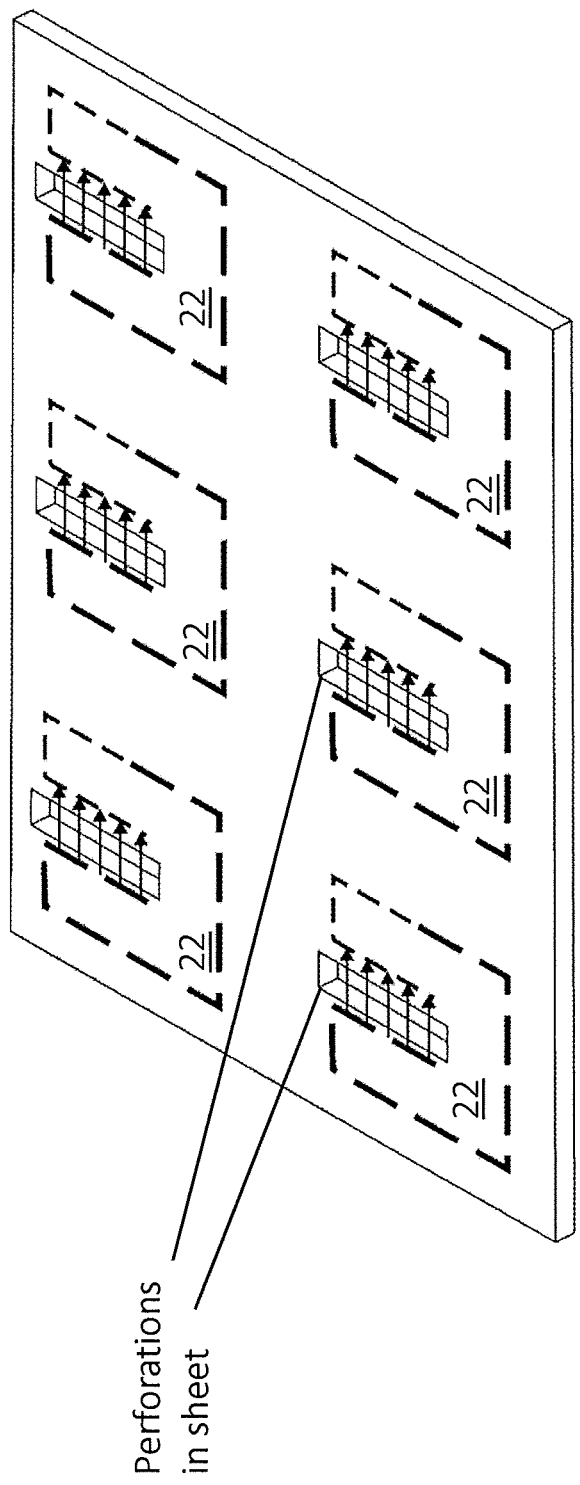

In one embodiment, the energy augmentators could be disposed on a perforated sheet, as shown in FIG. 7B. The perforations in one embodiment are in the regions of intensified electric field such that phosphors or other energy converting materials or devices could be disposed in the perforations.

In one embodiment (for color enhancement), the sheet product could be a laminate type of product applied to for example a nominally green object. Upon solar irradiation, the infrared part of the solar spectrum (normally only heating the surface) would generate the intensified electric field regions. In those regions, down converting phosphors converting blue, deep blue and ultraviolet light to green light would convert the blue, deep blue, and ultraviolet light of the solar spectrum to green light and the intensified electric field would enhance greater green light emission.

In one embodiment, the sheet product could be a laminate type of product applied to for example a nominally red object. Upon solar irradiation, the infrared part of the solar spectrum (normally only heating the surface) would generate the intensified electric field regions. In those regions, down converting phosphors converting green, blue, deep blue and ultraviolet light to red light would convert the green, blue, deep blue and ultraviolet light of the solar spectrum to red light and the intensified electric field would enhance greater red light emission.

Figure 7C:
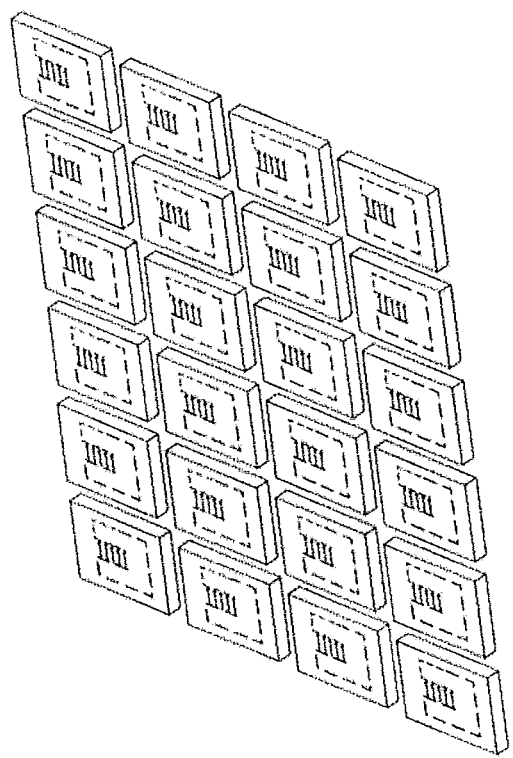

In one embodiment, the energy augmentators could be disposed on a sheet and then separated into distinct pieces, as shown in FIG. 7C, which could be readily added and mixed into a medium to be processed.

Figure 8:
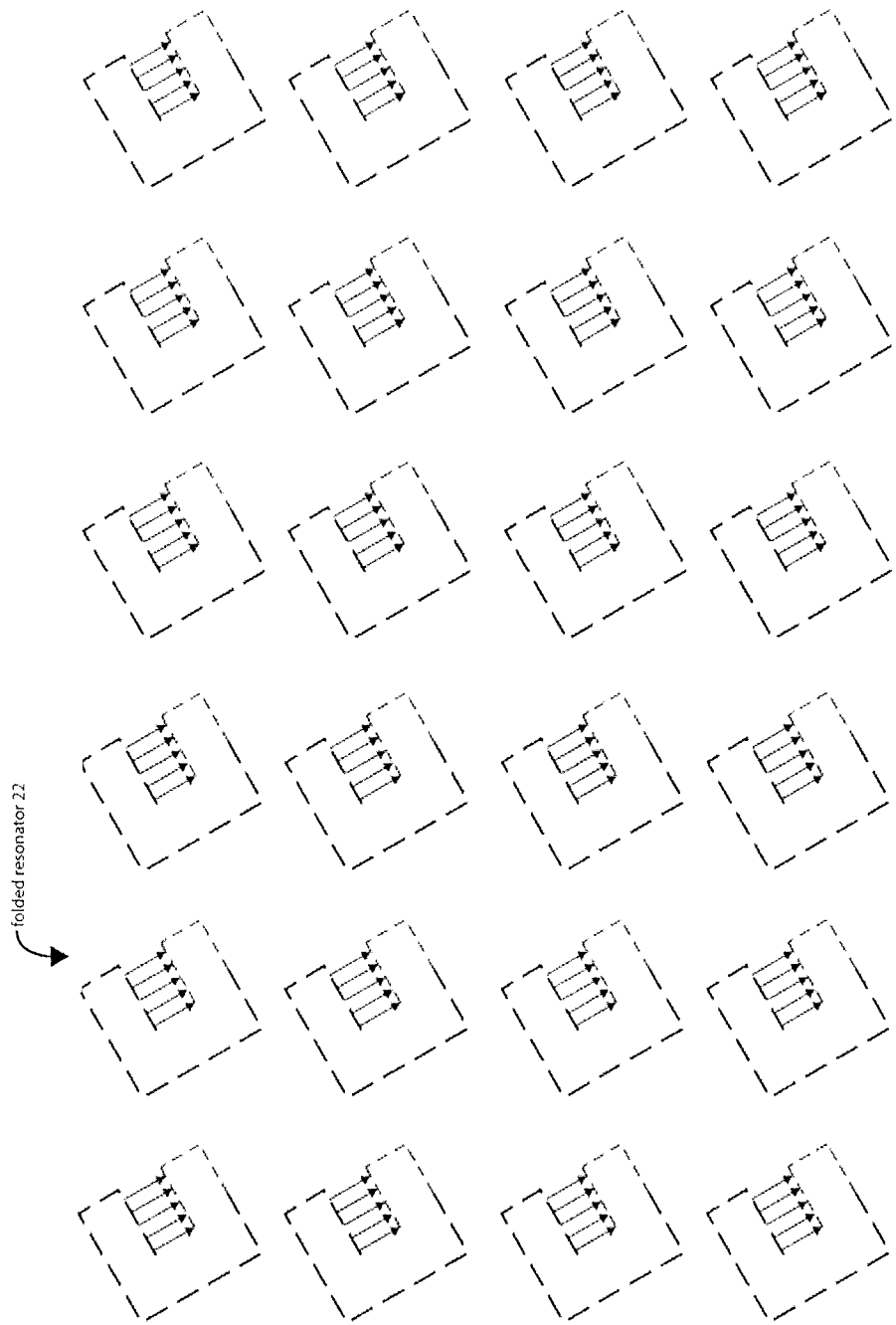
FIG. 8 is a diagram showing a pattern of ¾ λ folded resonators distributed in a plane or otherwise along a surface of an object and having a different orientation than in FIG. 7A.

FIG. 8 is a diagram showing a pattern of ¾ λ folded resonators 22 distributed in a plane or otherwise along a surface of an object and having a different orientation than in FIG. 7. By having different orientations, the rotating polarized sun light waves which may at one instance not have an electric field alignment conducive to driving the ¾ λ folded resonators, would have their electric field alignment conducive to driving resonators of a different orientation and therefore better aligned. Accordingly, if the sheet type products were used, layers of differently oriented ¾ λ folded resonators could be stacked together.

Figure 9:
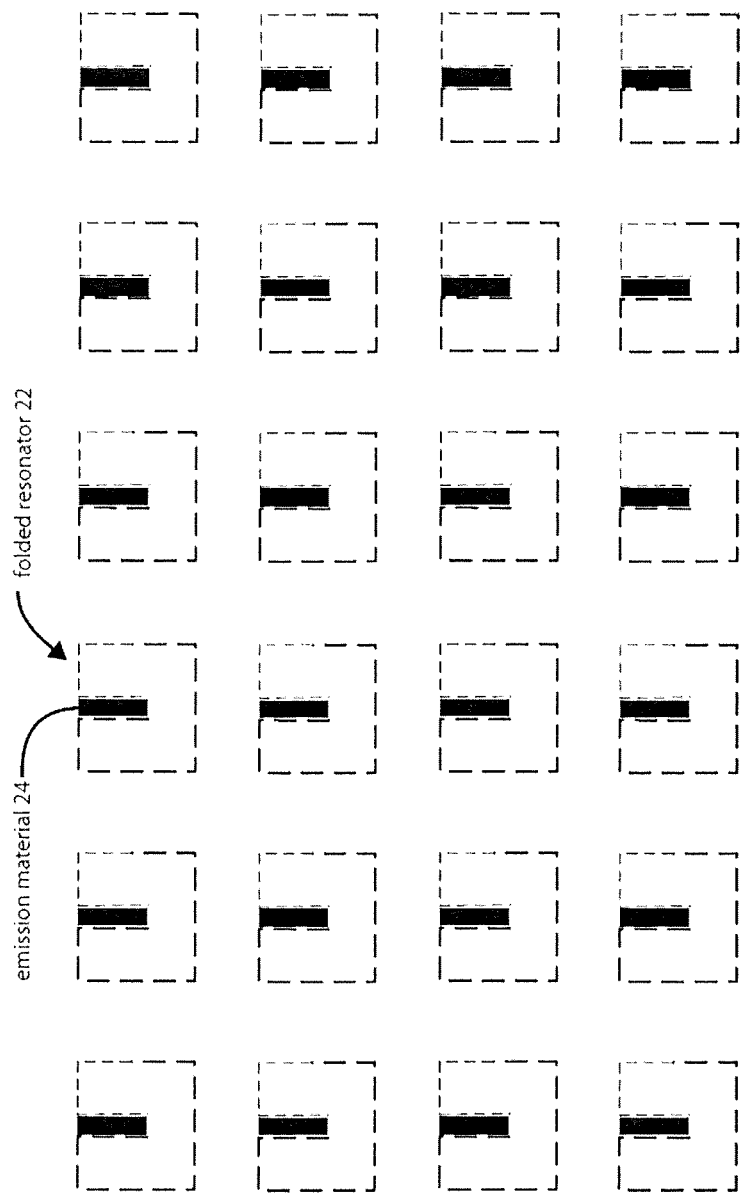
FIG. 9 is a diagram showing a pattern of ¾ λ folded resonators having a light or photon or electron emitting material deposited in the region of between the opposing electrodes.

FIG. 9 is a diagram showing a pattern of ¾ λ folded resonators 22 having an energy converter, a light or electron emitting material, or a color emitting or color converter material (i.e., emissive material 24) deposited in the region of between the opposing electrodes. Here, while shown in a plan view, the color converting or enhancing material deposited in the region of between the opposing electrodes may be deposited such that the color converting or enhancing material has an upper surface raised above the metal traces of the ¾ λ folded resonators. In this embodiment, the raised sections would intercept fringing fields of the intensified electric field between the opposing electrodes.

Figure 10:
FIG. 10 is a diagram showing a pattern of ¾ λ folded resonators having a patterned deposit of a light or photon or electron emitting material in the region of between the opposing electrodes.

FIG. 10 is a diagram showing a pattern of ¾ λ folded resonators 22 having an energy converter, a light or electron emitting material, or a color emitting or color converter material (i.e., emissive material 24) deposited in the region of between the opposing electrodes. Here, as before, the color converting or enhancing material deposited in the region of between the opposing electrodes may be deposited such that the color converting or enhancing material has an upper surface raised above the metal traces of the k folded resonators. In this embodiment, the raised sections would intercept fringing fields of the intensified electric field between the opposing electrodes. In this embodiment, the raised sections would extend around the corners where geometrically the corners would further intensify the electric field.

Figure 11:
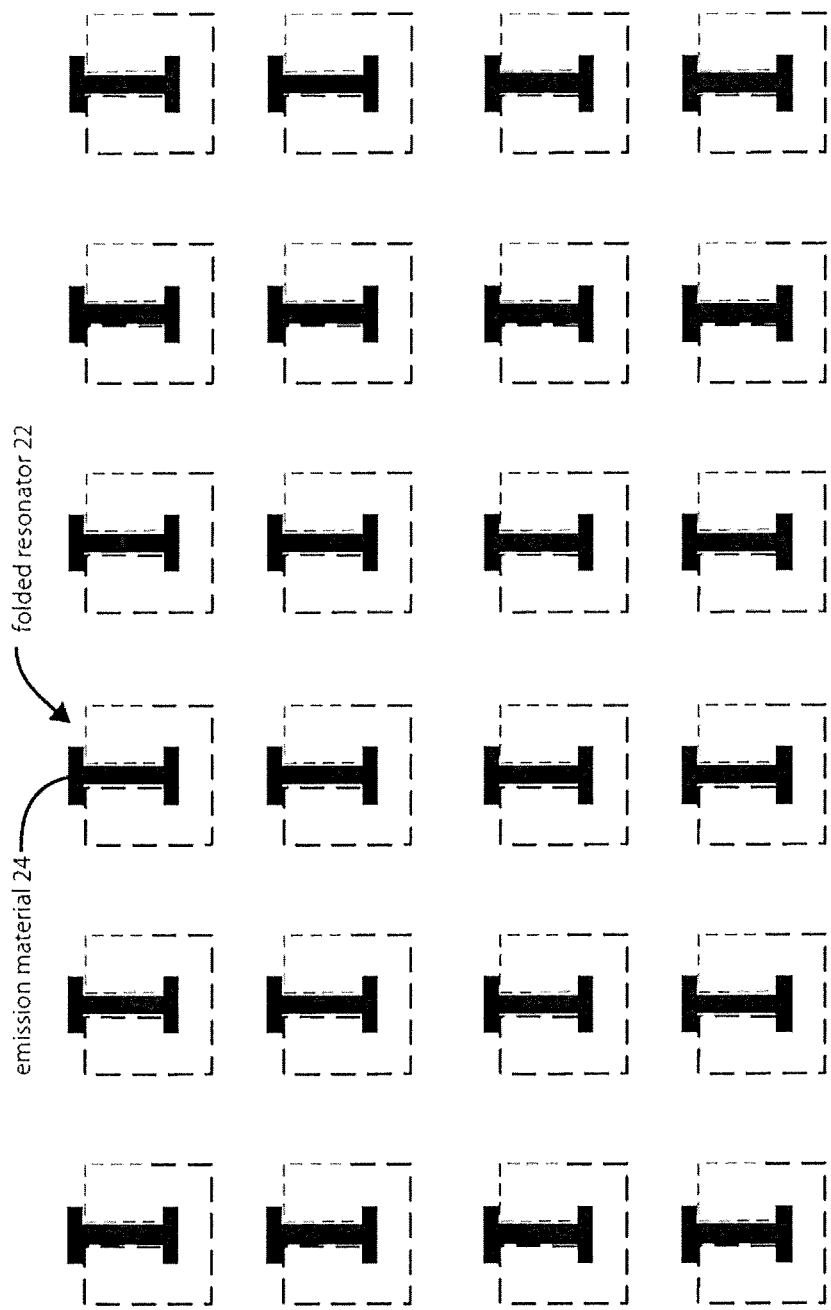
FIG. 11 is a diagram showing a pattern of ¾ λ folded resonators having a patterned deposit of a light or photon or electron emitting material in the region of between the opposing electrodes.

FIG. 11 is a diagram showing a pattern of ¾ λ folded resonators 22 having an energy converter, a light or electron emitting material, or a color emitting or color converter material (i.e., emissive material 24) deposited in the region of between the opposing electrodes. Here, as before, the color converting or enhancing material deposited in the region of between the opposing electrodes may be deposited such that the color converting or enhancing material has an upper surface raised above the metal traces of the ¾ λ folded resonators. In this embodiment, the raised sections would intercept fringing fields of the intensified electric field between the opposing electrodes. In this embodiment, the raised sections would extend around the corners where geometrically the corners would further intensify the electric field and would extend around the ends of the opposing electrodes.

In these embodiments shown in FIGS. 9, 10, and 11, the energy converters, or light or electron emitting materials, or color emitting or color converter materials (i.e., emissive materials 24) are disposed in a vicinity of one or more energy augmentation structures (i.e., the ¾ λ folded resonators). As such, the energy augmentation structures preferably are in a region of intensified electric field. The intensified electric field may represent a region of intensified energy especially if there is electrical current flow conductively coupling the energy converter to the one energy augmentation structures. In later embodiments, conductively coupling the energy converter to the one energy augmentation structures has advantages. Accordingly, the energy converters or color converting or enhancing materials disposed in a vicinity of one or more energy augmentation structures may have a physical conductive connection between the energy converter and the at least one energy augmentation structure. Alternatively, the coupling may be more that of radiatively or capacitively coupling the electric fields from the resonant structure into energy converters or color converting or enhancing materials disposed inside the energy augmentation structure, outside the energy augmentation structure, in a layer with the energy augmentation structure, or in a layer above or below the energy augmentation structure.

As used herein, in a vicinity of refers to the disposition of one thing inside the structure of another thing, outside and nearby or adjacent the structure of the other thing, and can include the disposition of one thing above or below the other thing in any three dimensional direction. Accordingly, in one embodiment of the present invention, the color converting or enhancing materials are disposed in a vicinity of the energy augmentation structures.

Figure 12:
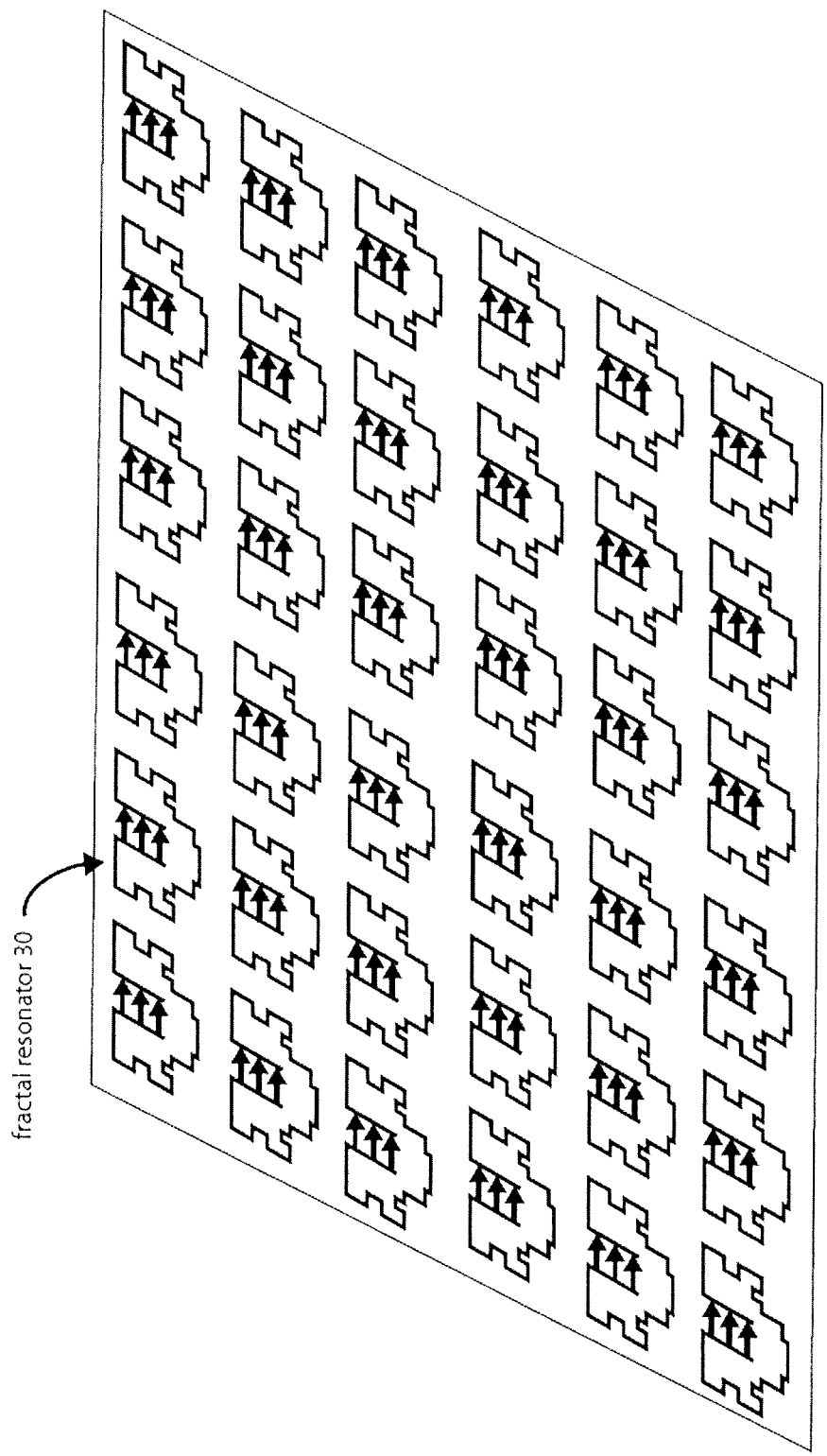
FIG. 12 is a diagram showing a pattern of ¾ λ folded resonators having for the metal traces a fractal pattern for the electrical path that loops around to connect the opposing electrodes.

FIG. 12 is a diagram showing a pattern of ¾ λ folded resonators 30 having for its metal traces a fractal pattern for the electrical path that loops around to connect the opposing electrodes. A fractal pattern for the electrical path with this pattern means that the metal trace can support various wavelengths resonating with the ¾ λ characteristics because of the multiplicity of possible loop paths available because the widths of each segment of the conductive path vary in width permitting electrical paths of different physical lengths to exist around the loop, FIG. 13 is a diagram showing another fractal antenna segment 32 where the straight-line sides of the metal pads have regions 24 of locally intensified electric field. Here, in one embodiment, the fractal antenna segment is designed for resonance in the infrared range, with the intensifies electric field regions 34 (for example as shown toward the straight-line sides of the metal pads being the place where blue phosphors and red phosphors (or other emissive materials 24) would be deposited such that their emission, would be enhanced the intensified electric fields in those regions 34.

Figure 14:
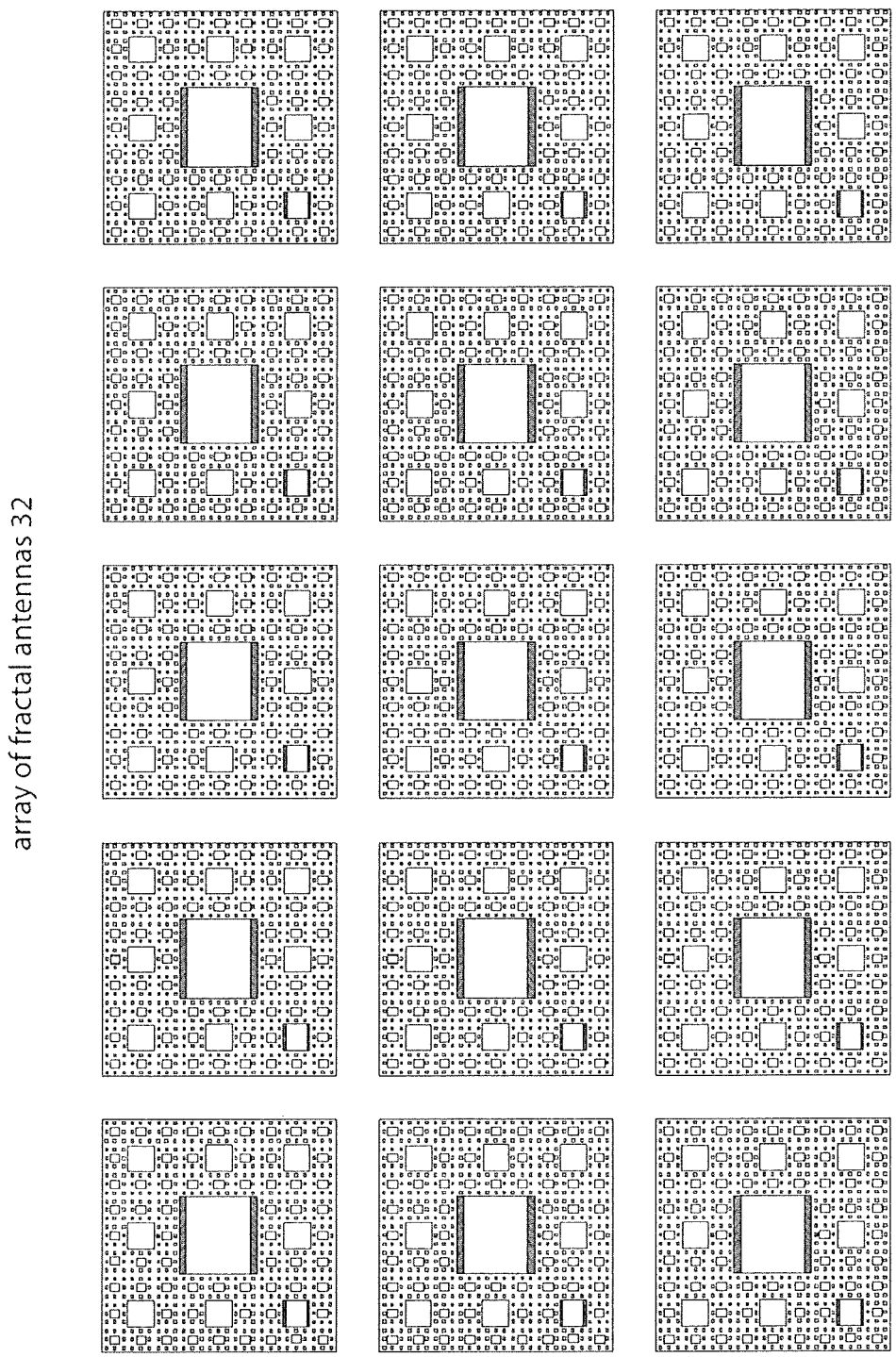
FIG. 14 is a diagram showing a repeated pattern of the fractal antenna segment of FIG. 13.

FIG. 14 is a diagram showing a repeated pattern (array) of the fractal antenna segments 32 of FIG. 13.

Figure 15:
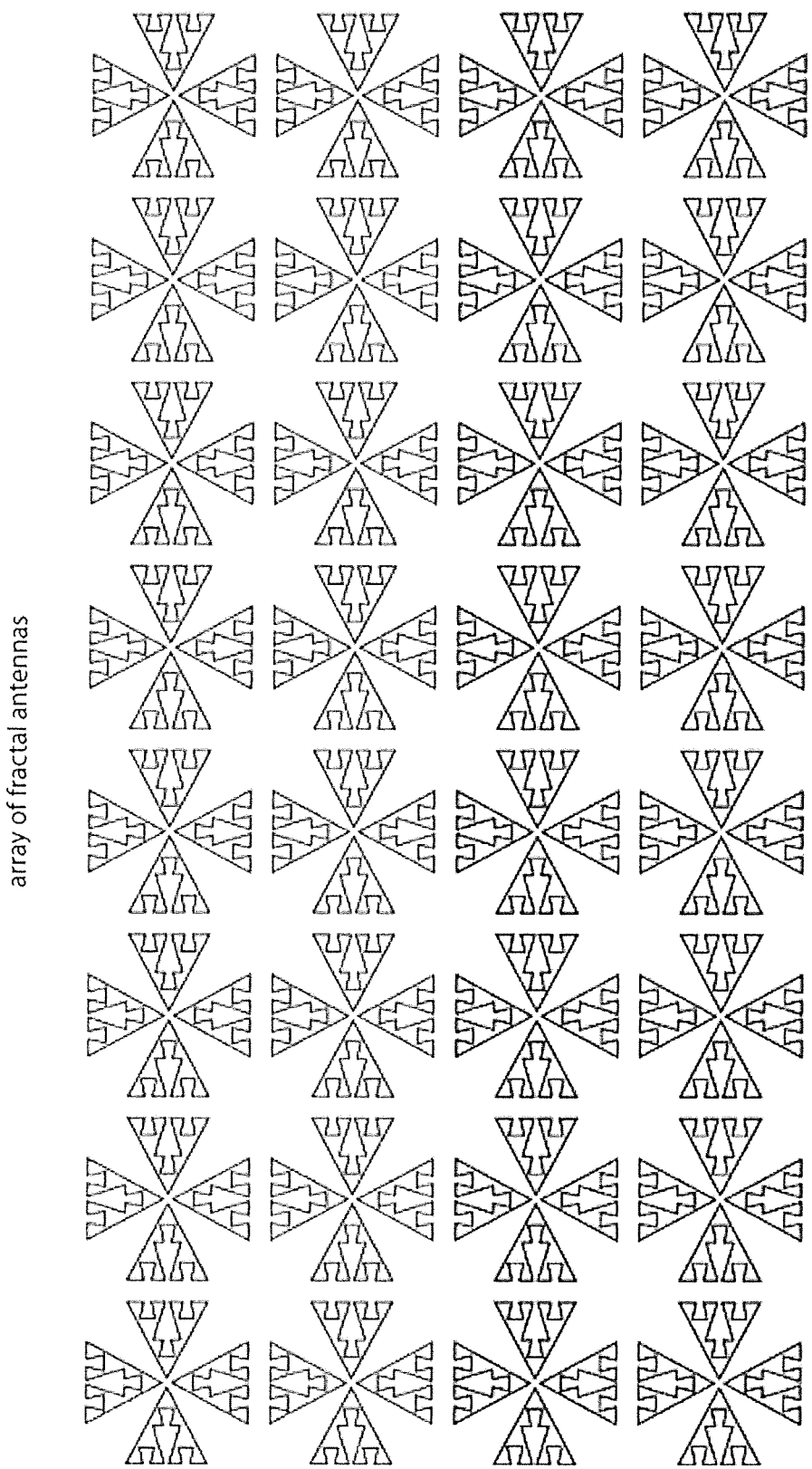
FIG. 15 is a diagram showing a pattern of bowtie fractal antenna segments.

FIG. 15 is a diagram showing a pattern (array) of bowtie fractal antenna segments, providing an alternative embodiment to the fractal antenna segments of FIG. 14.

In one embodiment of the invention, the resonant structures can comprise three-dimensional fractal patterns. Known in the art is the fabrication of three-dimensional fractal structures by nanoscale anisotropic etching of silicon such as described in Nanoscale etching of 3d fractal structures with many applications including 3d fractal antennas and structures for filters, by Brian Wang, Jun. 22, 2013, in the Journal of Micromechanics and Microengineering, (available at www.nextbigfuture.com/2013/06/nanoscale-etching-of-3d-fractal.html) the entire contents of which are incorporated herein by reference. In one embodiment of the invention, metal is deposited over a silicon three-dimensional fractal structure to form a multi-dimensional light collector.

Figure 16:
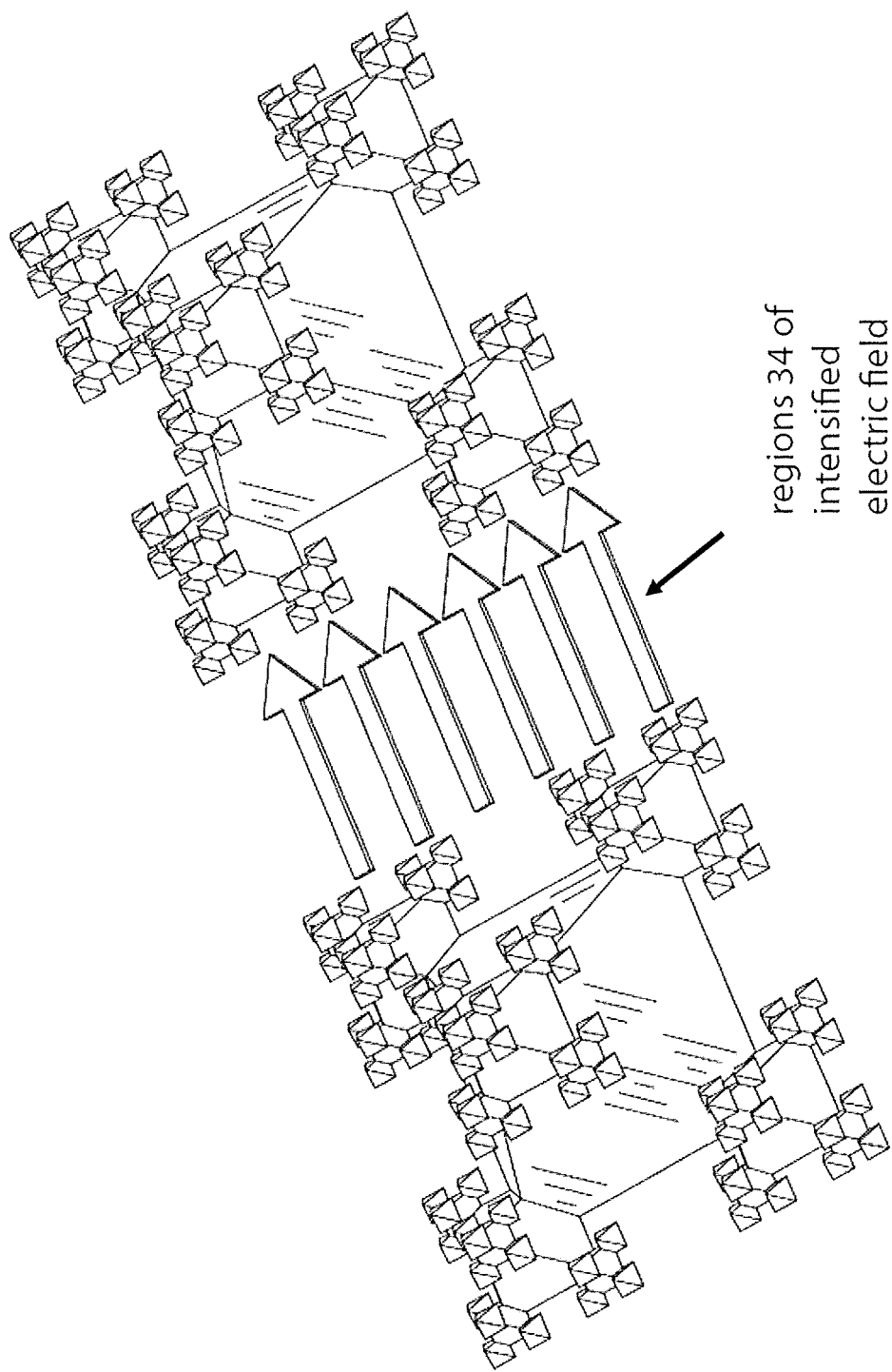

FIG. 16 is a diagram showing a paired three-dimensional fractal structure with regions 34 of an intensified electric field in between the pairs. The paired three-dimensional fractal structure is a color enhancement structure according to one embodiment of the invention. In one embodiment of the invention, these pyramidal type structures would be metallized with opposing faces metalized, a first loop conductor formed around the other sides of the first pyramid, then connecting across a region between the pair, and then a second loop formed around the sides of the second pyramid to the metallized opposing face of the second pyramid, to mimic (as seen from above) the ¾ λ folded resonators shown in FIG. 3.

In one embodiment, converter (emissive) materials 24 would be disposed nearby different sections of the pyramidal type structures and preferably between the opposing faces of the pair where the intensified electric field (depicted by the arrows) exists. With the three-dimensional aspect of this invention, red, yellow, green, and blue converters (or other designated emitters) could be disposed at different levels within this region of intensified electric field.

Figure 17:
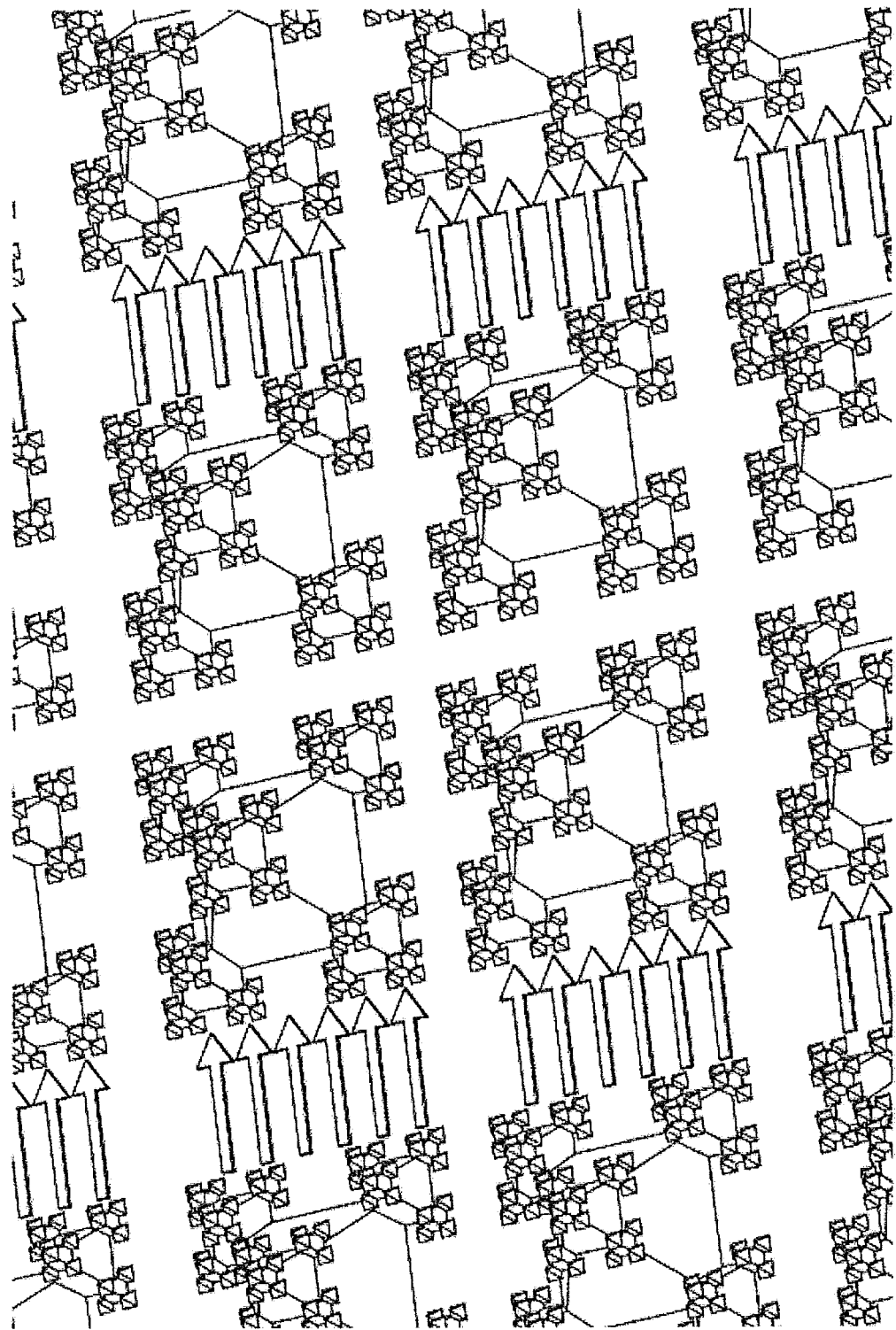
FIG. 17 is a diagram showing a pattern of the paired three-dimensional fractal structures.

FIG. 17 is a diagram showing a pattern (array) of the paired three-dimensional fractal structures of FIG. 16.

In these embodiments shown in FIGS. 12 to 17, the energy converters, or light or electron emitting materials, or color emitting or color converter materials (i.e., emissive materials 24) are disposed in a vicinity of one or more energy augmentation structures (i.e., the ¾ λ folded resonators). As such, the energy augmentation structures preferably are in a region of intensified electric field. The intensified electric field may represent a region of intensified energy especially if there is electrical current flow conductively coupling the energy converter to the one energy augmentation structures. In later embodiments, conductively coupling the energy converter to the one energy augmentation structures has advantages. Accordingly, the energy converters, or light or electron emitting materials, or color emitting or color converter materials disposed in a vicinity of one or more energy augmentation structures may have a physical conductive connection between the energy converter and the at least one energy augmentation structure. Alternatively, the coupling may be more that of radiatively coupling the electric fields from the resonant structure into energy converters or color converting or enhancing materials disposed inside the energy augmentation structure, outside the energy augmentation structure, in a layer with the energy augmentation structure, or in a layer above or below the energy augmentation structure.

Figure 18:
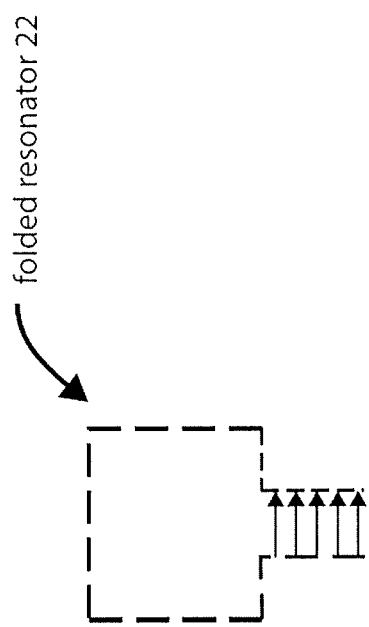
FIG. 18 is a diagram showing a ¾ wavelength resonator with the distal ends of the resonator antenna protruding outwardly while maintaining parallelism.

The energy augmentation structures are not limited to those shown above. Other variants are possible. Moreover, in one embodiment of the invention, the ¾ λ folded resonators need not to have the "folded sections" which fold inwards as shown in FIG. 3. Instead, as shown in FIG. 18, the ¾ λ resonators of the invention can have folded sections which fold outward with the regions of intensified electric field being outside of the "loop" of the resonator. The distal ends of the antenna protrude outwardly while maintaining parallelism. Specifically, FIG. 8 is a schematic of a ¾ λ external-electrode folded resonator 22. This external, opposed electrode pair design follows the general apportioning, scaling aspects, converter material placement, etc., shown in FIGS. 5 through 11 but with the internal folded sections being replaced by the external-electrode pair.

Figure 19:
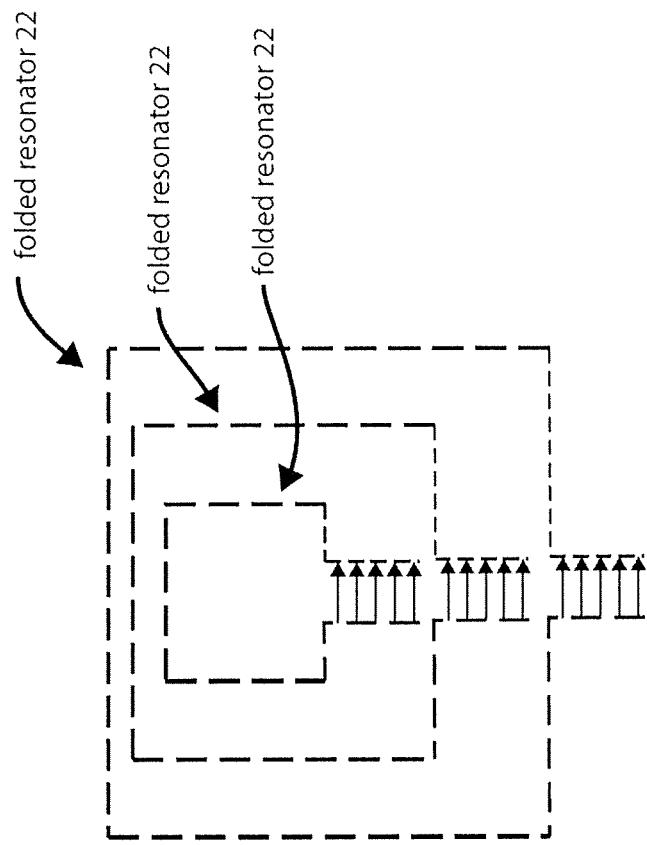
FIG. 19 is a diagram showing a packing configuration for three different ¾ wavelength resonators, that are maintained in plane with no overlapping distal ends.

In one embodiment of the invention, the ¾ λ external-electrode folded resonator 22 provides the capability to be packed in a concentric-type arrangement with progressively, increasing or decreasing size resonators. These resonators are maintained in plane with no overlapping distal ends. FIG. 19 is a schematic of a plurality of concentric-type ¾ λ external-electrode folded resonators 22. Since each of the k external-electrode folded resonators 22 has a different electrical length, the plurality of concentric-type ¾ λ external-electrode resonators will be "tuned" to the different wavelengths associated with the respective electrical lengths. Three different frequencies are therefore focused between the distal ends of the antennas.

Figure 20:
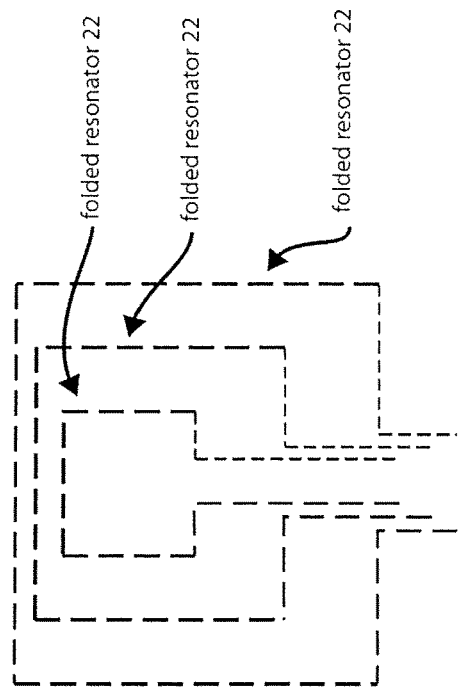
FIG. 20 is a diagram showing another packing configuration for three different ¾ wavelength resonators; that are maintained in plane with overlapping distal ends.

In another embodiment, FIG. 20 is a schematic of a plurality of concentric-type ¾ λ external-electrode folded resonators 22 with overlapping electrodes. In one embodiment, the overlapping provides a more concentrated/enhanced field region than in the non-overlapping arrangement of FIG. 19.

Figure 21:
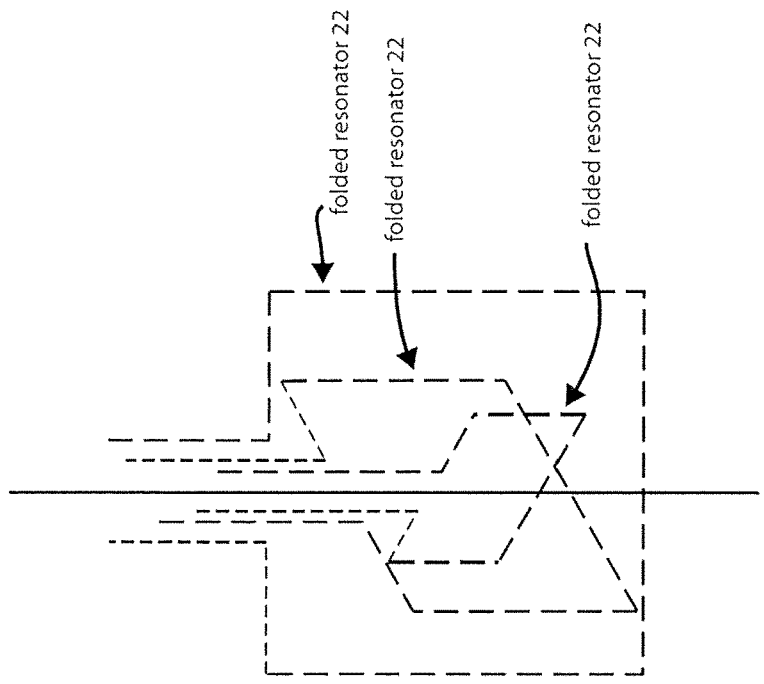
FIG. 21 is a diagram showing yet another packing configuration for the ¾ wavelength resonators, with an off (or out of) plane axial symmetry.

The present invention is not limited to planar concentric type packing arrangements as shown in FIG. 19 or 20. The three different wavelength resonators in FIG. 20 are maintained in plane with overlapping distal ends. These antennas are inductively coupled. In one embodiment, the present invention utilizes an off plane configuration with axial symmetry where the antennas are in an axially rotated, multiple frequency, interleaved % wave resonator structure. FIG. 21 is a schematic of an axially rotated, multiple frequency, interleaved ¾ wave resonators 22 showing (in this example) three differently sized resonators for multiple frequency resonance disposed about/along a common axis but axially rotated. In one embodiment, in this configuration, the resultant electric field is concentrated without one electrode section perturbing the electric fields from another.

In a further embodiment, there is provided an energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

Figure 22:
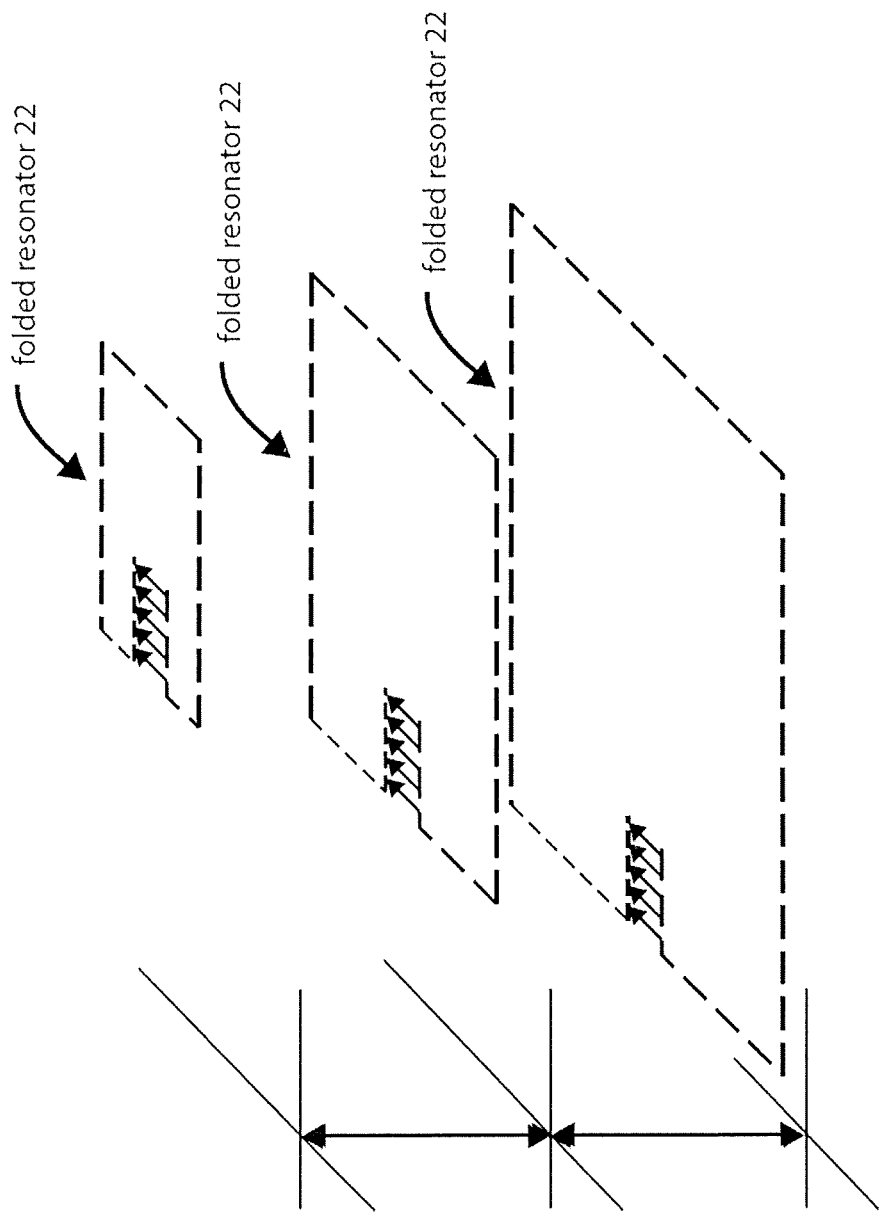
FIG. 22 is a diagram showing a multi-level packing configuration in parallel planes for the folded ¾ wavelength resonator shown.
Figure 23:
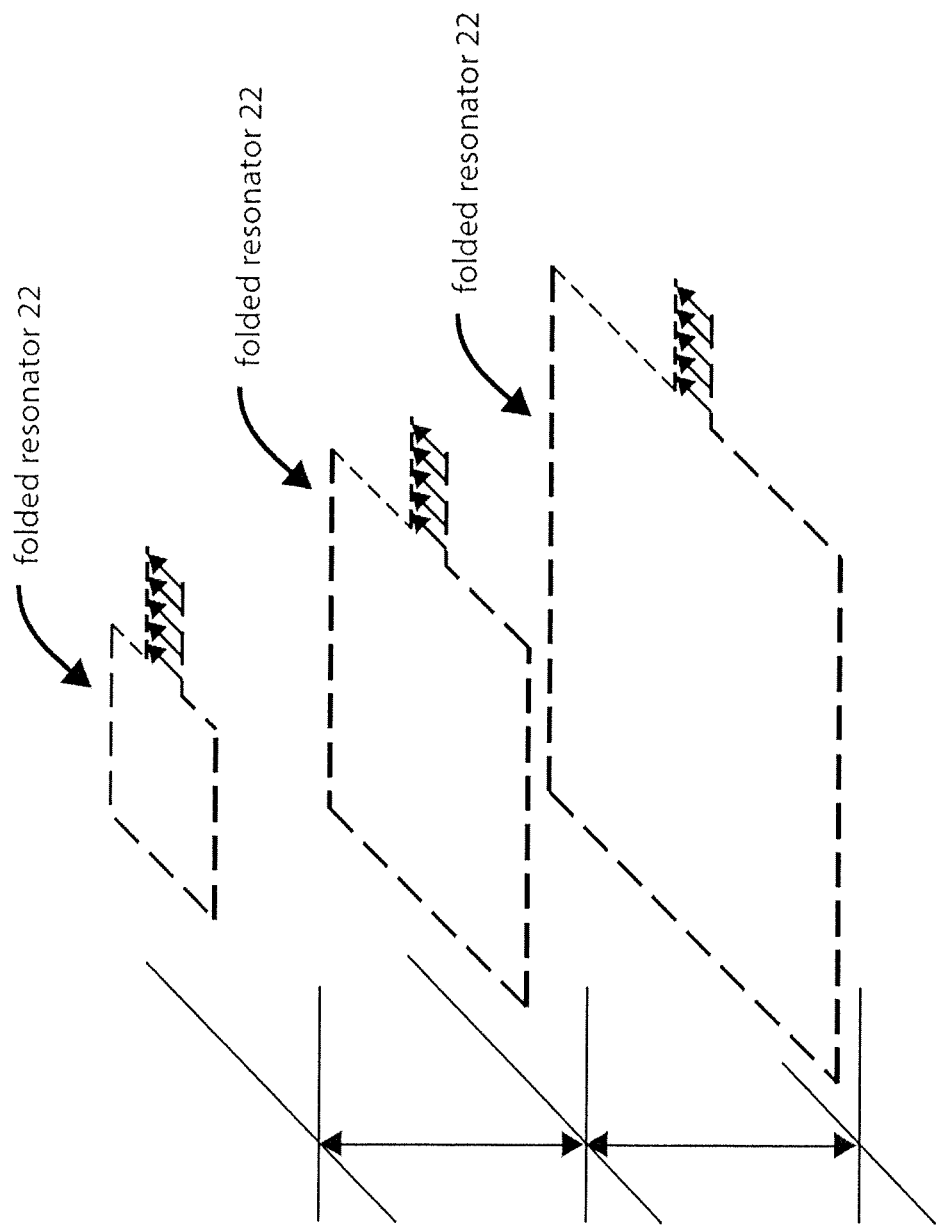
FIG. 23 is a diagram showing a multi-level packing configuration in parallel planes with distal ends protruding out for the ¾ wavelength resonator in FIG. 22.

In one embodiment, the present invention can use different levels for disposing $3/4$ $\lambda$ resonators thereon regardless of the resonators being $3/4$ $\lambda$ internally-folded resonators or $3/4$ $\lambda$ external-electrode resonators. This packing is shown in FIGS. 22 and 23 for configuration in parallel planes with distal ends folded in or protruding out respectively.

Figure 24A:
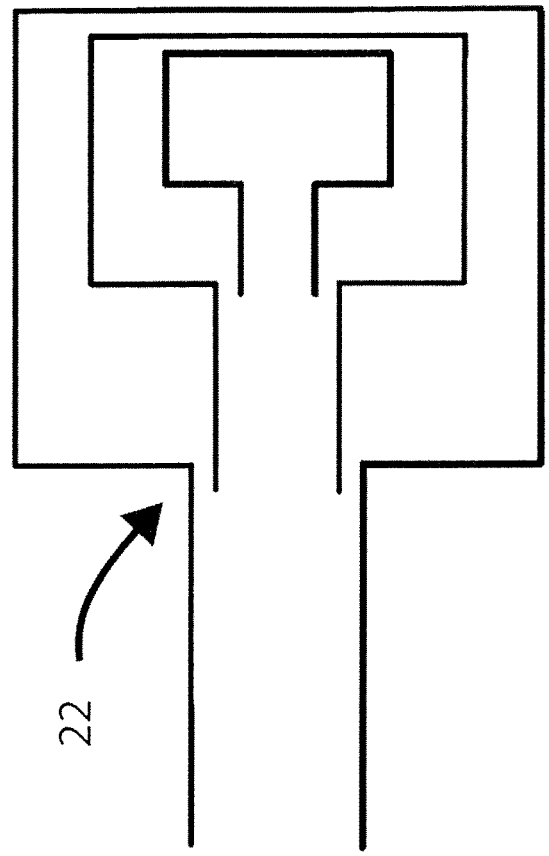
FIG. 24A is a diagram showing a different in-plane packing configuration.

In the embodiment of the invention depicted in FIG. 20 having a plurality of concentric-type $3/4$ $\lambda$ external-electrode resonators 22, the antennas are inductively decoupled. This configuration allows the electric field to be focused from three different frequencies in a longer path. This configuration can be used to create a mirror image configuration to extend the length of focused electric field as is illustrated in FIG. 24A.

Figure 24B:
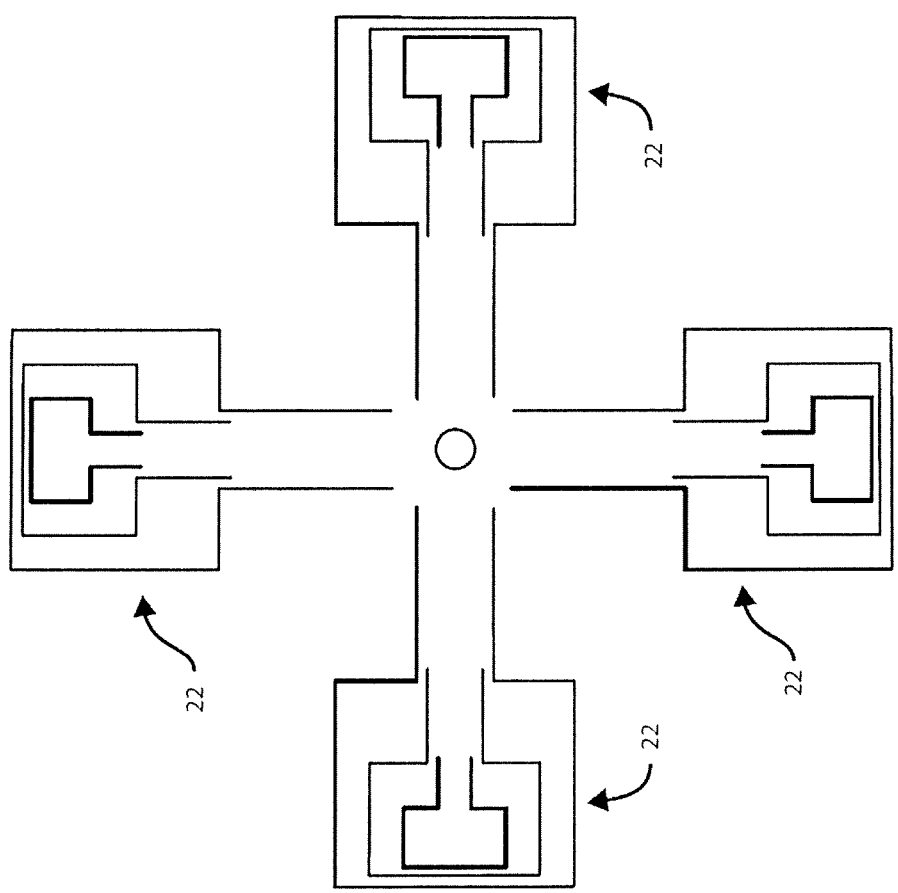
FIG. 24B is a diagram showing another different in-plane packing configuration.

The resonator configuration in this case is mirror imaged with another set of antennas (folded resonators 22) to create a longer path (doubled) of focused electric field. Furthermore, the resonator antenna configuration can be placed in more creative ways to enhance the electric field focusing around a target as is illustrated in the FIG. 24B.

The configuration in FIG. 25 allows the surrounding of a target within the plane of the resonator structure/antenna for the purpose of heating and focusing energy around the target. This prevents heat dissipation in silicon where the thermal conductivity is high. Time silicon substrate in such an instance can be single crystalline, polycrystalline or amorphous.

In one embodiment of the present invention, an "energy augmentation structure" represents a structure whereby a spatial region of the energy collector contains a converter material (or other light or electron emitting material) exposed to energy which stimulates emission of light at a different energy (wavelength) from that to which it is exposed while being in a spatial area/volume (e.g., between or around or in a vicinity of the folded structures or the external-electrode pairs) where there is an artificially induced higher electrical field and/or a higher energy density. These artificial regions can be produced for example by use of structures including, but not limited to, multiple level collection optics, resonators, fractal antennas, and electrical grid (or electrode) patterns.

By having the light or electron emitting materials disposed in a vicinity of the energy augmentation structures of this invention, regardless of the whether the energy augmentation structure is in a region of intensified electric field or otherwise outside the region of intensified electric field, the energy augmentation structures of the invention are able to produce light which can be used for a variety of applications, in particular for photo-stimulation of biological, chemical, and physical reactions such as for example photoactivation of photoreactive drugs, photoactivation of photosensitive materials such as adhesives or lithographic photoresists, or for direct interaction with biological and chemical agents in the environment of the augmentation structures, as in sterilization.

In one embodiment, the light or electron emitting materials noted above are disposed with an energy augmentation structure comprising one or more of an electromagnetic resonator structure, a folded resonator structure, and a fractal resonating structure, any of which having a region of an intensified electromagnetic field within the resonating structures.

In one embodiment, the energy converter or light or electron emitting materials noted above includes one or more luminescing materials. As described herein, there are uses of the energy augmentation structure and/or energy collector embodiments which enhance bioluminescence, chemo-luminescence, photoluminescence, fluorescence, mechano-luminescence, and/or electron emission.

In one embodiment, the energy converter or light emitting materials noted above includes for the one or more luminescent materials phosphorescent materials, fluorescent materials, electroluminescent materials, chemo-luminescent materials, bioluminescent materials, and mechano-luminescent materials used in conjunction with or not in conjunction with the energy augmentation structure noted above. When used in conjunction with the energy augmentation structure noted above, the emitted electromagnetic energy from the luminescent material is emitted with at least one augmented property compared to if the energy converter the luminescent material) were remote from the at least one energy augmentation structure.

In one embodiment, the bioluminescent materials are UV-emitting bioluminescent materials such as catalyzed luciferase and luminescent proteins.

In one embodiment, the energy converter or light emitting materials noted above includes for the one or more luminescing materials phosphorescent materials, fluorescent materials, electroluminescent materials, chemo-luminescent materials, bioluminescent materials, and mechano-luminescent materials used in conjunction with or not in conjunction with the energy augmentation structure noted above and which emit one of ultra-violet, visible, near infrared, and infrared light. In this embodiment, UV-emitting electroluminescent materials or mechano-luminescent devices and materials can be used. In this embodiment, in UV-emitting bioluminescent materials can be used.

In some embodiments, metallic patterns form a folded resonator having opposing electrodes with electric fields directed in between, and a converter is positioned between the opposing electrodes or within fringing electric field of the opposing electrodes or otherwise in a vicinity of the opposing electrodes. In one example, the folded resonator is a $3/4$ $\lambda$ folded resonator. In one example, metallic patterns comprise at least one of Au, Cu, Al, or transparent metal oxides. In another example, the metallic patterns can be formed with refractory metals such for example Ti, W, and Mo.

In some embodiments, the metallic patterns referenced above comprise an external external-electrode pair structure having opposing electrodes with electric fields directed in between, and a converter is positioned between the opposing electrodes or within fringing electric field of the opposing electrodes or otherwise in a vicinity of the opposing electrodes. In one example, the resonator is a $3/4$ $\lambda$ external-electrode pair resonator. In one example, metallic patterns comprise at least one of Au, Ag, Cu, Al, or transparent metal oxides. In another example, the metallic patterns can be formed with refractory metals such for example Ti, W, and Mo.

In some embodiments, plural resonators and plural converters are disposed at multiple positions throughout a light collector. In one example, the plural converters are positioned to convert light being internally scattered within the light collector.

In some embodiments of the energy augmentation structures, a first level of metallic patterns (or a second level of metallic patterns) comprises a metal core cladded with a high-K dielectric and a subsequent cladding of a low-K dielectric. In some embodiments of the energy augmentation structures, the first level of metallic patterns noted above (or the second level of metallic patterns) comprises a radial pattern of conductors. In some embodiments of the energy augmentation structures, the first level of metallic patterns noted above (or the second level of metallic patterns) comprises a fractal pattern. In one example, the fractal pattern is embedded within a dielectric material.

In some embodiments of the energy augmentation structures, the first level of metallic patterns noted above (or the second level of metallic patterns) comprises a three-dimensional fractal structure.

In some embodiments of the energy augmentation structures, there is provided a panel with the first level of metallic patterns and the second level of metallic patterns and optionally multiple converters formed therein or thereon. In some embodiments of the augmentation structures, there is provided a sheet with the first level of metallic patterns and the second level of metallic patterns and optionally multiple converters formed therein or thereon.

In some embodiments of the energy augmentation structures, the first level of metallic patterns noted above (or the second level of metallic patterns) of different sizes and/or orientations to each other of the first level of metallic patterns or with respect to the second level of metallic patterns.

In another embodiment, the energy augmentator can collect or distribute light.

Figure 25A:
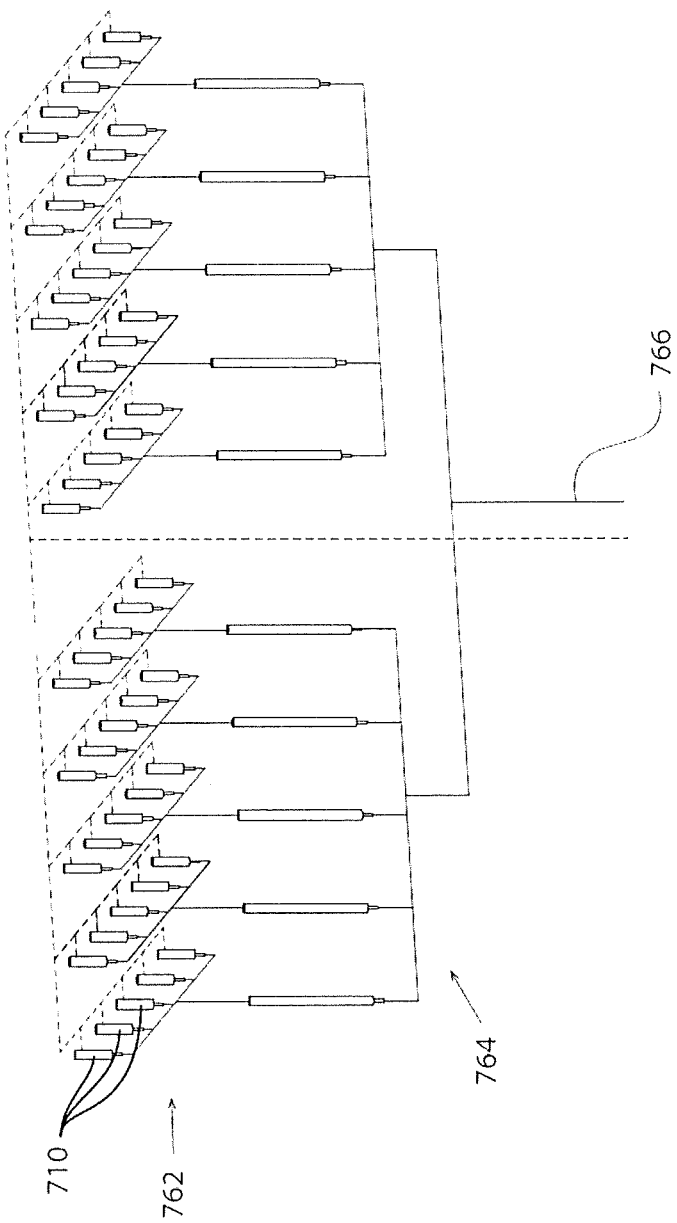
FIG. 25A is a schematic illustrating a distributed point light collector/transmitter of the invention.
Figure 25B:
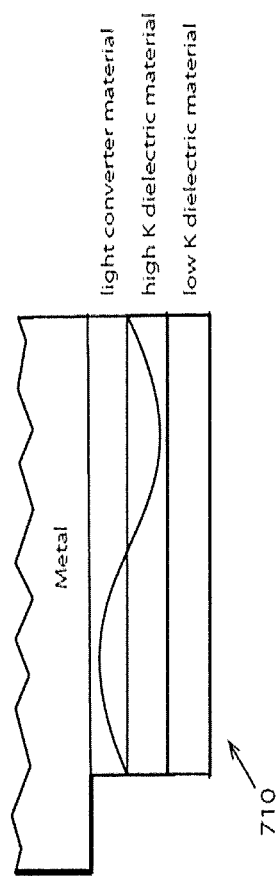
FIG. 25B is a schematic of a cross section of the collector/transmitter of FIG. 25A.

FIG. 25A is a schematic illustrating a distributed point light collector/transmitter of the invention showing a distribution of branches that can either collect light from distributed points 710 or conversely can distribute light from a central source 766 to the distributed points 710. The section of the collector/transmitter is shown in FIG. 25B showing a core metal, an optional light converter material, a high K dielectric, and a low K dielectric. In this arrangement, as shown, light is confined and not loss to scatter out of the collector/transmitter, except at the ends.

B. Energy Converters

In various embodiments of the invention, energy converters can be used with or without the energy augmentators described above. In some embodiments, the converters are for up conversion of light e.g., from the IR regime into visible electromagnetic radiation and for down conversion of light e.g., from the UV range into visible electromagnetic radiation. The invention in various embodiments up converts energy, preferably light in the visible spectrum. The invention encompasses a variety of applications where the up and down conversion materials with or without the energy augmentators are included to enhance electromagnetic energy emission, preferably light or photon emission. When an energy augmentator is present, it may be separate from or connected to the energy converter. In certain embodiments, the energy converter can have the energy augmentator formed on its surface through chemical vapor deposition ("CVD") or physical vapor deposition ("PVD") processes or other nanoscale "printing" methods. Such embodiments may be particularly useful in methods for treating human or animal patients, in which having such energy augmentators "imprinted" on a surface of the energy converter can guarantee proximity between the energy augmentator and the energy converter to maximize the interaction with the energy being applied. Alternatively, the energy augmentator can be formed on a surface of an inert non-energy converting particle, formed, for example, from silica or formed from a non-energy converting particle coated with an biologically and/or chemically inert coating (such as, for example, diamond, diamond-like carbon, or similar inert materials). Such an energy augmentator can then be co-administered with the energy converter to the human or animal patient.

Suitable energy modulation agents or energy converters (the two terms are used interchangeably herein) of the invention include, but are not limited to, a biocompatible is fluorescing metal nanoparticle, fluorescing dye molecule, gold nanoparticle, a water soluble quantum dot encapsulated by polyamidoamine dendrimers, a luciferase (bioluminescence), a biocompatible phosphorescent molecule, a combined electromagnetic energy harvester molecule, and a lanthanide chelate capable of intense luminescence.

Alternatively, the energy modulation agent or energy converter can emit energy in a form suitable for absorption at a target site or receptor. For example, the initiation energy source may be acoustic energy and one energy converter may be capable of receiving acoustic energy and emitting photonic energy (e.g. sonoluminescent molecules) to be received by another energy converter that is capable of receiving photonic energy. Other examples include energy converters that receive energy at x-ray wavelength and emit energy at UV wavelength, preferably at UV-A wavelength. A plurality of such energy converters may be used to form a cascade to transfer energy from initiation energy source via a series of energy converters.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a target site or a receptor such as a photoactivatable agent.

In a further embodiment, a biocompatible emitting source, such as a fluorescing metal nanoparticle or fluorescing dye molecule, is selected as an energy converter that emits in the UV-A band. In another embodiment, an energy converter comprising a UV-A emitting source can be a gold nanoparticle comprising for example a cluster of 5 gold atoms.

In another embodiment, an energy converter comprising a UV- or light-emitting luciferase is selected as the emitting source. A luciferase may be combined with ATP or another molecule, which may then be oxygenated with additional molecules to stimulate light emission at a desired wavelength. Alternatively, a phosphorescent emitting source may be used as the energy converter. One advantage of a phosphorescent emitting source is that the phosphorescent emitting molecules or other source may be electroactivated or photoactivated prior to insertion into the tumor either by systemic administration or direct insertion into the region of the tumor. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In one embodiment, the energy converters of the invention can include persistent after-glow phosphor materials emitting light in the visible to near ultraviolet and ultraviolet range. In one embodiment, Eu-doped strontium aluminate is used as an energy converter in which deep UV light or x-ray or electron beans "charge" the photoluminescence such that these phosphors can be charged outside for example a patient and then injected into target or diseased site where UV photons would be emitted. In another embodiment, gadolinium strontium magnesium aluminate is used as an energy converter in which deep UV light or x-ray or electron beans "charge" the photoluminescence such that these phosphors can be charged outside for example a patient and then injected into target or diseased site where UV photons would be emitted. U.S. Pat. Appl. Publ. No. 20070221883 (the entire contents of which are incorporated herein by reference) describes specifically gadolinium-activated strontium magnesium aluminate having an excitation maximum at about 172 nm, and which emits in a narrow-band UV emission at about 310 nm. The '883 publication also describes other useful energy converters for this invention, making note of emission spectra between 300 nm and 320 nm for a $Sr(Al, Mg)_{12}O_{19}$:Gd phosphor and two 312 nm line emitting phosphors, $YMgB_5O_{10}$:Gd, Ce and $YMgB_5O_{10}$, Gd, Ce, Pr. WO2016200349 (the entire contents of which are incorporated herein by reference) describes long lasting yellowish-green emitting phosphorescent pigments in the strontium aluminate (SrAl2O4) system, which could serve as energy converters in the present invention. WO 2016200348 (the entire contents of which are incorporated herein by reference) describes long lasting bluish-green emitting phosphorescent pigments in the strontium aluminate (Sr4Al14O25) system, which could serve as energy converters in the present invention. Xiong et al in "Recent advances in ultraviolet persistent phosphors," Optical Materials X 2 (2019) (the entire contents of which are incorporated herein by reference) describes a number of ultraviolet persistent phosphors that could as energy converters in the present invention. The table below provides a listing of such persistent phosphors:

| | | |
|---|---|---|
| SrO:$Pb^{2+}$ | 390 | >1 h |
| $CaAl_2O_4$:$Ce^{3+}$ $Tb^{3+}$ | 400 | >10 h |
| $CaAl_2O_4$:$Ce^{3+}$ $Tb^{3+}$ | 413 | >10 h |
| $Sr_2Al_2SiO_2$:$Ce^{3+}$ | 400 | several minutes |
| $SrZrO_3$ | 395 | <1000 s |
| $BaZrO_3$:$Mg^{2+}$ | 400 | >2400 s |
| $SrZrO_3$:$Pr^{3+}$ | 356 | |
| $CdSiO_3$:$Bi^{3+}$ | 360 | |
| $CdSiO_3$:$Bi^{3+}$ $Dy^{3+}$ | 360 | |
| $CdSiO_3$: $Bi^{3+}$ $Gd^{3+}$ | 344 | >6 h |
| $Sr_2MgGe_2O_7$:$Pb^{2+}$ | 370 | >12 h |
| $NaLuGeO_4$:$Bi^{3+}$ $Eu^{3+}$ | 400 | >63 h |

-continued

| | | |
|---|---|---|
| $CaZnGe_2O_6$: $Bi^{3+}$ | 300-700 | >12 h |
| $Cs_2NaYF_6$:$Pr^{3+}$ | 250 | >2 h |

In one embodiment, the phosphor described by Xiong et al as $CaAl_2O_4$:$Ce^{3+}$ having an emission peak of 400 nm and a persistent time of more than 10 h could be used, where it would be charged by x-ray irradiation outside a patient and then injected at a diseased site to provide internally generated. UV light.

In one embodiment, the persistent phosphors noted could be activated ex vivo and introduced along with psoralen (or other photoactivatable drug) into the patient by exchange of a bodily fluid or for example by supplying the persistent phosphors and the photoactivatable drug into a patient's blood stream.

In one embodiment, the persistent phosphors noted could be activated in vivo by injection of the phosphors into a diseased site and then exposure to x-rays.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. In another embodiment, a Stokes shift of an emitting source or a series of emitting sources arranged in a cascade is selected to convert a shorter wavelength energy, such as X-rays, to a longer wavelength fluorescence emission such an optical or UV-A.

In one embodiment, a lanthanide chelate capable of intense luminescence is used as an energy converter. In another embodiment, a biocompatible, endogenous fluorophore emitter is selected as an energy converter.

In one embodiment, the energy converters of the invention can include visible and UV-light emitting bioluminescent materials. In one embodiment, bioluminescent materials is such as coelenterate-type luciferin analogues could be used including amide monoanion known to emit at 480 nm and oxyluciferin known to emit at 395 nm.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

This invention in various embodiments can use a wide variety of down conversion materials (or mixtures of down conversion materials) with or without the energy augmentators to enhance light or photon emission. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties. Accordingly, the down conversion materials to enhance light or photon emission can convert energy from one of ultraviolet light, x-rays, and high energy particles to visible light. The down conversion materials to enhance light or photon emission can convert energy from higher energy visible light to lower energy visible light.

In one embodiment of the invention, a quantum dot mixture with or without the energy augmentators can be used for the multiple nanoparticles. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted. Quantum dots represent one way to down convert ultraviolet light of the spectrum to a targeted wavelength or energy emission. Quantum dots represent one way to down convert blue light of the spectrum to a targeted wavelength or energy emission.

As described in U.S. Pat. No. 6,744,960 (the entire contents of which are incorporated by reference), different size quantum dots produce different color emissions. In that work and applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot 18, may range from about 2 to 10 nm, Since the size of these particles is so small, quantum physics governs many of the electrical and optical properties of the quantum dot. One such result of the application of quantum mechanics to the quantum dot 18 is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 μm Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example; for 5.0 nm diameter CdSe quantum dots light having wavelengths shorter than about 625 nm is absorbed to produce emission at about 625 nm while for 2.2 nm quantum dots comprising CdSe light having wavelengths smaller than about 500 rum is absorbed and re-emitted at about 500 nm. In practice; however, the excitation or pump radiation is at least about 50 nanometers shorter than the emitted radiation.

Specifically, in one embodiment of the invention, a quantum dot mixture (ODM) coating can be deposited using CVD and or sol-gel techniques using standard precipitation techniques. The ODM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl, Nos. 2008/0057096; 2006/0275368; and 2010/0023101.

Further, the down conversion materials for the invention described here can be coated with insulator materials such as for example silica which will reduce the likelihood of any chemical interaction between the luminescent particles and the medium the particles are included therein. These and the other conversion materials described here can be used with or without energy augmentators. For biocompatible applications of inorganic nanoparticles, one of the major limiting factors is their toxicity. Generally speaking, all semiconductor nanoparticles are more or less toxic. For biocompatible applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS; SrS and $Y_2O_3$ are less toxic. In addition; the toxicity of nanoparticles can result from their inorganic stabilizers, such as TGA, or from dopants such as $Eu^{2+}$, $Cr^{3+}$ or $Nd^{3+}$. Other suitable down conversion materials which would seem the most biocompatible are zinc sulfide, $ZnS:Mn^{2+}$, ferric oxide, titanium oxide, zinc oxide, zinc oxide containing small amounts of $Al_2O_3$, and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine. Bismuth Germinate, Cadmium Tungstate, and CsBr doped with divalent Eu.

In various embodiments of the invention, the following luminescent polymers with or without energy augmentators are also suitable as conversion materials: poly(phenylene ethynylene), poly(phenylene vinylene), poly(p-phenylene), poly(thiophene), poly(pyridyl vinylene), poly(pyrrole), poly (acetylene), poly (vinyl carbazole), poly(fluorenes), and the like, as well as copolymers and/or derivatives thereof.

In various embodiments of the invention, the following materials with or without energy augmentators can be used similar to that detailed in U.S. Pat. No. 7,090,355, the entire contents of which are incorporated herein by reference. For down-conversion, the following materials can be used. Inorganic or ceramic phosphors or nano-particles, including but not limited to metal oxides, metal halides, metal chalcogenides (e.g. metal sulfides); or their hybrids, such as metal oxo-halides, metal oxo-chalcogenides. Laser dyes and small organic molecules, and fluorescent organic polymers. Semiconductor nano-particles; such as II-VI or HIV compound semiconductors, e.g. fluorescent quantum dots. Organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The metal elements are chemically bonded to organic groups to prevent the quenching of the fluorescence from the hosts or solvents. Phosphors can be used including the Garnet series of phosphors: $(Y_m A_{1-m})_3 (Al_n B_{1-n})_5 O_{12}$, doped with Ce; where $0 \leq m$, $n \leq 1$, where A includes other rare earth elements, B includes B, Ga. In addition, phosphors containing metal silicates, metal borates, metal phosphates, and metal aluminates hosts can be used. In addition, nano-particulates phosphors containing common rare earth elements (e.g. Eu, Tb, Ce, Dy, Er, Pr, and Tm) and transitional or main group elements (e.g. Mn, Cr, Ti, Ag, Cu, Zn, Bi, Pb, Sn, and Tl) as the fluorescent activators, can be used. Materials such as Ca, Zn, Cd in tungstates, metal vanadates, ZnO, etc. can be used.

The commercial laser dye materials obtained from several laser dye vendors, including Lambda Physik, and Exciton, etc. can also be used with or without energy augmentors. A partial list of the preferred laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc. have been used in optoelectronic devices, such as polymer light emitting diodes (PLED). Such fluorescent polymers can be used directly as the fluorescent layer of the transparent 2-D display screen with and without energy augmentors.

As noted above, semiconductor nanoparticles (e.g., quantum dots) can be used with or without energy augmentors. The terms "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nano-particle is luminescent). The nanoparticle can be either a homogeneous nano-crystal, or comprises of multiple shells. For example, the nanoparticle can include a "core" of one or more first semiconductor materials, and may be to surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, Sffe, BaS, BaSe, BaTe, and the like) and III-V (GaN, GaP, GaAs, GaSb, InP, InAs, InSb, and the like) and IV (Ge, Si, and the like) materials, and an alloy or a mixture thereof.

Fluorescent organometallic molecules containing rare earth or transitional element cations can be used for down conversion materials with or without energy augmentors. Such molecules include a metal center of rare earth elements including Eu, Tb, Ir, Tm, Ce protected with organic chelating groups. The metal center may also include transitional elements such as Zn, Mn, Cr, Jr, etc. and main group elements such as B, Al, Ga. Such organometallic molecules can readily dissolve in liquid or transparent solid host media. Some examples of such fluorescent organometallic molecules include: 1. Tris(dibenzoylmethane)mono(phenanthroline)europium(III); 2. Tris(8-hydroxyquinoline)erbium, 3: Tris(1-phenyl-3-methyl-4-(2,2-dimethylpropan-1-oyl)pyrazolin-5-one)terbium(III), 4. Bis(2-methyl-8-hydroxyquinolato)zinc; 5. Diphenylborane-8-hydroxyquinolate.

Specific examples of down-conversion materials for red emission include those discussed above and europium complexes such as those described in JP Laid-open Patent Publication (Kokai) No. 2003-26969, constructed such that β-diketone ligand is coordinated to europium forming an europium complex capable of emitting red fluorescence. Other specific examples of the rare earth element complexes include complexes include lanthanum (Ln), europium (Eu), terbium (Tb), and gadolinium (Gd) and combinations thereof. An europium (Eu) complex is capable of emitting red fluorescence when irradiated with ultraviolet rays having a wavelength ranging from 365 nm to 410 nm, Terbium (Tb) is capable of emitting green fluorescence when irradiated with ultraviolet rays having a wavelength of 365 nm.

In other down-conversion embodiments, the down conversion materials which emit red light may include europium, light emitting particles which emit green light may include Terbium, and light emitting particles which emit blue or yellow light may include cerium (and/or thulium). In up-conversion embodiments, up conversion materials which emit red light may include praseodymium, light emitting particles which emit green light may include erbium, and light emitting particles which emit blue light may include thulium. In embodiments, the conversion materials can be light emitting particles made of fluorescent molecules that emit different colors (e.g. red, green, and blue), or different wavelengths or energies of light. In embodiments, the conversion materials can be light emitting particles made of pure organic or organo-metallic dyes with or without energy augmentors.

In addition to the combinations of rare earth complexes, such as a combination of a europium complex and a terbium complex, it is also possible employ a combination of a europium complex and a green-emitting fluorescent substance which is not a complex, or a combination of a terbium complex and a red-emitting fluorescent substance which is not a complex.

Other down converter materials (which can be used with or without energy augmentors) include for example ZnS, PbS, SbS$_3$, MoS$_2$, PbTe, PbSe, BeO, MgO, Li$_2$CO$_3$, Ca(OH)$_2$, MoO$_3$, SiO$_2$, Al$_2$O$_3$, TeO$_2$, SnO$_2$, KBr, KCl, and NaCl. These materials can include dopants to tailor the emission properties, as noted above. Examples of doped (or alloyed) glass systems suitable for the include Y$_2$O$_3$:Gd, Y$_2$O$_3$:Dy, Y$_2$O$_3$:Tb, Y$_2$O$_3$:Ho, Y$_2$O$_3$:Er, Y$_2$O$_3$:Tm, Gd$_2$O$_3$:Eu, Y$_2$O$_2$S:Pr, Y$_2$O$_2$S:Sm, Y$_2$O$_2$S:Eu, Y$_2$O$_2$S:Tb, Y$_2$O$_2$S:Ho, Y$_2$O$_2$S:Er, Y$_2$O$_2$S:Dy, Y$_2$O$_2$S:Tm, ZnS:Ag:Cl (blue), ZnS:Cu:Al (green), Y$_2$O$_2$S:Eu (red), Y$_2$O$_3$:Eu (red), YVO$_4$:Eu (red), and Zn$_2$SiO$_4$:Mn (green).

With regard more specifically to down converter materials suitable for the invention, U.S. Pat. No. 4,705,952 (the contents of which are hereby incorporated herein by reference) describes an infrared-triggered phosphor that stores energy in the form of visible light of a first wavelength and released energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention with or without energy augmentors. In one example, the infrared-triggered phosphors would be used in conjunction with the folded resonators, and the receipt of a microwave or IR signal would locally heat and trigger emission. (This application would be particularly well suited for color enhancement and/or security applications.)

In other embodiments of the invention, the down converter materials (or mixtures of down converters materials (which can be used with or without energy augmentators) can include $Y_2O_3$: Li. Sun et al "Luminescent properties of Li+ doped nanosized $Y_2O_3$:Eu," Solid State Comm. 119 (2001) 393-396 (the entire contents of which are incorporated herein by reference) describe such materials. Hou et al "Luminescent properties nano-sized $Y_2O_3$:Eu fabricated by co-precipitation method," Journal of Alloys and Compounds, vol. 494, issue 1-2, 2 Apr. 2010, pages 382-385 (the entire contents of which are incorporated herein by reference) describe that nano-sized yttria ($Y_2O_3$) powders have been successfully synthesized by a co-precipitation method. The powders were well crystallized, and the grains were almost spherical with good dispersibility. The quenching concentration of $Eu^{3+}$ ions is 9 mol % which is much higher than micro-scaled powders. The incorporation of Li+ ions greatly improved the luminescence intensity. The highest emission intensity was observed with 4 mol % Li+ doped $Y_2O_3$:Eu powder (($Y_{0.87}Eu_{0.09}Li_{0.04})_2O_3$) and the fluorescence intensity was increased by as much as 79%. Yi et al "Improved cathodoluminescent characteristics of $Y_2O_3$: $Eu^{3+}$ thin films by Li-doping," Appl. Phys. A 87, 667-671 (2007) (the entire contents of which are incorporated herein by reference) describe cathodoluminescent spectra for both $Y_2O_3$:$Eu^{3+}$ and Li-doped $Y_2O_3$:$Eu^{3+}$ films and methods for making these materials.

Specific downconverting materials may also include at least one or more of $Y_7O_3$, $Y_2O_3$:Gd, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS, ZnSe, MgS, CaS, $Zn_2SiO_4$:Mn, LaOBr:Tm and alkali lead silicate including compositions of $SiO_2$, $B_2O_3$, $Na_2O$, $K_2O$, PbO, MgO, or Ag, and combinations or alloys or layers thereof. Furthermore, the down-converting materials can be sulfur containing phosphors, which can help for example in the rubber vulcanization or other photoactivated processes. An example of such a sulfur containing phosphor is: (Sr, Ca)$Ga_2S_4$. Other examples wherein said phosphor particles comprise a thiogallate host material selected from the group consisting of $SrGa_2S_4$, $CaGa_2S_4$ $BaGa_2S_4$, $MgGa_2S_4$ and solid solutions thereof. The particle size of such phosphor can be controlled from 25 nm to 300 microns in size as described in U.S. Pat. No. 6,153,123A. The downconverting materials can include a dopant including at least one of Er, Eu, Yb, Tm, Nd, Mn, Sb, Tb, Ce, Y, U, Pr, La, Gd and other rare-earth species or a combination thereof. The dopant can be included at a concentration of 0.01%-50% by mol concentration. At times it is preferable to have a combination of dopants rather than one dopant such is the case for a Mn and Sb in silicate matrices.

The invention in other embodiments can use a wide variety of up conversion materials (or mixtures of up converters) with or without the energy augmentators to enhance a particular wavelength or energy of light emitted from a material or surface. These up conversion materials can include similar materials as discussed above with regard to down conversion but typically included doped or impurity states in a host crystal that provide a is mechanism for up conversion pumping. Accordingly, the up conversion materials to enhance wavelength or energy emission can convert energy from one of near infrared, infrared, and microwave irradiation. The upconversion materials to enhance color emission can convert energy from lower energy visible light to higher energy visible light.

In one example, a nanoparticle of a lanthanide doped oxide can be excited with near infrared light such as laser light at 980 nm and 808 nm to produce visible light in different parts of the red, green, blue spectrum (different wavelengths or energies) depending on the dopant trivalent rare earth ion(s) chosen, their concentration, and the host lattice.

The lanthanide doped oxides suitable for this invention differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the $NaYF_4$ such that the $Yb^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/7}$ energy state. In other words, the energy state at $^2F_{5/2}$ of the $Yb^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as $Er^{3+}$ doped $BaTiO_3$ nanoparticles and $Yb^{3+}$ doped $CsMnCl_3$) are suitable in various embodiments of the invention with or without the energy augmentators.

Further, materials specified for up conversion materials in the invention (with or without energy augmentation) include CdTe, CdSe, ZnO; CdS; $Y_2O_3$, MgS, CaS; SrS and in BaS. Such up conversion materials may be any semiconductor and more specifically, but not by way of limitation, sulfide, telluride, selenide; and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, 0<z≤1, and 0<y≤1). Complex compounds of the above-described semiconductors are also contemplated for use in the invention—e.g. $(M_{1-z}N_z)_{1-x}Mn_xA_{1-y}B_y$, (M=Zn, Cd, Pb, Ca, Ba, Sr, Mg; N=Zn, Cd, Pb, Ca, Ba, Sr, Mg; A=S, Se, Te, O; B=S; Se, Te, O; 0<x≤1, 0<y≤1, 0<z≤1). Two examples of such complex compounds are $Zn_{0.4}Cd_{0.4}Mn_{0.2}S$ and $Zn_{0.2}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn, Yb; MgS; Mn, Yb; CaS; Mn, Yb etc., and their complex compounds: $(M_{1-z}N_z)_{1-x}(Mn_qR_{1-q})_xA_{1-y}B_y$, (M=Zn, Cd; Pb, Ca, Ba; Sr, Mg; N=Zn, Cd, Pb, Ca, Ba; Sr, Mg; A=S, Se, Te, O; B=S, . . . 0<z≤1, o<q≤1).

Some nanoparticles such as ZnS:$Tb^{3+}$, $Er^{3+}$; ZnS:$Tb^{3+}$; $Y_2O_3$:$Tb^{3+}$; $Y_2O_3$:$Tb^{3+}$, Er3+; ZnS:$Mn^{2+}$; ZnS:Mn, $Er^{3+}$ are known in the art, to function for both down-conversion luminescence and upconversion luminescence and would be suitable for the invention with or without energy augmentators. In up-conversion embodiments, light emitting particles which emit red light may include praseodymium, light emitting particles which emit green light may include erbium, and light emitting particles which emit blue light may include thulium.

In general, the upconversion process generally requires one of more rare-earth dopants, such as Er, Eu, Yb, Tm, Nd, Tb, Ce, Y; U, Pr, La; Gd and other rare-earth species or a combination thereof, doped into a dielectric crystal (of any size >0.1 nm), including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, where incident radiation is at longer wavelength than emissive radiation from the crystal. The wavelength emitted in based entirely on the dopant ion(s) chosen and their associated and relative concentration in the host crystal. For the example of upconversion in a $Y_2O_3$ host crystal, to achieve a blue emission (~450-480 nm) one could synthesize [$Y_2O_3$; Yb (3%), Tm (0.2%)], where the Yb and Tm are the percentages doped in the crystal relative to the Y atoms being 100%. Likewise, typical green upconversion materials are [$Y_2O_3$; Yb (5%), Ho (1%)] and [$Y_2O_3$; Yb (2%), Er (1%)], and typical red upconversion materials are [$Y_2O_3$; Yb (10%), Er (1%)] and [$Y_2O_3$; Yb (5%), Eu (1%)]. The concentrations of dopants relative to each other and the crystal matrix must be tuned for every combination, and there are multiple ways to achieve multiple wavelength or energy emissions from even the same dopants.

Up-conversion of red light with a wavelength of about 650 nm in $Tm^{3+}$ doped is flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. The emission intensities of both bands have been observed by others to vary quadratically with the excitation power. For glasses with a 717 $m^{3+}$ concentration of 0.2 mol % and greater, cross-relaxation processes occur which decrease the up-conversion efficiency.

The emission of visible light upon excitation in the near-infrared (NIR) has been observed in optically clear colloidal solutions of $LuPO_4$:$Yb^{3+}$ and $YbPO_4$:$Er^{3+}$ nanocrystals in chloroform. Excitation at 975 nm has been shown by others to produce visible emission in the blue, green, or red spectral regions.

Tellurium and germanium oxides (tellurites and germanates) are also suitable upconverters. These glasses can be doped with Tm. Yb, Ho, Er, Pr, for example.

$Yb^{3+}$ doped $BaZrO_3$ is also suitable for upconversion. $Er^{3+}$ and/or $Tm^{3+}$ doping are also suitable for tailoring the emission wavelengths.

In another embodiment, $Nd^{3+}$:$Cs_2NaGdCl_6$ and $Nd^{3+}$, $Yb^{3+}$:$Cs_2NaGdCl_6$ polycrystalline powder samples prepared by Morss method have been reported to be up converters and are suitable for the present invention. These materials, under 785 nm irradiation, have shown upconversion emissions near 538 nm (Green), 603 nm (Orange), and 675 nm (Red) were observed and assigned to 4G7/2→4I9/2, (4G7/2→4I11/2; 4G5/2→4I9/2), and (4G7/2→4I13/2; 4G5/2→4I11/2), respectively.

In another embodiment, $Nd^{3+}$ and $Ho^{3+}$ co-doped-based $ZrF_4$ fluoride glasses under 800 nm excitation have been reported to be up converters and are suitable for the present invention. Among the up-conversion luminescences for the $ZrF_4$ fluoride glasses, the green emission was seen to be extremely strong and the blue and red emission intensities were very weak.

In another embodiment, $Tm^{3+}$/$Yb^{3+}$-codoped $TeO_2$—$Ga_2O_3$—$R_2O$ (R=Li, Na, K) glasses have been reported to be up converters and are suitable for the present invention. These materials, under excitation at 977 nm, showed intense blue upconversion emission centered at 476 nm along with a weak red emission at 650 nm.

In another embodiment, metal-to-ligand charge transfer (MIXT) transition in [Ru(dmb)$_3$]$^{2+}$ (dmb=4,4'-dimethyl-2,2'-bipyridine) in the presence of anthracene or 9,10-diphenylanthracene have been reported to be up converters and are suitable for the present invention. Upconverted singlet fluorescence resulting from triplet-triplet annihilation at low excitation power has been reported. In particular 9,10-diphenylanthracene (DPA) (substituted for anthracene) showed higher efficiencies for upconversion. In these experiments, workers with this material system assumed that DPA's increased singlet fluorescence quantum yield (=0.95) relative to anthracene (=0.27)7. This work lead to an approximate 24.4±6.1 enhancement of green-to-blue light upconversion permitting direct visualization of the process at low excitation power, for example by a commercial green laser pointer ($\lambda_{ex}$=532 nm, <5 mW' peak power).

In certain embodiments, further energy converters include, but are not limited to, (not ranked by order of preference or utility):

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$, and $LuPO_4$:$Pr^{3+}$. Examples further include the alkali earth chalcogenide phosphors which are in turn exemplified by the following non-inclusive list: MgS:$Eu^{3+}$, CaS:$Mn^{2+}$, CaS:Cu, CaS:Sb, CaS:$Ce^{3+}$, CaS:$Eu^{2+}$, CaS:$Eu^{2+}Ce^{3+}$, CaS:$Sm^{3+}$, CaS:$Pb^{2+}$, CaO:$Mn^{2+}$, CaO:$Pb^{2+}$.

Further examples include the ZnS type phosphors that encompass various derivatives: ZnS:Cu, Al(Cl), ZnS:Cl(Al), ZnS:CuI(Cl), ZnS:Cu, ZnS:Cu, In.

Also included are the compound IIIb-Vb phosphors which include the group IIIb and Vb elements of the periodic table. These semiconductors include BN, BP, BSb, AlN, AlP, AlAs, AlSb, GaN, GaP, GaAs, GaSb, InN, InP, InSb and these materials may include donors and acceptors that work together to induce light emission diodes. These donors include, but are not limited to, Li, Sn, Si, Li, Te, Se, S, O and acceptors include, but are not limited to, C, Be, Mg, Zn, Cd, Si, Ge. Further included are the major GaP light emitting diodes which include, but are not limited to, GaP:Zn, O, GaP:NN, Gap:N and GaP, which emit colors Red, Yellow, Green and Pure Green respectively.

The materials can further include such materials as GaAs with compositional variation of the following sort: $In_{1-y}(Ga_{1-x}Al_x)_yP$.

Also included is silicon carbide SiC, which has commercial relevancy as a luminescent platform in blue light emitting diodes. These include the polytypes 3C—SiC, 6H—SiC, 4H—SiC with donors such as N and Al and acceptors such as Ga and B.

Further examples include multiband luminescent materials include, but not limited to, the following compositions (Sr, Ca, Ba)$_5$(PO$_4$)$_3$Cl:$Eu^{2+}$, BaMg$_2$Al$_{16}$O$_{27}$:$Eu^{2+}$, CeMgAl$_{11}$O$_{19}$:$Ce^{3+}$:$Tb^{3+}$, LaPO$_4$:$Ce^{3+}$:$Tb^{3+}$, GdMgB$_5$O$_{10}$:Ce$_3$:$Tb^{3+}$, $Y_2O_3$:$Eu^{3+}$, (Ba, Ca, Mg)$_5$(PO$_4$)$_3$Cl:$Eu^{2+}$, 2SrO$_{0.84}$P2O50.16B2O3:$Eu^{2+}$, Sr$_4$Al$_{14}$O$_{25}$:$Eu^{2+}$.

Materials typically used for fluorescent high pressure mercury discharge lamps are also included. These can be excited with X-Ray and are exemplified by way of family designation as follows: Phosphates (Sr, MXPO$_4$)$_2$:Sn$^{22+}$, Mg or Zn activator, Germanate 4MgO.GeO$_2$:Mn$^{4+}$, 4(MgO, MgF$_2$)GeO$_2$:Mn$^{4+}$, Yttrate Y$_2$O$_3$:Eu$^{3+}$, Vanadate YVO$_4$: Eu$^{3+}$, Y(P, V)O$_4$:Eu$^{3+}$, Y(P, V)O$_4$:In$^+$, Halo-Silicate Sr$_2$Si$_3$O$_{82}$SrCl$_2$:Eu$^{2+}$, Aluminate (Ba, Mg)$_2$Al$_{16}$O$_{24}$.Eu$^{2+}$, (Ba, Mg)$_2$Al$_{16}$O$_{24}$:Eu$^{2+}$, Mn$^{2+}$, Y$_2$O$_3$Al$_2$O$_3$:Tb$^{3+}$.

Another grouping by host compound includes chemical compositions in the halophosphates phosphors, phosphate phosphors, silicate phosphors, aluminate phosphors, borate phosphors, tungstate phosphors, and other phosphors. The halophosphates include, but are not limited to: 3Ca$_3$(PO$_4$)$_2$.Ca(F, Cl)$_2$:Sb$^{3+}$, 3Ca$_3$(PO$_4$)$_2$.Ca(F, Cl)$_2$:Sb$^{3+}$/Mn$^{2+}$, Sr$_{10}$(PO$_4$)$_6$Cl$_2$:Eu$^{2+}$, (Sr,Ca)$_{10}$(PO$_4$)$_6$Cl$_2$:Eu$^{2+}$, (Sr,Ca)$_{10}$(PO$_4$)$_6$.nB$_2$O$_3$:Eu$^{3+}$, (Sr, Ca, Mg)$_{10}$(PO$_4$)$_6$Cl$_2$:Eu$^{2+}$. The phosphate phosphors include, but are not limited to: Sr$_2$P$_2$O$_7$:Sn$^{2+}$, (Sr, Mg)$_3$(PO$_4$)$_2$:Sn$^{2+}$, Ca$_3$(PO$_4$)$_2$.Sn$^{2+}$, Ca$_3$(PO$_4$)$_2$:Tl$^+$, (Ca, Zn)$_3$(PO$_4$)$_2$:Tl$^+$, Sr$_2$P$_2$O$_7$:Eu$^{2+}$, SrMgP$_2$O$_7$:Eu$^{2+}$, Sr$_3$(PO$_4$)$_2$:Eu$^{2+}$, LaPO$_4$:Ce$^{3+}$, Tb$^{3+}$, La$_2$O$_3$.0.2SiO$_2$.0.9P$_2$O$_5$:Ce$^{3+}$.Tb$^{3+}$, BaO.TiO$_2$.P$_2$O$_5$. The silicate phosphors Zn$_2$SiO$_4$:Mn$^{2+}$, CaSiO$_3$:Pb$^{2+}$/Mn$^{2+}$, (Ba, Sr, Mg).3Si$_2$O$_7$:Pb$^{2+}$, BaSi$_2$O$_5$:Pb$^{2+}$, Sr$_2$Si$_3$O$_8$,2SrCl$_2$:Eu$^{2+}$, Ba$_3$MgSi$_2$O$_8$:Eu$^{2+}$, (Sr, Ba)Al$_2$Si$_2$O$_8$:Eu$^{2+}$.

The aluminate phosphors include, but are not limited to: LiAlO$_2$:Fe$^{3+}$, BaAl$_8$O$_{13}$:Eu$^{2+}$, BaMg$_2$Al$_{16}$O$_{27}$:Eu$^{2+}$, BaMg$_2$Al$_{16}$O$_{27}$:Eu$^{2+}$/Mn$^{2+}$, Sr$_4$Al$_{14}$O$_{25}$:Eu$^{2+}$, CeMgAl$_{11}$O$_{19}$:Ce$^{3+}$/Tb$^{3+}$.

The borate phosphors include: Cd$_2$B$_2$O$_5$:Mn$^{2+}$, SrB$_4$O$_7$F:Eu$^{2+}$, GdMgB$_5$O$_{10}$:Ce$^{3+}$/Tb$^{3+}$, GdMgB$_5$O$_{10}$:Ce$^{3+}$/Mn$^{3+}$, GdMgB$_5$O$_{10}$:Ce$^{3+}$/Tb$^{3+}$/Mn$^{2+}$.

The tungstate phosphors include, but are not limited to: CaWO$_4$, (Ca, Pb)WO$_4$, MgWO$_4$. Other phosphors Y$_2$O$_3$: Eu$^{3+}$, Y(V, P)O$_4$:Eu$^{2+}$, YVO$_4$:Dy$^{3+}$, MgGa$_2$O$_4$:Mn$^{2+}$, 6MgO.As$_2$O$_5$:Mn$^{2+}$, 3.5MgO.0.5MgF$_2$.GeO$_2$:Mn$^{4+}$.

The activators to the various doped phosphors include, but are not limited to: Tl$^+$, Pb$^{2+}$, Ce$^{3+}$, Eu$^{2+}$, WO$_4^{2+}$, Sn$^{2+}$, Sb$^{3+}$, Mn$^{2+}$, Tb$^{3+}$, Eu$^{3+}$, Mn$^{4+}$, Fe$^{3+}$. The luminescence center Tl$^+$ is used with a chemical composition such as: (Ca, Zn)$_3$(PO$_4$)$_2$:Tl$^+$, Ca$_3$(PO$_4$)$_2$:Tl$^+$. The luminescence center Mn$^{2+}$ is used with chemical compositions such as MgGa$_2$O$_4$:Mn$^{2+}$, BaMg$_2$Al$_{16}$O$_{27}$:Eu$^{2+}$/Mn$^{2+}$, Zn$_2$SiO$_4$:Mn$^2$, 3Ca$_3$(PO$_4$)$_2$.Ca(F, Cl)$_2$:Sb$^{2+}$/Mn$^{2+}$, CaSiO$_3$:Pb$^{2+}$/Mn$^{2+}$, Cd$_2$B$_2$O$_5$:Mn$^{2+}$, CdB$_2$O$_5$:Mn$^{2+}$, GdMgB$_5$O$_{10}$:Ce$^{3+}$/Mn$^{2+}$, GdMgB$_5$O$_{10}$:Ce$^{3+}$/Tb$^{3+}$/Mn$^{2+}$. The luminescence center Sn2+ is used with chemical compositions such as: Sr$_2$P$_2$O$_7$:Sn$^{2+}$, (Sr, Mg)$_3$(PO$_4$)$_2$:Sn$^{2+}$. The luminescence center Eu$^{2+}$ is used with chemical compositions such as: SrB$_4$O$_7$F:Eu$^{2+}$, (Sr, Ba)Al$_2$Si$_2$O$_8$:Eu$^{2+}$, Sr$_3$(PO$_4$)$_2$:Eu$^{2+}$, Sr$_2$P$_2$O$_7$:Eu$^{2+}$, Ba$_3$MgSi$_2$O$_8$:Eu$^{2+}$, Sr$_{10}$(PO$_4$)$_6$Cl$_2$:Eu$^{2+}$, BaMg$_2$Al$_{16}$O$_{27}$:Eu$^{2+}$/Mn$^{2+}$, (Sr,Ca)$_{10}$(PO$_4$)$_6$Cl$_2$:Eu$^{2+}$. The luminescence center Pb$^{2+}$ is used with chemical compositions such as: (Ba, Mg, Zn)$_3$Si$_2$O$_7$:Pb$^{2+}$, BaSi$_2$O$_5$:Pb$^{2+}$, (Ba, Sr)$_3$Si$_2$O$_7$:Pb$^{2+}$.

The luminescence center Sb$^{2+}$ is used with chemical compositions such as: 3Ca$_3$(PO$_4$)$_2$.Ca(F, Cl)$_2$:Sb$^{3+}$, 3Ca$_3$(PO$_4$)$_2$.Ca(F, Cl)$_2$:Sb$^{3+}$/Mn$^{2+}$.

The luminescence center Tb$^{3+}$ is used with chemical compositions such as: CeMgAl$_{11}$O$_{19}$:Ce$^{3+}$/Tb$^{3+}$, LaPO$_4$: Ce$^{3+}$/Tb$^{3+}$, Y$_2$SiO$_5$:Ce$^{3+}$/Tb$^{3+}$, GdMgB$_5$O$_{10}$:Ce$^{3+}$/Tb$^{3+}$. The luminescence center Eu$^{3+}$ is used with chemical compositions such as: Y$_2$O$_3$:Eu$^{3+}$, Y(V, P)O$_4$:Eu$^{3+}$. The luminescence center Dy$^{3+}$ is used with chemical compositions such as: YVO$_4$:Dy$^{3+}$. The luminescence center Fe$^3$ is used with chemical compositions such as: LiAlO$_2$:Fe$^{3+}$. The luminescence center Mn$^{4+}$ is used with chemical compositions such as: 6MgO.As$_2$O$_5$:Mn$^{4+}$, 3.5MgO0.5MgF$_2$.GeO$_2$: Mn$^{4+}$. The luminescence center Ce$^{3+}$ is used with chemical compositions such as: Ca$_2$MgSi$_2$O$_7$:Ce$^{3+}$ and Y$_2$SiO$_5$:Ce$^{3+}$. The luminescence center WO$_4^{2-}$ is used with chemical compositions such as: CaWO$_4$, (Ca, Pb)WO$_4$, MgWO$_4$. The luminescence center TiO$_4^{4-}$ is used with chemical compositions such as: BaO.TiO$_2$.P$_2$O$_5$.

Additional phosphor chemistries of interest using X-Ray excitations include, but are not limited to, the k-edge of these phosphors. Low energy excitation can lead to intense luminescence in materials with low k-edge. Some of these chemistries and the corresponding k-edge are listed below:

| | |
|---|---|
| BaFCl:Eu$^{2+}$ | 37.38 keV |
| BaSO$_4$:Eu$^{2+}$ | 37.38 keV |
| CaWO$_4$ | 69.48 keV |
| Gd$_2$O$_2$S:Tb$^{3+}$ | 50.22 keV |
| LaOBr:Tb$^{3+}$ | 38.92 keV |
| LaOBr:Tm$^{3+}$ | 38.92 keV |
| La$_2$O$_2$S:Tb$^{3+}$ | 38.92 keV |
| Y$_2$O$_2$S:Tb$^{3+}$ | 17.04 keV |
| YTaO$_4$ | 67.42 keV |
| YTaO$_4$:Nb | 67.42 keV |
| ZnS:Ag | 9.66 keV |
| (Zn,Cd)S:Ag | 9.66/26.7 keV |

These materials can be used alone or in combinations of two or more. A variety of compositions can be prepared to obtain the desired output wavelength or spectrum of wavelengths.

In the present invention, the phosphor selection could be chosen such that under x-ray or other high energy source irradiation, the light emitted from the phosphors could, for example, have exemplary characteristics including:

Emissions in 190-250 nm wavelength range;

Emissions in the 330-340 nm wavelength range.

Mechanoluminescent Materials (Organic and Inorganic):

In another embodiment of the invention, mechano-luminescent materials can be used as energy converters and optionally can be used with the energy augmentation structures described above.

Mechano-luminescent materials convert ultrasonic or mechanical energy (such as vibrations naturally existing on an article such as motor or vibrations from driven by transducers) into visible light. Here, for example, the mechano-luminescent materials would be placed in a vicinity (e.g., between or around or inside) the folded structures or the external-electrode pairs.

In one embodiment, an electromagnetic wave energy augmentator captures one or more wavelengths of electromagnetic energy, and augments the one or more wavelengths of electromagnetic energy in at least one property (such as electric field intensity in a vicinity of the mechano-luminescent materials), while at the same time the mechano-luminescent materials can be considered an energy converter converting the ultrasonic or mechanical energy into electromagnetic radiation (i.e., emitted light).

In one embodiment of the invention, the increased electric field in the folded structure or the external electrode pair increases the luminescence of the mechano-luminescent materials. The energy used to build the electric field in the folded structure or the external electrode pair being provided separately from the mechanical energy driving the mechano-luminescence.

Various mechano-luminescent materials suitable for the present invention with or without energy augmentators include ZnS:Mn$^{2+}$, SrAl$_2$O$_4$:Eu$^{2+}$, ZnS:Cu, SrAMgSi$_2$O$_7$: Eu$^{2+}$ (A=Ca, Sr, Ba), KCl, KI, KBr, NaF, NaCl, LiF, RbCl, RbBr, RbI, MgO, $SrAl_2O_4$, $CaAl_2O_4$, $Sr_{1-x}Ba_xAl_2O_4$ (x=0, 0.1, 0.2, 0.4), $Sr_{0.9}Ca_{0.1}Al_2O_4$, $Zn_2Ge_{0.9}Si_{0.1}O_4$, $MgGa_2O_4$, $ZnGa_2O_4$, $ZnAl_2O_4$, ZnS, ZnTe, $(ZnS)_{1-x}(MnTe)_{cx}(x<¼)$, CaZnOS, BaZnOS, $Ca_2MgSi_2O_7$, $Sr_2MgSi_2O_7$, $Ba_2MgSi_2O_7$, $SrCaMgSi_2O_7$, $SrBaMgSi_2O_7$, $Sr_6MgSi_2O_{8+n}$ (1≤n≤2), $Ca_2Al_2SiO_7$, $Sr_2Al_2SiO_7$, $CaYAl_3O_7$, $CaAl_2Si_2O_8$, $Ca_{1-x}Sr_xAl_2Si_2O_8$ (x<0.8), $SrMg_2(PO_4)_2$, $Ba_{1-x}Ca_xTiO_3$ (0.25<x<0.8), $Ba_{1-x}Ca_xTiO_3$, $LiNbO_3$, $Sr_2SnO_4$, (Ca, Sr, Ba)$_2SnO_4$, $Sr_3Sn_2O_7$, $Sr_3(Sn, Si)_2O_7$, $Sr_3(Sn, Ge)_2O_7$, $Ca_3Ti_2O_7$, $CaNb_2O_6$, $Ca_2Nb_2O_7$, $Ca_3Nb_2O_8$, $BaSi_2O_2N_2$, $SrSi_2O_2N_2$, $CaZr(PO_4)_2$, $ZrO_2$.

In one embodiment, a europium-holmium co-doped strontium aluminate can be used as a mechano-luminescent material (i.e., an energy converter) alone or in conjunction with the energy augmentors. The europium-holmium co-doped strontium aluminate and the other mechano-luminescent materials convert sonic or acoustic energy into photon emissions which may or may not be placed in a vicinity of the energy augmentors.

Yanim Jia, in "Novel Mechano-Luminescent Sensors Based on Piezoelectric/Electroluminescent Composites," Sensors (Basel). 2011; 11(4): 3962-396, the entire contents of which are incorporated by reference, describes a mechanoluminescent composite made of a piezoelectric material and an electroluminescent material. In this composite device, when a stress is applied to the piezoelectric layer, electrical charges will be induced at both the top and bottom faces of piezoelectric layer due to the piezoelectric effect. These induced electrical charges will result in a light output from the electroluminescent layer due to the electroluminescent effect.

Here, in one embodiment of the present invention with or without energy augmentors, such composites made of a piezoelectric material and an electroluminescent material, hereinafter "composite mechano-luminescent emitters," provides a structure that, upon stimulation with mechanical or vibrational energy such as from an acoustic or ultrasonic transducer, emit light.

Electroluminescent and phosphorescent materials (organic and inorganic): The present invention in various embodiments can utilize organic fluorescent molecules or inorganic particles capable or fluorescence and phosphorescence having crystalline, polycrystalline or amorphous micro-structures for the converters (optionally including the energy augmentation structures described above).

The list of inorganic molecules that can be used with or without energy augmentors for the electroluminescence and phosphorescent materials described below include but is not limited to the following inorganic electroluminescent phosphor materials:

$SrS:Ce^{3+}$ $CaGa_2S_4:Ce^{3+}$ $SrS:Cu^+$ $CaS:Pb^{2+}$ $BaAl_2S_4:Eu^{2+}$ $ZnS:Tb^{3+}$ $ZnMgS:Mn_2^{2+}$ $SrGa_2S_4:Eu^{2+}$ $CaAl_2S_4:Eu^{2+}$ $BaAl_2S_4:Eu^{2+}$ $ZnS:Mn^{2+}$ $MgGa_2O_4:Eu^{3+}$ $(Ca, Sr)Y_2S_4:Eu^{2+}$ $BaAl_2S_4:Eu^{2+}$

Organic molecules that can phosphoresce under the influence of an electric field are also of interest in the present application. The organic fluorescent compounds with high quantum yield include by way of illustration:

Naphthalene,
Pyrene,
Perylene,
Anthracene,
Phenanthrene,
p-Terphenyl,
p-Quartphenyl,
Trans-stilbene,
Tetraphenylbutadiene,
Distyrylbenzene,
2,5-Diphenyloxazole,
4-Methyl-7-diethylaminocoumarin,
2-Phenyl-5-(4-biphenyl)-1,3,4-oxadiazole,
3-Phenylcarbostyryl,
1,3,5-Triphenyl-2-pyrazoline,
1,8-Naphthoylene-1',2'-bezimidazole,
4-Amino-N-phenyl-naphthalimide.

The inorganic fluorescent and phosphorescent materials detailed here are numerous, and various examples are given by way of illustration rather than limitation and can be used with or without energy augmentors. Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds could include (not ranked by order of preference or utility) the following material examples:

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAlsO_8$, $LiA_1O_2$, $CaPO_3$, $AlF_3$.

Further included are alkali earth chalcogenide phosphors which are in turn exemplified by the following non-inclusive list:

$MgS:Eu^{3+}$, $CaS:Mn^{2+}$, CaS:Cu, CaS:Sb, $CaS:Ce^{3+}$, $CaS:Eu^{2+}$, $CaS:Eu^{2+}Ce^{3+}$, $CaS:Sm^{3+}$, $CaS:Pb^{2+}$, $CaO:Mn^{2+}$, $CaO:Pb^{2+}$.

The examples include the ZnS type phosphors that encompass various derivatives:

ZnS:Cu, Al(CL), ZnS:Cl(Al), ZnS:Cu, I(Cl), ZnS:Cu, ZnS:Cu, In.

Compound IIIb-Vb phosphors which include the group IIIb and Vb elements of the periodic table are suitable for converter materials. These semiconductors include BN, BP, BSb, AlN, AlP, AlAs, AlSb, GaN, GaP, GaAs, GaSb, InN, InP, InAs, InSb and these materials have donors and acceptors that work in together to induce light emission diodes. The donors include Li, Sn, Si, Li, Te, Se, S, O, and acceptors include C, Be, Mg, Zn, Cd, Si, Ge. As an example, GaP light emitting diodes include GaP:Zn, O, GaP:NN, Gap:N and GaP which emit colors Red, Yellow, Green and Pure Green respectively.

The compounded materials further include such materials as GaAs with compositional variation of the following sort: $In_{1-y}(Ga_{1-x}Al_x)_yP$ (provides a simple example). Silicon Carbide SiC as a luminescent platform has commercial relevancy if the blue light emitting diodes. These include the polytypes 3C—SiC, 6H—SiC, 4H—SiC with donors such as N and Al and acceptors such as Ga and B.

Multiband luminescent materials suitable for converter materials include for example the following compositions: $(Sr, Ca, Ba)_5(PO_4)_3Cl:Eu^{2+}$, $BaMg_2Al_{16}O_{27}:Eu^{2+}$, $CeMgAl_{11}O_{19}:Ce^{3+}:Tb^{3+}$, $LaPO_4:Ce^{3+}:Tb^{3+}$, $GdMgB_5O_{10}:Ce^{3+}:Tb^{3+}$, $Y_2O_3:Eu^{3+}$, $(Ba,Ca,Mg)_5(PO_4)_3Cl:Eu^{2+}$, $2SrO_{0.84}P_2O_5 \cdot 0.16B_2O_3:Eu^{2+}$, $Sr_4Al_{14}O_{25}:Eu^{2+}$.

Other materials suitable for converter materials include those materials used for fluorescent high pressure mercury discharge lamps can be excited with X-Ray and are exemplified by way of family designation as follows: Phosphates $(Sr, MXPO_4)_2:Sn^{2+}$, Mg or Zn activator, Germanate $4MgO \cdot GeO_2:Mn^{4+}$, $4(MgO, MgF_2)GeO_2:Mn^{4+}$, Yttrate $Y_2O_3:Eu^{3+}$, Vanadate $YVO_4:Eu^{3+}$, $Y(P,V)O_4:Eu^{3+}$, $Y(P,V)O_4:In^+$, Halo-Silicate $Sr_2Si_3O_8 \cdot 2SrCl_2:Eu^{2+}$, Aluminate $(Ba,Mg)_2Al_{16}O_{24}:Eu^{2+}$, $(Ba, Mg)_2Al_{16}O_{24}:Eu^{2+},Mn^{2+}$, $Y_2O_3 \cdot Al_2O_3:Tb^{3+}$.

Another grouping of materials suitable for converter materials by host compound include chemical compositions in the Halophosphates phosphors, Phosphate phosphors, Silicate phosphors, Aluminate phosphors, Borate phosphors, Tungstate phosphors, and other phosphors.

The halophosphates include by way of illustration: $3Ca_3(PO_4)_2 \cdot Ca(F,Cl)_2:Sb^{3+}$, $3Ca_3(PO_4)_2 \cdot Ca(F,Cl)_2:Sb^{3+}/Mn^{2+}$, $Sr_{10}(PO_4)_6Cl_2:Eu^{2+}$, $(Sr,Ca)_{10}(PO_4)_6Cl_2:Eu^{2+}$, $(Sr,Ca)_{10}(PO_4)_6 \cdot nB_2O_3:Eu^{3+}$, $(Sr, Ca,Mg)_{10}(PO_4)_6Cl_2:Eu^{2+}$.

The phosphate phosphors include by way of illustration $Sr_2P_2O_7:Sn^{2+}$, $(Sr,Mg)_3(PO_4)_2:Sn^{2+}$, $Ca_3(PO_4)_2 \cdot Sn^{2+}$, $Ca_3(PO_4)_2:Tl^+$, $(Ca,Zn)_3(PO_4)_2:Tl^+$, $Sr_2P_2O_7:Eu^{2+}$, $SrMgP_2O_7:Eu^{2+}$, $Sr_3(PO_4)_2:Eu^{2+}$, $LaPO_4:Ce^{3+}$, $Tb^{3+}$, $La_2O_3 \cdot 0.2SiO_2 \cdot 0.9P_2O_5:Ce^{3+} \cdot Tb^{3+}$, $BaO \cdot TiO_2 \cdot P_2O_5$. The silicate phosphors $Zn_2SiO_4:Mn^{2+}$, $CaSiO_3:Pb^{2+}/Mn^{2+}$, $(Ba, Sr, Mg) \cdot 3Si_2O_7:Pb^{2+}$, $BaSi_2O_5:Pb^{2+}$, $Sr_2Si_3O_8 \cdot 2SrCl_2:Eu^{2+}$, $Ba_3MgSi_2O_8:Eu^{2+}$, $(Sr,Ba)Al_2Si_2O_8:Eu^{2+}$.

The aluminate phosphors include:
$LiAlO_2:Fe^{3+}$, $BaAl_8O_{13}:Eu^{2+}$, $BaMg_2Al_{16}O_{27}:Eu^{2+}$, $BaMg_2Al_{16}O_{27}:Eu^{2+}/Mn^{2+}$, $Sr_4Al_{14}O_{25}:Eu^{2+}$, $CeMgAl_{11}O_{19}:Ce^{3+}/Tb^{3+}$.

The borate phosphors include:
$Cd_2B_2O_5:Mn^{2+}$, $SrB_4O_7F:Eu^{2+}$, $GdMgB_5O_{10}:Ce^{3+}/Tb^{3+}$, $GdMgB_5O_{10}:Ce^{3+}/Mn^{3+}$, $GdMgB_5O_{10}:Ce^{3+}/Tb^{3+}/Mn^{2+}$.

The tungstate phosphors include:
$CaWO_4$, $(Ca,Pb)WO_4$, $MgWO_4$. Other phosphors $Y_2O_3:Eu^{3+}$, $Y(V,P)O_4:Eu^{2+}$, $YVO_4:Dy^{3+}$, $MgGa_2O_4:Mn^{2+}$, $6MgO \cdot As_2O_5:Mn^{2+}$, $3.5MgO \cdot 0.5MgF_2 \cdot GeO_2:Mn^{4+}$.

Activators of relevance to the various doped phosphors include the following list:
$Tl^+$, $Pb^{2+}$, $Ce^{3+}$, $Eu^{2+}$, $WO_4^{2+}$, $Sn^{2+}$, $Sb^{3+}$, $Mn^{2+}$, $Tb^{3+}$, $Eu^{3+}$, $Mn^{4+}$, $Fe^{3+}$.

In various embodiments, the luminescence center Tl+ can be used with a chemical composition such as:
$(Ca,Zn)_3(PO_4)_2:Tl^+$, $Ca_3(PO_4)_2:Tl^+$.

Similarly, the luminescence center Mn2+ can be used with chemical compositions such as
$MgGa_2O_4:Mn^{2+}$, $BaMg_2Al_{16}O_{27}:Eu^{2+}/Mn^{2+}$, $Zn_2SiO_4:Mn^{2+}$, $3Ca_3(PO_4)_2 \cdot Ca(F,Cl)_2:Sb^{2+}/Mn^{2+}$, $CaSiO_3:Pb^{2+}/Mn^{2+}$, $Cd_2B_2O_5:Mn^{2+}$, $CdB_2O_5:Mn^{2+}$, $GdMgB_5O_{10}:Ce^{3+}/Mn^{2+}$, $GdMgB_5O_{10}:Ce^{3+}/Tb^{3+}/Mn^{2+}$.

Further, the luminescence center $Sn^{2+}$ can be used with chemical compositions such as:
$Sr_2P_2O_7:Sn^{2+}$, $(Sr,Mg)_3(PO_4)_2:Sn^{2+}$.

The luminescence center $Eu^{2+}$ can also be used with chemical compositions such as:
$SrB_4O_7F:Eu^{2+}$, $(Sr,Ba)Al_2Si_2O_8:Eu^{2+}$, $Sr_3(PO_4)_2:Eu^{2+}$, $Sr_2P_2O_7:Eu^{2+}$, $Ba_3MgSi_2O_8:Eu^{2+}$, $Sr_{10}(PO_4)_6Cl_2:Eu^{2+}$, $BaMg_2Al_{16}O_{27}:Eu^{2+}/Mn^{2+}$, $(Sr,Ca)_{10}(PO_4)_6Cl_2:Eu^{2+}$.

The luminescence center $Pb^{2+}$ can be used with chemical compositions such as:
$(Ba,Mg,Zn)_3Si_2O_7:Pb^{2+}$, $BaSi_2O_5:Pb^{2+}$, $(Ba,Sr)_3Si_2O_7:Pb^{2+}$.

The luminescence center $Sb^{2+}$ can be used with chemical compositions such as:
$3Ca_3(PO_4)_2 \cdot Ca(F,Cl)_2:Sb^{3+}$, $3Ca_3(PO_4)_2 \cdot Ca(F,Cl)_2:Sb^{3+}/Mn^{2+}$.

The luminescence center Tb3+ can be used with chemical compositions such as:
$CeMgAl_{11}O_{19}:Ce^{3+}/Tb^{3+}$, $LaPO_4:Ce^{3+}/Tb^{3+}$, $Y_2SiO_5:Ce^{3+}/Tb^{3+}$, $GdMgB_5O_{10}:Ce^{3+}/Tb^{3+}$.

The luminescence center $Eu^{3+}$ can be used with chemical compositions such as:
$Y_2O_3:Eu^{3+}$, $Y(V,P)O_4:Eu^{3+}$.

The luminescence center $Dy^{3+}$ can be used with chemical compositions such as:
$YVO_4:Dy^{3+}$.

The luminescence center $Fe^{3+}$ can be used with chemical compositions such as:
$LiAlO_2:Fe^{3+}$.

The luminescence center $Mn^{4+}$ can be used with chemical compositions such as:
$6MgO \cdot As_2O_5$: $Mn^{4+}$, $3.5MgO \cdot 0.5MgF_2 \cdot GeO_2:Mn^{4+}$.

The luminescence center $Ce^{3+}$ can be used with chemical compositions such as:
$Ca_2MgSi_2O_7:Ce^{3+}$ and $Y_2SiO_5:Ce^{3+}$.

The luminescence center $WO_4^{2-}$ can be used with chemical compositions such as:
$CaWO_4$, $(Ca,Pb)WO_4$, $MgWO_4$.

The luminescence center $TiO_4^{4-}$ can be used with chemical compositions such as:
$BaO \cdot TiO_2 \cdot P_2O_5$.

In various embodiments of this invention, the phosphor chemistry utilized in x-ray excitations can be used with or without energy augmentators. Of particular interest is the k edge of these phosphors. Low energy excitation can lead to intense luminescence in materials with low k-edge. Some of these chemistries and the corresponding k-edge are included as follows:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4:Nb$ | 67.42 keV |
| $ZnS:Ag$ | 9.66 keV |
| $(Zn,Cd)S:Ag$ | 9.66/26.7 keV |

In one embodiment of this invention, light from these materials (excited for example by high energy particles including x-rays, gamma rays, protons, and electrons) can have their emissions modulated by having those materials included in a vicinity of (including inside) the color enhancing structures described herein. For example, in medical treatments where x-ray excites phosphorescence to photo-stimulate reactions in a patient, simultaneous with irradiation by the high energy particles, there could be applied infrared irradiation to drive resonance in the energy augmentation structures described herein, where the x-ray phosphors would have enhanced light emissions when in the presence of the intensified electric fields. In another example, in medical or scientific instruments, for simultaneous with irradiation by the high energy particles, there could be applied electric fields to enhance emissions from these x-ray phosphors.

Electro Luminescent Materials: Various materials used for the electroluminescence in the present invention with or without energy augmentators can include but are not limited to:

4,4',4''-Tris[phenyl(m-tolyl)amino]triphenylamine (m-MTDATA)

N,N'-Bis(3-methylphenyl)-N,N'-diphenylbenzidine (TPD)

4,4',4''-Tris[phenyl(m-tolyl)amino]triphenylamine (m-MTDATA)

N,N'-Bis(3-methylphenyl)-N,N'-diphenylbenzidine (TPD)

Tris-(8-hydroxyquinoline)aluminum 2,4,6-Tris(2-pyridyl)-s-triazine (TPT)

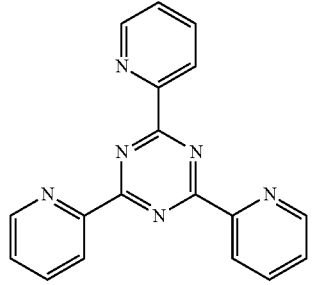 [SMILES: c1ccc(-c2nc(-c3ccccn3)nc(-c3ccccn3)n2)nc1]

2,2',2''-(1,3,5-Benzinetriyl)-tris(1-phenyl-1-H-benzimidazole)Alq

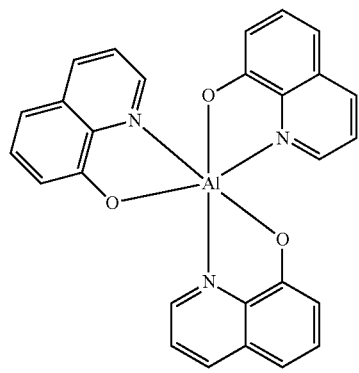

2,2',2''-(1,3,5-Benzinetriyl)-tris(1-phenyl-1-H-benzimidazole)TPBI

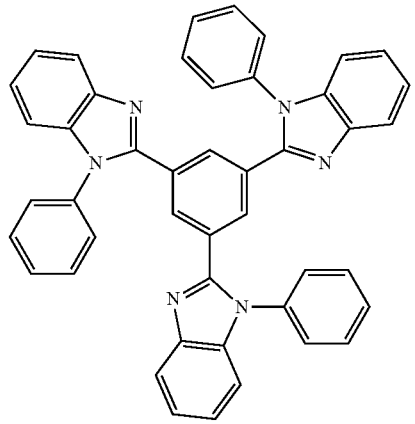 [SMILES: c1ccc(-n2c(-c3cc(-c4nc5ccccc5n4-c4ccccc4)cc(-c4nc5ccccc5n4-c4ccccc4)c3)nc3ccccc32)cc1]

2,9-Dimethyl-4,7-diphenyl-1,10-phenanthroline, BCP2,9-Dimethyl-4,7-diphenyl-1,10-phenanthroline, BCP

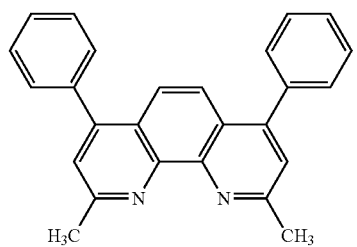 [SMILES: Cc1cc(-c2ccccc2)c2ccc3c(-c4ccccc4)cc(C)nc3c2n1]

Figure 26:
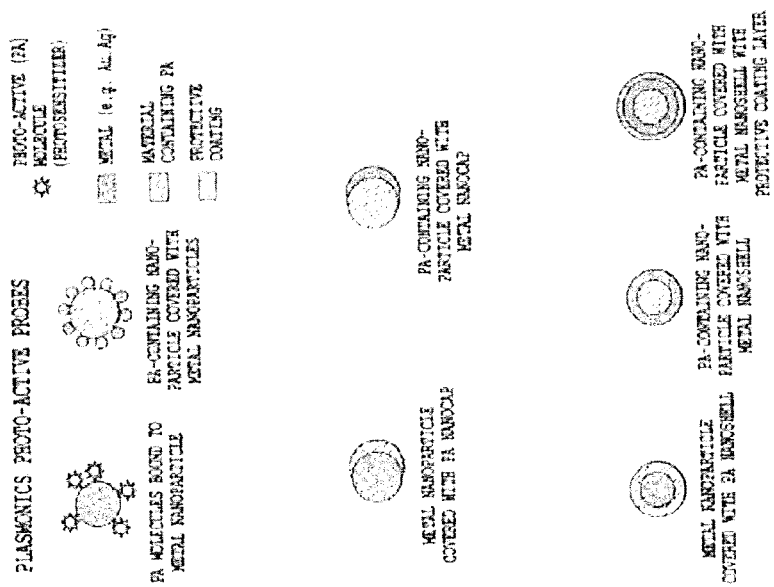
FIG. 26 is a schematic illustrating various converter structures of the invention.

Plasmonic enhancement structures: FIG. 26 is a schematic of a depiction of an upconverter or a down converter material (i.e., a photoactive material) according to one embodiment of the invention to be utilized in the color enhancement/augmentation structures noted herein with or without energy augmentators. FIG. 26 shows a number of structural configurations for placement of a dielectric core upconverter or a down converter material (which is of a nanometer sized scale) in proximity to a metal shell. Incident light at a wavelength $\lambda_1$ interacts with the upconverting dielectric core. The interaction of light $\lambda_1$ with the dielectric core produces a secondary emission at a frequency $\lambda_2$ which has a shorter wavelength than $\lambda_1$ and accordingly has a higher energy than $\lambda_1$. While the exact physical mechanisms for the upconversion may depend on the particular upconversion material and process being used in a particular application, for the purposes for discussion and illustration, the following explanation is offered.

In the context of FIG. 26, when a wavelength $\lambda_1$ interacts with a dielectric material core, three separate processes are well understood for the upconversion process involving trivalent rare earth ions. These three processes are:
1) excited state absorption whereby two photons are absorbed sequentially by the same ion to excite and populate one or more states;
2) energy transfer upconversion which is a transfer of excitation from one ion to another already in an excited state; and
3) a cooperative process of multiphotons where two nearby ions in excited states are emitting collectively from a virtual state.

Regardless of which one of these processes is occurring between the chosen ion(s) and the host lattice, the end result is a photon of energy greater than the excitation energy being emitted from the host lattice for the upconversion or down conversion process.

Therefore, the particular ion being activated (whether it be a dopant ion or a host ion of a lattice such as in the neodymium oxide) will be chosen based on the host material being processed, in order that the dopant ion or the host ion in the dielectric core provide ion states which are pumpable by a NIR source to generate the resultant emission $\lambda_2$.

Hence, the invention in one embodiment provides an upconversion or a down conversion material configured, upon exposure to a first wavelength $\lambda_1$ of radiation, to generate a second wavelength $\lambda_2$ of radiation having an energy higher or lower than the first wavelength $\lambda_1$. The system can include a metallic structure disposed in relation to the nanoparticle (e.g. a metallic shell covering a fraction of the nanoparticle). The system may include a receptor disposed in the medium in proximity to the nanoparticle. The receptor upon activation by the second wavelength $\lambda_2$ may itself fluoresce producing visible light. In one embodiment of the invention, a physical characteristic of metallic structure (such as those described above and below in the drawings) is set to a value where a surface plasmon resonance in the metallic structure resonates at a frequency which provides spectral overlap with either the first wavelength $\lambda_1$ or the second wavelength $\lambda_2$. This system with a metallic structure disposed in relation to an up-conversion or a down-conversion nanoparticle becomes the converter utilized in the color enhancement/augmentation structures noted herein.

Within the context of the invention, the term "physical characteristic" of the metallic shell or core can relate to any characteristic of the metal itself or the shell or core dimensions or shape which affects the surface plasmon resonance frequency. Such physical characteristics can include, but are not limited to, a conductivity, a radial dimension, a chemical composition or a crystalline state of the metal shell or core.

In various embodiments, the metallic structures can be a metallic shell encapsulating at least a fraction of the nanoparticle in the metallic shell wherein a conductivity, a radial dimension, or a crystalline state of the metallic shell sets the surface plasmon resonance in the metallic structure to resonate at a frequency which provides spectral overlap with either the first wavelength $\lambda_1$ or the second wavelength $\lambda_2$. In various embodiments, the metallic structures can be a multi-layer metallic shell encapsulating at least a fraction of the nanoparticle in the metallic shell wherein a conductivity, a radial dimension, or a crystalline state of the metallic shell sets the surface plasmon resonance in the metallic structure to resonate at the first wavelength $\lambda_1$ and the second wavelength $\lambda_2$. This capability permits radiation at $\lambda_1$ and $\lambda_2$ to be amplified.

In various embodiments, the metallic structures can be a metallic particle existing in one or more multiple structures. These multiple structures can have a variety of shapes including for example sphere, spheroid, rod, cube, triangle, pyramid, pillar, crescent, tetrahedral shape, star or combination thereof disposed adjacent the nanoparticle wherein a conductivity, a dimension (e.g. a lateral dimension or a thickness), or a crystalline state of the metallic structure sets the surface plasmon resonance in the metallic particle or rod to resonate at a frequency which provides spectral overlap with either the first wavelength $\lambda_1$ or the second wavelength $\lambda_2$. Such shapes are described in the present figures and in the figures in U.S. Ser. No. 12/401,478 which is incorporated by reference in its entirety. The shape choice can affect the frequency of the surface plasmon resonance. It is known that the plasmon band is changed by the shape of nanoparticles (e.g., prolate and obloid spheroids). The paper "Spectral bounds on plasmon resonances for Ag and Au prolate and oblate nanospheroids," in the Journal of Nanophotonics, Vol. 2, 029501 (26 Sep. 2008), the entire contents of which are incorporated by reference, shows plasmon resonance shifts for shaping of Ag and plasmon resonance shifts for shaping of Au of prolate and obloid spheroids. In one embodiment of the invention, with an increasing aspect ratio for a metallic structure of the invention, the prolate spheroid resonance is red shifted relative to a sphere with no lower limit (under the assumptions of a Drude dispersion model). On the other hand, the oblate resonances are "blue shifted" as the spheroid becomes increasingly flat, but up to a limit.

In various embodiments, the metallic structures disposed in relation to an up-conversion or a down-conversion nanoparticle can be a metallic structure disposed interior to the nanoparticle wherein a conductivity or a dimension (e.g. a lateral dimension or a thickness) of the metallic structure sets the surface plasmon resonance in the metallic structure to resonate at a frequency which provides spectral overlap with either the first wavelength $\lambda_1$ or the second wavelength $\lambda_2$. In various embodiments, the metallic structures can be a metallic multi-layer structure disposed interior to the nanoparticle wherein a conductivity or a dimension (e.g. a lateral dimension or a thickness) of the metallic structure sets the surface plasmon resonance in the metallic structure to resonate at the first wavelength $\lambda_1$ and the second wavelength $\lambda_2$. This capability once again permits radiation at $\lambda_1$ and $\lambda_2$ to be amplified.

In another embodiment, the invention provides a nanoparticle structure including a sub 1000 nm dielectric core and a metallic structure disposed in relation to the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. Such nanoparticle structures can exhibit in certain embodiments surface plasmon resonance in the metallic structures to enhance upconversion of light from a first wavelength $\lambda_1$ to a second wavelength $\lambda_2$.

As described above, a shell (or other structure) is in particular designed with a layer thickness (or for example a lateral dimension) to enhance the photon upconversion process through plasmonic enhancement. The thickness of the shell (or other physical characteristic) is "tuned" in its thickness to the absorption process by having a dimension in which plasmons (i.e., electrons oscillations) in shell have a resonance in frequency which provides spectral overlap with the absorption band targeted. Thus, if the upconversion is to be stimulated by 980 nm NIR light, then the thickness of the shell is "tuned" in a thickness to where a plasmon resonance resonates at a frequency also of 980 nm (or in the neighborhood thereof as plasmon resonances are typically broad at these wavelengths).

Figure 27:
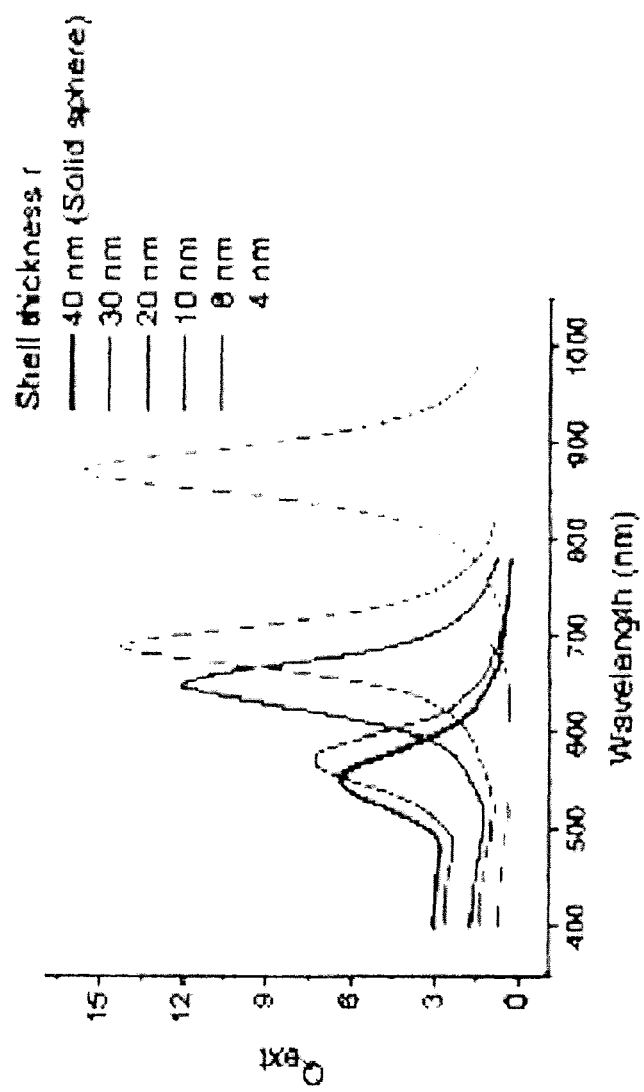
FIG. 27 is a schematic illustration of plasmon resonance as a function of shell thickness.

A plasmon resonating shell can be made of numerous transition metals, including though not limited to gold, silver, platinum, palladium, nickel, ruthenium, rhenium, copper, and cobalt or a combination or alloys or layers thereof. Such a plasmon resonating shell can be also made of a combination of metals and non-metals. When formed of a gold nanoshell, the recommended thickness to resonate with 980 nm light is approximately 3.5 nm surrounding an 80 nm upconverting core, as projected by extended Mie theory calculations. (See Jain et al., *Nanaleu.* 2007, 7(9), 2854 the entire contents of which are incorporated herein by reference.) FIG. 27 is reproduced from Jain et al and illustrates the capability in the invention to "tune" the metal shell to have a spectral overlap with the excitation and/or emission radiation wavelengths.

In one embodiment of the invention, the metallic structures disposed in relation to an up-conversion or a down-conversion nanoparticle can be an alloy such as for example a Au:Ag alloy. The alloy content can be set to adjust the frequency of the surface plasmon resonance. In one embodiment of the invention, the metallic structures can be an alloy such as for example a Pt:Ag alloy. The alloy content can be set to adjust the frequency of the surface plasmon resonance. In one embodiment of the invention, the metallic structures can be an alloy such as for example a Pt:Au alloy. The alloy content can be set to adjust the frequency of the surface plasmon resonance.

In one embodiment of the invention, the converter nanoparticle can be an alloy of two or more materials. In this embodiment, the alloy can have a composition between the two or more materials which is set to a compositional value where excitation of the alloy at first wavelength $\lambda_1$ produces emission at the second wavelength $\lambda_2$. In one embodiment of the invention, the nanoparticle can be a zinc sulfide and zinc selenide alloy. In one embodiment of the invention, the nanoparticle can be a zinc sulfide and cadmium sulfide alloy.

In one embodiment of the invention, the zinc sulfide and zinc selenide nanoparticle alloy can have an alloy content set to provide a predetermined surface plasmon resonance. In one embodiment of the invention, the zinc sulfide and cadmium sulfide nanoparticle alloy can have an alloy content is set to provide a predetermined surface plasmon resonance.

Some techniques for producing nanoparticles and nanoparticle alloys which are suitable for the invention are described in the following documents, all of which are incorporated herein in their entirety: U.S. Pat. Nos. 7,645,318; 7,615,169; 7,468,146; 7,501,092; U.S. Pat. Appl. Publ. No. 2009/0315446; 2008/0277270; 2008/0277267; 2008/0277268; and WO 2009/133138.

In one embodiment of the invention, the thickness of the metal shell disposed in relation to an up-conversion or a down-conversion nanoparticle is set depending on the absorption frequency (or in some cases the emission frequency) of the particular dopant ions in the dielectric core to enhance the total efficiency of the emission process of the upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall net process.

Additionally, plasmon-phonon coupling may be used to reduce a resonance frequency through the tuning of the bands to a degree off resonance. This may be useful in optimizing resonance energy transfer processes for the purpose of shifting the outputted color to a color desirable for a painted, colored, or displayed surface. In one example, FIG. 27 shows an example of the plasmon resonance shift as a function of shell thickness.

Here, in one embodiment of the invention, the capability to produce stimulated emission at a targeted wavelength or color or energy is complemented by the ability to design nanoparticles that have designed absorption bands. Such absorption materials could for example further serve to improve the monochromaticity of light observed from a paint, ink, dye, or otherwise reflecting surface treated with the color enhancing compositions of the invention.

Details of the preparation of this nanoparticle system are included in U.S. Ser. No. 12/725,108, the entire contents of which are incorporated herein by reference. The absorption spectrum of $Y_2O_3$ alone (lower trace) is fairly featureless, showing absorption due to the tri-arginine near 200 nm and a gentle slope associated with scattering and absorption by the $Y_2O_3$ nanoparticles extending into the visible portion of the spectrum. The gold-coated $Y_2O_3$ (upper trace), on the other hand, exhibit a strong absorption band at 546 nm, which is characteristic of the plasmonics resonance band due to the gold shell around the $Y_2O_3$ cores. The red-shifting of the plasmon absorption to 546 nm is consistent with the presence of a gold shell around a dielectric core.

In one embodiment of the invention, the converter materials for the upconverter dielectric core can include a wide variety of dielectric materials, as described above. In various embodiments of the invention, the upconverter dielectric core includes more specifically lanthanide doped oxide materials. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y) and scandium (Sc). Hence, suitable dielectric core materials include $Y_2O_3$, $Y_2O_2S$, $NaYF_4$, $NaYbF_4$, Na-doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. These dielectric cores can be doped with Er, Eu, Yb, Tm, Nd, Tb, Ce, Y, U, Pr, La, Gd and other rare-earth species or a combination thereof.

Lanthanides usually exist as trivalent cations, in which case their electronic configuration is (Xe) $4f^n$, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled 5s and 5p orbitals, thus giving rise to line-like spectra. The f-f electronic transitions are LaPorte forbidden, leading to long excited state lifetimes, in the micro- to millisecond range.

Accordingly, examples of doped materials in the invention include oxides such as yttrium oxide and neodymium oxide and aluminum oxide as well as sodium yttrium fluoride and nanocrystalline perovskites and garnets such as yttrium aluminum garnet (YAG) and yttrium aluminum perovskite (YAP). Of these materials, doping is required for some, but not all of these materials, for promoting upconversion efficiencies. In various embodiments of the invention, the host nanocrystals are doped with trivalent rare earth lanthanide ions from those lanthanide series elements given above.

More specifically, in various embodiments of the invention, pairs of these dopants are introduced in order to make accessible more energy states in the host crystal. The activation and pumping of these energy states follows closely the principles discussed above. Doping concentrations in the invention can range from 0.2% to 20% roughly per ion into the host lattice or in a weight or mol % variation. The efficiency of the upconversion processes of specific bands in these materials can be modulated by the percentages doped to induce and enhance targeted emissions. Lanthanide doped upconverters while not limited to, can use the following mol percent dopant compositions: 5% Er, 10% Yb, 0.2% Tm+3% Yb, and 1% Er+10% Yb.

The size of the nanocrystal will also have an effect on the efficiency of the upconversion process, as a larger nanocrystal will have more sites for dopant ions to be accommodated into the host lattice, therefore enabling more emissions from the same doped host than if the nanocrystal were smaller. While the dopant percentages listed above are not rigidly fixed, these numbers provide a rudimentary teaching of the typical percentages one would use in obtaining a particular dielectric core material of the invention.

Moreover, some of these host crystals (e.g., neodymium oxide) in one embodiment of the invention may require no specific doping to facilitate upconversion, which has been seen in one instance in $Nd_2O_3$ with an excitation wavelength of 587 nm producing emissions at 372 nm, 402 nm, and 468 nm. See Que, W et al. Journal of Applied Physics 2001, vol 90, pg. 4865, the entire contents of which are incorporated herein by reference. Doping neodymium oxide with $Yb^{3+}$, in one embodiment of the invention, would enhance upconversion through sensitizing the $Nd^{3+}$ ions with a lower energy $Yb^{3+}$ activator.

In one embodiment of the invention, the dielectric core is coated, such as for example with a metallic shell, to enhance electron-phonon coupling and thereby increase up conversion or down conversion efficiency, as discussed above. In another embodiment of the invention, the shell can include a $SiO_2$— and/or $TiO_2$-coating, and this coating is in one embodiment coated on doped $Y_2O_3$ upconverting nanoparticles to thereby, in some instances, increase the upconversion efficiency relative to an uncoated nanocrystal. In another embodiment of the invention, the shell can include a $SiO_2$— and/or $TiO_2$-coating, and this coating is in one embodiment coated on doped $Y_2O_3$ down converting nanoparticles to thereby, in some instances, increase the down conversion efficiency relative to an uncoated nanocrystal. Further, in one embodiment of the invention, the coating can be a polymer. In one embodiment, this coating is provided on $NaYF_4$:Ln/$NaYF_4$ dielectric core. Such coatings can increase the upconversion efficiency relative to an uncoated upconverter.

In another embodiment of the invention, phonon modes of undoped host-lattice (e.g., $Y_2O_3$) nanocrystals are modulated, for example, by Au, Ag, Pt, and Pd shells of varying thicknesses. In various embodiments of the invention, the upconverter dielectric core and the shell system includes as upconverting nanocrystals $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure disposed in relation to an up-conversion or a down-conversion nanoparticle can exist inside the dielectric and the relative position of the metal structure to the dielectric structure can enhance plasmon resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter.

In various embodiments of the invention, the upconverter or down converter dielectric core can be coated with thiol-terminated silanes to provide a coating of $SiO_2$ about the core of similar reactivity to $Y_2O_3$. In one embodiment of the invention, the above-described methodology is used to synthesize core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells where core and shell diameters varying from 2 to 20 nm. In these material systems, the tuned ratio of core-to-shell diameter may permit a plasmon-phonon resonance which should amplify absorption of NIR light and/or upconverted emission. In these material systems, control of the core and shell diameters is one factor determining the size dependent effect and subsequent tuning of plasmon-phonon resonance.

In one embodiment of the invention, the upconverter dielectric core can be mixed core-shell materials including for example semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag,Pt, Pd) or undoped $Y_2O_3$ and $NaYF_4$ matrices which have the potential to enhance or tune the phonon modes needed for energy transfer in the upconversion process. Solubility can be enhanced, for example, by addition of thiolated organics (Au shell), organic chain triethanolsilane ($Y_2O_3$ shell), and tri-octylphosphine-oleic amine ($NaYF_4$ shell). All core-shell nanoparticles may further be solubilized into a colloidal suspension with the addition of triarginine peptide, polyethylene glycol, and polyethyleneimine surfactants.

Figure 28A:
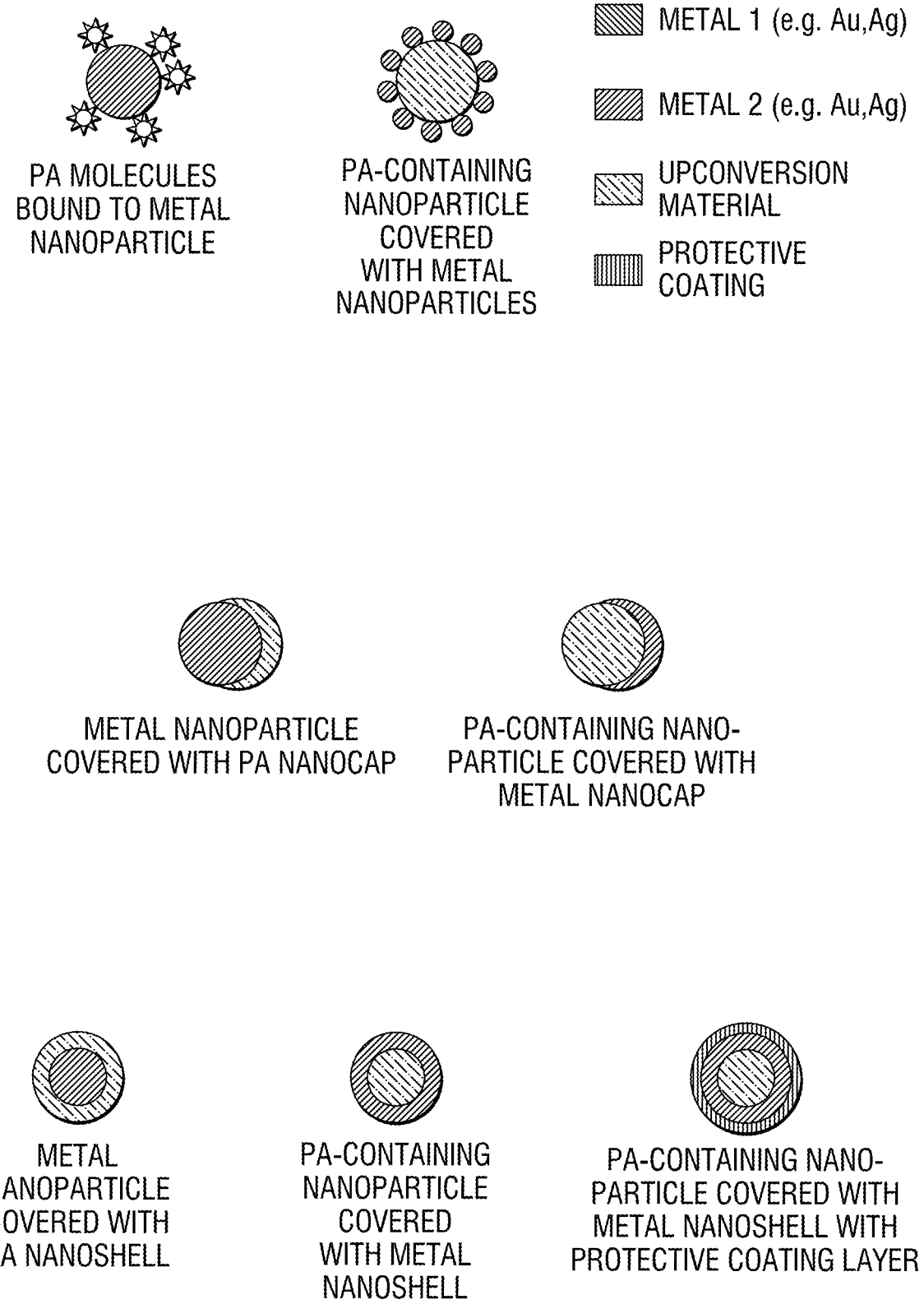
FIG. 28A is a schematic illustrating other various converter structures of the invention.

FIG. 28A shows some of the various embodiments of the converter structures of the invention that can be designed: (a) a structure including upconverter (UC) molecules bound to a metal (gold) nanoparticle; (b) a structure including an UC-containing nanoparticle covered with metal nanoparticles, (c) a metal nanoparticle covered with an UC-containing nanocap; (d) an UC-containing nanoparticle covered with metal nanocap, (e) a metal nanoparticle covered with UC nanoshell, (f) an UC-containing nanoparticle covered with metal nanoshell, (g) an UC-containing nanoparticle covered with metal nanoshell with protective coating layer.

Figure 28B:
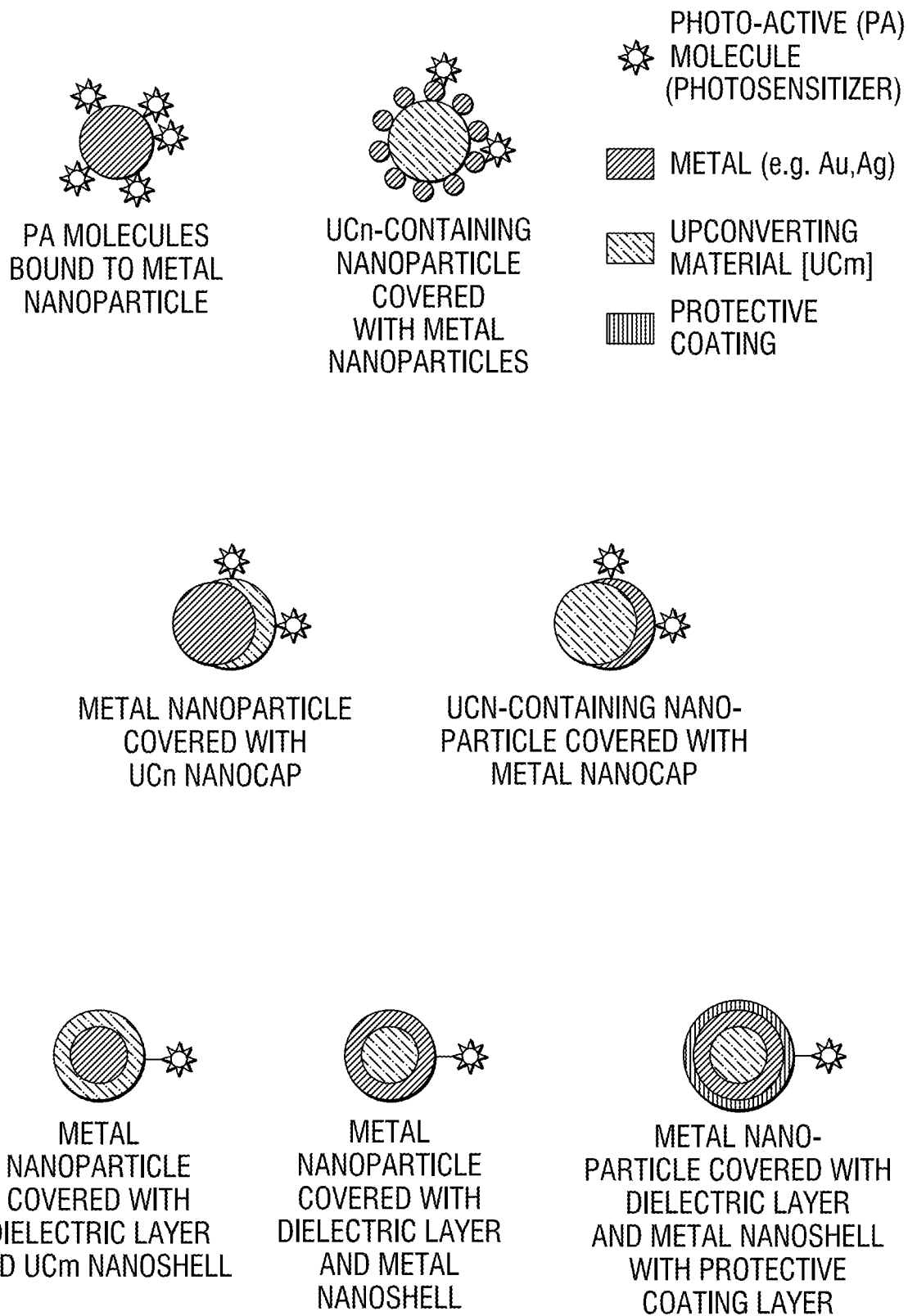
FIG. 28B is a further schematic illustrating other various converter structures of the invention.

The configurations (while shown in the FIG. 28A with UC-containing materials) would be applicable for enhancement for down converting materials such as the quantum dots or phosphors described herein. Moreover, in one embodiment of the invention, dielectric spacers (for examples silicates as discussed below) can be used with the structure of FIG. 6A-b to space apart the particle type metallic structures. In another embodiment of the invention, dielectric spacers can be used with the structure of FIG. 28A to space apart the metal layers, whether or not these layers are partial metal layers or continuous metal layers. See the schematics in FIG. 28B In various embodiments of the invention, multi-layer metallic nanoshells discussed in this application have the potential capability to enhance electromagnetically two spectral regions. Accordingly, the metallic structures of the invention can be used in the upconverting mode to enhance both the excitation at wavelength $\lambda_1$ and the emission at wavelength $\lambda_2$. This feature also can be used in the down converting to enhance primarily the emission at wavelength $\lambda_2$ and potentially the excitation at wavelength $\lambda_1$.

Such metallic structures in various embodiments of the invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Similarly, in various embodiments of the invention, the up or down converting materials can include at least one of a dielectric, a glass, or a semiconductor. The up or down converting materials can include an alloy of two or more dielectric materials, an alloy of two or more glasses, or an alloy of two or more semiconductors.

Accordingly, FIG. 28A represents embodiments of the invention where the dielectric core is supplemented with a shell. The shell can include a metal layer of a prescribed thickness. The metal layer can include materials such as nickel, gold, iron, silver, palladium, platinum and copper and combinations thereof. The metal layer can be also made of a combination of metals and non-metals. The shell functions as a plasmonic shell where surface plasmons can form in the metal between the dielectric core and the outer environment acting as an exterior dielectric. The shell (as shown) may not be a complete shell. Partial metallic shells or metallic shells of varying thicknesses are also acceptable in the invention.

As discussed below, the metallic shells in another embodiment of the invention serve as scattering centers for UV light where UV light which, even if absorbed in a paint or coating layer contributes at a minimum to localized heating of the paint or coating layer material, will be scattered from the paint or coated layer.

FIG. 28C shows still further embodiments of plasmonics-active nanostructures having upconverting (UC) materials that can be designed: (a) a metal nanoparticle, (b) an UC nanoparticle core covered with metal nanocap, (c) a spherical metal nanoshell covering an UC spheroid core, (d) an oblate metal nanoshell covering UC spheroid core, (e) a metal nanoparticle core covered with UC nanoshell, (f) a metal nanoshell with protective coating layer, (g) multi-layer metal nanoshells covering an UC spheroid core, (h) multi-nanoparticle structures, (i) a metal nanocube and nanotriangle/nanoprism, and (j) a metal cylinder.

Figure 28D:
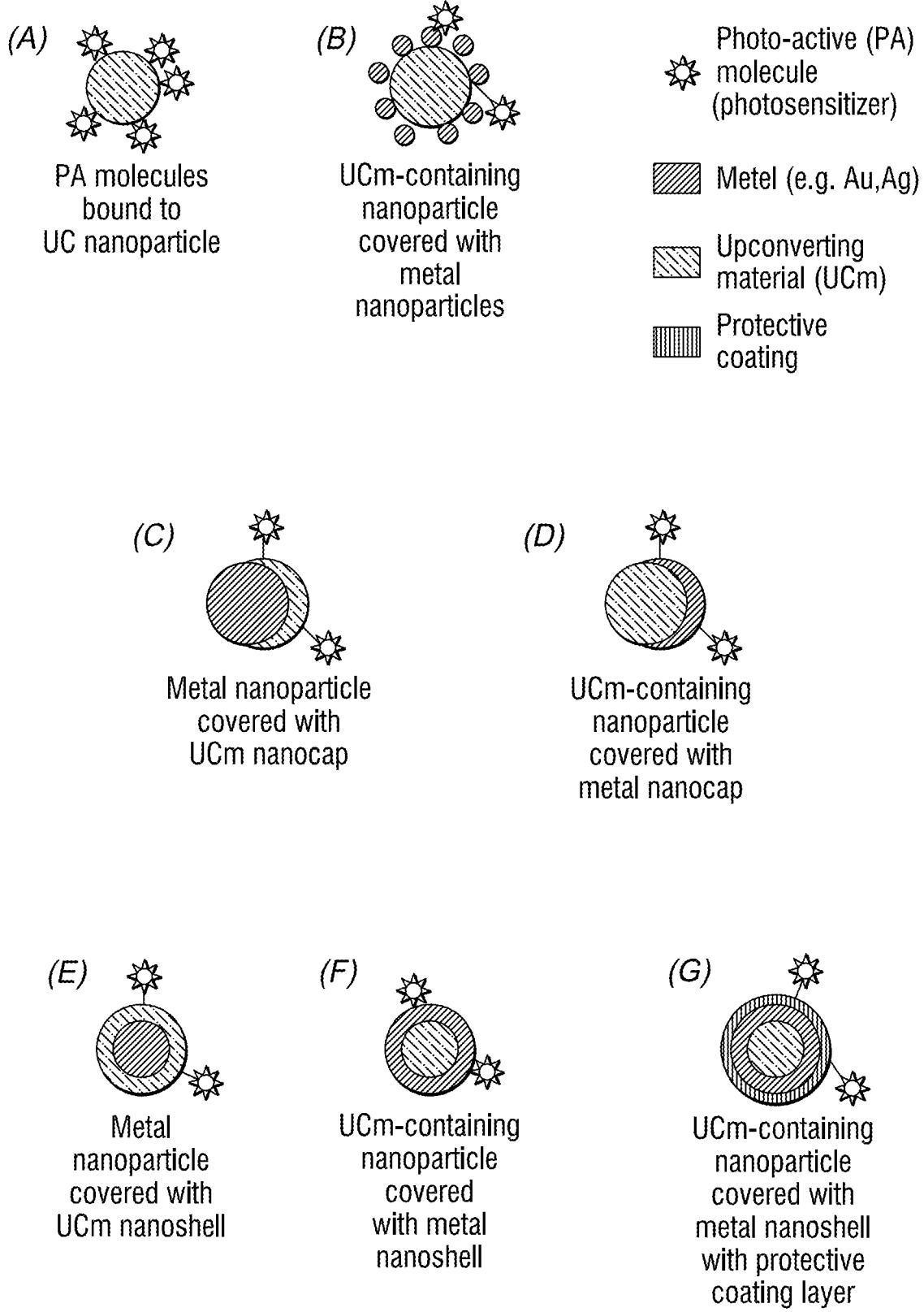
FIG. 28D is a schematic illustration of photo-active molecules inked to plasmonics-active upconverter structures of the invention.

FIG. 28D shows yet other embodiments of plasmonics-active nanostructures having upconverting materials with linked photo-active (PA) molecules that can be designed. For example, for the case of psoralen (as the PA molecule), the length of the linker between the PA molecule and the UC material or the metal surface is tailored such that it is sufficiently long to allow the PA molecules to be active (attach to DNA) and short enough to allow efficient excitation of light from the UC to efficiently excite the PA molecules. FIG. 28D shows (a) PA molecules bound to an UC nanoparticle, (b) an UC material-containing a nanoparticle covered with metal nanoparticles, (c) a metal nanoparticle covered with UC material nanocap, (D) an UC material-containing nanoparticle covered with metal nanocap, (e) a metal nanoparticle covered with an UC material nanoshell, (f) an UC material-containing nanoparticle covered with metal nanoshell, (g) an UC material-containing nanoparticle covered with metal nanoshell with protective coating layer.

With the upconverter and down converter structures of the invention, a plasmonics effect is advantageous. A plasmonics effect can increase the local intensity of the received light or the local intensity of the emitted light from the up and/or down converter structures of the invention. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NIR region, respectively.

In various embodiments, nanoparticles of neodymium and ytterbium doped yttrium oxide, europium and ytterbium doped yttrium oxide, and any combination of rare earth trivalent ions doped into a neodymium oxide nanocrystal can be used. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nano-scale. There are advantages offered by these yttrium oxide nanostructures of the invention. The small scale synthetic methodology for creating nanoscale yttrium oxide is easier to control and produce in yttrium oxide than in YAG. The host structure of yttrium oxide scintillates by down conversion. These combinations of dopants in yttrium oxide for example can provide predetermined emission colors for the yttrium oxide nanocrystal for the color shifting of the invention.

In one embodiment of the invention, a dual dopant permits excitation of either ion in the host glass. For instance, excitation by 980 nm light excites an ytterbium ion, where through transfer of energy from one excited state of the ytterbium ion to another dopant provides a mechanism for upconversion emission of light in the visible and NIR spectral regions.

Up-conversion phosphors similar in chemical compositions to the down-conversion fluorescent materials discussed above can be used. The up-conversion phosphors can include laser dyes, e.g., the organic small molecules that can be excited by the absorption of at least two infrared photons with emission of visible light. The up-conversion phosphors can include fluorescent polymers, e.g., the class of polymers that can be excited by the absorption of at least two infrared photons with emission of visible light. The up-conversion phosphors can include inorganic or ceramic particles or nano-particles, including the conventional up-conversion phosphors (e.g. metal fluorides, metal oxides) that can be excited by the absorption of at least two infrared photons with emission of visible light. The up-conversion phosphors can include semiconductor particles, including nano-particles such as II-VI or III-V compound semiconductors, e.g. quantum dots, described in details in the "down-conversion" semiconductors above.

Fluorescent up-conversion inorganic phosphors can include but are not limited to metal oxides, metal halides, metal chalcogenides (e.g. sulfides), or their hybrids, such as metal oxo-halides, metal oxo-chalcogenides. Fluorescent up-conversion inorganic phosphors are usually doped with rare earth elements (e.g. $Yb^{3+}$, $Er^{3+}$, $Tm^{3+}$). Some host examples include, but are not limited to: $NaYF_4$, $YF_3$, $BaYF_5$, $LaF_3$, $La_2Moo_8$, $LaNbO_4$, $LnO_2S$; where Ln is the rare earth elements, such as Y, La, Gd).

These converters (and the other energy converters described herein which receive energy and generate light or electron emission) can optionally include any of the energy augmentation structures described above.

In various embodiments of the invention, energy converters can be used with the energy augmentators described above for color enhancement. In some embodiments, the converters are up conversion of light e.g., from the IR regime into visible electromagnetic radiation and for down conversion of light e.g., from the UV range into visible electromagnetic radiation. The invention in various embodiments up converts energy, preferably light in the visible spectrum. The invention encompasses a variety of applications where the up and down conversion materials with or without energy augmentators are included to enhance the color of the object being displayed. These application areas can include paints on signs, walls, cars, buildings, boats, airplanes. These application areas can include display monitors, computer monitors, telephone displays, watch dials, instrument dials to name but a few.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

This invention in various embodiments can use a wide variety of down conversion materials (or mixtures of down conversion materials) with or without the energy augmentators to enhance a particular color of light observable to an observer. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties. Accordingly, the down conversion materials to enhance color emission can convert energy from one of ultraviolet light, x-rays, and high energy particles to visible light. The down conversion materials to enhance color emission can convert energy from higher energy visible light to lower energy visible light with or without the energy augmentators.

In one embodiment of the invention, a quantum dot mixture with or without the energy augmentators can be used for color enhancement. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted. Quantum dots represent one way to down convert ultraviolet light of the spectrum to a targeted color emission, such as for example a green light emission. Quantum dots represent one way to down convert blue light of the spectrum to a targeted color emission, such as for example a green light emission.

As described in U.S. Pat. No. 6,744,960 (the entire contents of which are incorporated by reference), different size quantum dots produce different color emissions. In that work and applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot 18, may range from about 2 to 10 nm. Since the size of these particles is so small, quantum physics governs many of the electrical and optical properties of the quantum dot. One such result of the application of quantum mechanics to the quantum dot 18 is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 μm. Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm. In practice, however, the excitation or pump radiation is at least about 50 nanometers shorter than the emitted radiation.

Specifically, in one embodiment of the invention, a quantum dot mixture (QDM) coating can be deposited using CVD and or sol-gel techniques using standard precipitation techniques to be used with or without the energy augmentators. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

Further, the down conversion materials for the invention described here can be coated with insulator materials such as for example silica which will reduce the likelihood of any chemical interaction between the luminescent particles and the medium the particles are included therein. These and the other conversion materials here can be used with or without the energy augmentators. For biocompatible applications of inorganic nanoparticles, one of the major limiting factors is their toxicity. Generally speaking, all semiconductor nanoparticles are more or less toxic. For biocompatible applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable down conversion materials which would seem the most biocompatible are zinc sulfide, ZnS:$Mn^{2+}$, ferric oxide, titanium oxide, zinc oxide, zinc oxide containing small amounts of $Al_2O_3$, and AgI nanoclusters encapsulated in zeolite. For non medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, BaFBr:$Eu^{2+}$ nanoparticles, Cesium Iodine, Bismuth Germanate, Cadmium Tungstate, and CsBr doped with divalent Eu.

In various embodiments of the invention, the following luminescent polymers are also suitable as conversion materials with or without the energy augmentators: poly(phenylene ethynylene), poly(phenylene vinylene), poly(p-phenylene), poly(thiophene), poly(pyridyl vinylene), poly (pyrrole), poly(acetylene), poly(vinyl carbazole), poly (fluorenes), and the like, as well as copolymers and/or derivatives thereof.

In various embodiments of the invention, the following materials can be used similar to that detailed in U.S. Pat. No. 7,090,355, the entire contents of which are incorporated herein by reference. For down-conversion, the following materials can be used with or without the energy augmentators. Inorganic or ceramic phosphors or nano-particles, including but not limited to metal oxides, metal halides, metal chalcogenides (e.g. metal sulfides), or their hybrids, such as metal oxo-halides, metal oxo-chalcogenides. Laser dyes and small organic molecules, and fluorescent organic polymers. Semiconductor nano-particles, such as II-VI or III-V compound semiconductors, e.g. fluorescent quantum dots. Organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The metal elements are chemically bonded to organic groups to prevent the quenching of the fluorescence from the hosts or solvents. Phosphors can be used including the Garnet series of phosphors: $(Y_mA_{1-m})_3(Al_nB_{1-n})_5O_{12}$, doped with Ce; where 0≤m, n≤1, where A includes other rare earth elements, B includes B, Ga. In addition, phosphors containing metal silicates, metal borates, metal phosphates, and metal aluminates hosts can be used. In addition, nanoparticulates phosphors containing common rare earth elements (e.g. Eu, Tb, Ce, Dy, Er, Pr, Tm) and transitional or main group elements (e.g. Mn, Cr, Ti, Ag, Cu, Zn, Bi, Pb, Sn, Tl) as the fluorescent activators, can be used. Materials such as Ca, Zn, Cd in tungstates, metal vanadates, ZnO, etc. can be used with or without the energy augmentators.

The commercial laser dye materials obtained from several laser dye vendors, including Lambda Physik, and Exciton, etc. can also be used with or without the energy augmentators. A partial list of the preferred laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc. have been used in optoelectronic devices, such as polymer light emitting diodes (PLED). Such fluorescent polymers can be used directly as the fluorescent layer of the transparent 2-D display screen.

As noted above, semiconductor nanoparticles (e.g., quantum dots) can be used with or without the energy augmentators. The terms "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nano-particle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Fluorescent organometallic molecules containing rare earth or transitional element cations can be used for down conversion materials with or without the energy augmentators. Such molecules include a metal center of rare earth elements including Eu, Tb, Er, Tm, Ce protected with organic chelating groups. The metal center may also include transitional elements such as Zn, Mn, Cr, Ir, etc. and main group elements such as B, Al, Ga. Such organometallic molecules can readily dissolve in liquid or transparent solid host media. Some examples of such fluorescent organometallic molecules include: 1. Tris(dibenzoylmethane)mono (phenanthroline)europium(III); 2. Tris(8-hydroxyquinoline) erbium; 3. Tris(1-phenyl-3-methyl-4-(2,2-dimethylpropan-1-oyl)pyrazolin-5-one)terbium(III); 4. Bis(2-methyl-8-hydroxyquinolato)zinc; 5. Diphenylborane-8-hydroxyquinolate.

Specific examples of down-conversion materials for red emission include those discussed above and europium complexes such as those described in JP Laid-open Patent Publication (Kokai) No. 2003-26969, constructed such that β-diketone ligand is coordinated to europium forming an europium complex capable of emitting red fluorescence. Other specific examples of the rare earth element complexes include complexes include lanthanum (Ln), europium (Eu), terbium (Tb), and gadolinium (Gd) and combinations thereof. A europium (Eu) complex is capable of emitting red fluorescence when irradiated with ultraviolet rays having a wavelength ranging from 365 nm to 410 nm. Terbium (Tb) is capable of emitting green fluorescence when irradiated with ultraviolet rays having a wavelength of 365 nm.

In other down-conversion embodiments with or without the energy augmentators, the down conversion materials which emit red light may include europium, light emitting particles which emit green light may include Terbium, and light emitting particles which emit blue or yellow light may include cerium (and/or thulium). In up-conversion embodiments, up conversion materials which emit red light may include praseodymium, light emitting particles which emit green light may include erbium, and light emitting particles which emit blue light may include thulium. In embodiments, the conversion materials can be light emitting particles made of fluorescent molecules that emit different colors (e.g. red, green, and blue). In embodiments, the conversion materials can be light emitting particles made of pure organic or organo-metallic dyes with or without the energy augmentators.

In addition to the combinations of rare earth complexes, such as a combination of a europium complex and a terbium complex, it is also possible employ a combination of a europium complex and a green-emitting fluorescent substance which is not a complex, or a combination of a terbium complex and a red-emitting fluorescent substance which is not a complex.

Other down converter materials with or without the energy augmentors include for example ZnS, PbS, SbS$_3$, MoS$_2$, PbSe, BeO, MgO. Li$_2$CO$_3$, Ca(OH)$_2$, MoO$_3$, SiO$_2$, Al$_2$O$_3$, TeO$_2$, SnO$_2$, KBr, KCl, and NaCl. These materials can include dopants to tailor the emission properties, as noted above. Examples of doped (or alloyed) glass systems suitable for the include Y$_2$O$_3$:Gd, Y$_2$O$_3$:Dy, Y$_2$O$_3$:Tb, Y$_2$O$_3$:Ho, Y$_2$O$_3$:Er, Y$_2$O$_3$:Tm, Gd$_2$O$_3$:Eu, Y$_2$O$_2$S:Pr, Y$_2$O$_2$S:Sm, Y$_2$O$_2$S:Eu, Y$_2$O$_2$S:Tb, Y$_2$O$_2$S:Ho, Y$_2$O$_2$S:Er, Y$_2$O$_2$S:Dy, Y$_2$O$_2$S:Tm, ZnS:Ag:Cl (blue), ZnS:Cu:Al (green), Y$_2$O$_2$S:Eu (red), Y$_2$O$_3$:Eu (red), YVO$_4$:Eu (red), and Zn$_2$SiO$_4$:Mn (green).

With regard more specifically to down converter materials suitable for the invention with or without the energy augmentors, U.S. Pat. No. 4,705,952 (the contents of which are hereby incorporated herein by reference) describes an infrared-triggered phosphor that stores energy in the form of visible light of a first wavelength and released energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention with or without the energy augmentors.

In other embodiments of the invention, the down converter materials (or mixtures of down converters materials) can include Y$_2$O$_3$: Li. Sun et al "Luminescent properties of Li+ doped nanosized Y$_2$O$_3$:Eu," Solid State Comm. 119 (2001) 393-396 (the entire contents of which are incorporated herein by reference) describe such materials. Hou et al "Luminescent properties nano-sized Y$_2$O$_3$:Eu fabricated by co-precipitation method," Journal of Alloys and Compounds, vol. 494, issue 1-2, 2 Apr. 2010, pages 382-385 (the entire contents of which are incorporated herein by reference) describe that nano-sized yttria (Y$_2$O$_3$) powders have been successfully synthesized by a co-precipitation method. The powders were well crystallized, and the grains were almost spherical with good dispersibility. The quenching concentration of Eu$^{3+}$ ions is 9 mol % which is much higher than micro-scaled powders. The incorporation of Li+ ions greatly improved the luminescence intensity. The highest emission intensity was observed with 4 mol % Li+ doped Y$_2$O$_3$:Eu powder ((Y$_{0.87}$Eu$_{0.09}$Li$_{0.04}$)$_2$O$_3$) and the fluorescence intensity was increased by as much as 79%. Yi et al "Improved cathodoluminescent characteristics of Y$_2$O$_3$:Eu$^{3+}$ thin films by Li-doping," Appl. Phys. A 87, 667-671 (2007) (the entire contents of which are incorporated herein by reference) describe cathodoluminescent spectra for both Y$_2$O$_3$:Eu$^{3+}$ and Li-doped Y$_2$O$_3$:Eu$^{3+}$ films and methods for making these materials.

The invention in other embodiments can use a wide variety of up conversion materials (or mixtures of up converters) with or without the energy augmentors to enhance a particular color of light observable from reflective material or surface. These up conversion materials can include similar materials as discussed above with regard to down conversion but typically included doped or impurity states in a host crystal that provide a mechanism for up conversion pumping. Accordingly, the up conversion materials to enhance color emission can convert energy from one of near infrared, infrared, and microwave irradiation. The upconversion materials to enhance color emission can convert energy from lower energy visible light to higher energy visible light.

Upconversion materials with or without the energy augmentors can be used in various ways to enhance visible light emission by way of conversion of infrared light from a solar spectrum (as in daylight exposure) or a black body spectrum (as in an incandescent lamp). In one example, a nanoparticle of a lanthanide doped oxide can be excited with near infrared light such as laser light at 980 nm and 808 nm to produce visible light in different parts of the red, green, blue spectrum depending on the dopant trivalent rare earth ion(s) chosen, their concentration, and the host lattice.

The lanthanide doped oxides suitable for this invention differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the NaYF$_4$ such that the Yb$^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the Yb$^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as Er$_{3+}$ doped BaTiO$_3$ nanoparticles and Yb$^{3+}$ doped CsMnCl$_3$) are suitable in various embodiments of the invention with or without the energy augmentors.

Further, materials specified for up conversion materials in the invention with or without the energy augmentors include CdTe, CdSe, ZnO, CdS, Y$_2$O$_3$, MgS, CaS, SrS and BaS. Such up conversion materials may be any semiconductor and more specifically, but not by way of limitation, sulfide, telluride, selenide, and oxide semiconductors and their nanoparticles, such as Zn$_{1-x}$Mn$_x$S$_y$, Zn$_{1-x}$Mn$_x$Se$_y$, Zn$_{1-x}$Mn$_x$Te$_y$, Cd$_{1-x}$MnS$_y$, Cd$_{1-x}$Mn$_x$Se$_y$, Cd$_{1-x}$Mn$_x$Te$_y$, Pb$_{1-x}$Mn$_x$S$_y$, Pb$_{1-x}$Mn$_x$Se$_y$, Pb$_{1-x}$Mn$_x$Te$_y$, Mg$_{1-x}$Mn$_x$S$_y$, Ca$_{1-x}$Mn$_x$S$_y$, Ba$_{1-x}$Mn$_x$S$_y$, and Sr$_{1-x}$, etc. (wherein, 0<x≤1, and 0<y≤1). Complex compounds of the above-described semiconductors are also contemplated for use in the invention—e.g. (M$_{1-z}$N$_z$)$_{1-x}$Mn$_x$A$_{1-y}$B$_y$ (M=Zn, Cd, Pb, Ca, Ba, Sr, Mg; N=Zn, Cd, Pb, Ca, Ba, Sr, Mg; A=S, Se, Te, 0; B=S, Se, Te, O; 0<x≤1, 0<y≤1, 0<z≤1). Two examples of such complex compounds are Zn$_{0.4}$Cd$_{0.4}$Mn$_{0.2}$S and Zn$_{0.9}$Mn$_{0.1}$S$_{0.8}$Se$_{0.2}$. Additional conversion materials include insulating and nonconducting materials such as BaF$_2$, BaFBr, and BaTiO$_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er;

CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$, (M=Zn, Cd, Pb, Ca, Ba, Sr, Mg; N=Zn, Cd, Pb, Ca, Ba, Sr, Mg; A=S, Se, Te, O; B=S, . . . 0<z≤1, o<q≤1).

Some nanoparticles such as $ZnS:Tb^{3+}$; $Er^{3+}$; $ZnS:Tb^{3+}$; $Y_2O_3:Tb^{3+}$; $Y_2O_3:Tb^{3+}$, $Er3^+$; $ZnS:Mn^{2+}$; $ZnS:Mn,Er^{3+}$ are known in the art to function for both down-conversion luminescence and upconversion luminescence and would be suitable for the invention with or without the energy augmentators. In up-conversion embodiments, light emitting particles which emit red light may include praseodymium, light emitting particles which emit green light may include erbium, and light emitting particles which emit blue light may include thulium.

In general, the upconversion process generally requires one of more rare-earth dopants, such as Er, Eu, Yb, Tm, Nd, Tb, Ce, Y, U, Pr, La, Gd and other rare-earth species or a combination thereof, doped into a dielectric crystal (of any size >0.1 nm), including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, where incident radiation is at longer wavelength than emissive radiation from the crystal. The wavelength emitted in based entirely on the dopant ion(s) chosen and their associated and relative concentration in the host crystal. For the example of upconversion in a $Y_2O_3$ host crystal, to achieve a blue emission (~450-480 nm) one could synthesize [$Y_2O_3$; Yb (3%), Tm (0.2%)], where the Yb and Tm are the percentages doped in the crystal relative to the Y atoms being 100%. Likewise, typical green upconversion materials are [$Y_2O_3$; Yb (5%), Ho (1%)] and [$Y_2O_3$; Yb (2%), Er (1%)], and typical red upconversion materials are [$Y_2O_3$; Yb (10%), Er (1%)] and [$Y_2O_3$; Yb (5%), Eu (1%)]. The concentrations of dopants relative to each other and the crystal matrix must be tuned for every combination, and there are multiple ways to achieve multiple colors from even the same dopants with or without the energy augmentators.

Up-conversion of red light with a wavelength of about 650 nm in $Tm^{3+}$ doped flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. The emission intensities of both bands have been observed by others to vary quadratically with the excitation power. For glasses with a $Tm^{3+}$ concentration of 0.2 mol % and greater, cross-relaxation processes occur which decrease the up-conversion efficiency.

The emission of visible light upon excitation in the near-infrared (NIR) has been observed in optically clear colloidal solutions of $LuPO_4:Yb^{3+}$, $Tm^{3+}$, and $YbPO_4:Er^{3+}$ nanocrystals in chloroform. Excitation at 975 nm has been shown by others to produce visible luminescence in the blue, green, or red spectral regions.

Tellurium and germanium oxides (tellurites and germinates) are also suitable upconverters. These glasses can be doped with Tm, Yb, Ho, Er, Pr, for example.

$Yb^{3+}$ doped $BaZrO_3$ is also suitable for upconversion. $Er^{3+}$ and/or $Tm^{3+}$ doping are also suitable for tailoring the emission wavelengths.

In another embodiment, $Nd^{3+}:Cs_2NaGdCl_6$ and $Nd^{3+}$, $Yb^{3+}:Cs_2NaGdCl_6$ polycrystalline powder samples prepared by Morss method have been reported to be up converters and are suitable for the present invention. These materials, under 785 nm irradiation, have shown upconversion emissions near 538 nm (Green), 603 nm (Orange), and 675 nm (Red) were observed and assigned to 4G7/2→4I9/2, (4G7/2→4I11/2; 4G5/2→4I9/2), and (4G7/2→4I13/2; 4G5/2→4I11/2), respectively.

In another embodiment, $Nd^{3+}$ and $Ho^{3+}$ co-doped-based $ZrF_4$ fluoride glasses under 800 nm excitation have been reported to be up converters and are suitable for the present invention. Among the up-conversion luminescences for the $ZrF_4$ fluoride glasses, the green emission was seen to be extremely strong and the blue and red emission intensities were very weak.

In another embodiment, $Tm^{3+}/Yb^{3+}$-codoped $TeO_2$—$Ga_2O_3$—$R_2O$ (R=Li, Na, K) glasses have been reported to be up converters and are suitable for the present invention. These materials, under excitation at 977 nm, showed intense blue upconversion emission centered at 476 nm along with a weak red emission at 650 nm.

In another embodiment, metal-to-ligand charge transfer (MLCT) transition in [Ru(dmb)$_3$]$^{2+}$(dmb=4,4'-dimethyl-2,2'-bipyridine) in the presence of anthracene or 9,10-diphenylanthracene have been reported converters and are suitable for the present invention. Upconverted to be up converters and are suitable for the present invention. Upconverted singlet fluorescence resulting from triplet-triplet annihilation at low excitation power has been reported. In particular 9,10-diphenylanthracene (DPA) (substituted for anthracene) showed higher efficiencies for upconversion. In these experiments, workers with this material system assumed that DPA's increased singlet fluorescence quantum yield (=0.95) relative to anthracene (=0.27)7. This work lead to an approximate 24.4±6.1 enhancement of green-to-blue light upconversion permitting direct visualization of the process at low excitation power, for example by a commercial green laser pointer ($\lambda_{ex}$=532 nm, <5 mW peak power).

The structures described herein for color enhancement with the energy augmentation structures are denoted as color enhancing/energy augmentation structures or as energy enhancing/augmentation structures.

By having the energy converters or color converting or enhancing materials disposed in a vicinity of the energy augmentation structures of this invention, regardless of the whether the energy augmentation structure is in a region of intensified electric field or otherwise outside the region of intensified electric field, the color enhancing/energy augmentation structures or the energy enhancing/augmentation structures of the invention are able to produce light which can be used for a variety of applications, in particular for photo-stimulation of biological, chemical, and physical reactions such as for example photoactivation of photoreactive drugs, photoactivation of photosensitive materials such as adhesives or lithographic photoresists, or for direct interaction with biological and chemical agents in the environment of the augmentation structures, as in sterilization.

Accordingly, in one embodiment of the invention, the color enhancement structures described herein can receive polychromatic light from a variety of sources such as sunlight, incandescent bulbs, fluorescent tube, and LED light sources with each having different wavelengths or wavelength bands. For these wavelength different bands, the resonators are "matched" or "tuned" to those wavelengths such that an intense electric field is established especially between the external-electrode pairs, or the folded resonator electrode pairs if used. In those regions of intense electric field can be disposed color converters (up and/or down phosphors) which can take light from one of the different wavelengths or wavelength bands, and have light of another wavelength or of different wavelength bands be emitted therefrom. In one embodiment, the intense electric field increases the intensity of the emitted light from the phosphors. Moreover, unlike the above-noted plasmonics where the electric field enhancement is restricted to regions within 100 to 200 nm of the metal, the resonators establish an increased electric field within the volume of the external-electrode pair, or the folded resonator electrode pairs if used, such that the phosphor material in a vicinity and within the external-electrode pair (or the folded resonator electrode pairs) exhibits an intensity larger than if the converter were remote from the resonator.

In view of the above, this invention is directed in general to methods and systems for color enhancement utilizing a color enhancement structure having a) an energy collector comprising at least one energy augmentation structure, and b) an energy converter capable of converting a second wavelength/quantum of electromagnetic energy into and emitting therefrom a third wavelength of light shifted in wavelength/energy from the second wavelength/quantum of electromagnetic energy. In one embodiment, the energy converter is disposed in a vicinity of the at least one energy augmentation structure such that the light shifted in wavelength is emitted with an intensity larger than if the converter were remote from the at least one energy augmentation structure. For ease of understanding, the term "wavelength" will be used to describe the electromagnetic energy entering into the energy converter, even though that electromagnetic energy may be better described in certain embodiments based upon its energy level or strength.

By having the energy converters or color converting or enhancing materials disposed in a vicinity of the energy augmentation structures of this invention, regardless of the whether the energy augmentation structure is in a region of intensified electric field or otherwise outside the region of intensified electric field, the color enhancing/augmentation structures or the energy enhancing/augmentation structures of the invention are able to enhance the conversion of one form of energy to another, as a conversion from one or more wavelengths of light to other wavelengths of light, or as a conversion from the one or more wavelengths of light to electrical energy, or as a conversion from the one or more wavelengths of light to heat.

Conversion from the one or more wavelengths of light to other wavelengths of light is useful for color shifting and color enhancement applications. Conversion from the one or more wavelengths of light to electrical energy is useful for harvesting solar energy using for example photovoltaic cells. Conversion from the one or more wavelengths of light to heat is useful also for harvesting solar energy using for example thermoelectric cells or other heat-to-electrical energy devices such as thermoelectric generators.

In some embodiments of the color enhancing/energy augmentation structures, the color enhancing structure includes a multi-dimensional light collector comprising a first level of metallic patterns and a second level of metallic patterns offset in at least one of a lateral or axial direction from the first level of metallic patterns. At least one of the metallic patterns optionally comprises a first resonator dimensioned to be resonant with a first wavelength of light. The first resonator can be one of a folded structure or an external-electrode pair structure as noted above. The color enhancement structure has a converter capable of converting a second wavelength of light into and emitting therefrom a third wavelength of light shifted in wavelength from the second wavelength of light. The converter is disposed with the first resonator such that the light shifted in wavelength is emitted with an intensity larger than if the converter were remote from the first resonator.

In some embodiments, the energy converter being disposed in a vicinity of the at least one energy augmentation structure is conductively coupled the energy converter to the at least one energy augmentation structure.

For example, in some embodiments, the energy converter being disposed in a vicinity of the at least one energy augmentation structure comprises a physical conductive connection between the energy converter and the at least one energy augmentation structure.

In some embodiments of the color enhancing/energy augmentation structures, the color enhancing structure, the energy converter comprises a down converter converting ultraviolet or blue light into red, yellow, or green light. In some embodiments of the color enhancing/augmentation structures, the energy converter comprises an up converter converting infrared or red light into yellow, green light, or blue light.

In some embodiments of the color enhancing/energy augmentation structures, the metallic patterns referenced above comprises a folded resonator having opposing electrodes with electric fields directed in between, and the converter is positioned between the opposing electrodes or within fringing electric field of the opposing electrodes or otherwise in a vicinity of the opposing electrodes. In one example, the folded resonator is a 3 folded resonator. In one example, metallic patterns comprise at least one of Au, Ag, Cu, Al, or transparent metal oxides. In another example, the metallic patterns can be formed with refractory metals such for example Ti, W, and Mo.

In some embodiments of the color enhancing/energy augmentation structures, the metallic patterns referenced above comprises an external external-electrode pair structure having opposing electrodes with electric fields directed in between, and the converter is positioned between the opposing electrodes or within fringing electric field of the opposing electrodes or otherwise in a vicinity of the opposing electrodes. In one example, the resonator is a 3 external-electrode pair resonator. In one example, metallic patterns comprise at least one of Au, Ag, Cu, Al, or transparent metal oxides. In another example, the metallic patterns can be formed with refractory metals such for example Ti, W, and Mo.

In some embodiments of the color enhancing/energy augmentation structures, the color enhancing structure, there is an antireflection film disposed on at least one of the metallic patterns or on the converter.

In some embodiments of the color enhancing/energy augmentation structures, the color enhancing structure, the first resonator noted above comprises plural resonators, the converter noted above comprises plural converters, and the plural converters are disposed at multiple positions throughout the light collector. In one example, the plural converters are positioned to convert light being internally scattered within the light collector.

In some embodiments of the color enhancing/energy augmentation structures, the first level of metallic patterns noted above (or the second level of metallic patterns) comprises a metal core cladded with a high-K dielectric and a subsequent cladding of a low-K dielectric. In some embodiments of the color enhancing/energy augmentation structures, the first level of metallic patterns noted above (or the second level of metallic patterns) comprises a radial pattern of conductors. In some embodiments of the color enhancing/energy augmentation structures, the first level of metallic patterns noted above (or the second level of metallic patterns) comprises a fractal pattern. In one example, the fractal pattern is embedded within a dielectric material.

In some embodiments of the color enhancing/energy augmentation structures, the first level of metallic patterns noted above (or the second level of metallic patterns) comprises a three-dimensional fractal structure.

In some embodiments of the color enhancing/energy augmentation structures, the light collector comprises a transparent panel with the first level of metallic patterns and the second level of metallic patterns and optionally multiple converters formed therein. In some embodiments of the color enhancing/augmentation structures, the light collector comprises a transparent sheet with the first level of metallic patterns and the second level of metallic patterns and optionally multiple converters formed therein.

In some embodiments of the color enhancing/energy augmentation structures, the first level of metallic patterns noted above (or the second level of metallic patterns) are of different sizes and/or orientations to each other of the first level of metallic patterns or with respect to the second level of metallic patterns.

Figure 29:
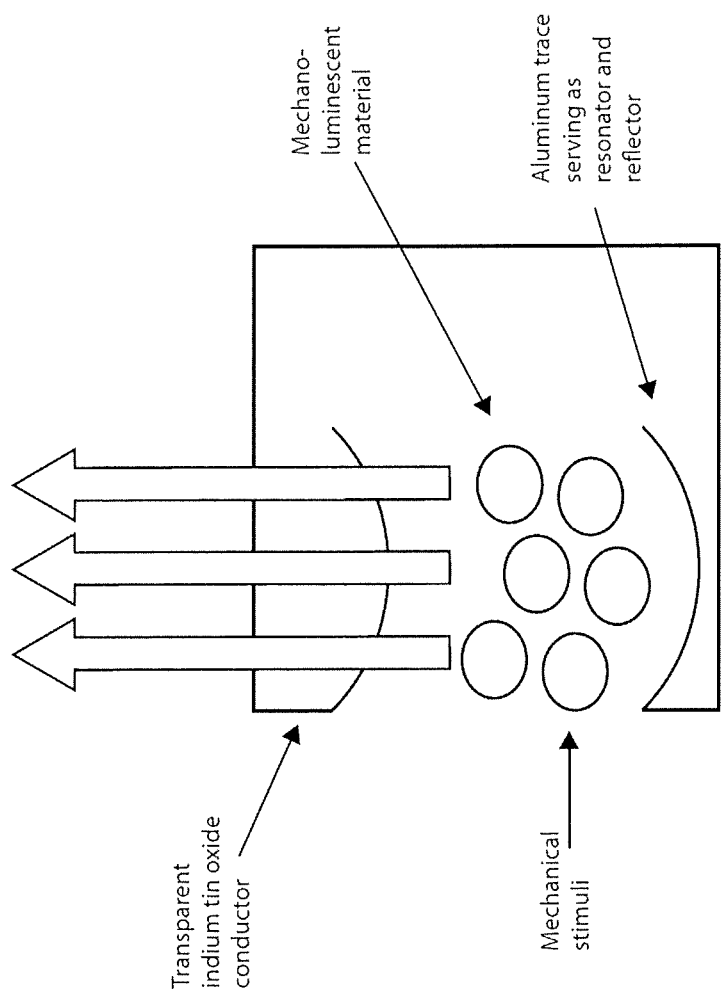
FIG. 29 is a diagram showing a mechanoluminescent emitter of the present invention.

Indeed, FIG. 29 is a schematic of a reflective resonator of this invention including mechano-luminescent materials, in this example the mechano-luminescent materials being placed between a folded resonator structure, although mechano-luminescent materials could be placed between an external electrode pair resonator structure. Thus, in one embodiment, an electromagnetic wave energy augmentator captures one or more wavelengths of electromagnetic energy, and augments the one or more wavelengths of electromagnetic energy in at least one property (such as electric field intensity in a vicinity of the mechano-luminescent materials), while at the same time the mechano-luminescent materials can be considered an energy converter converting the ultrasonic or mechanical energy into electromagnetic radiation (i.e., emitted light).

In one embodiment of the invention, the increased electric field in the folded structure or the external electrode pair increases the luminescence of the mechano-luminescent materials. The energy used to build the electric field in the folded structure or the external electrode pair being provided separately from the mechanical energy driving the mechano-luminescence.

For example, the reflective resonator of FIG. 29 could be placed adjacent an exhaust stack of an engine or other waste heat dissipating machine. In one embodiment, the reflective resonator of FIG. 29 would be mounted on a stainless steel arm connected to the heat stack. The stainless steel would couple mechanical vibrations to the reflective resonator while thermally isolating the reflective resonator from the exhaust stack, thereby permitting even inorganic mechano-luminescent materials to be used.

When the engine began to show higher levels of vibration or vibrations at different frequencies, the intensity of the light emitted would change providing a visible light signal that the engine or machine was under stress from power loads or wear or mechanical failure.

In one embodiment of the invention, the reflective structure shown in FIG. 29 need not include the resonator and its resonating elements. In one embodiment of the invention, the reflective structure shown in FIG. 29 could be placed directly on a machine operating at a relatively cold temperature around 100° C. In this embodiment, the reflective structure need not include the resonator and its resonating elements. However, if the resonator and its resonating elements were present, a laser such as 656 nm laser could "probe" the resonator and intensify "on demand" the mechano-luminescence. In this way, early detection of developing mechanical problems could be detected.

Various mechano-luminescent materials suitable for the present invention include $ZnS:Mn^{2+}$, $SrAl_2O_4:Eu^{2+}$, $ZnS:Cu$, $SrAMgSi_2O_7:Eu^{2+}$(A=Ca, Sr, Ba), KCl, KI, KBr, NaF, NaCl, LiF, RbCl, RbBr, RbI, MgO, $SrAl_2O_4$, $CaAl_2O_4$, $Sr_{1-x}Ba_xAl_2O_4$ (x=0, 0.1, 0.2, 0.4), $Sr_{0.9}Ca_{0.1}Al_2O_4$, $Zn_2Ge_{0.9}Si_{0.1}O_4$, $MgGa_2O_4$, $ZnGa_2O_4$, $ZnAl_2O_4$, ZnS, ZnTe, $(ZnS)_{1-x}(MnTe)_x$ (x<¼), CaZnOS, BaZnOS, $Ca_2MgSi_2O_7$, $Sr_2MgSi_2O_7$, $Ba_2MgSi_2O_7$, $SrCaMgSi_2O_7$, $SrBaMgSi_2O_7$, $Sr_nMgSi_2O_{5+n}$(1≤n≤2), $Ca_2Al_2SiO_7$, $Sr_2Al_2SiO_7$, $CaYAl_3O_7$, $CaAl_2Si_2O_8$, $Ca_{1-x}Sr_xAl_2Si_2O_8$ (x<0.8), $SrMg_2(PO_4)_2$, $Ba_{1-x}Ca_xTiO_3$ (0.25<x<0.8), $Ba_{1-x}Ca_xTiO_3$, $LiNbO_3$, $Sr_2SnO_4$, (Ca, Sr, Ba)$_2SnO_4$, $Sr_3Sn_2O_7$, $Sr_3(Sn, Si)_2O_7$, $Sr_3(Sn, Ge)_2O_7$, $Ca_3Ti_2O_7$, $CaNb_2O_6$, $Ca_2Nb_2O_7$, $Ca_3Nb_2O_8$, $BaSi_2O_2N_2$, $SrSi_2O_2N_2$, $CaZr(PO_4)_2$, $ZrO_2$.

Yanim Jia, in "Novel Mechano-Luminescent Sensors Based on Piezoelectric/Electroluminescent Composites," Sensors (Basel). 2011; 11(4): 3962-396, the entire contents of which are incorporated by reference, describes a mechano-luminescent composite made of a piezoelectric material and an electroluminescent material. In this composite device, when a stress is applied to the piezoelectric layer, electrical charges will be induced at both the top and bottom faces of piezoelectric layer due to the piezoelectric effect. These induced electrical charges will result in a light output from the electroluminescent layer due to the electroluminescent effect.

Here, in one embodiment of the present invention, such composites made of a piezoelectric material and an electroluminescent material, hereinafter "composite mechano-luminescent emitters," provides a structure that, upon stimulation with mechanical or vibrational energy such as from an acoustic or ultrasonic transducer, emit light. Details of various electroluminescent materials that can be used for the composite mechano-luminescent emitters are provided in the next section where electroluminescent materials alone are placed in vicinity of the opposing resonator electrodes.

Figure 30:
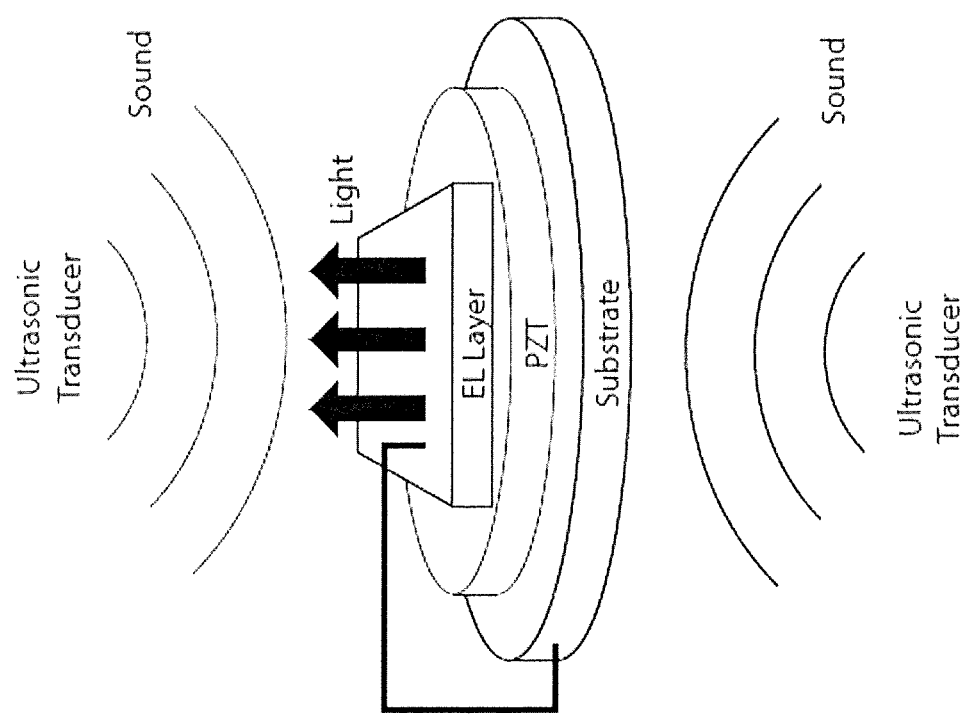
FIG. 30 is a diagram showing a composite piezoelectric/electroluminescent emitter of the present invention.

FIG. 30 is a schematic of composite mechano-luminescent emitter composed of a piezoelectric material and an electroluminescent material which, in one embodiment, could be mechano-luminescent light emitters in FIG. 29.

Figure 31:
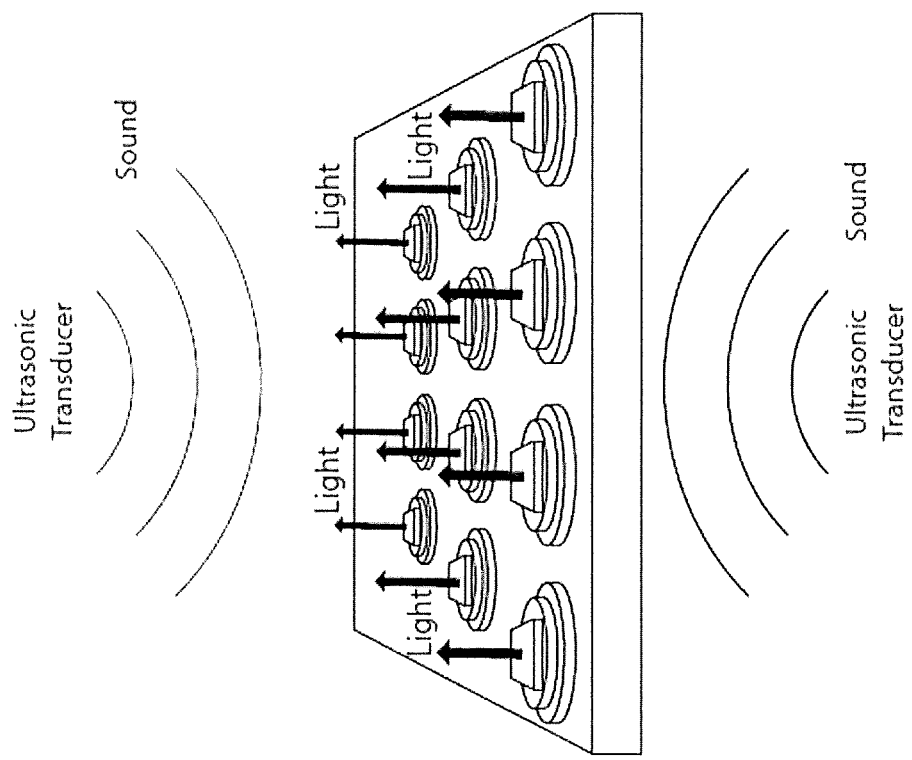
FIG. 31 is a diagram showing a distribution of the composite emitters of FIG. 30 across a surface for light emission.

In another embodiment, the composite mechano-luminescent emitters could be used without need for any resonator structure. FIG. 31 is schematic showing the composite mechano-luminescent emitters distributed across a sector of interest for generation of light therefrom. FIG. 31 shows that an ultrasonic transducer can be used for stimulation/activation of these composite mechano-luminescent emitters.

In color enhancement applications, application of ultrasonic energy could change the color emission from a surface. Such applications could be for security systems where an item would contain a pattern of the composite mechano-luminescent emitters. The pattern would not be apparent until it was activated with ultrasonic or acoustic energy upon which time light of a predetermined wavelength would be emitted. The light emitted might be visible or infrared light depending on the type of detector used to detect the emitted light.

Figure 32:
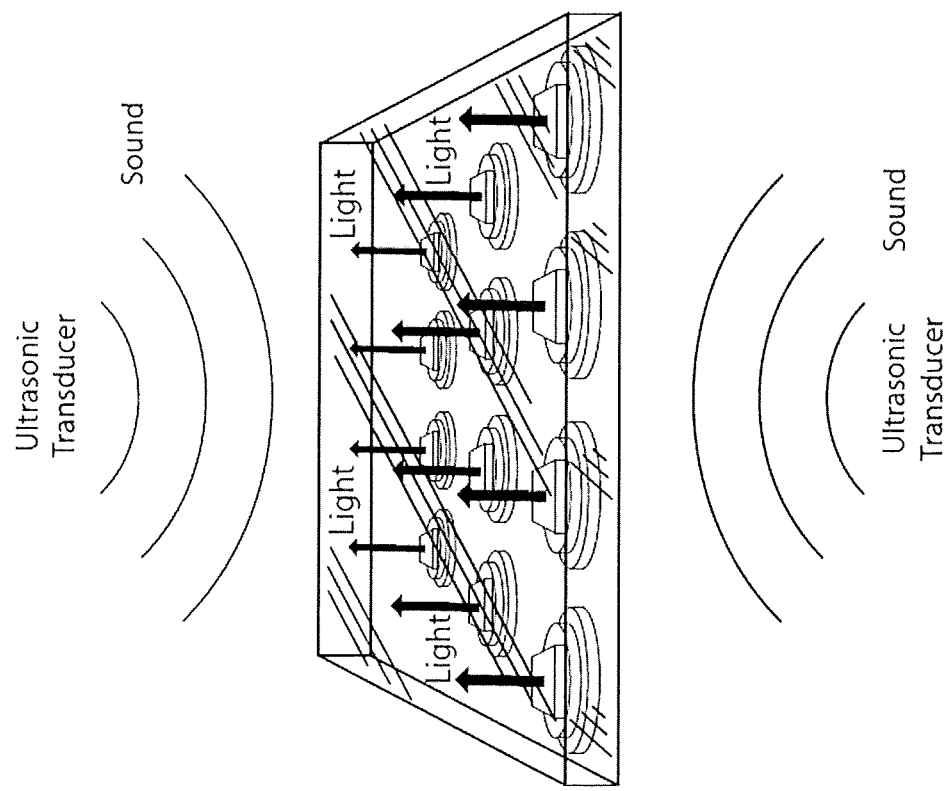
FIG. 32 is a diagram showing a distribution of the composite emitters of FIG. 30 within a target region for light emission.

In a related application of these composite mechano-luminescent emitters, FIG. 32 is schematic showing the composite mechano-luminescent emitters distributed inside a medium of interest for generation of light therein or therefrom. With the present invention, light can be turned on and off with the on/off status of an ultrasonic transducer and the intensity of the light can be varied. There are no power leads to run into the medium of interest. There is no space taken up by batteries or control elements to turn power on and off. The composite mechano-luminescent emitters can be miniaturized. The composite mechano-luminescent emitters could be agglomerated in a container. In some embodiments, the container would not be completely packed permitting the tilting of the container to relocate the composite mechano-luminescent emitters within the container.

Electroluminescent and phosphorescent materials (organic and inorganic): The present invention in various embodiments with or without energy augmentors can utilize in organic fluorescent molecules or inorganic particles capable or fluorescence and phosphorescence having crystalline, polycrystalline or amorphous micro-structures for the converters (optionally including the energy augmentation structures described above).

The list of inorganic molecules that can be used in the resonating structures to enhance the color emission include but is not limited to the following inorganic electroluminescent phosphor materials:

$SrS:Ce^{3+}$ $CaGa_2S_4:Ce^{3+}$ $SrS:Cu^+$ $CaS:Pb^{2+}$ $BaAl_2S_4:Eu^{2+}$ $ZnS:Tb^{3+}$ $ZnMgS:Mn^{2+}$ $SrGa_2S_4:Eu^{2+}$ $CaAl_2S_4:Eu^{2+}$ $BaAl_2S_4:Eu^{2+}$ $ZnS:Mn^{2+}$ $MgGa_2O_4:Eu^{3+}$ $(Ca, Sr)Y_2S_4:Eu^{2+}$ $BaAl_2S_4:Eu^{2+}$

The organic molecules that can phosphoresce under the influence of an electric field are also of interest in the present application. The organic fluorescent compounds with high quantum yield include by way of illustration:
  Naphthalene,
  Pyrene,
  Perlene,
  Anthracene,
  Phenanthrene,
  p-Terphenyl,
  p-Quartphenyl,
  Trans-stilbene,
  Tetraphenylbutadiene,
  Distyrylbenzene,
  2,5-Diphenyloxazole,
  4-Methyl-7-diethylaminocoumarin,
  2-Phenyl-5-(4-biphenyl)-1,3,4-oxadiazole,
  3-Phenylcarbostyryl,
  1,3,5-Triphenyl-2-pyrazoline,
  1,8-Naphthoylene-1',2'-bezimidazole,
  4-Amino-N-phenyl-naphthalimide.

The inorganic fluorescent and phosphorescent materials detailed here are numerous, and various examples are given by way of illustration rather than limitation. Furthermore, these materials can be doped with specific ions (activators or a combination of activators) that occupy a site in the lattice structure in the case of crystalline or polycrystalline materials and could occupy a network forming site or a bridging and/or non-bridging site in amorphous materials. These compounds could include (not ranked by order of preference or utility) the following material examples:

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$.

Further included are alkali earth chalcogenide phosphors which are in turn exemplified by the following non-inclusive list:

$MgS:Eu^{3+}$, $CaS:Mn^{2+}$, CaS:Cu, CaS:Sb, $CaS:Ce^{3+}$, CaS: $Eu^{2+}$, CaS: $Eu^{2+}Ce^{3+}$, CaS: $Sm^{3+}$, $CaS:Pb^{2+}$, $CaO:Mn^{2+}$, $CaO:Pb^{2+}$.

The examples include the ZnS type phosphors that encompass various derivatives:

ZnS:Cu,Al(Cl), ZnS:Cl(Al), ZnS:Cu,I(Cl), ZnS:Cu, ZnS:Cu,In.

Compound IIIb-Vb phosphors which include the group IIIb and Vb elements of the periodic table are suitable for converter materials. These semiconductors include BN, BP, BSb, AlN, AlP, AlAs, AlSb, GaN, GaP, GaAs, GaSb, InN, InP, InAs, InSb and these materials have donors and acceptors that work in together to induce light emission diodes. The donors include Li, Sn, Si, Li, Te, Se, S, O, and acceptors include C, Be, Mg, Zn, Cd, Si, Ge. As an example, GaP light emitting diodes include GaP:Zn, O, GaP:NN, Gap:N and GaP which emit colors Red, Yellow, Green and Pure Green respectively.

The compounded materials further include such materials as GaAs with compositional variation of the following sort: In1-y(Ga1-xAlx)yP (provides a simple example). Silicon Carbide SiC as a luminescent platform has commercial relevancy if the blue light emitting diodes. These include the polytypes 3C—SiC, 6H—SiC, 4H—SiC with donors such as N and Al and acceptors such as Ga and B.

Multiband luminescent materials suitable for converter materials include for example the following compositions: (Sr, Ca, Ba)$_5$(PO$_4$)$_3$Cl:Eu$^{2+}$, BaMg$_2$Al$_{16}$O$_{27}$:Eu$^{2+}$, CeMgAl$_{11}$O$_{19}$:Ce$^{3+}$:Tb$^{3+}$, LaPO$_4$:Ce$^{3+}$:Tb$^{3+}$, GdMgB$_5$O$_{10}$:Ce$^{3+}$:Tb$^{3+}$, Y$_2$O$_3$:Eu$^{3+}$, (Ba,Ca,Mg)$_5$(PO$_4$)$_3$Cl:Eu$^{2+}$, 2SrO$_{0.84}$P$_2$O$_5$.0.16B$_2$O$_3$:Eu$^{2+}$, Sr$_4$Al$_{14}$O$_{25}$:Eu$^{2+}$.

Other materials suitable for converter materials include those materials used for fluorescent high pressure mercury discharge lamps can be excited with X-Ray and are exemplified by way of family designation as follows:

Phosphates (Sr, MXPO$_4$)$_2$:Sn$^{2+}$, Mg or Zn activator, Germanate 4MgO.GeO$_2$:Mn$^{4+}$, 4(MgO, MgF$_2$)GeO$_2$:Mn$^{4+}$, Yttrate Y$_2$O$_3$:Eu$^{3+}$, Vanadate YVO$_4$:Eu$^{3+}$, Y(P,V)O$_4$:Eu$^{3+}$, Y(P,V)O$_4$:In$^+$, Halo-Silicate Sr2Si3O$_8$.2SrCl$_2$:Eu$^{2+}$, Aluminate (Ba,Mg)$_2$Al$_{16}$O$_{24}$:Eu$^{2+}$, (Ba, Mg)$_2$Al$_{16}$O$_{24}$:Eu$^{2+}$,Mn$^{2+}$, Y$_2$O$_3$Al$_2$O$_3$:Tb$^{3+}$.

Another grouping of materials suitable for converter materials by host compound include chemical compositions in the Halophosphates phosphors, Phosphate phosphors, Silicate phosphors, Aluminate phosphors, Borate phosphors, Tungstate phosphors, and other phosphors.

The halophosphates include by way of illustration:
3Ca$_3$(PO$_4$)$_2$.Ca(F,Cl)$_2$:Sb$^{3+}$, 3Ca$_3$(PO$_4$)$_2$.Ca(F,Cl)$_2$:Sb$^{3+}$/Mn$^{2+}$, Sr$_{10}$(PO$_4$)$_6$Cl$_2$:Eu$^2$, (Sr,Ca)$_{10}$(PO$_4$)$_6$Cl$_2$:Eu$^{2+}$, (Sr, Ca)$_{10}$(PO$_4$)$_6$.nB$_2$O$_3$:Eu$^{3+}$, (Sr, Ca,Mg)$_{11}$(PO$_4$)$_6$Cl$_2$:Eu$^{2+}$.

The phosphate phosphors include by way of illustration $Sr_2P_2O_7:Sn^{2+}$, $(Sr,Mg)_3(PO_4)_2:Sn^{2+}$, $Ca_3(PO_4)_2.Sn^{2+}$, $Ca_3(PO_4)_2:Tl^+$, $(Ca,Zn)_3(PO_4)_2:Tl^+$, $Sr_2P_2O_7:Eu^{2+}$, $SrMgP_2O_7:Eu^{2+}$, $Sr_3(PO_4)_2:Eu^{2+}$, $LaPO_4:Ce^{3+}$, $Tb^{3+}$, $La_2O_3.0.2SiO_2.0.9P_2O_5:Ce^{3+}.Tb^{3+}$, $BaO.TiO_2P_2O_5$. The silicate phosphors $Zn_2SiO_4:Mn^{2+}$, $CaSiO_3:Pb^{2+}/Mn^{2+}$, $(Ba, Sr, Mg)_3Si_2O_7:Pb^{2+}$, $BaSi_2O_5:Pb^{2+}$, $Sr_2Si_3O_8.2SrCl_2:Eu^{2+}$, $Ba_3MgSi_2O_8:Eu^{2+}$, $(Sr,Ba)Al_2Si_2O_8:Eu^{2+}$.

The aluminate phosphors include:
$LiAlO_2:Fe^{3+}$, $BaAl_8O_{13}:Eu^{2+}$, $BaMg_2Al_{16}O_{27}:Eu^{2+}$, $BaMg_2Al_{16}O_{27}.Eu^{2+}/Mn^{2+}$, $Sr_4Al_{14}O_{25}:Eu^{2+}$, $CeMgAl_{11}O_{19}:Ce_{3+}/Tb^{3+}$.

The borate phosphors include:
$Cd_2B_2O_5:Mn^{2+}$, $SrB_4O_7F:Eu^{2+}$, $GdMgB_5O_{10}:Ce^{3+}/Tb^{3+}$, $GdMgB_5O_{10}:Ce^{3+}/Mn^{3+}$, $GdMgB_5O_{10}:Ce^{3+}/Tb^{3+}/Mn^{2+}$.

The tungstate phosphors include:
$CaWO_4$, $(Ca,Pb)WO_4$, $MgWO_4$. Other phosphors $Y_2O_3:Eu^{3+}$, $Y(V,P)O_4:Eu^{2+}$, $YVO_4:Dy^{3+}$, $MgGa_2O_4:Mn^{2+}$, $6MgO.As_2O_5:Mn^{2+}$, $3.5MgO.0.5MgF_2GeO_2:Mn^{4+}$.

Activators of relevance to the various doped phosphors include the following list:
$Tl^+$, $Pb^{2+}$, $Ce^{3+}$, $Eu^{2+}$, $WO_4^{2-}$, $Sn^{2+}$, $Sb^{3+}$, $Mn^{2+}$, $Tb^{3+}$, $Eu^{3+}$, $Mn^{4+}$, $Fe^{3+}$.

In various embodiments, the luminescence center Tl+ can be used with a chemical composition such as:
$(Ca,Zn)_3(PO_4)_2:Tl^+$, $Ca_3(PO_4)_2:Tl^+$.

Similarly, the luminescence center $Mn^{2+}$ can be used with chemical compositions such as
$MgGa_2O_4:Mn^{2+}$, $BaMg_2Al_{16}O_{27}:Eu^{2+}/Mn^{2+}$, $Zn_2SiO_4:Mn^{2+}$, $3Ca_3(PO_4)_2.Ca(F,Cl)_2:Sb^{2+}/Mn^{2+}$, $CaSiO_3:Pb^{2+}/Mn^{2+}$, $Cd_2B_2O_5:Mn^{2+}$, $CdB_2O_5:Mn^{2+}$, $GdMgB_5O_{10}:Ce^{3+}/Mn^{2+}$, $GdMgB_5O_{11}:Ce^{3+}/Tb^{3+}/Mn^{2+}$.

Further, the luminescence center $Sn^{2+}$ can be used with chemical compositions such as:
$Sr_2P_2O_7:Sn^{2+}$, $(Sr,Mg)_3(PO_4)_2:Sn^{2+}$.

The luminescence center $Eu^{2+}$ can also be used with chemical compositions such as:
$SrB_4O_7F:Eu^{2+}$, $(Sr,Ba)Al_2Si_2O_8:Eu^{2+}$, $Sr_3(PO_4)_2:Eu^{2+}$, $Sr_2P_2O_7:Eu^{2+}$, $Ba_3MgSi_2O_8:Eu^{2+}$, $Sr_{10}(PO_4)_6Cl_2:Eu^{2+}$, $BaMg_2Al_{16}O_{27}:Eu^{2+}/Mn^{2+}$, $(Sr,Ca)_{10}(PO_4)_6Cl_2:Eu^{2+}$.

The luminescence center $Pb^{2+}$ can be used with chemical compositions such as:
$(Ba,Mg,Zn)_3Si_2O_7:Pb^{2+}$, $BaSi_2O_5:Pb^{2+}$, $(Ba,Sr)_3Si_2O_7:Pb^{2+}$.

The luminescence center $Sb^{2+}$ can be used with chemical compositions such as:
$3Ca_3(PO_4)_2.Ca(F,Cl)_2:Sb^{3+}$, $3Ca_3(PO_4)_2Ca(F,Cl)_2:Sb^{3+}/Mn^{2+}$.

The luminescence center Tb3+ can be used with chemical compositions such as:
$CeMgAl_{11}O_{19}:Ce^{3+}/Tb^{3+}$, $LaPO_4:Ce^{3+}/Tb^{3+}$, $Y_2SiO_5:Ce^{3+}/Tb^{3+}$, $GdMgB_5O_{10}:Ce^{3+}/Tb^{3+}$.

The luminescence center $Eu^{3+}$ can be used with chemical compositions such as:
$Y_2O_3:Eu^{3+}$, $Y(V,P)O_4:Eu^{3+}$.

The luminescence center $Dy^{3+}$ can be used with chemical compositions such as:
$YVO_4:Dy^{3+}$.

The luminescence center $Fe^{3+}$ can be used with chemical compositions such as:
$LiAlO_2: Fe^{3+}$.

The luminescence center $Mn^{4+}$ can be used with chemical compositions such as:
$6MgO.As_2O_5:Mn^{4+}$, $3.5MgO.0.5MgF_2.GeO_2:Mn^{4+}$.

The luminescence center $Ce^{3+}$ can be used with chemical compositions such as:
$Ca_2MgSi_2O_7:Ce^{3+}$ and $Y_2SiO_5:Ce^{3+}$.

The luminescence center $WO_4^{2-}$ can be used with chemical compositions such as:
$CaWO_4$, $(Ca,Pb)WO_4$, $MgWO_4$.

The luminescence center $TiO_4^{4-}$ can be used with chemical compositions such as:
$BaO.TiO_2.P_2O_5$.

In various embodiments of this invention, the phosphor chemistry utilized in X-Ray excitations can be used. Of particular interest is the k-edge of these phosphors. Low energy excitation can lead to intense luminescence in materials with low k-edge. Some of these chemistries and the corresponding k-edge are included as follows:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4:Nb$ | 67.42 keV |
| $ZnS:Ag$ | 9.66 keV |
| $(Zn,Cd)S:Ag$ | 9.66/26.7 keV |

In one embodiment of this invention, light from these materials (excited for example by high energy particles including x-rays, gamma rays, protons, and electrons) can have their emissions modulated by having those materials included in a vicinity of (including inside) the color enhancing structures described herein. For example, in medical treatments where x-ray excites phosphorescence to photo-stimulate reactions in a patient, simultaneous with irradiation by the high energy particles there could be applied infrared irradiation to drive resonance in the color enhancing structures/energy augmentation structures described herein, where the x-ray phosphors would have enhanced emissions when in the presence of the intensified electric fields. In another example, in medical or scientific instruments, simultaneous with irradiation by the high energy particles there could be applied electric fields to enhance emissions from these x-ray phosphors.

Adhesives

In one embodiment of this invention, a class of curable adhesives is utilized by the present invention in combination with an adhesion promoter or an adhesion promoting treatment with or without the energy augmentors. This class of adhesives has one or more of the following desirable attributes:

a—Cure without line of sight (bond line where the adhesion takes place is internal to structures to be bonded)

b—Cure without depth of penetration limitation (Bond line can be deep inside materials without compromising the cure kinetics)

c—Cure without thermal expansion mismatch (ability to bond at room temp and to avoid compressive and tensile stresses at the bond line)

d—Cure adhesive selectively (only where the adhesive has an energy converting particle does the adhesive form a network; this can be used to generate selective curing geometries)

e—The adhesives have suitable Properties (electrical—including dielectric non-conductive to anisotropically semiconductive to conductive, mechanical—rigidity or compliancy (use of a second phase flexibilizer), optical—from transparent to opaque, Acid vs. Base Control—ability to withstand a variety of environments from Inks to aqueous solutions, Adhesive Bond strength of a desirable range)

These attributes make it possible to achieve certain adhesive curing applications which were not previously attainable, as well as improve on already existing adhesive curing applications. The present invention adhesive curing leads to novel assemblies and processing methods that are advantageous compared to the state of the art.

In one embodiment, the present invention provides a way with or without the energy augmentators to bond materials at ambient temperature using photoinitiator chemistries that convert absorbed light energy (typically UV light) to chemical energy in the form of initiating species such as free radicals or cations and thereby initiate a polymerization reaction in a monomer-containing adhesive. In another aspect, the invention provides a way to perform photoinitiation in situations where the area to be bonded is not accessible to an external light source.

According to one embodiment of the invention, the adhesive composition comprises: an organic vehicle comprising at least one polymerizable monomer; at least one photoinitiator responsive to a selected wavelength of light; at least one energy converting material selected to emit the selected wavelength of light when exposed to a selected imparted radiation; and optionally the energy augmentators.

According to another aspect of the invention, the method of adhesive bonding comprises the steps of: a) placing a polymerizable adhesive composition with or without the energy augmentators, including at least one photoinitiator and at least one energy converting material, in contact with two or more components to be bonded to form an assembly; and, b) irradiating the assembly with radiation at a first wavelength, capable of conversion by the at least one energy converting material, preferably a down converting material such as a phosphor, to a second wavelength capable of activating the at least one photoinitiator.

According to yet another aspect of the invention, the method of adhesive bonding comprises the steps of: a) attaching the at least one photoinitiator and at least one energy converting material with one another using such methods as adsorption or chemical bonding through a tether and then mixing the chemistry hence formed into the mix with a resin with or without the energy augmentators.

According to a further embodiment of the invention, a method for creating joints and establishing adhesion between two different substrates comprises using an adhesive system with or without the energy augmentators that in turn contains a plurality of synthetic polymeric chains and at least one photoinitiator that is a photoactive cross-linking agent. In this case the role of the at least one photoinitiator as a photo-active cross-linking agent is to link one polymer chain to another by forming bonds that can be covalent or ionic in nature. In this case the initial viscous material is transformed to a solid material through the formation of a 3D network structure achieved by creating links between pre-existing chains in a resin system. Such cross-linking can be applicable to both synthetic polymers (for adhesives) and to natural polymers (such as protein or DNA).

The inventive material of one embodiment of the present invention with or without the energy augmentators comprises two primary components: first, a monomer composition including at least one photoinitiator; and second, at least one energy converting material capable of absorbing an imparted energy and converting the energy to produce photons in a spectral range that can be absorbed by the at least one photoinitiator, and thus initiate polymerization of the monomer composition. Preferably, the energy converting material is a downconverting material capable of absorbing higher-energy photons (typically X-rays) and down-converting to produce lower-energy photons (typically UV, but also visible light) in a spectral range that can be absorbed effectively by the photoinitiator. Optional components include, without limitation: organic and inorganic fillers such as oxides, dielectrics, conductors, fibers, etc.; plasticizers; pore-formers; and other physical additives.

In an alternative embodiment, the curable adhesive composition with or without the energy augmentators comprises a plurality of cross-linkable polymer chains rather than the polymerizable monomer. In this embodiment, the photoinitiator is one that is capable, upon activation, of creating crosslinks between the cross-linkable polymer chains to form a 3D polymer network, thus curing the adhesive composition by crosslinking. While many of the embodiments below are described based upon the embodiment using a curable adhesive composition comprising polymerizable monomer, this description is merely for convenience and use of the curable adhesive composition comprising the plurality of cross-linkable polymer chains can be equally substituted in the described embodiments.

In the present invention, the energy converting material can be any material that can convert the imparted energy either into higher energy photons ("upconverting material") or into lower energy photons ("downconverting material"). Suitable upconverting materials and downconverting materials are described in U.S. provisional patent application 61/161,328, filed Mar. 18, 2009; U.S. provisional patent application 61/259,940, filed Nov. 10, 2009; U.S. Provisional Application Ser. Nos. 60/954,263, filed Aug. 6, 2007, and 61/030,437, filed Feb. 21, 2008; U.S. application Ser. No. 12/059,484, filed Mar. 31, 2008; U.S. application Ser. No. 11/935,655, filed Nov. 6, 2007; U.S. Provisional Application Ser. Nos. 61/042,561, filed Apr. 4, 2008; 61/035,559, filed Mar. 11, 2008; and 61/080,140, filed Jul. 11, 2008; U.S. patent application Ser. No. 12/401,478 filed Mar. 10, 2009; U.S. patent application Ser. No. 11/935,655, filed Nov. 6, 2007; U.S. patent application Ser. No. 12/059,484, filed Mar. 31, 2008; U.S. patent application Ser. No. 12/389,946, filed Feb. 20, 2009; and U.S. patent application Ser. No. 12/417,779, filed Apr. 3, 2009, the entire disclosures of each of which are hereby incorporated by reference. The imparted energy can be any desired energy as needed to penetrate the material between the imparted energy source and the adhesive composition itself. For example, the imparted energy can be near-infrared (NIR), with an upconverting material to convert the imparted energy into UV photons that can be absorbed by the photoinitiator used. Preferably, the imparted energy is X-ray energy, with the energy converting material being a downconverting material, such as a phosphor or scintillator. For convenience, the following discussion will refer to downconverting materials and the use of X-rays as the imparted energy. However, this is not intended to be limiting of the present invention and any desired combination of imparted energy and energy converting material can be used, so long as the photons generated by the energy converting material are capable of being absorbed by the photoinitiator. Suitable energy converters for adhesive processing are also described in the section of this application entitled B. ENERGY CONVERTERS. Moreover, the plasma capsules described elsewhere can be used as energy converters and light emitters. Of particular note also are the x-ray induced persistent phosphors, the mechano-luminescent devices, and the piezoluminescent materials. Furthermore, adhesive processing may occur by exposure of the curable adhesive medium directly to x-rays or via an x-ray fluorescent material emitting lower energy x-rays after being exposed to higher energy x-rays.

In one embodiment, the energy augmentators could be added into the curable adhesive composition as a perforated sheet containing the energy augmentators, such as shown above in FIG. 7B. The curable adhesive composition with or without energy converters could then be pressed onto and into the perforations.

In one embodiment, the energy augmentators (as discrete pieces shown in FIG. 7C) could be added to the curable adhesive composition.

The associated method comprises two essential steps: a) placing a polymerizable adhesive composition with or without the energy augmentators, including a photoinitiator and down-converting material, in contact with two or more components to be bonded to form an assembly; and, b) irradiating the assembly with radiation at a first wavelength, capable of down-conversion by the phosphor to a second wavelength capable of activating the photoinitiator. Optional steps include, without limitation: dispensing the adhesive in a selected pattern through a needle or screen printing the adhesive through a mask having a selected pattern; photo-patterning the adhesive; pre-forming the adhesive into a sheet having isotropic or anisotropic conductivity; and applying pressure to the adhesive bond during the curing process.

The dispensing of the adhesive and the adhesive properties can preferably be adjusted to meet the following:

The dispensing can be performed using any conventional dispensing system, including, but not limited to, dispensing using piston or auger pumps, spin coating, spray coating, or screen printing.

The adhesive can contain a tracer element for inspection, if desired.

The adhesive can contain a pigment for optical inspection, if desired.

The adhesive can be made to change color after curing, if desired.

For reference purposes, listed below are generally accepted approximate wavelength, frequency, and energy limits of the various regions of the electromagnetic spectrum:

|  | Wavelength (m) | Frequency (Hz) | Energy (J) |
| --- | --- | --- | --- |
| Radio | $>1 \times 10^{-1}$ | $<3 \times 10^{9}$ | $<2 \times 10^{-24}$ |
| Microwave | $1 \times 10^{-3} - 1 \times 10^{-1}$ | $3 \times 10^{9} - 3 \times 10^{11}$ | $2 \times 10^{-24} - 2 \times 10^{-22}$ |
| Infrared | $7 \times 10^{-7} - 1 \times 10^{-3}$ | $3 \times 10^{11} - 4 \times 10^{14}$ | $2 \times 10^{-22} - 3 \times 10^{-19}$ |
| Optical | $4 \times 10^{-7} - 7 \times 10^{-7}$ | $4 \times 10^{14} - 7.5 \times 10^{14}$ | $3 \times 10^{-19} - 5 \times 10^{-19}$ |
| UV | $1 \times 10^{-8} - 4 \times 10^{-7}$ | $7.5 \times 10^{14} - 3 \times 10^{16}$ | $5 \times 10^{-19} - 2 \times 10^{-17}$ |
| X-ray | $1 \times 10^{-11} - 1 \times 10^{-8}$ | $3 \times 10^{16} - 3 \times 10^{19}$ | $2 \times 10^{-17} - 2 \times 10^{-14}$ |
| Gamma-ray | $<1 \times 10^{-11}$ | $>3 \times 10^{19}$ | $>2 \times 10^{-14}$ |

One issue associated with the bonding of two substrates together is that, while the photo initiated curing can partially or completely cure the polymerizable adhesive composition, the adhesions of those materials to the respective substrates being bonded together requires additional selection of structures or materials which have the capacity to bond to either substrate.

According one embodiment of the invention, the method of adhesive bonding comprises the steps of: a) treating a surface of an element to be bonded to provide an adherent structure on said surface; b) placing a polymerizable adhesive composition with or without the energy augmentators, including at least one photoinitiator and at least one energy converting material, in contact with the adherent structure and two or more components to be bonded to form an assembly; c) irradiating the assembly with radiation at a first wavelength, capable of conversion by the at least one energy converting material, preferably a down converting material such as a phosphor, to a second wavelength capable of activating the at least one photoinitiator to produce from the polymerizable adhesive composition a cured adhesive composition; and d) adhesively joining the two or more components by way of the adherent structure and the cured adhesive composition. With the energy augmentators present, this invention can generate local regions of intense electric fields to enhance light emission from the energy converters in proximity to those local regions generating the light within the polymerizable adhesive composition to be cured.

In one embodiment, the adhesive composition includes curable polymer system comprising an adherent structure attached to a low energy surface of an element to be bonded (the surface having a surface energy less than 50 mJ/m$^2$), at least one polymerizable adhesive composition with or without the energy augmentators for adhesive attachment to the adherent structure, at least one photoinitiator responsive to a selected wavelength of light, and at least one energy converting material selected to emit the wavelength of light when exposed to an imparted radiation.

In one embodiment, the adhesive composition includes an adhesive transfer member comprising a release substrate, one or more rubber compounds disposed on a surface of the release element, and an energy converting material with or without the energy augmentators intermixed with said one or rubber compounds in the surface of the release element.

The methods and systems described herein as part of the invention permit the at least one energy converting material to be either a downconverting material, and upconverting material or a combination of thereof to process curable adhesive materials. In one aspect of the invention, the downconverting material can comprise inorganic particulates selected from the group consisting of: metal oxides; metal sulfides; doped metal oxides; and mixed metal chalcogenides. In one aspect of the invention, the downconverting material can comprise at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS; ZnSe; MgS; CaS and alkali lead silicate including compositions of $SiO_2$, $B_2O_3$, $Na_2O$, $K_2O$, PbO, MgO, or Ag, and combinations or alloys or layers thereof. In one aspect of the invention, the downconverting material can include a dopant including at least one of Er, Eu, Yb, Tm, Nd, Mn Tb, Ce, Y, U, Pr, La, Gd and other rare-earth species or a combination thereof. The dopant can be included at a concentration of 0.01%-50% by mol concentration.

In one aspect of the invention, the downconverting material can comprise materials such as ZnSeS:Cu, Ag, Ce, Tb; CaS: Ce,Sm; $La_2O_2S$:Tb; $Y_2O_2S$:Tb; $Gd_2O_2S$:Pr, Ce, F; $LaPO_4$. In other aspects of the invention, the downconverting material can comprise phosphors such as ZnS:Ag and ZnS:Cu, Pb. In other aspects of the invention, the downconverting material can be alloys of the ZnSeS family doped with other metals. For example, suitable materials include $ZnSe_xS_y$:Cu, Ag, Ce, Tb, where the following x, y values and intermediate values are acceptable: x:y; respectively 0:1; 0.1:0.9; 0.2:0.8; 0.3:0.7; 0.4:0.6; 0.5:0.5; 0.6:0.4; 0.7:0.3; 0.8:0.2; 0.9:0.1; and 1.0:0.0.

In other aspects of the invention, the downconverting material can be materials such as sodium yttrium fluoride (NaYF$_4$), lanthanum fluoride (LaF$_3$), lanthanum oxysulfide (La$_2$O$_2$S), yttrium oxysulfide (Y$_2$O$_2$S), yttrium fluoride (YF$_3$), yttrium gallate, yttrium aluminum garnet (YAG), gadolinium fluoride (GdF$_3$), barium yttrium fluoride (BaYF$_5$, BaY$_2$F$_8$), gadolinium oxysulfide (Gd$_2$O$_2$S), calcium tungstate (CaWO$_4$), yttrium oxide:terbium (Yt$_2$O$_3$Tb), gadolinium oxysulphide:europium (Gd$_2$O$_2$S:Eu), lanthanum oxysulphide:europium (La$_2$O$_2$S:Eu), and gadolinium oxysulphide:promethium, cerium, fluorine (Gd$_2$O$_2$S:Pr,Ce, F), YPO$_4$:Nd, LaPO$_4$:Pr, (Ca,Mg)SO$_4$:Pb, YBO$_3$:Pr, Y$_2$SiO$_5$:Pr, Y$_2$Si$_2$O$_7$:Pr, SrLi$_2$SiO$_4$:Pr,Na, and CaLi$_2$SiO$_4$: Pr.

In these methods and systems, the wavelength of radiation capable of energy conversion by the at least one energy converting material can be at least one of X-rays, electron beams, deep UV light (e.g., 160-400 nm for down conversion). In these methods and systems to process curable adhesive materials with or without the energy augmentators, the wavelength of radiation capable of conversion by the at least one energy converting material can be near infrared (e.g., for up conversion).

In these methods and systems to process curable adhesive materials with or without the energy augmentators, down converting and/or upconverting materials (such as those described herein) can be included in an organic vehicle which is cured by activation of a photoinitiator contained therein or by vulcanization of a sulfur containing compound therein.

In these methods and systems, the organic vehicle (e.g., a polymerizable adhesive composition with or without the energy augmentators) can comprise a monomer forming a thermoset resin. The thermoset resin can be selected from the group consisting of: acrylics, phenolics, urethanes, epoxies, styrenes, and silicones. In these methods and systems, the at least one photoinitiator can be selected from the group consisting of: benzoin ethers, benzil ketals, α-dialkoxyacetophenones, α-aminoalkylphenones, acylphosphine oxides, benzophenones/amines, thioxanthones/amines, and titanocenes. In these methods and systems, the polymerizable adhesive composition further comprises inorganic particulates selected from the group consisting of: metals and metal alloys, ceramics and dielectrics, and metal-coated polymers. The polymerizable adhesive composition can further comprise an organic component selected from the group consisting of: solvents, viscosity modifiers, surfactants, dispersants, and plasticizers.

In these methods and systems, the adherent structure can be provided by way of a solution containing natural or synthetic rubber (i.e., rubber-like) compounds which are disposed on the surface of an element to be bonded, the solvent can be removed (e.g., by evaporation), and the rubber compounds can be polymerized.

Natural Rubber, Isoprene and PolyIsoprene:

Natural rubber has a long fatigue life and high strength even without reinforcing fillers. It can be used to approximately 100° C., and sometimes above. It can maintain flexibility down to −60° C. if compounded for the purpose. It has suitable creep and stress relaxation resistance and is low cost.

Furthermore, natural rubber as utilized in various embodiments of this invention includes milled grades of the natural rubber. Natural rubber as shown above can be a naturally-occurring polyisoprene elastomer recovered from the sap of rubber trees (*Hevea brasiliensis*) and certain other trees and plants. Natural rubber as a commodity can generally be supplied in solid form or as alkali-stabilized latex.

In one embodiment of this invention, the "rubber-like" compounds can include isoprene. Isoprene can be derived from many plants. Isoprene, or 2-methyl-1,3-butadiene, is a common organic compound used across a wide range of industrial applications and can be found with the following formula CH$_2$=C(CH$_3$)CH=CH$_2$. Isoprene has the advantage of being a colorless volatile liquid and therefore can be blended with various other compounds that are compatible with its miscibility characteristics.

An example of polyisoprene is shown below, where a poly cis-1,4 isoprene is shown as the building block of a longer chain.

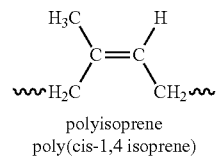

polyisoprene
poly(cis-1,4 isoprene)

Once the longer chain is crosslinked, the crosslinked material develops elastomeric properties. The elongation of the material depends on the number of crosslinks that are imparted to form the network. When under a tensile stress, the networked material can stretched. When the stress is removed, the material fully recovers (as long as it has been stressed below its non-elastic deformation threshold).

For solvent-based adhesives or primers utilized in various embodiments of this invention, the solid natural rubber is usually masticated on a two-roll mill prior to being dissolved in hydrocarbon solvents. Although it is possible to prepare solutions of unmilled natural rubber, milling reduces gels, thereby affecting viscosity, stability, uniformity and speed of dissolving. Solvents such as toluene can and have been used to dissolve the natural rubber compounds into a mixture that which can be applied to the surfaces of substrate a and substrate b.

Natural rubber can be utilized in various embodiments of this invention with or without the energy augmentators where the natural rubber bonds are cross-linked by the assistance of ultraviolet light generated from at least one or more of down converting or up converting materials (such as the ones described above). The natural rubber formulations in the present invention (prior to inclusion of energy converters or energy augmentators) then follows, for example, conventional formulations and preparations such as those described in "UV-curable natural rubbers such as those described in "Ultraviolet curing of acrylated liquid natural rubber for surface coating application," Songklanakarin J. Sci. Technol. 31 (1), 49-55, January-February 2009, the entire contents of which are incorporated herein by reference.

Accordingly, in one aspect of the present invention, ultraviolet light generated from at least one or more of down converting or up converting materials (such as the ones described above with or without the energy augmentators) can be used to cross-link the following liquid natural rubber (LNR) samples:

1) The liquid natural rubber (LNR) obtained by degradation of 20% DRC natural rubber latex with hydrogen peroxide of 0.5 phr and cobalt acetylacetonate of 1 phr by means of mechanical stirrer in a round bottom flask at 65° C. for 72 hrs. LNR was precipitated in methanol and then dried in a hot oven at 40° C.

2) Epoxidized liquid natural rubber (ELNR) obtained from 10% w/v LNR in toluene. Formic acid and hydrogen peroxide in ratio of 30:60 (mol % with respect to isoprene unit) added drop wise and stirred at 50° C. for 2 hrs. ELNR was then washed in 5.0% $NaHCO_3$ solution, precipitated in methanol and dried at 40° C.

In one aspect of the present invention, ultraviolet light generated from at least one or more of down converting or up converting materials with or without the energy augmentators (such as the ones described above) cross links a rubber prepared from the liquid natural rubber compounds noted above, and/or other liquid natural rubber compounds. For example, the ultraviolet light generated from at least one or more of down converting or up converting materials (such as the ones described above) can serve to cross link a surface coating material obtained by the mixing of LNR with 80 phr tripropylene glycol diacrylate and 10 phr Irgacure 651.

Moreover, in one embodiment, natural and synthetic rubber compounds with or without the energy augmentators can be directly activated by x-ray flux to bond and be used as the interface material between the respective substrates and the cured polymers. Such natural and synthetic rubber compounds can be prepared in a fine powder form, applied to the surfaces, and then exposed to x-ray energy for example energy at 320 kVp, 160 kVp or 106 kVp. Higher or lower KVp energies can be used in various embodiments of the invention. In one embodiment of the invention, MVp energies are used to penetrate more deeply into the object being cured. In one embodiment of the invention, 10-100 kVp energies are used where the object being cured is on a surface of an article or relatively close to the surface or inside of a low mass number material such as a plastic. In general, the selection of the kVp will depend on a number of factors including the geometry and construction of the material being cured, the x-ray dose, and the rate of production desired. Higher kVp sources could be used for deep penetration, and an x-ray fluorescing substance such as iodine-containing compounds can be used in the rubber article to be cured to convert the higher kVp x-rays to softer energies such as 28.5 KeV ad 3.78-5.18 KeV. Indeed, almost all elements have characteristic x-ray fluorescent lines, and by selecting an element for preferably heavier than carbon, oxygen, nitrogen, and the other elements in the adhesives, the incident higher energy x-rays will be absorbed as the site of the heavier atoms, and secondary x-ray fluorescent lines will be emitted. The additives to the rubber can have a particle size distribution in the nano- or micron-scale. The nano-sized particles can also serve double duty by impacting the rheology of the rubber more than the micron sized particles in view of the nano-sized particles' higher surface area.

In one embodiment of the invention, the rubber-containing bonding compounds (upon being exposed to an x-ray flux) have the capacity to bond to low energy substrates. Energy converters such as the down converters and upconverter described herein are not necessarily needed. In one embodiment of the invention, once these rubber compounds have been bonded to the respective substrates, then one of the photo initiated curing processes described below can be used to form a robust adhesion of substrates through the primer interface and the intermediate cured polymer resin between the substrates. In one embodiment of the invention, these rubber compounds with or without the energy augmentators bonded to the respective substrates can be directly bonded together without necessarily using the intermediate cured polymer resin between the substrates. Under the appropriate combination of pressure, thermal energy (heat) and ionizing energy (X-ray, e-beam and gamma ray), free radicals can be created on each side of an interface which could lead to bonding across the interface. This can be done with or without the energy augmentators.

Accordingly, the natural rubber compounds provide a double-bond backbone which can be activated by x-ray alone or either by UV light generated by x-ray phosphors (discussed below with or without the energy augmentators) which emit UV light upon exposure to x-rays or an e-beam flux. When using down converters, the UV light is used to specifically open a double bond in the natural rubbers.

Accordingly, in the methods and systems of this invention, the polymerization of disposed rubber compounds on the surface of the element to be bonded can be accomplished with or without the energy augmentators by exposing the rubber compounds to at least one of x-rays, e-beam, or UV flux. While not tied to any particular theory, the exposing can break or "open up" double bonds in the rubber compounds, followed in turn by bonding of the rubber compounds to the surface of the element to be bonded. With this approach, the solution is provided with a concentration of the natural or synthetic rubber compounds between 33% and 45%. Other concentrations are also possible.

With regard to e-beam activation, electrons of an energy range of 80-450 keV, for example, can break chemical bonds and generate free radicals either directly or through intermediate ions, which then initiate polymerization. Electron beams having an energy of 80-450 keV capable of curing even pigmented resins of about 400 μm as well as clear coatings of up to 500 μm thickness for the cured coatings. The present invention is not limited to this range of e-beam energies. Other (in particular) higher energy e-beams can be used. Prior rubber compound vulcanization studies have reported the use of e-beam induced vulcanization from electrons out of a 1.8 MeV accelerator with an output power of 10.8 kW.

The paper entitled "Comparison between electron-beam and chemical crosslinking of silicone rubber" in Nuclear Instruments and Methods in Physics Research B 243 (206) 354-358, the entire contents of which are incorporated herein by reference, describes silicone rubber compounds being irradiated by electron beams in the absence of chemical reagents. The silicone rubber compounds described therein are useful in various embodiments of this invention where x-rays, e-beam, or UV flux (from for example the down converters or up converters described herein) initiate chemical crosslinking without necessarily the need to add chemical reagents to promote the crosslinking.

Additionally, under the appropriate conditions, a linear accelerator capable of delivering X-ray photon beams and or e-beam can be used. In this case a 6 MeV to 15 MeV energies are commonly used. At 15 MeV, it would be possible to generate Cerenkov (alternately called Cherenkov) radiation. This radiation is commonly observable when charged particles (electrons in this case) inside the medium travel at a higher that the phase velocity of light in that medium.

The following is a list of rubber compounds suitable for the present invention which can be used with or without energy augmentators. (The present invention is not limited to this list.) The list includes four kinds of rubber samples:

NR (natural rubber), EPDM (ethylene-propylene terpolymer) rubber, EVA (ethylene vinyl acetate) rubber and CPE (chlorinated polyethylene).

NR rubber:
  NR+0 phr TMPT, containing 62.70% NR and 37.30% filler;
  NR+3 phr TMPT, containing 61.52% NR. 1.85% TMPT and 36.63% filler;
  NR+6 phr TMPT, containing 60.42% NR. 3.63% TMPT and 35.95% filler;
  NR+9 phr TMPT, containing 59.35% NR. 5.34% TMPT and 35.31% filler. EPDM rubber:
  EPDM+0 phr TMPT, containing 62.70% EPDM and 37.30% filler;
  EPDM+3 phr TMPT, containing 61.52% EPDM. 1.85% TMPT and 36.63% filler;
  EPDM+6 phr TMPT, containing 60.42% EPDM. 3.63% TMPT and 35.95% filler;
  EPDM+9 phr TMPT, containing 59.35% EPDM. 5.34% TMPT and 35.31% o filler.
  EPDM+12 phr TMPT, containing 58.31% EPDM. 7.00% TMPT and 34.69% filler. EVA rubber:
  EV A+0 phr T AC, containing 62.70% EVA and 37.30% filler;
  EVA+3 phr T AC, containing 61.52% EVA. 1.85% T AC and 36.63% filler;
  EVA+6 phr TAC, containing 60.42% EVA. 3.63% TAC and 35.95% filler;
  EVA+9 phr T AC, containing 59.35% EVA. 5.34% T AC and 35.31% filler. CPE rubber:
  CPE+0 phr TAC, containing 62.70% CPE and 37.30% filler;
  CPE+3 phr TAC, containing 61.52% CPE. 1.85% TAC and 36.63% filler;
  CPE+6 phr T AC, containing 60.42% CPE. 3.63% T AC and 35.95% filler;
  CPE+9 phr T AC, containing 59.35% CPE. 5.34% T AC and 35.31% filler.

In one embodiment of the present invention, blended rubber compounds such as for example acrylonitrile butadiene rubber-poly vinyl chloride (NBR-PVC) blends can be exposed to e-beams to affect a cure. Energy converters with or without the energy augmentators such as the down converters and upconverter described herein can be included, but are not necessarily needed. Dose rates from 25 to 150 kGy can be effective in curing these blends.

Blends of acrylonitrile butadiene rubber (NBR) and poly vinyl chloride (PVC), with a density of 0.7-1.2 g/cm$^3$, are commercially available and can be used with or without the energy augmentators. Acrylonitrile butadiene rubber-poly vinyl chloride (NBR-PVC) is a miscible physical mixture of commercial importance. The NBR can act as a permanent plasticizer for PVC. The presence of PVC improves aging resistance of NBR as both PVC and NBR are polar and blending NBR with PVC increases the compatibility. The aim in blending plastic and rubber is to improve the physical, thermal, and mechanical properties as well as to modify the processing characteristics and cost reduction of the final product. When used, as described above, this invention can generate local regions of intense electric fields to enhance light emission from the energy converters in proximity to those local regions, locally generating or enhancing light emission or localized internal heating within the rubber compounds to be cured.

Crosslinking and Vulcanization:

The formation of a network in a "rubbery" material can be done using various methods. When dealing with a "rubbery" material, the most common way of forming a network between chains is called vulcanization.

Vulcanization of rubber is well known and can be generally defined as the formation of crosslinks between the polymeric chains using sulfur, heat, curing agents, accelerators and other sensitizing chemistries.

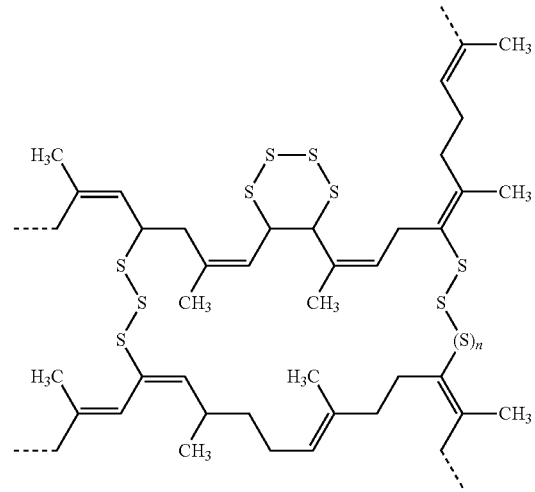

Sulfur Cross Linking

Vulcanization is an example of cross-linking. The schematic above is an illustration of two "polymer chains" (a lower chain and an upper chain) cross-linked after the vulcanization of natural rubber with sulfur (n=0, 1, 2, 3 . . . ).

Alternatively, the crosslinks between rubber chains can be achieved using peroxides, UV light, electron beam, microwave, etc. The use of peroxides as crosslinking agents is well known and offers the potential to carry out the cross-linking process at lower temperatures. In fact all low temperature process alternatives have the potential of reducing degradation by oxidation and limit rubber blooming when compared to the standard sulfur based vulcanization. However, the properties developed with standard vulcanization are considered superior to those developed with alternate methods. Commercial products such as ethylene-propylene rubber (EPM), fluoro-elastomers (FKM) can undergo peroxide cure to undergo crosslinks formation between chains and result in the formation of a stable network with good properties. This crosslinking is done via the covalent carbon-carbon bonds. Both unsaturated and saturated polymers can be processed using peroxide curing methods. The mechanical properties and thermal stability that are obtained are directly related to the number of crosslinking taking place in the network. Higher crosslink density would result in more stable rubbery compounds.

In the present invention, peroxide curable rubbers with or without the energy augmentators are activated through a down conversion from X-Ray energy to UV light using phosphor materials (and other energy converters both down conversion and up conversion described herein). One of the advantages of the present invention is that the rubbers can be activated with no direct line of site. This allows the rubber doped with peroxide generators and the phosphors to remain un-reactive until such a time that X-Ray activation is performed. Incidentally, the same phosphors can convert energy from an Electron Beam (EB) to UV energy suitable for peroxide activation and initiation of the curing. A further advantage of this method is the low energies required to carry out the curing. The X-Ray energy/dose and the e-beam energy/dose used for activation can be range from 20 mGy to 3 Gy as opposed to standard EB ionization that can require up to 10 kGy.

In one embodiment of the present invention, the natural and synthetic rubber compounds and/or the blends noted above are applied with or without the energy augmentators to surface and then vulcanized to form a cured product bonded to the substrate. Vulcanization may be considered to have occurred when two radicals produced on neighboring polymer units recombine. These radicals can produced by a chemical agent, such as peroxide or sulfur. In general, vulcanization is a process for converting rubber or related polymers into more durable materials via the addition of sulfur or other equivalent curatives or accelerators. These additives modify the polymer by forming crosslinks (or bridges) between individual polymer chains (as shown above). Vulcanized materials are typically less sticky and have superior mechanical properties. In one embodiment of the present invention, radiation, such as electron beam or gamma radiation can be used to cause vulcanization of polymers. These and other vulcanization techniques can be used in the present invention. As used herein, vulcanization is the process of converting natural or synthetic rubbers from their natural state into a more robust durable state where the natural or synthetic rubbers are cross linked.

In one embodiment of the present invention, the interaction of electron beam radiation with a polymer results in the formation of free radicals by dissociation of the excited state or by ion molecular reaction. The vulcanization reaction occurs during the irradiation of the polymer. Coagents, such as ethylene glycol dimethacrylate (EDMA), trimethylol propane trimethacrylate (TMPTMA), or trim ethyl-propane trimethacrylate (TPTA) can be used to reduce the dose required for cross-linking.

In one embodiment of the present invention, the natural and synthetic rubber compounds and/or the blends noted above with or without the energy augmentators can also be activated by UV light emitted for example from a downconverter converting x-ray (or e-beams) into UV light to cure or otherwise vulcanize the natural and synthetic rubber compounds and/or the blends noted above. In one embodiment of the present invention, the natural and synthetic rubber compounds and/or the blends noted above with or without the energy augmentators can also be activated by visible light emitted for example from a downconverter converting x-ray or e-beams into visible light or for example from an upconverter converting infrared light into visible light to cure or otherwise vulcanize the natural and synthetic rubber compounds and/or the blends noted above.

One of the most common agents used for vulcanization is sulfur. Sulfur, by itself, is a slow vulcanizing agent and does not vulcanize synthetic polyolefins. Even with natural rubber, large amounts of sulfur, as well as high temperatures and long heating periods are necessary. Vulcanization accelerators are used including activators like zinc oxide and stearic acid. The accelerators and activators are catalysts. An additional level of control is achieved by retarding agents that inhibit vulcanization until some optimal time or temperature.

In one embodiment of the present invention, vulcanization is achieved by the activation of sulfur-containing compounds added to the polymerizable adhesive compositions. The sulfur-containing compounds with or without the energy augmentators can themselves by phosphors and can be activated by UV light or directly by x-ray or electron beam exposure. While not bound to a particular theory, upon activation (i.e., exposure to UV light or direct exposure to x-rays or electron beams or other high energy particles), free radicals are generated which serve to cross link the natural or synthetic rubber compounds.

More specifically, in one embodiment of this invention, a low temperature sulfur based crosslinking occurs. In one embodiment, natural rubber is mixed with a media with or without the energy augmentators that undergoes a partial degradation under X-Ray to release a substantial level of sulfur. Once the sulfur is released between the polyisoprene chains, it can be made to react further in the presence of X-Ray or EB energy. In the case the chemical reaction can be carried out under thermal heat or not. Higher temperatures were found to accelerate the curing. However, even in the presence of room temperature, the curing is enhanced when X-Ray of EB energy is supplied to the material undergoing the reaction. The chemistries employed can remain partially cured for days and accelerated toward full cure by X-Ray energy when needed. This is advantageous from a manufacturing standpoint since production line stoppage can take place and work in process can be maintained in a queue until such time that X-Ray or EB energy is applied to the materials.

This aspect of the present invention reduces the amount of energy required to obtain X-Ray and/or EB curing. This is very useful in view of the fact that historically radiation curing has limited adoption in the manufacturing environment due to the high level of energies required and due to the high cost of radiation equipment capable of delivering high levels of energy. By reducing the energy level required, the present invention can be utilized in more industrial applications.

X-Ray Curable Rubber Containing Sulfur Chemistry:

The compounded rubbers in the present invention included in the following working example, Cake Rubber (that has undergone a mastication process consisting of shear through a milling machine), a Tackifying resin (C5 & C9 resins), a Wood Rosin (turpine based short chain), Kraton (a synthetic polymer) and Xylene (a solvent). These components were mixed and prepared to form a rubber base. The prepared rubber based was then used to form a curable rubber. The curable rubber in this case was formed by adding Iron Sulfate hydrated 10:1 in water to the rubber base. Eight grams of the rubber base was used to which 0.25 grams of the hydrated Iron Sulfate were added, followed by the addition of 0.25 grams of IRGACURE 250 (which contains an iodonium salt). Furthermore, one gram of a sulfur containing phosphor was added. Phosphors such as CaS phosphor and/or ZnSeS are suitable. The mixture was then stirred and allowed to homogenize.

0.5 grams was applied to a silicone treated Mylar film to cover a surface area of 1 in by 4 in. The silicone treated Mylar makes it easy to release the films. The rubber mixture was then flattened to have a thickness of about 1 mm. The Mylar containing this rubber pattern was allowed to dry in air or under 60° C. heat. The solvent was removed in less than 10 minutes, and the rubber coupon on the Mylar firm was dried. At this stage the rubber coupon is very tacky but malleable.

The Mylar film was removed from the hot plate. The rubber coupon was aligned with a low energy substrate. In this working example, the rubber coupon and the low energy substrate were pressed together to make intimate contact. In one embodiment, the energy augmentators could be added to the mixture or added as a perforated sheet containing the energy augmentators (such as that depicted in FIG. 7B).

In the following working example, the Mylar film without the energy augmentators was then removed from the rubber coupon and then rubber coupon was therefore left in contact and on top of the low energy substrate. The low energy substrate was unprimed and yet the tackiness of the rubber coupon was good enough to provide enough mechanical interlocking to hold the substrates in contact. Another substrate was then placed on top of the rubber coupons to form a sandwich where the rubber coupon was maintained under pressure.

The assembly formed by the two substrates sandwiching the rubber coupon was then exposed to X-Ray energy. A total of five such assemblies were exposed to X-Ray energy, and a total of three such assemblies were prepared but not exposed to X-Ray energy. The X-Ray energy exposure consists of 180 sec under energy produced using 320 kVp, 10 mA in a Precision X-Ray machine. The assemblies were then tested for peel strength.

This was done by splitting one end of the assembly apart. About half an inch (0.5 in) was slices apart at the join line where the rubber coupon is located. One end of the low energy substrate was attached to a fix location while the end of the second substrate was attached to a five pound weight. In this configuration the rubber coupon was subjected to peel (which is a known test in the industry). The three assemblies that were not processed under X-Ray were also tested for peel. The elapsed time for the five pound weight to peel the three and half in length of the bonded assembly was then measure. The faster the time to rip through the joint the weaker is the rubber coupon. The longer it takes the weight to fall the more crosslinks have formed and the more indication of curing has taken place. The average time for the five pound weight to fall for the three assemblies that were not processed under X-Ray was 2 seconds. The average time for the five pound weight to fall for the five assemblies that were processed under X-Ray was three and half minutes. This indicated that crosslinking did take place in this working example.

X-Ray Curable Rubber Containing Sulfur Chemistry as Well as Peroxide:

Another category forming a rubber base chemistry was prepared using the mixture described above as well as the inclusion of additional agents (e.g., with or without the energy augmentators and other agents) to accelerate the cure and was found to be effective in networking the rubber coupon forming the joint. In this case, a chain transfer agent (mercaptopropionate) was added. Also, the rubber base included a trifunctional monomer. Also, the addition of cobalt-acetate or copper-naphthenate promotes the kinetics.

In this case, the cure can proceed with the sulfur-vulcanization as well as a peroxide based curing. Assemblies have a peel time of close to five minutes were made which indicate that the formation of crosslink of the rubber.

Multifunctional monomers (MFM) can be added to enhance the properties various chemistries can be used. MFM are more important in the case of the peroxide curable rubbers. Multi-functional agents which can be added to the mixture are organic molecules with a high reactivity to free radicals. A tri-functional monomer as part of the rubber mix for either the peroxide cure or for an addition to the Natural Rubber cured with sulfur under X-Ray.

In one embodiment of this invention, multifunctional co-agents such as described in Chapter 1 of "Aspects Regarding Radiation Crosslinking of Elastomers," by Manaila et al, are suitable for the present invention. The "Aspects Regarding Radiation Crosslinking of Elastomers," the contents of which are incorporated herein by reference in entirety. Multifunctional co-agents can be classified in two groups: Type I and Type II co-agents.

Type I: Addition and hydrogen abstraction reactions: these co-agents consist of rather polar molecules with a low molecular weight and activated double bonds. Their main characteristic is that they are highly reactive towards radicals, so scorch takes place very fast, which sometimes can be a disadvantage. By using this kind of coagents not only the rate of cure is increased but also the crosslink density or state of cure. A disadvantage that may be present when using this type of co-agents is that, due to polarity, the compatibility of these co-agents with the polymer matrix is limited. Some examples of Type I co-agents are: acrylates, methacrylates, bismaleimides and zinc salts.

Type II: Addition reactions: these co-agents are, in general, less polar molecules, which form more stable free radicals. The use of these co-agents leads to an increase in crosslink density but unlike Type I, Type II co-agents do not typically increase the cure rate. Due to their low polarity, Type II co-agents have a good compatibility with many elastomers. Some examples are: high-vinyl 1,2-polybutadiene, divinylbenzene, allyl esters of cyanurates, isocyanurates and sulphur.

One liquid rubber compound that successfully cured using peroxide chemistry was Hypro 1300 X43 VTBN—liquid rubber (methacrylate terminated butadiene-acrylonitrile). Two chemistries were prepared as follows. The first chemistry was prepared with Hypro 1300 80%, Dipropylene glycol diacrylate 14%; 6% TPO (thermoplastic polyolefin). The second chemistry was prepared using the following mixture of Hypro 1300 80%, Pentaerythritol tetraacrylate (PETA) 14%; 6% TPO. To both of these chemistries were added a LaOBr Phosphor for activating peroxide based curing. These chemistries were effective in curing various high energy substrates; however, these chemistries were not as compatible with the low energy substrates and therefore did not wet the surface as well as the other examples evaluated.

Additional agents such as the energy augmentators can be added to accelerate the cure. An example of such accelerator is QDO (Quinone Dioxime) from Lord Corporation. QDO is a non-sulfur vulcanizing agent that can be added to synthetic elastomers to accelerate the curing kinetics.

Figure 33B:
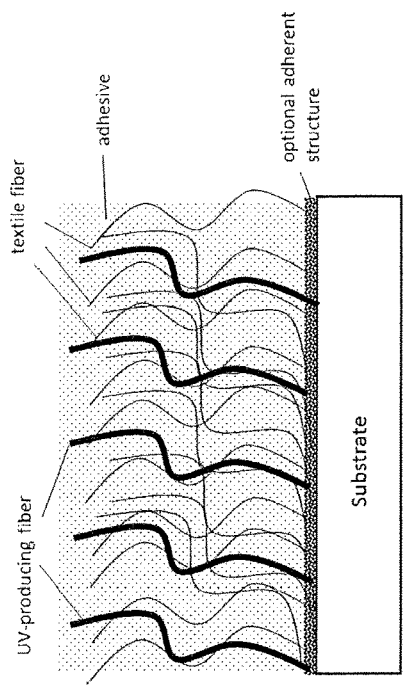
FIG. 33B is a schematic depicting a textile bonded to a substrate using the methods and systems of the present invention.
Figure 33D:
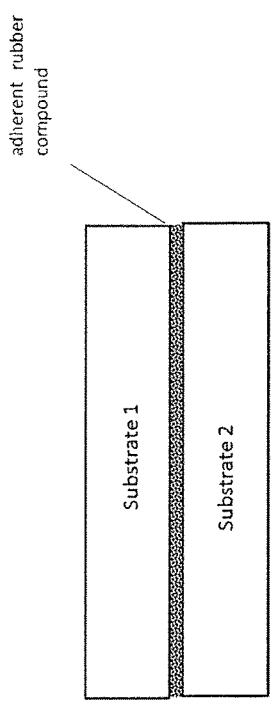
FIG. 33D is a schematic depicting the bonding of two substrates together using rubber compounds of the present invention FIG. 34A provides an emission spectrum of a material that emits in the UVA regime, upon irradiation with X-rays.
Figure 33A:
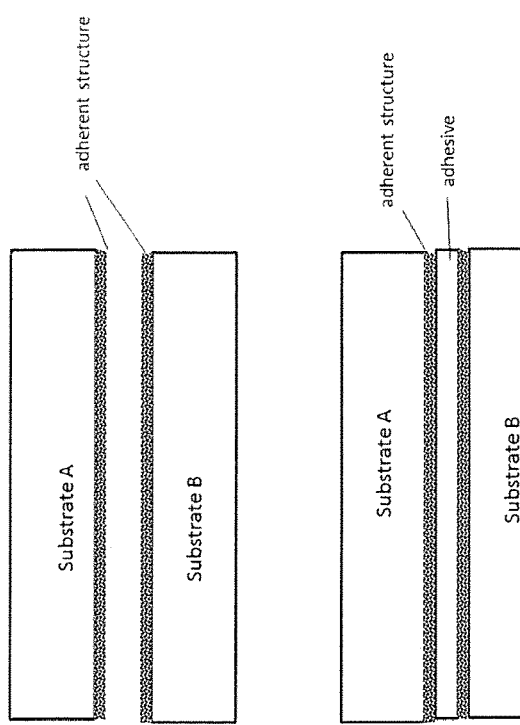
FIG. 33A is a schematic depicting two substrates bonded together using the methods and systems of the present invention.

The Formation of Adherent Structures:

FIG. 33A shows two substrates where an adherent structure without the energy augmentators has been formed on the surfaces thereof. However, in one embodiment of the invention, the energy augmentators could have been placed in the adhesive shown on FIG. 33A. A variety of adherent structures are described elsewhere, but for the purpose of illustration, the adherent structure in FIG. 33A can be considered by way of an example the to be cured or vulcanized natural and synthetic rubber compounds and/or the blends noted above. Once the adherent structure has been formed, the polymerizable adhesive compositions noted above and described in more detail in other sections of this specification can be applied in between the substrates, the substrates pressed together, and the polymerizable adhesive composition cured to form the structure in the lower half of FIG. 33A.

In these methods and systems, the surface of the element to be bonded can comprise a low energy material having a surface energy of less than 50 $mJ/m^2$, less than 40 $mJ/m^2$, or less than 30 $mJ/m^2$.

In these methods and systems, the surface of the element to be bonded (and optionally the interior) can comprise at least one of a polytetrafluoroethylene, a poly(perfluoroalkylacrylate), a polystyrene, a polyacrylate, a poly(methyl methacrylate), a poly(dimethylsiloxane), a polyethylene, a polychlorotrifluoroethylene, a polypropylene, a polyvinyl chloride, a polyvinyl fluoride, a polyvinylidenedichloride, a polyvinylidenedifluoride, a polyacrylamide, a polyethylene terephthalate, a poly(6-aminocoproicacid), and a poly(11-aminoundecaroicacid). In these methods and systems, the surface of the element to be bonded (and optionally the interior) can comprise at least one of a silicone and a poly (dimethyl siloxane).

In one embodiment of this invention, besides priming the substrates as described above, other processes can be used such as a plasma etch (for example an air plasma which would be cost effective) and or a chemical etch to form the adherent structures noted above. Accordingly, in various methods and systems of this invention, the adherent structure can be formed onto or into the surface of the element to be bonded by modifying the surface of the element to increase a surface energy thereof. In these methods and systems, the adherent structure without the energy augmentators can be formed onto or into the surface of the element to be bonded by exposing the surface to a plasma treatment. The plasma treatment can be at reduced pressures or at or above atmospheric pressure conditions. In these methods and systems, the adherent structure can be formed onto or into the surface of the element to be bonded by exposing the surface to a chemical etchant. In another embodiment, the surface treatment could comprise a thermal torch that is applied to the surface at an adequate distance and for a predetermined time to overcome the bonding of surface elements, side groups and/or molecules which ultimately leads to the formation of free radicals. The thermal treatment (torching) can optionally be used along with an air plasma to form free radicals more efficiently, if desired.

In these various methods and systems, the adherent structure can be formed onto or into the surface of the element to be bonded by applying a primer to said surface of the element to be bonded. The primer can comprise a two-component urethane-based primer. The two-component urethane-based primer can be a moisture activated primer.

One issue associated with the use of inorganic phosphors is that typically these phosphors tend to be fairly large in dimension on the order of microns, although it is possible to have the inorganic phosphors be in the nano-scale. In one embodiment of the invention, luminescing organic pigments are used as for example organic phosphors described elsewhere. Organic phosphors are typically much smaller in size than the inorganic phosphors noted above. Accordingly, organic phosphors with or without the energy augmentators can be integrally mixed into the polymerizable adhesive composition or into the rubber-containing bonding compounds. This organic or "molecular" type of phosphor then allows for the concentration of phosphor in the curing and bonding layers to be minimized relative to that which will be necessary for the larger organic size phosphors. Accordingly the cross linking between the phosphors may generate a more robust and complete chemical bond between substrates. When using inorganic phosphors, care is needed to avoid compromising the mechanical properties of the polymers under curing. Depending on the inorganic phosphor under consideration, it is sometimes desirable to have the phosphors coated with a coating that allows some bonding between the coating (on the phosphors) and the rest of the polymers in the vicinity. Inorganic phosphors that have a platelet morphology lead to weaker mechanical properties than those having needle like features at their surfaces. For these reasons, a coating can be applied, such as PMMA (polymethyl methacrylate) or ethyl cellulose, using an organic vehicle dissolved in a solvent. Alternative coatings can be applied via chemical vapor deposition, or physical vapor deposition. These coatings can be diamond or diamond-like carbon coatings, nitrides, carbides and others.

Alternatively, the surfaces of the substrates to be bonded can be coated with special coatings using processes such as CVD and PVD. These coatings can be of various kinds provided they are suitable for the bonding requirements specified by the manufacturer of the assemblies to be produced. The requirements can be economical, aesthetic, and/or mechanical in nature.

In the various methods and systems of this invention, the at least one energy converting material can be an organic phosphor. The at least one photoinitiator is configured to be activated by emitted light from one or more of organic phosphors. The organic phosphor can be at least one of anthracene, sulfoflavine, fluorescein, eosin, polyvinyltoluene, styrene, fluors, and rhodamine. The organic phosphor can be linked to the at least one photoinitiator.

In one embodiment of this invention, primers (as noted above) can be applied to the surfaces (for example the commercially available primer known as from ATPRIME® from Reichhold) which involves a two part primer part A and part B. A primer is particularly advantageous for the bonding together dissimilar substrates.

In one embodiment of the invention, fluorescent organic molecules without the energy augmentators can be attached to different reaction sites and serve as the photo-initiators. In one embodiment, these fluorescent organic molecules can be rolled into a polymer chain. The polymer chain can support side group attachments or chain terminations and can be a part of a network including the fluorescent organic molecules and the polymerizable adhesive compositions.

In one embodiment of this invention, the substrate can be considered a textile or a fabric. The fabric can then include a set of fibers that includes the fluorescent molecules woven into a thread of the textile. The interweaving or threading of the fluorescent organic molecules through the textile allows for activation of the polymerizable adhesive composition disposed at the interface between the textile and a further object. The infiltration of polymerizable adhesive composition with or without the energy augmentators into the interstices of the textile itself can promote the bonding and adherence the textile to the opposing substrate.

FIG. 33B is a schematic depicting a textile bonded to a substrate by way of UV (light emitting) fibers in the textile activating a polymerizable adhesive composition which had previously been supplied. As shown in FIG. 33B, adherent structures on the surface of the substrate can be used if needed.

In an associated method, without limitation: the polymerizable adhesive composition can be dispensed in a selected pattern through a needle or screen printing, jetted in place through an adhesive sprayer, or otherwise through a mask having a selected pattern; or otherwise through photo-patterning; or otherwise through pre-forming the adhesive composition into a sheet (optionally with isotropic or anisotropic conductivity). Pressure can be applied to the polymerizable adhesive composition if necessary, to assist in the bonding.

Figure 33C:
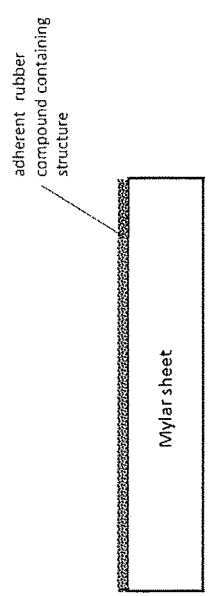
FIG. 33C is a schematic depicting an adhesive transfer sheet for transfer of natural or synthetic rubber compounds onto a substrate to be bonded

In one embodiment of this invention, an adhesive transfer sheet with or without energy augmentators can be used to transfer the above-noted natural or synthetic rubber compounds onto a substrate to be bonded. FIG. 33C is a schematic depicting an adhesive transfer sheet for transfer of natural or synthetic rubber compounds onto a substrate to be bonded. With this approach, a sheet made of Mylar (for example) is pulled through a solution of the above-noted natural or synthetic rubber compounds in which various down converters and/or up converters with or without the energy augmentators are also in suspension. In one embodiment, the energy augmentators may be placed or formed on the Mylar sheet, and released from the Mylar sheet along with the rubber containing compound.

The rubber compounds and the down and/or up converters with or without the energy augmentators transfer to the Mylar sheet forming a continuous or quasi-continuous coating (having some exclusion zones) thereof. In one embodiment, the energy augmentators could be added to the Mylar sheet as a perforated sheet containing the energy augmentators. In this approach, the coated sheet with or without energy augmentators is now able to be cut or otherwise shaped to fit prescribed regions where two or more substrates such as the low energy substrates (noted elsewhere) are to be bonded together. Once applied to one of the substrates, the adhesive transfer sheet with or without energy augmentators is pressed and the rubber compounds with the down and/or up converters are transferred to the first substrate, and the Mylar sheet removed. This transfer process can conform or otherwise dispose the rubber compounds (with the down and/or up converters and with or without energy augmentators) to a surface of the first substrate. In some embodiments, the down and/or up converters may be omitted if the vulcanization of the rubber compound is to occur by direct x-ray inducement or other high energy particle bombardment, such as electron beam induced curing of the rubber compounds.

Subsequently, a second substrate (or more substrates) can be pressed into contact with the transferred rubber compounds (with the down and/or up converters with or without energy augmentators), and thereafter upon x-ray or other appropriate activation energy the rubber compounds can be used to cure or otherwise vulcanize the rubber compounds, thus binding the substrates together.

FIG. 33D is a schematic depicting the bonding of two substrates together using rubber compounds of the present invention without energy augmentators.

Thus, in one embodiment of this invention, there is provided an adhesive transfer member including a release substrate, one or more rubber compounds disposed on a surface of the release element, and an energy converting material with or without the energy augmentators intermixed with one or rubber compounds. The adhesive transfer member can include a downconverting or an upconverting material (such as those described above or below). Specific downconverting materials can include inorganic particulates selected from the group consisting of: metal oxides; metal sulfides; doped metal oxides; and mixed metal chalcogenides. Specific downconverting materials may also include at least one of $Y_2O_3$, $Y_2O_3$:Gd, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS, ZnSe, MgS, CaS, $Zn_2SiO_4$:Mn, LaOBr:Tm and alkali lead silicate including compositions of $SiO_2$, $B_2O_3$, $Na_2O$, $K_2O$, PbO, MgO, or Ag, and combinations or alloys or layers thereof. The down-converting materials can be sulfur containing phosphors to help in the rubber vulcanization. An example of such sulfur containing phosphor is: $(Sr,Ca)Ga_2S_4$. Other examples wherein said phosphor particles comprise a thiogallate host material selected from the group consisting of $SrGa_2S_4$, $CaGa_2S_4BaGa_2S_4$, $MgGa_2S_4$ and solid solutions thereof. The particle size of such phosphor can be controlled from 25 nm to 300 microns in size as described in U.S. Pat. No. 6,153,123A. The downconverting materials can include a dopant including at least one of Er, Eu, Yb, Tm, Nd, Mn, Sb, Tb, Ce, Y, U, Pr, La, Gd and other rare-earth species or a combination thereof. The dopant can be included at a concentration of 0.01%-50% by mol concentration. At times it is preferable to have a combination of dopants rather than one dopant such is the case for a Mn and Sb in silicate matrices.

Specific upconverting materials can include at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

Several application domains can benefit from this new class of adhesive and methods used to cure such new class of adhesives and these include:

Bonding of semiconductors: Such as wafer bonding, die to wafer bonding, die on die bonding, package on package assembly at room temperature, etc. This is a particularly useful area for anisotropically conductive adhesives.

Encapsulation of semiconductors: Such as glob top, dam and fill, molding (PMC), insertion molding and flip chip underfill.

Semiconductor lithography: The present invention adhesive compositions with or without the energy augmentators and corresponding constituent material chemistries can be used in front end semiconductors to pattern semiconductor device structures. The photolithography applications include the use of photoresist materials that have negative or positive tones and development. The exposure of X-rays can be gated by adjustable apertures (particularly those made from lead), with programmable distances to allow X-rays to interact with specific areas of the dispensed adhesive. Furthermore, patterning using X-rays can be performed by masks containing heavy metals that attenuate X-ray in some areas and not others.

Other methods of patterning can bypass all mask work by using imprint lithography. In this case, dip transfer methods and stamping methods can be used to deposit a pattern that contains the adhesive composition with features containing energy converting particles with or without the energy augmentators. In this case X-ray would cure the adhesive areas with the conversion particles contained within.

The present invention also provides the ability to prepare novel composites. A novel ply (the fundamental Building Block for composites) contains fibers coated with polymer resins with or without the energy augmentators, energy converting particles and suitable catalyst/photoinitiator systems. This prepreg material is used for the buildup process (Cross-ply, unidirectional ply) used in composites to yield light weight structures and shapes ranging from simple shapes to complex 3D shapes and structures (such as a round vessel). The stack up or build up is then exposed to X-ray for curing and solidification.

Bonding of composites: The present invention permits the bonding of composites to other composites (especially to low energy surface materials), to metals and metal alloys, to rubbers, to leather and to inorganic materials (such as ceramics), particularly useful in bonding of non-like materials to one another. In one embodiment, the bonding to the low energy surface materials in turn permits the polymerizable adhesive compositions with or without the energy augmentators including the adherent surface structures to in turn be bonded to variety of other materials including those described above and below.

Attaching mechanical fasteners to composites: The present invention permits the bonding of small metallic components to large composite panels such as rivets which can be useful to fasten two separate structures. Conventionally, this requires the use of metal on metal contact to accomplish a welded connection. The present invention's polymerizable adhesive compositions with or without the energy augmentators including the adherent surface structures permit a much wider manufacturing freedom of operation. For aerospace and automotive applications, for example, a KUKA robot (sold by KUKA Aktiengesellschaft of Augsburg, Germany) can be equipped with an adhesive applicator (such as a dispenser) and an X-ray source as well as a pick and place machine to: dispense the adhesive, perform optical inspection, place a rivet and hold it in place, and cure with X-ray. Furthermore, the advantage of room temperature bonding minimizes warpage.

Natural composites: The present invention permits the fabrication of large wood beams, or other natural composite materials, which has been conventionally accomplished, for example, from small wood pieces by resin coating the wood pieces and bonding the assembly under high pressure and heat to cure the adhesive. The present invention's polymerizable adhesive compositions with or without the energy augmentators including the adherent surface structures allow room temperature bonding and no moisture needs to be volatized during cure. This is far better than the conventional methods of making such composites which typically use microwaves for heat generation, but creates enormous amounts of heat in the process, sometimes even resulting in the workpiece catching fire.

Bonding of metals: The present invention permits the bonding of metallic chassis and doors in automotives (to replace conventional induction heating). Alternatively the present invention can work alongside induction heating to reduce the energy requirement to accomplish the bonding process. Metal sheets can be bent in special shapes and then adhesively bonded together by the present invention's polymerizable adhesive compositions with or without the energy augmentators including the adherent surface structures by first forming the adherent surface structures and then dispensing a bead of the polymerizable adhesive composition around the chassis and mating the metallic pieces, fixing their position, followed by curing.

Fluidic Channels: The present invention permits the creation of fluidic channels in plastics, metals and inorganic substrates by bonding patterned substrates (with or without the energy augmentators) together to form fluidic channels. The joining of dissimilar plastics, the joining of semiconductors to plastic can be done by first forming the adherent surface structures and then dispensing the polymerizable adhesive composition onto respective surfaces to form and seal the fluidic channels Multichip modules: The present invention permits die on KOVAR substrate, as well as lid sealing on multi-chip-modules to be bonded by first forming the adherent surface structures and then dispensing the polymerizable adhesive composition (with or without the energy augmentators) onto respective surfaces to adhere the die to the KOVAR.

MEMS: The present invention permits sealing MEMS with glass wafers at room temperature (without head shift), bonded by first forming the adherent surface structures on the glass wafers and then dispensing the polymerizable adhesive composition with or without the energy augmentators onto respective surfaces to adhere the MEMS and glass wafer together.

Optoelectronics: The present invention permits alignment of optoelectronics for maximizing light intensity yield (DWDM), applying adhesive with or without the energy augmentators, and curing at room temperature (these steps maintaining maximum light intensity passage). The present invention permits alignment of optical fiber(s) in V-groove, curing with or without the energy augmentators, aligning multi-channels fibers, and curing, all while maintaining light intensity passage.

Attaching deformable substrates, particularly dissimilar substrates: The present invention permits the attaching rubber to foam, leather to rubber, leather to leather, or fabric to fabric, or any combination of deformable substrates which can be provided by first forming the adherent surface structures on at least one of the mating surface and then dispensing the polymerizable adhesive composition with or without the energy augmentators onto the respective surfaces to adhere the elements together.

Furthermore, the present invention extends to the use of conductive polymers on wearable fabrics. In this case a conductive bead (such as conductive silicone) is applied to a stretchable fabric and cured. The conductive bead can therefore route a signal (bus a signal) between two points in the fabric. Such provision can be extended to include the connection of the wearable fabric with a peripheral device (such as a cell phone) or another wearable item such as a running shoe. These conductive silicones (to name but one example) can used to make electronic garments that allow interconnectivity anywhere in the body.

Furthermore, the concepts of conductive polymers on fabrics can be used for the textiles used in car seats, airplanes, trucks and train and various other vehicles in the transportation industry.

Other preferred applications of the present invention to adhesives technology with or without the energy augmentators include, but are not limited to:

Adhesive bonding of living tissue, not only at the surface but internally. This eliminates the need for sutures or staples. Currently, cyanoacrylate ("SuperGlue") type adhesives are used for these applications. However, cyanoacrylates generally generate heat as they cure, which can lead to cell ablation.

Activation of a coagulant to treat bleeding—most valuable in a trauma or extensive surgery. The present invention adhesives could be used as temporary "stop-gap" measures in trauma patients, giving the caregiver more time to address injuries without the patient bleeding out.

Remote curing of construction materials, best suited for local repair with a uniform cure throughout the articles to be cured.

Bonding of fabrics such as foul weather gear, without heat, eliminating melting created at a heat bond, and the need for putting (stitch) holes into impervious materials.

One particularly preferred application domain is in the field of microelectronics assembly, where thermoset adhesives are used to bond bare die to substrate, establish conductive contacts, and perform various roles in packaging and sealing structures such as glob-top and die-underfill structures. Commercially available materials are formulated to meet various requirements, and in addition to the monomer(s) may contain particulate fillers such as metal or dielectric powders, as well as various additives to control viscosity and other properties. The materials are typically dispensed as a thixotropic fluid in precise locations, and after all the parts are placed, the entire assembly is heated to a temperature necessary to polymerize the monomers.

The present invention in one embodiment avoids the need to heat the entire assembly and can generate curing of the adhesive without risking warpage or other heat damage to the microelectronics. Here, with the energy augmentors present, this invention can generate local regions of intense electric fields to enhance light emission from the energy converters in proximity to those local regions. The internally generated light would activate photoinitiator chemistries. Alternatively, with the energy augmentors present, this invention can provide localized internal heating within the medium to be cured. The localized internal heating would activate thermosetting polymers and adhesives.

As modern electronic components evolve to smaller sizes, and integrated circuits include ever-smaller features such as ultra-shallow junctions, the permissible thermal budget during assembly continues to decrease. Similarly, polymer composites used for dental restorations must be cured without subjecting the patient to high curing temperatures. To address these issues, many photo-curing polymer systems have been developed. In general, these systems employ a photoinitiator, which, when exposed to UV light, releases chemical energy in the form of free radicals or cations to initiate the reaction of the monomers at substantially ambient temperatures.

The clear conventional limitation of photoinitiators is the need to have direct access to a suitable light source. This prevents the use of conventional materials for advanced processes such as multilayer stacks of individual silicon dies, because there is no way to get the UV light into the interior of the stack. These limitations are not present with the present invention adhesives, since the present invention adhesives can be readily cured by application of ionizing radiation, such as X-rays to cure the adhesive in place with minimal heat generated.

In the description that follows, various aspects of the invention will be described in greater detail so that the skilled artisan may gain a fuller understanding of how the invention may be made and used. Although the present description discusses the use of X-ray as the triggering radiation for the curing process, other types of ionizing radiation can be used as the triggering radiation, using similar down-converting agents, including, but not limited to, gamma rays or particle beams, such as proton beams or electron beams.

The mismatch between the coefficients of thermal expansion of different materials can be illustrated through the following table. The present invention in one embodiment allows for the joining of materials without excessive heat and hence circumvents the stresses that are typically trapped during thermal heating necessitated by thermal curing adhesives globally throughout the adhesive. The present invention in one embodiment enables curing between materials of drastically different CTEs.

TABLE 1

| Material | Coefficient OF Thermal Expansion/ppm/C |
|---|---|
| Silica Glass | 0.6 |
| E-Glass | 4.8 |
| Alumina | 8.7 |
| Steel | 14 |
| Aluminum | 23-24 |
| Polyimide | 38-54 |
| Epoxy | 45-65 |
| Polyester | 55-100 |
| Polystyrene | 60-80 |
| Polypropylene | 85-200 |
| Silicone resin | 160-180 |

TABLE 1-continued

One component of the adhesive material is a monomer system including a photoinitiator. The radical polymerization of formulations based on acrylate or styrene has been widely developed. It typically relies on radiation curing using near UV (300-400 nm range), although photoinitiators are now available in the visible up to the IR range as well as into the deep UV range. Cationic photoinitiators, which produce either a Lewis or Bronsted acid, may be used as initiators for cationically polymerizing materials (e.g., epoxies) and for resins that are capable of crosslinking via polycondensation reactions.

Photoinitiators are typically divided into two classes: Type I photoinitiators which undergo a unimolecular bond cleavage when irradiated, yielding free radicals, and Type II photoinitiators which undergo a bimolecular reaction, in which the excited state of the photoinitiator interacts with a second molecule (called a coinitiator) to generate free radicals. UV photoinitiators may be of either Type I or Type II, whereas visible light photoinitiators are almost exclusively Type II.

Type I UV photoinitiators include, but are not limited to, the following classes of compounds: benzoin ethers, benzil ketals, α-dialkoxyacetophenones, α-aminoalkylphenones, and acylphosphine oxides. Type II UV photoinitiators include, but are not limited to, benzophenones/amines and thioxanthones/amines. Visible photoinitiators include, but are not limited to, titanocenes.

It will be appreciated that the most efficient system will be one in which the particular photoinitiator is selected based on two considerations, viz., the type of monomer system and the type of light available.

A large number of useful photoinitiator compounds are known in the art. The following compounds [available from Sigma-Aldrich Corp., St. Louis, Mo.] have been characterized and their UV absorbance spectra are available: Acetophenone, 99%; Anisoin, 95%; Anthraquinone, 97%; Anthraquinone-2-sulfonic acid, sodium salt monohydrate, 97%; (Benzene) tricarbonylchromium, 98%; Benzil, 98%; Benzoin, sublimed, 99.5+%; Benzoin ethyl ether, 99%; Benzoin isobutyl ether, tech., 90°% o; Benzoin methyl ether, 96%; Benzophenone, 99%; Benzophenone/1-Hydroxycyclohexyl phenyl ketone, 50/50 blend; 3,3',4,4'-Benzophenonetetracarboxylic dianhydride, sublimed, 98%; 4-Benzoylbiphenyl, 99%; 2-Benzyl-2-(dimethylamino)-4'-morpholinobutyrophenone, 97%; 4,4'-Bis(diethylamino)benzophenone, 99+%; 4,4'-Bis(dimethylamino)benzophenone, 98%; Camphorquinone, 98%; 2-Chlorothioxanthen-9-one, 98%; (Cumene)cyclopentadienyliron(II) hexafluorophosphate, 98%; Dibenzosuberenone, 97%; 2,2-Diethoxyacetophenone, 95%; 4,4'-Dihydroxybenzophenone, 99%; 2,2-Dimethoxy-2-phenylacetophenone, 99%; 4-(Dimethylamino)benzophenone, 98%; 4,4'-Dimethylbenzil, 97%; 2,5-Dimethylbenzophenone, tech., 95%; 3,4-Dimethylbenzophenone, 99%; Diphenyl(2,4,6-trimethylbenzoyl)phosphine oxide/2-Hydroxy-2-methylpropiophenone, 50/50 blend; 4'-Ethoxyacetophenone, 98%; 2-Ethylanthraquinone, 97+%; Ferrocene, 98%; 3'-Hydroxyacetophenone, 99+%; 4'-Hydroxyacetophenone, 99%; 3-Hydroxybenzophenone, 99%;

4-Hydroxybenzophenone, 98%; 1-Hydroxycyclohexyl phenyl ketone, 99%; 2-Hydroxy-2-methylpropiophenone, 97%; 2-Methylbenzophenone, 98%; 3-Methylbenzophenone, 99%; Methybenzoylformate, 98%; 2-Methyl-4'-(methylthio)-2-morpholinopropiophenone, 98%; Phenanthrenequinone, 99+%; 4'-Phenoxyacetophenone, 98%; Thioxanthen-9-one, 98%; Triarylsulfonium hexafluoroantimonate salts, mixed, 50% in propylene carbonate; and Triarylsulfonium hexafluorophosphate salts, mixed, 50% in propylene carbonate.

Other suitable photoinitiators include the various IRGACURE products commercially available from BASF Corporation. The Key Products Selection Guide 2003 for Photoinitiators for UV Curing is hereby incorporated by reference in its entirety. A representative chemical class of photoinitiators is provided as examples. It would be appreciated that derivatives of such chemistries is also included. The representative list includes α-Hydroxyketone and derivatives based on (1-Hydroxy-cyclohexyl-phenyl-ketone; 2-Hydroxy-2-methyl-1-phenyl-1-propanone; 2-Hydroxy-1-[4-(2-hydroxyethoxy) phenyl]-2-methyl-1-propanone). Phenylglyoxylate and derivatives based on (Methylbenzoylformate; oxy-phenyl-acetic acid 2-[2 oxo-2 oxy-phenyl-acetic acid 2-[2 oxo-2 phenyl-acetoxy-ethoxy]-ethyl ester and oxy-phenyl-acetic 2-[2-hydroxy-ethoxy]-ethyl ester). Benzyldimethyl-ketal and derivatives based on (α,α-dimethoxy-α-phenylacetophenone). Alpha-Aminoketone and derivatives based on (2-Benzyl-2-(dimethylamino)-1-[4-(4-morpholinyl) phenyl]-1-butanone; 2-Methyl-1-[4-(methylthio)phenyl]-2-(4-morpholinyl)-1-propanone/IRGACURE 369 (30 wt %)+IRGACURE 651 (70 wt %). Mono Acyl Phosphine (MAPO) and derivatives based on (Diphenyl (2,4,6-trimethylbenzoyl)-phosphine oxide. MAPO α-Hydroxyketone and derivatives based on DAROCUR TPO (50 wt %)+DAROCUR 1173 (50 wt %). Bis Acyl Phosphine (BAPO) and derivatives based on Phosphine oxide, phenyl bis (2,4,6-trimethyl benzoyl). BAPO Dispersion based on (IRGACURE 819 (45% active) dispersed in water). BAPO/α-Hydroxyketone (IRGACURE 819 (20 wt %)+DAROCUR 1173 (80 wt %). Metallocene (Bis (eta 5-2,4-cyclopentadien-1-yl), Bis [2,6-difluoro-3-(1H-pyrrol-1-yl), phenyl]titanium). Iodonium salt and derivatives based on Iodonium, (4-methylphenyl) [4-(2-methylpropyl) phenyl]-, hexafluorophosphate(1-).

The polymerizable adhesive composition of the present invention with or without the energy augmentors can comprise a polymerizable composition or a crosslinkable composition. The term organic vehicle is used herein to indicate the portion of the curable adhesive composition that ultimately forms the resin upon curing, whether by polymerization or crosslinking. Thus, a polymerizable organic vehicle can comprise at least one polymerizable monomer. A crosslinkable organic vehicle thus comprises a plurality of crosslinkable polymer chains. Ideally, the organic vehicle is of a suitable viscosity for dispensing/applying to the desired substrate.

The monomer system may be selected based upon overall requirements such as strength, flexibility or compliance, matching with substrate properties, and the type of bonding involved, such as electrically conductive bonding versus a strictly structural adhesive bond.

Some suitable monomer systems that may be used for various applications of the invention include, without limitation: epoxies, phenolics, urethanes, acrylics, cyanoacrylates, silicones, polysulfides, polyimides, polyphenylquinoxalines, and styrenes. A source for suitable monomer chemistries is "Engineered Materials Handbook: Adhesives and Sealants, Volume III (v. 3)" CRC Press, 1990, by Cyril A. Dostal, the contents of which are hereby incorporated by reference. In one particularly interesting embodiment of the present invention, the adhesive can be used to bond living tissue to living tissue, such as in adhesive suturing of wounds or surgical openings. Any monomer system resulting in a polymer that is biocompatible can be used in such applications, with preference given to the cyanoacrylates commonly already used in wound care, but with an X-ray initiated cure by down converting the X-ray into an energy sufficient to promote the curing of monomer based adhesive. The X-ray based curing described herein further includes adhesives based on crosslinking polymeric chains through activation of appropriate cross-linking agents.

One component of the adhesive material is a material capable of converting the imparted energy and converting it to photons in a spectral range that can be absorbed effectively by the photoinitiator. Preferably, the energy converting material is a downconverting material capable of absorbing higher-energy photons (typically from ionizing radiation such as X-rays and electron-beam) and down-converting to produce lower-energy photons (typically UV) in a spectral range that can be absorbed effectively by the photoinitiator. These materials are broadly classified in two classes: scintillators and phosphors. Many down-converter materials are known, including, without limitation: metal oxides; metal sulfides; doped metal oxides; or mixed metal chalcogenides. Also included in this category are organic-inorganic hybrid scintillators such as disclosed by Kishimoto et al. (Appl. Phys Lett. 2008, 93, 261901), the contents of which are incorporated herein by reference.

Phosphor selection criteria were based on peak intensity of the emission, peak position with UV of the emission, the need to have a workable phosphor with minimal storage requirements, handling and packaging, the ability of the phosphor to couple to X-ray energy, the control over its particle size and particle size distribution; and, finally their surface chemistry.

The addition to photo-initiators, metallic particles that can effectively generate secondary electrons in the presence of X-Ray can be used to speed up cure kinetics. As such, metallic powders can be added to any chemistry described above and results in a cure speed improvement. Such metallic powders can include, Al, Cu, Ag, Au, Ni, Ti and others to name but a few examples.

In one embodiment, the peak emission target is between 200 nm and 400 nm or simply the UVA through UVC spectrum. It is desirable to have the maximum conversion of X-ray intensity into UVA intensity. This conversion described in various interrelated terms. Sometimes, it is referred to as the quantum yield or probability of interaction between X-ray and phosphors. These interrelated terms include the coupling efficiency, emission effectiveness or the Effective-Z between the X-ray and the phosphor. A list of some of the best X-ray phosphors is reported in the table below.

TABLE

| # | Phosphor | Emission Spectrum Peak Emission (nm) | X-ray Absorption | | | Microstructure | | Hygroscopic |
|---|---|---|---|---|---|---|---|---|
| | | | Emiss Eff (%) | Eff (Z) | K-edge (keV) | Specific Gravity | Crystal Structure | |
| 1 | BaFCl:Eu$^{2+}$ | 380 | 13 | 49.3 | 37.38 | 4.7 | Tetragonal | N |
| 2 | BaSO$_4$—:Eu$^{2+}$ | 390 | 6 | 45.5 | 37.38 | 4.5 | Rhombic | N |
| 3 | LaOBr:Tm$^{3+}$ | 360, 460 | 14 | 49.3 | 38.92 | 6.3 | Tetragonal | N |
| 4 | YTaO$_4$ | 337 | | 59.8 | 67.42 | 7.5 | Monolithic | N |
| 5 | YTaO$_4$:Nb (*) | 410 | 11 | 59.8 | 67.42 | 7.5 | Monolithic | N |
| 6 | CaWO$_4$ | 420 | 5 | 61.8 | 69.48 | 6.1 | Tetragonal | N |
| 7 | LaOBr:Tb$^{3+}$ | 420 | 20 | 49.3 | 38.92 | 6.3 | Tetragonal | N |
| 8 | Y$_2$O$_2$S:Tb$^{3+}$ | 420 | 18 | 34.9 | 17.04 | 4.9 | Hexagonal | N |
| 9 | ZnS:Ag | 450 | 17 | 26.7 | 9.66 | 3.9 | Hexagonal | N |
| 10 | (Zn,Cd)S:Ag | 530 | 19 | 38.4 | 9.66/26.7 | 4.8 | Hexagonal | N |
| 11 | Gd$_2$O$_2$S:Tb$^{3+}$ | 545 | 13 | 59.5 | 50.22 | 7.3 | Hexagonal | N |
| 12 | La$_2$O$_2$S:Tb$^{3+}$ | 545 | 12.5 | 52.6 | 38.92 | 6.5 | Hexagonal | N |

In some applications the desirable incident or initiation energy is different than X-ray (such as EUV) while the desirable down-converted output intensity remains in the UVA. In other applications the desirable incident or initiation energy is X-ray but the desirable down-converted energy output of the phosphor is in the UVB. Yet in other cases the desirable incident or initiation energy is X-ray but the desirable down-converted energy output of the phosphor is in the UVA and the UVB. The selected phosphors are chosen according to the invention to work with excitation sources including X-ray, extreme UV and e-beam. Within the X-ray regime, the selected phosphors can couple to a flux of X-ray photons emanating from commercially available equipment sources such as for example presently used for therapeutic tumor treatments, medical imaging and semiconductor inspection.

Figure 34B:
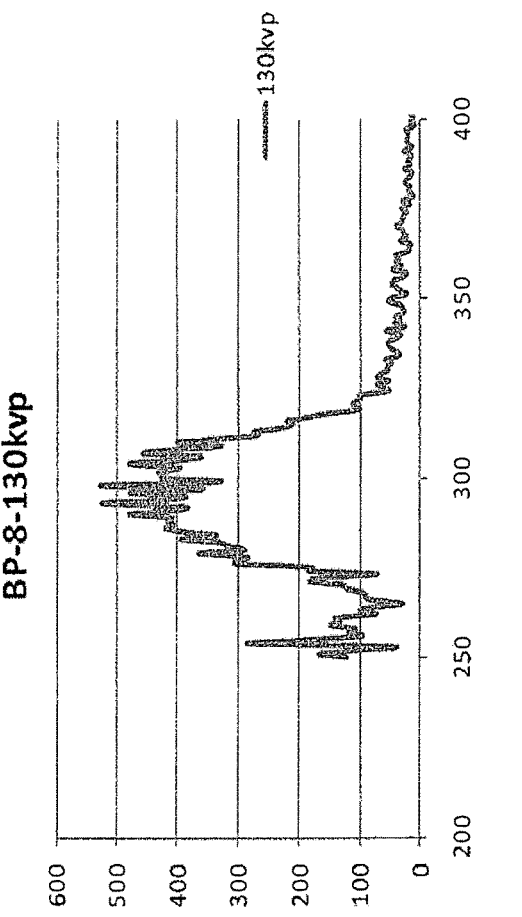
FIG. 34B provides an emission spectrum of a material that emits in the UVB regime, upon irradiation with X-rays.
Figure 34A:
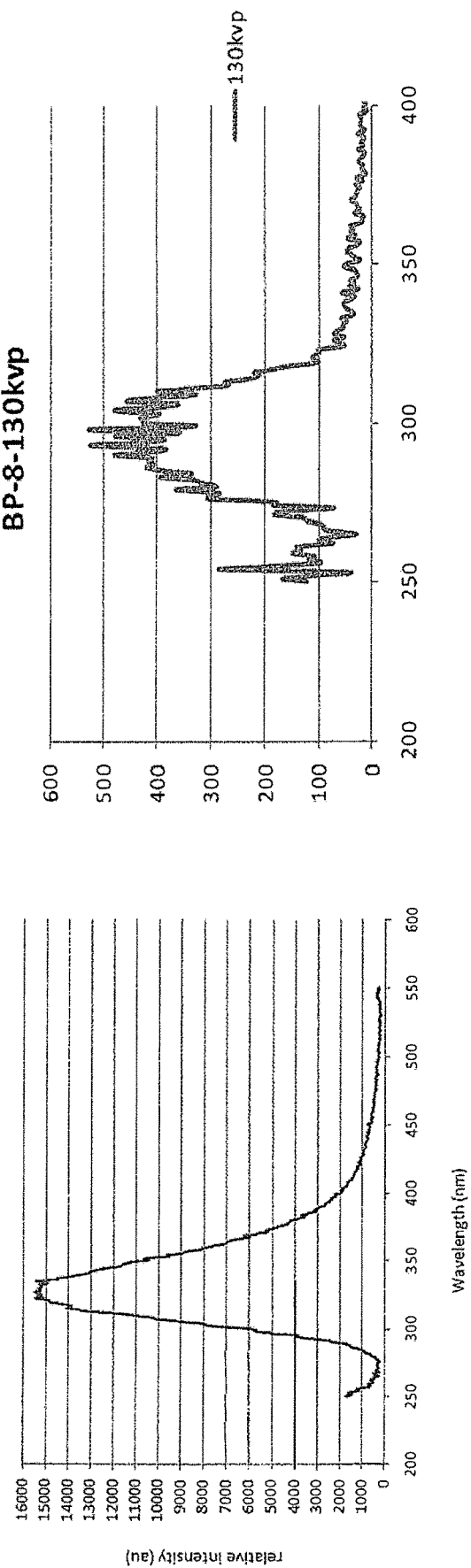
Figure 35:
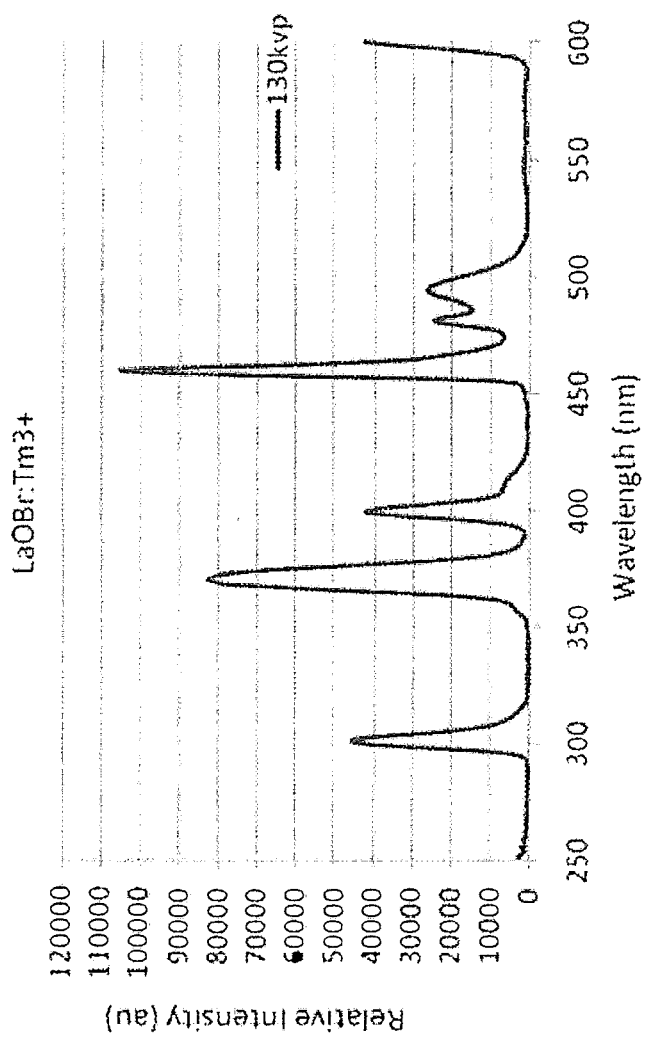
FIG. 35 provides an emission spectrum of a material that emits in the UVA, UVB, and visible regimes, upon irradiation with X-rays.

An example of a material that emits in the UVA regime is provided in FIG. 34A. The X-ray system used to carry out the experiment was the Fulton X-ray System. An example of a material having an output in the UVB is provided in FIG. 34B. An example of a material having an output in the UVA, UVB and the visible is provided in FIG. 35.

Accordingly, in various embodiments of the present invention, the phosphors noted above with or without the energy augmentators activate the photoinitiators noted above to produce UV light and affect curing of the adhesive medium between two or more substrates. In other embodiments, the phosphors promote curing or vulcanization of the natural or synthetic rubber compounds noted above.

Mixed or Alloyed Phosphors (with or without the Energy Augmentators)

Figure 36:
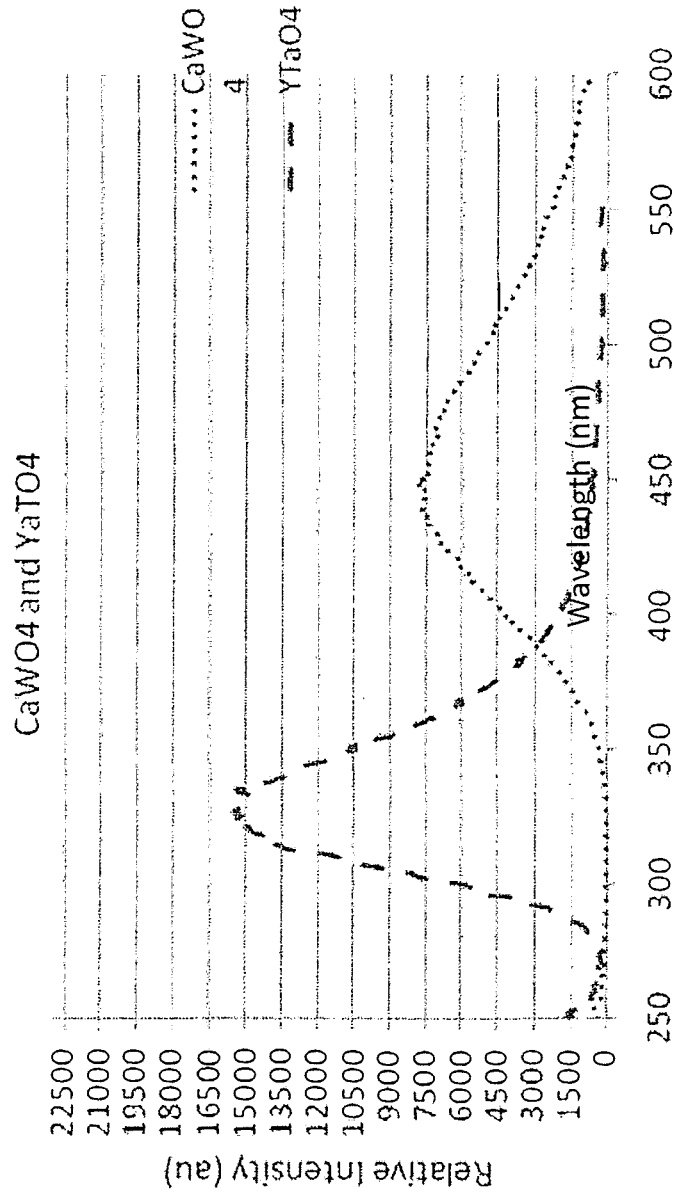
FIG. 36 provides emission spectra of two separate materials, $CaWO_4$ and $YaTO_4$, upon irradiation with X-rays.
Figure 37:
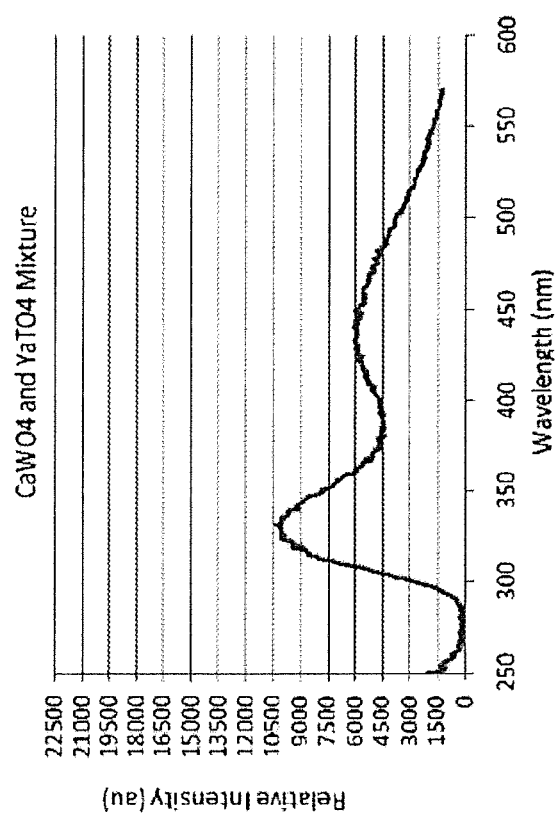
FIG. 37 provides an emission spectrum of a mixture of $CaWO_4$ and $YaTO_4$, upon irradiation with X-rays.

Another possibility of interest is the ability to mix at least two phosphors with or without the energy augmentators to broaden the output of the mixture compared with the starting phosphors. In this example, two phosphors each emitting in a distinct region were mixed together and the output spectral output was measured to demonstrate the ability to influence the output intensity of the mixture compared to the starting materials. (See FIGS. 36 and 37.)

Figure 38:
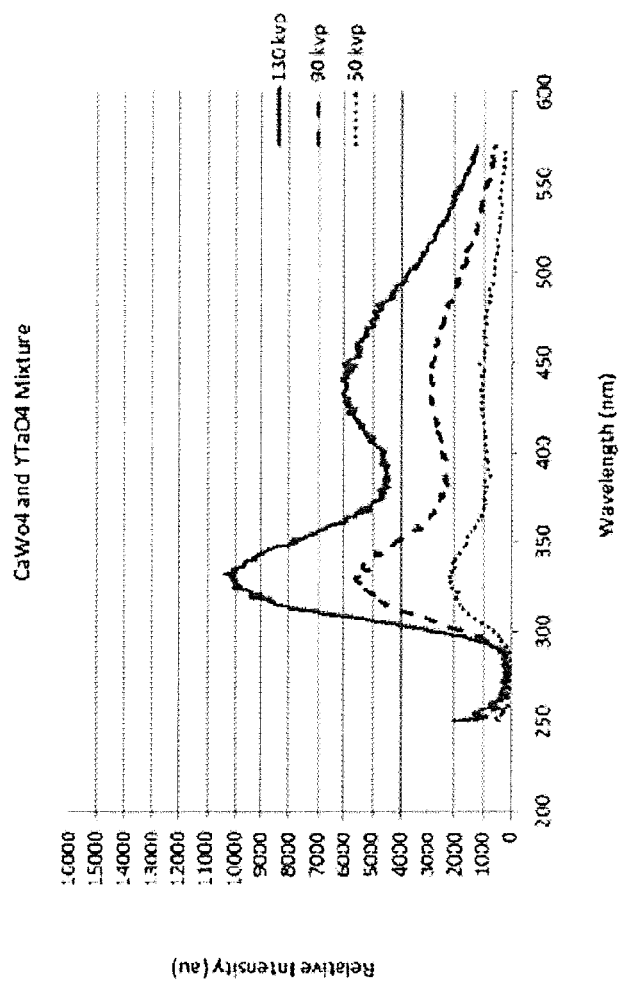
FIG. 38 provides emission spectra of a mixture of $CaWO_4$ and $YaTO_4$, upon irradiation with X-rays at intensities of 50, 90, and 130 kVp.

The intensity of the initiation energy (X-ray in this case) influences the UV output of the phosphor. The following examples are provided to illustrate how modifying the intensity of photonic energy of X-ray can modulate the light output of the X-ray. The relative intensity output of a phosphor (CaOW$_4$) was measured as a function of the energy of the X-ray photons. The X-ray energy was modified by modifying the peak voltages that exist between the filament and the target. The target in this case was tungsten. The measurements were carried out using the same mass of phosphor under 50 kVp, 90 kVp and 130 kVp. The relative intensity of the emission in arbitrary units is indicative but not conclusive in terms of comparing different materials. However, within the same conditions used to conduct measurements, it is clear that the higher X-ray intensity the higher the relative intensity of the emitted wavelength. (See FIG. 38.)

The phosphors can be synthesized from different chemicals and using different processes to control their morphology, influence their properties and light intensity output but more importantly their stability in ambient air environments. It is preferred to have phosphors that are not hygroscopic. Phosphors are easier to handle and to work with when they are stable in water and do not contain dopants that are toxic; however, even when phosphors are not stable in water and do contain dopants that are toxic. The particles of the phosphors can be coated using chemistry synthesis methods that leads to the build-up of a protective coating which shields the phosphor from the environment (water for example) and shields the environment from the toxic dopant in the phosphor (bromide for example). The protective coating can be silica or can be diamond or diamond-like carbon. Silica can be formed using sol-gel derived techniques. Diamond and diamond-like carbon can be derived from chemical vapor deposition (CVD) based on hydrogen-methane gas mixtures. Handling and packaging of phosphors can be achieved through dispersion in solution or in powder form. It was found that silica coated phosphors make a good powder that does not agglomerate. These coated phosphors can be used with or without energy augmentators.

In addition to high intensity, emission at the correct wavelengths, another desirable attribute of phosphors is to have low specific gravity (if possible). A low specific gravity may help avoid sedimentation and settling when the phosphors are mixed into another media such as a resin or a resin blend containing photo-initiators.

Accordingly, in various embodiments of the present invention, the mixed phosphors noted above with or without energy augmentators activate the photoinitiators noted above to affect curing of the adhesive medium between two or more substrates. In other embodiments, the mixed phosphors promote curing or vulcanization of the natural or synthetic rubber compounds noted above.

The particle size of the phosphor is a relevant factor. The smaller the particle size the higher the surface area. The small particles were found to alter the rheology of resins containing photo-catalysts more effectively than larger phosphor particles. The larger the particles size the higher the intensity output. The phosphors were found to perform well in terms of conversion of X-ray into UVA and activating photo-catalysts inside resin systems when they contain a particle size distribution (not a mono-modal particle size distribution). The phosphors having small particles (i.e. having a high surface area) were successfully used to increase the viscosity of the resin without the use of active silica (or AEROSIL). In one embodiment, phosphor nano-particles are added to adjust viscosity in-lieu of active silica. The best photo-activation and viscosity adjustment was found when nano-particles were used with a phosphor having particles up to the 5 microns particle size. In essence bimodal distribution of particles can help the packing factor (or loading content of phosphors into the resin) as well as helps in terms of rheological control and UVA light intensity generation for the formulation of adhesives having controllable viscosity, good curing under X-ray. A tri-modal or large distribution of particle sizes are effective in balancing rheology of the adhesive and cure response of the adhesive under X-ray. The higher surface area can effectively increase the cure speed provided the rheology of the mix is not too high in viscosity pushing the adhesive beyond a workable range for dispensing or screening or jetting.

In addition to the inorganic compounds (or phosphors) described in this invention, organic compounds can be used with or without energy augmentators to achieve the same or a similar purpose to affect curing of the adhesive medium between two or more substrates or to promote curing or vulcanization of the natural or synthetic rubber compounds noted above. For example, anthracene and anthracene-based compounds can be used to achieve the objective of the invention (curing with no line of sight and thermal energy). Anthracene exhibits a blue (400-500 nm peak) fluorescence under ultraviolet light. Furthermore, it was found that anthracene exhibits fluorescence under X-Ray energy.

Various plastic scintillators, plastic scintillator fibers and related materials are made of polyvinyltoluene or styrene and fluors. These and other formulations are commercially available, such as from Saint Gobain Crystals, as BC-414, BC-420, BC-422, or BCF-10.

| Phosphor | Product Reference | Peak Emission (nm) |
|---|---|---|
| Organic | BC-414 | 392 |
| Organic | BC-420 | 391 |
| Organic | BC-422 | 370 |

Other polymers are able to emit in the visible range and these include:

| Phosphor (Fiber Forms) | Product Reference | Peak Emission (nm) | # of Photons Per MeV |
|---|---|---|---|
| Organic | BCF-10 | 432 | 8000 |
| Organic | BC-420 | 435 | 8000 |
| Organic | BC-422 | 492 | 8000 |

Furthermore, these organic compounds that can convert X-ray to UV energy can be interwoven into synthetic polymer chains. Here, the plasma or chemical treatments described above may be an excellent way to form the adherent structures on the surface of the synthetic polymer or graft it onto the backbone of the synthetic polymer chains to permit binding and adhesion. These chains can be used as the base resin system for a cross-linking adhesive; hence leading to the formation of a new set of X-ray activatable resin systems.

UV receptive chemistries can be made more reactive by adding photo-sensitizers. This process is referred to as photo-sensitization. Certain photosensitive chemical compounds can be added to supplement photonic energy to the reactant and the reactant site to promote or enhance curing.

For UV curing applications, it is of interest to have chemistries that upon exposure to the UV radiation would form an intermediate in an excited state that in turn emits light of the correct wavelength for further curing to take place. In other words, a sensitizer can play a role in energy transfer.

Many light sensitizing chemistries are known and widely used in the industry and these include to name but a few, acenaphthene quinone, aceanthrene quinone, or a mixture thereof with anthrone and/or naphthaquinone, violanthrone, isoviolanthrone, fluoresceine, rubrene, 9,10-diphenylanthracene, tetracene, 13,13'-dibenzantronile, levulinic acid.

Accordingly, in various embodiments of the present invention, the energy converters noted above, and particularly the organic phosphors noted above, activate the photoinitiators noted above to affect curing of the adhesive medium between two or more substrates. In other embodiments, the organic phosphors promote curing or vulcanization of the natural or synthetic rubber compounds noted above.

The table below shows a wide variety of energy converters which can be used in this invention. This list is not inclusive of all the possibilities.

| Phosphor Color | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|
| Zn3(PO4)2:Tl+ | 310 | | | | | | N |
| BaF2 | 310 | | | | | | Slightly |
| CsI | 315 | | | | | | N |
| Ca3(PO4)2:Tl+ | 330 | | | | | | N |
| YTaO4 | 337 | 59.8 | | 67.42 | 7.5 | Monolithic | N |
| CsI:Na | 338 | | | | | | Y |
| BaSi2O5:Pb2+ | 350 | | | | | | N |
| Borosilicate | 350 | | | | | | N |
| LaCl3(Ce) | 350 | | | | | | Y |
| SrB4O7F:Eu2+ | 360 | | | | | | N |
| RbBr:Tl+ | 360 | | | | | | ? |
| (Ba,Sr,Mg)3Si2O7:Pb2+ | 370 | | | | | | N |
| YAlO3:Ce3+ | 370 | | | | | | N |

-continued

| Phosphor | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|
| Color | | | | | | | |
| BC-422 | 370 | | | | | Organic | ? |
| BaFCl:Eu2+ | 380 | 13 | 49.3 | 37.38 | 4.7 | Tetragonal | N |
| BaSO4—:Eu2+ | 390 | 6 | 45.5 | 37.38 | 4.5 | Rhombic | N |
| BaFBr:Eu2+ | 390 | | | | | | ? |
| BC-420 | 391 | | | | | Organic | ? |
| BC-414 | 392 | | | | | Organic | ? |
| SrMgP2O7:Eu2+ | 394 | | | | | | N |
| BaBr2:Eu2+ | 400 | | | | | | N |
| (Sr,Ba)Al2Si2O8:Eu2+ | 400 | | | | | | N |
| YTaO4:Nb (*) | 410 | 11 | 59.8 | 67.42 | 7.5 | Monolithic | N |
| Y2SiO5:Ce3+ | 410 | | | | | | N |
| CaWO4 | 420 | 5 | 61.8 | 69.48 | 6.1 | Tetragonal | N |
| LaOBr:Tb3+ | 420 | 20 | 49.3 | 38.92 | 6.3 | Tetragonal | N |
| Y2O2S:Tb3+ | 420 | 18 | 34.9 | 17.04 | 4.9 | Hexagonal | N |
| La2SiO5:Ce3+ | 420 | | | | | | N |
| La1.8Y0.2SiO5:Ce | 420 | | | | | | N |
| ZnS:Ag | 450 | 17 | 26.7 | 9.66 | 3.9 | Hexagonal | N |
| CdWO4 | 475 | | | | | | Slightly |
| Bi4Ge3O12 (BGO) | 480 | | | | | | N |
| (Zn,Cd)S:Ag | 530 | 19 | 38.4 | 9.66/26.7 | 4.8 | Hexagonal | N |
| Gd2O2S:Tb3+ | 545 | 13 | 59.5 | 50.22 | 7.3 | Hexagonal | N |
| La2O2S:Tb3+ | 545 | 12.5 | 52.6 | 38.92 | 6.5 | Hexagonal | N |
| Y3Al5O12 (Ce) | 550 | | | | | | N |
| LaOBr:Tm3+ | 360, 460 | 14 | 49.3 | 38.92 | 6.3 | Tetragonal | N |
| CaF2(Eu) | 435/300 | | | | | | N |

Further energy converters include, but are not limited to, (not ranked by order of preference or utility):

$CaF_2$, $ZnF_2$, $KMgF_3$, $ZnGa_2O_4$, $ZnAl_2O_4$, $Zn_2SiO_4$, $Zn_2GeO_4$, $Ca_5(PO_4)_3F$, $Sr_5(PO_4)_3F$, $CaSiO_3$, $MgSiO_3$, ZnS, $MgGa_2O_4$, $LaAl_{11}O_{18}$, $Zn_2SiO_4$, $Ca_5(PO_4)_3F$, $Mg_4Ta_2O_9$, $CaF_2$, $LiAl_5O_8$, $LiAlO_2$, $CaPO_3$, $AlF_3$, and $LuPO_4:Pr^{3+}$. Examples further include the alkali earth chalcogenide phosphors which are in turn exemplified by the following non-inclusive list: $MgS:Eu^{3+}$, $CaS:Mn^{2+}$, CaS:Cu, CaS:Sb, $CaS:Ce^{3+}$, $CaS:Eu^{2+}$, $CaS:Eu^{2+}Ce^{3+}$, $CaS:Sm^{3+}$, $CaS:Pb^{2\%}$ $CaO:Mn^{2+}$, $CaO:Pb^{2+}$.

Further examples include the ZnS type phosphors that encompass various derivatives: ZnS:Cu,Al(Cl), ZnS:Cl(Al), ZnS:Cu,I(Cl), ZnS:Cu, ZnS:Cu,In.

Also included are the compound IIIb-Vb phosphors which include the group IIIb and Vb elements of the periodic table. These semiconductors include BN, BP, BSb, AlN, AlP, AlAs, AlSb, GaN, GaP, GaAs, GaSb, InN, InP, InAs, InSb and these materials may include donors and acceptors that work together to induce light emission diodes. These donors include, but are not limited to, Li, Sn, Si, Li, Te, Se, S, O and acceptors include, but are not limited to, C, Be, Mg, Zn, Cd, Si, Ge. Further included are the major GaP light emitting diodes which include, but are not limited to, GaP:Zn,O, GaP:NN, Gap:N and GaP, which emit colors Red, Yellow, Green and Pure Green respectively.

The materials can further include such materials as GaAs with compositional variation of the following sort: $In_{1-y}(Ga_{1-x}Al_x)_yP$.

Also included is silicon carbide SiC, which has commercial relevancy as a luminescent platform in blue light emitting diodes. These include the polytypes 3C—SiC, 6H—SiC, 4H—SiC with donors such as N and Al and acceptors such as Ga and B.

Further examples include multiband luminescent materials include, but not limited to, the following compositions $(Sr, Ca, Ba)_5(PO_4)_3Cl:Eu^{2+}$, $BaMg_2Al_{16}O_{27}:Eu^{2+}$, $CeMgAl_{11}O_{19}:Ce^{3+}:Tb^{3+}$, $LaPO_4:Ce^{3+}:Tb^{3+}$, $GdMgB_5O_{10}:Ce_3:Tb^{3+}$, $Y_2O_3:Eu^{3+}$, $(Ba,Ca,Mg)_5(PO_4)_3Cl:Eu^{2+}$, $2SrO_{0.84}P_2O50.16B2O3:Eu^{2+}$, $Sr_4Al_{14}O_{25}:Eu^{2+}$.

Materials typically used for fluorescent high pressure mercury discharge lamps are also included. These can be excited with X-Ray and are exemplified by way of family designation as follows: Phosphates $(Sr, M)(PO_4)_2:Sn^{2+}$, Mg or Zn activator, Germanate $4MgO.GeO_2:Mn^{4+}$, $4(MgO, MgF_2)GeO_2:Mn^{4+}$, Yttrate $Y_2O_3:Eu^{3+}$, Vanadate $YVO_4:Eu^{3+}$, $Y(P,V)O_4:Eu^{3+}$, $Y(P,V)O_4:In^+$, Halo-Silicate $Sr_2Si_3O_{82}SrCl_2:Eu^{2+}$, Aluminate $(Ba,Mg)_2Al_{16}O_{24}:Eu^{2+}$, $(Ba, Mg)_2Al_{16}O_{24}:Eu^{2+},Mn^{2+}$, $Y_2O_3Al_2O_3:Tb^{3+}$.

Another grouping by host compound includes chemical compositions in the halophosphates phosphors, phosphate phosphors, silicate phosphors, aluminate phosphors, borate phosphors, tungstate phosphors, and other phosphors. The halophosphates include, but are not limited to: $3Ca_3(PO_4)_2.Ca(F,Cl)_2:Sb^{3+}$, $3Ca_3(PO_4)_2.Ca(F,Cl)_2:Sb^{3+}/Mn^{2+}$, $Sr_{10}(PO_4)_6Cl_2:Eu^{2+}$, $(Sr,Ca)_{10}(PO_4)_6Cl_2:Eu^{2+}$, $(Sr,Ca)_{10}(PO_4)_6.nB_2O_3:Eu^{3+}$, $(Sr, Ca,Mg)_{10}(PO_4)_6Cl_2:Eu^{2+}$. The phosphate phosphors include, but are not limited to: $Sr_2P_2O_7:Sn^{2+}$, $(Sr,Mg)_3(PO_4)_2:Sn^{2+}$, $Ca_3(PO_4)_2.Sn^{2+}$, $Ca_3(PO_4)_2:Tl^+$, $(Ca,Zn)_3(PO_4)_2:Tl^+$, $Sr_2P_2O_7:Eu^{2+}$, $SrMgP_2O_7:Eu^{2+}$, $Sr_3(PO_4)_2:Eu^{2+}$, $LaPO_4:Ce^{3+}$, $Tb^{3+}$, $La_2O_3.0.2SiO_2.0.9P_2O_5:Ce^{3+}.Tb^{3+}$, $BaO.TiO_2.P_2O_5$. The silicate phosphors $Zn_2SiO_4:Mn^{2+}$, $CaSiO_3:Pb^2/Mn^{2+}$, $(Ba, Sr, Mg).3Si_2O_7:Pb^{2+}$, $BaSi_2O_5:Pb^{2+}$, $Sr_2Si_3O_8.2SrCl_2:Eu^{2+}$, $Ba_3MgSi_2O_8:Eu^{2+}$, $(Sr,Ba)Al_2Si_2O_8:Eu^{2+}$.

The aluminate phosphors include, but are not limited to: $LiAlO_2:Fe^{3+}$, $BaAl_8O_{13}:Eu^{2+}$, $BaMg_2Al_{16}O_{27}:Eu^{2+}$, $BaMg_2Al_{16}O_{27}:Eu^{2+}/Mn^{2+}$, $Sr_4Al_{14}O_{25}:Eu^{2+}$, $CeMgAl_{11}O_{19}:Ce^{3+}/Tb^{3+}$.

The borate phosphors include: $Cd_2B_2O_5:Mn^{2+}$, $SrB_4O_7F:Eu^{2+}$, $GdMgB_5O_{10}:Ce^{3+}/Tb^{3+}$, $GdMgB_5O_{10}:Ce^{3+}/Mn^{3+}$, $GdMgB_5O_{10}:Ce^{3+}/Tb^{3+}/Mn^{2+}$.

The tungstate phosphors include, but are not limited to: $CaWO_4$, $(Ca,Pb)WO_4$, $MgWO_4$. Other phosphors $Y_2O_3:Eu^{3+}$, $Y(V,P)O_4:Eu^{2+}$, $YVO_4:Dy^{3+}$, $MgGa_2O_4:Mn^{2+}$, $6MgO.As_2O_5:Mn^{2+}$, $3.5MgO.0.5MgF_2.GeO_2:Mn^{4+}$.

The activators to the various doped phosphors include, but are not limited to: $Tl^+$, $Pb^{2+}$, $Ce^{3+}$, $Eu^{2+}$, $WO_4^{2+}$, $Sn^{2+}$, $Sb^{3+}$, $Mn^{2+}$, $Tb^{3+}$, $Eu^{3+}$, $Mn^{4+}$, $Fe^{3+}$. The luminescence center $Tl^+$ is used with a chemical composition such as: $(Ca,Zn)_3(PO_4)_2:Tl^+$, $Ca_3(PO_4)_2:Tl^+$. The luminescence center $Mn^{2+}$ is used with chemical compositions such as $MgGa_2O_4:Mn^{2+}$, $BaMg_2Al_{16}O_{27}:Eu^{2+}/Mn^{2+}$, $Zn_2SiO_4:Mn^{2+}$, $3Ca_3(PO_4)_2.Ca(F,Cl)_2:Sb^{2+}/Mn^{2+}$, $CaSiO_3:Pb^{2+}/Mn^{2+}$, $Cd_2B_2O_5:Mn^{2+}$, $CdB_2O_5:Mn^{2+}$, $GdMgB_5O_{10}:Ce^{3+}/Mn^{2+}$, $GdMgB_5O_{10}:Ce^{3+}/Tb^{3+}/Mn^{2+}$. The luminescence center Sn2+ is used with chemical compositions such as: $Sr_2P_2O_7:Sn^{2+}$, $(Sr,Mg)_3(PO_4)_2:Sn^{2+}$. The luminescence center $Eu^{2+}$ is used with chemical compositions such as: $SrB_4O_7F:Eu^{2+}$, $(Sr,Ba)Al_2Si_2O_8:Eu^{2+}$, $Sr_3(PO_4)_2:Eu^2$, $Sr_2P_2O_7:Eu^2$, $Ba_3MgSi_2O_8:Eu^2$, $Sr_{10}(PO_4)_6Cl_2:Eu^{2+}$, $BaMg_2Al_{16}O_{27}:Eu^{2+}/Mn^{2+}$, $(Sr,Ca)_{10}(PO_4)_6Cl_2:Eu^{2+}$. The luminescence center $Pb^{2+}$ is used with chemical compositions such as: $(Ba,Mg,Zn)_3Si_2O_7:Pb^{2+}$, $BaSi_2O_5:Pb^{2+}$, $(Ba,Sr)_3Si_2O_7:Pb^{2+}$.

The luminescence center $Sb^{2+}$ is used with chemical compositions such as: $3Ca_3(PO_4)_2.Ca(F,Cl)_2:Sb^{3+}$, $3Ca_3(PO_4)_2.Ca(F,Cl)_2:Sb^{3+}/Mn^{2+}$.

The luminescence center $Tb^{3+}$ is used with chemical compositions such as: $CeMgAl_{11}O_{19}:Ce^{3+}/Tb^{3+}$, $LaPO_4:Ce^{3+}/Tb^{3+}$, $Y_2SiO_5:Ce^{3+}/Tb^{3+}$, $GdMgB_5O_{10}:Ce^{3+}/Tb^{3+}$. The luminescence center $Eu^{3+}$ is used with chemical compositions such as: $Y_2O_3:Eu^{3+}$, $Y(V,P)O_4:Eu^{3+}$. The luminescence center $Dy^{3+}$ is used with chemical compositions such as: $YVO_4:Dy^{3+}$. The luminescence center $Fe^{3+}$ is used with chemical compositions such as: $LiAlO_2:Fe^{3+}$. The luminescence center $Mn^{4+}$ is used with chemical compositions such as: $6MgO.As_2O_5:Mn^{4+}$, $3.5MgO0.5MgF_2.GeO_2:Mn^{4+}$. The luminescence center $Ce^{3+}$ is used with chemical compositions such as: $Ca_2MgSi_2O_7:Ce^{3+}$ and $Y_2SiO_5:Ce^{3+}$. The luminescence center $WO_4^{2-}$ is used with chemical compositions such as: $CaWO_4$, $(Ca,Pb)WO_4$, $MgWO_4$. The luminescence center $TiO_4^{4-}$ is used with chemical compositions such as: $BaO.TiO_2.P_2O_5$.

Additional phosphor chemistries of interest using X-Ray excitations include, but are not limited to, the k-edge of these phosphors. Low energy excitation can lead to intense luminescence in materials with low k-edge. Some of these chemistries and the corresponding k-edge are listed below:

| | |
|---|---|
| $BaFCl:Eu^{2+}$ | 37.38 keV |
| $BaSO_4:Eu^{2+}$ | 37.38 keV |
| $CaWO_4$ | 69.48 keV |
| $Gd_2O_2S:Tb^{3+}$ | 50.22 keV |
| $LaOBr:Tb^{3+}$ | 38.92 keV |
| $LaOBr:Tm^{3+}$ | 38.92 keV |
| $La_2O_2S:Tb^{3+}$ | 38.92 keV |
| $Y_2O_2S:Tb^{3+}$ | 17.04 keV |
| $YTaO_4$ | 67.42 keV |
| $YTaO_4:Nb$ | 67.42 keV |
| $ZnS:Ag$ | 9.66 keV |
| $(Zn,Cd)S:Ag$ | 9.66/26.7 keV |

These materials can be used alone or in combinations of two or more. A variety of compositions can be prepared to obtain the desired output wavelength or spectrum of wavelengths.

In the present invention, the phosphor selection could be chosen such that under x-ray or other high energy source irradiation, the light emitted from the phosphors could, for example, have exemplary characteristics including:

Emissions in 190-250 nm wavelength range;
Emissions in the 330-340 nm wavelength range.

It will be appreciated that the most efficient system will be one in which the particular photo-initiator is selected based on its absorption, its photo-catalysis sensitivity to the intensity of the incident radiation (i.e.; the efficiency of energy transfer).

The emission wavelength in many embodiments of the present invention depends on the particular down converter material chosen to carry out the cure of the photo-catalytic reaction under consideration. Accordingly, to ensure the most efficient energy transfer from the phosphor to the photoinitiator, the phosphors are paired with the correct photoinitiators to match the emitted frequency/wavelength from the down-converter material to the peak absorption of the photo-initiator. This is referred to as a spectral match in the current invention. The spectral matching mentioned above increases the chances of energy transfer by increasing the number of successful attempts needed to overcome the activation energy barrier gating reactions.

Table 6 shows the relative peak absorption of certain photo-initiators and the relative peak emissions of certain phosphors. The pairing of photo-initiators and phosphors was done accordingly to the table below.

| Photoinitiator | Absorption Peaks | Peak Absorption | Phosphor | Peak Emission |
|---|---|---|---|---|
| IRGACUR 784 | 398, 470 | 398 | LaOBr:Tm3+ (coated) | 360, 460 |
| DAROCUR 4265 | 240, 272, 380 | 380 | CWO4:Pb | 425 |
| IRGACUR 2100 | 275, 370 | 370 | YTaO4:Nb (*) | 410 |
| IRGACUR 2022 | 246, 282, 370 | 370 | Y2SiO5:Ce | 410 |
| IRGACUR 819DW | 295, 370 | 370 | BaSO4-:Eu2+ (coated) | 390 |
| IRGACUR 819 | 295, 370 | 370 | SrB6O10:Pb | 360 |
| DAROCUR TPO | 295, 368, 380, 393 | 368 | BaSi2O5:Pb2+ | 350 |
| IRGACURE 651 | 250, 340 | 340 | CsI:Na (Coated) | 338 |
| IRGACURE 184 | 246, 280, 333 | 333 | YTaO4 | 337 |
| IRGACURE 500 | 250, 332 | 332 | | |
| DAROCUR 1173 | 245, 280, 331 | 331 | | |
| IRGACURE 754 | 255, 325 | 325 | | |
| DAROCUR MBF | 255, 325 | 325 | | |
| IRGACURE 369 | 233, 324 | 324 | | |
| IRGACURE 1300 | 251, 323 | 323 | | |
| IRGACURE 907 | 230, 304 | 304 | | |
| IRGACURE 2959 | 276 | 270 | | |

Accordingly, in various embodiments of the present invention, the spectrally-matched phosphors (inorganic or organic) noted above with or without energy augmentors can activate photoinitiators to affect curing of the adhesive medium between two or more substrates. In other embodiments, the spectrally-matched phosphors (inorganic or organic) promote curing or vulcanization of the natural or synthetic rubber compounds noted above.

Furthermore, the distance between a phosphor particle and a photo-initiator influences the efficiency of energy transfer. The shorter the distance between the photo-initiators and the phosphors the better chances of energy transfer leading to successful reactions will take place. Inside a mixture of a curable system there are many particles and a relatively elevated concentration of photo-initiators. As a result, there is more than one distance between particles and photo-initiators. In these cases, the average distance between phosphor particles and photo-initiators is used as a metric, but other distance metrics could be used.

The photo-initiators can be attached onto the surface of phosphor particles using tethering of adsorption techniques among others. In the case of tethering, a high vs. low molecular weight would be an effective way to controllably change the distance between the photo-initiators and the particles respective surfaces. In the case of deposition through adsorption, the distance between the surface of the phosphors and the photo-initiators can be altered by inner-layering a coating that is transparent to the UV energy emitted by the phosphors. $SiO_2$ is an example of such inner layer since it is transparent to UV.

Packing factor and average distance between the phosphors and the photo-initiators can be impacted using a surface coating. The packing factor of a phosphor having innate surface chemistry would therefore be different than that for a phosphor having a relatively thick coating.

The combination of the spectral match defined above, the average distance between the photo-initiators and the phosphors, the intensity of radiation generated by the phosphor particles under an initiation radiation, the particle size distribution constitutes the most efficient embodiment of the present invention.

In regards to the packing factor of the phosphors, a "large enough" silica coating deposited on the surfaces of particles would change the effective packing factor or the effective density of the powder (i.e.; mass per unit volume of powder). Similarly, a phosphor coated with a coating having an irregular shape can further lower the mass per unit volume. As an example a powder of an average particle size of 5 microns can be coated with enough silica to obtain an average size of 15 microns.

The phosphor itself becomes more or less responsive to the incident X-ray beam as a result of the coating that can alter its effective density of the mass of the powder per unit volume. The probability of interaction between the X-ray energy and the phosphors decreases with increasing coating wall thickness. An illustration is provided in FIG. 39 where the same amount of phosphor (i.e.; the X-ray coupling agent) can occupy a larger thickness.

Figure 40:
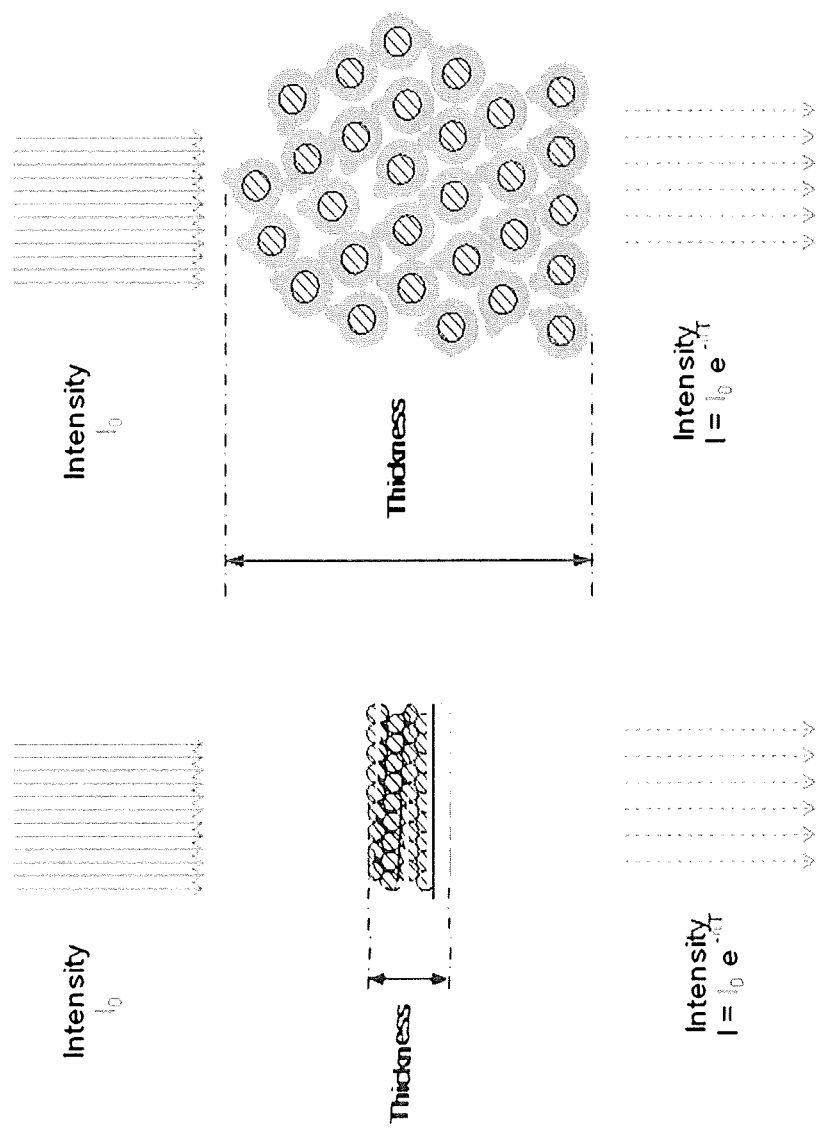
FIG. 40 provides the changes in attenuation of intensity of X-ray between a phosphor that has a coating and an innate phosphor surface.

By virtue of changing the concentration of phosphor or by changing the effective packing factor of the phosphor, the probability of interaction of the X-ray energy with the phosphor filled resin can be altered. The intensity of X-ray can be attenuated differently between a phosphor that has a coating and an innate phosphor surface (see FIG. 40).

As noted above, in one embodiment of this invention, organic phosphors can be used having a significantly smaller size than convention inorganic polymers.

The coated phosphors can be used as the filler in the resin system. The widely used filler in the industry is silica. In some cases, alumina and boron-nitride can be used as fillers. The fillers with or without energy augmentators in effect can be used to substitute some of the resin volume without degrading the properties of curable material. The filling of silica powder leads to cost savings. Filled systems are typically more mechanically stable and more cost effective than the unfilled systems.

Accordingly, in various embodiments of the present invention, the coated phosphors (inorganic or organic) noted above activate the photoinitiators to affect curing of the adhesive medium between two or more substrates in the presence of absence of energy augmentators. In other embodiments, the coated phosphors (inorganic or organic) promote curing or vulcanization of the natural or synthetic rubber compounds noted above.

The UV curing materials can be diverse; but, as a general categorization, the following materials sets are outlined by specific resin families, associated initiators, cure mechanism and appropriate application. This is by no means an inclusive list but just a general categorization to further illustration. The present invention is compatible with each of these categories including radical cross-linking or polymerization, cationic crosslinking, base catalyzed crosslinking.

Radical Crosslinking:

Radical cross-linking or polymerization utilizes resin systems such as acrylates, maleates, and styrenes. These resin systems can be used with or without energy augmentators. The initiators used in these cases include aromatic ketones such as phenyl-glyoxylates, phenyl-glyoxylates, alpha-amino ketones, benzildimethyl ketal, bisacylphosphine oxides, monoacylphosphine oxides, benzophenones.

The photoinitiators for free-radical polymerization can generate reactive chemical intermediates such as those that occur in homolytic bond cleavage, hydrogen abstraction, photo-charge transfer. The addition of phosphors is compatible with the photoreactive species and does not interfere with the basis of free radical polymerization including the 2-photons based processes.

By way of illustration, a two-photon photoleachable photoinitiator such as bisacylphosphine oxides may absorb a first photon of a given wavelength range (for example below 430 nm) to split into another photo-initiator type such as monoacylphosphine oxides that in turn can be activated using another photon of another wavelength range (below 415 nm) and lead to further radical species able to promote the formation of high molecular weight polymers.

The application of free radical cure encompasses a broad set of applications including coatings, electronic materials, and adhesives. The method described herein extends the use of such free-radical cure into no line of site applications that cannot be accomplished otherwise and renders the use of deeply penetrating initiating radiation the source of energy that indirectly triggers the cure.

Cationic Crosslinking:

Cationic crosslinking utilizes resin systems such as epoxides, vinyl ethers, and oxetanes. These resin systems can also be used with or without energy augmentators. The initiators used in these cases include diaryl iodonium salts, triaryl sulfonium salts and onium salts to name a few. The applications of such cationic crosslinking are found in electronic materials, inks and adhesives. The addition of these special salts triggers curing by proton generation which leads to cationic polymerization. The phosphors described herein, and the other energy converters or energy emitters described herein are applicable to cationic curing materials and their applications.

As an example of a curing with a photochemical initiators, a compound such as bisazide 4,4'-diazidodibenzalacetone-2,2'-disulfonic acid disodium salt can be added to a mix. This compound initiates the crosslinking upon irradiation at a wavelength of 360-370 nm which is a readily available wavelength. Another example include benzophenone can be used as a photo initiator in UV-curing applications such as inks.

Base Catalyzed Crosslinking:

Base catalyzed crosslinking utilizes resin systems such as epoxy, polyol/isocyanate, and Michael addition. These resin systems can also be used with or without energy augmentators. The mechanism of curing is based on Lewis base generators. Applications of the base catalyzed crosslinking extend according to this invention to coatings and adhesives.

Direct X-Ray Cure:

Direct curing with x-ray energy (with or without the use of phosphors with or without energy augmentators) is also possible in the present invention. For example, one can add a chemical compound that has the capability of being activated directly under x-ray energy, such as methyl ethyl ketone peroxide (MEKP), which is an organic peroxide, to assist in initiating the polymerization. Also, benzoyl peroxide, another compound in the peroxide family that has two benzoyl groups bridged by a peroxide link, can be used to assist in the initiation of the polymerization under x-ray. The effect of phosphors and these peroxide based chemicals can be additive.

Figure 41:
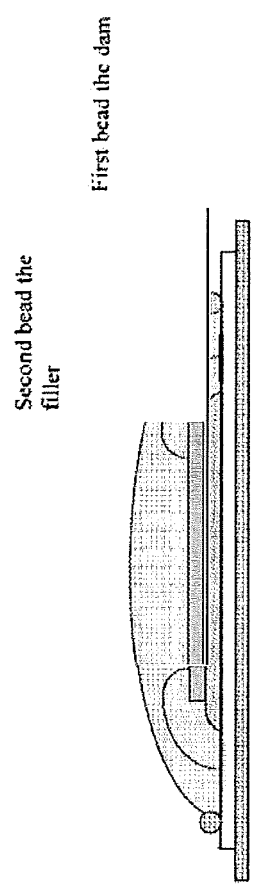
FIG. 41 provides a representation of an embodiment of a dam-and-fill application of the present invention.

Co-Curing:

In some applications it is useful to have two adhesive beads with or without energy augmentators. One adhesive bead is filled with a phosphor having a high effective packing density and another adhesive bead having a lower packing density. In this case, under the same X-ray energy intensity, one bead would cure faster than the other. In some dam and fill applications, such as in RF-ID, one could apply a dam, cure it, and then fill and cure the fill. (See FIG. 41)

However, one could co-cure the two adhesive beads using the method described here by the ability to couple more initiation energy into the containment bead as compared with the filler. These methods allow the curing of the containment bead and the filler material at the same time (co-curing) or curing one after the other (sequential curing). The same base adhesive can be used for both cases (possibly the same chemical formulation) with the containment bead having a phosphor of a different conversion efficiency than that of the filler material. This can be readily done by proper choice of the phosphor, or content of the phosphor. In a way the adhesive beads can be cured effectively at the same time but one sees more UV intensity than the other and cure faster than the other under the same X-ray beam.

Figure 42:
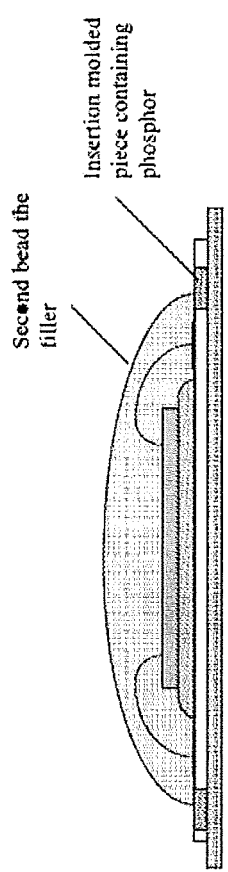
FIG. 42 provides a representation of an embodiment of the present invention using an insertion molded piece placed in the substrate to intensify the UV output.

Yet in another embodiment of the present invention, an insertion molded piece of plastic containing the appropriate amount of phosphor with or without energy augmentators is added as part of the material to be cured. (See FIG. 42.) As a molded frame this acts as the source of UV under X-ray energy. In this case the inserted molded piece gives extra UV energy to the dam (or perimeter area) and leads to faster curing. This allows the materials to cure more selectively at the borders.

Accordingly, in one embodiment of the present invention, the polymerizable adhesive compositions with or without energy augmentators including the adherent surface structures are utilized to improve and enhance the bonding strength.

Additionally photo-sensitizing chemistries can be used to enhance the photo-catalytic based reactions.

Accordingly, in various embodiments of the present invention, the light activated curing of the adhesive medium between two or more substrates can be assisted by other curing mechanisms and can be assisted with energy augmentators. In other embodiments, the curing or vulcanization of the natural or synthetic rubber compounds noted above can be assisted by the other curing mechanisms and can be assisted with energy augmentators.

Surface Modification for Phosphors.

Synthesizing phosphors in the micron and nanometer particle sizes can be done using various methods. Once synthesized, these phosphors can be used with or without energy augmentators. Also, various phosphors may have different surface chemistries. Some phosphors could be potentially hygroscopic or toxic in high doses. One way to enable the use of hygroscopic or potentially toxic phosphors is to encapsulate them by forming a containing barrier layer around phosphor particles. This has the double benefit of standardizing different phosphor chemistries to have the same common surface chemistry with predictable behavior as well as shield the phosphor inside a barrier layer. A sol-gel derived silicate coating is one method by which this can be achieved. Silica happens to be UV transparent and is congruent with most oxides and most phosphors that are not hygroscopic (as listed in the phosphor table).

The protective coating can be silica or can be diamond or diamond-like carbon. Silica can be formed using sol-gel derived techniques. Diamond and diamond-like carbon can be derived from chemical vapor deposition (CVD) based on hydrogen-methane gas mixtures, or from physical vapor deposition (PVD) based on vaporized and ionized carbon accelerated toward the target. These are but representative examples of the methods that are possible.

Dispersion:

The uniformity of dispersion of phosphors inside a resin is quite important. A uniform distribution of phosphors inside a curable system influences the homogeneity of the curable material and therefore the mechanical and optical properties of the curable material. The mixing uniformity and the particles size distribution have an influence on the curing system response in terms of cure extent as a function of time under the initiation energy. The uniformity of the dispersion can be short lived if the phosphors have a high specific density leading to settling in the resin. For this reason, some surface modification techniques can be desirable to maintain the phosphors in suspension.

Dispersants:

The surface of the phosphors can be modified for two general purposes. One method leads to tethering or adsorbing the photo-initiators onto the surface of the phosphors. The other method is to add dispersant chemistries to the surface of phosphors to enable the phosphors to remain in suspension after the adhesive is formulated and the ingredients have been mixed together. In general phosphors are preferred to be in powder form with minimal aggregation between particles. The dispersion of phosphor powder in a resin system can be achieved using various methods. These dispersion methods keep the phosphors in suspension by limiting or preventing the potential re-flocculation caused by the particles' Brownian motion at room temperature or at temperatures above room temperatures by 20° C. to 30° C. These slightly elevated above room temperature are useful in dispensing the adhesives through a needle using a piston or an auger pump.

The surface modification of the phosphors to maintain a uniform dispersion after mixing is important. Various organic polymer agents can be used to increase the wetting characteristics of the phosphors into the resin chemistry. Similarly, various dispersing agents can be added to maintain the phosphor particles in suspension inside the mix. The dispersing agents are built from polyurethane or polyacrylate polymeric structures having high molecular weight (3000-50000). Various dispersing agent are available in the market. The dispersants can be anchored onto inorganic surface by virtue of surface charge (the electrostatic attraction of oppositely charged surfaces) and can be anchored or adsorbed to the organic substances like the chains in the resin by virtue of dipolar interactions, hydrogen bonding and London/van-der-Waals forces. Once anchored in place the high molecular weight dispersants increase the steric hindrance for particles to diffuse too close to one another hence preventing agglomeration of phosphors.

Tethering:

The downconverting particles and photo-initiators used in the present invention can be added as separate components to a curable adhesive formulation having or not having the energy augmentators, or can be tethered to one another to provide increased likelihood of activation of the photoinitiator upon emission from the downconverting particles.

Tethering of photoinitiators to the downconverting particles can be done by any conventional chemistry, so long as it does not interfere with the emission characteristics of the downconverting particles (other than potential slight movement of the peak emission in the red or blue direction), and so long as it does not interfere with the ability of the photoinitiator to initiate polymerization of the curable adhesive composition. One may also use combinations of two or more phosphors, two or more photoinitiators, or both, to achieve more complex curing kinetics. Further, one can use organic downconverters, such as anthracene, rather than the various inorganic downconverters noted above. With the organic downconverters, there are additional possibilities including, but not limited to, use of the organic downconverter material as a separate component in the curable adhesive composition, tethering the organic downconverter to the photoinitiator, as described for the inorganic downconverter particles above, or even incorporation of the organic downconverter groups into one or more of the monomer components of the curable adhesive composition.

Figure 93:
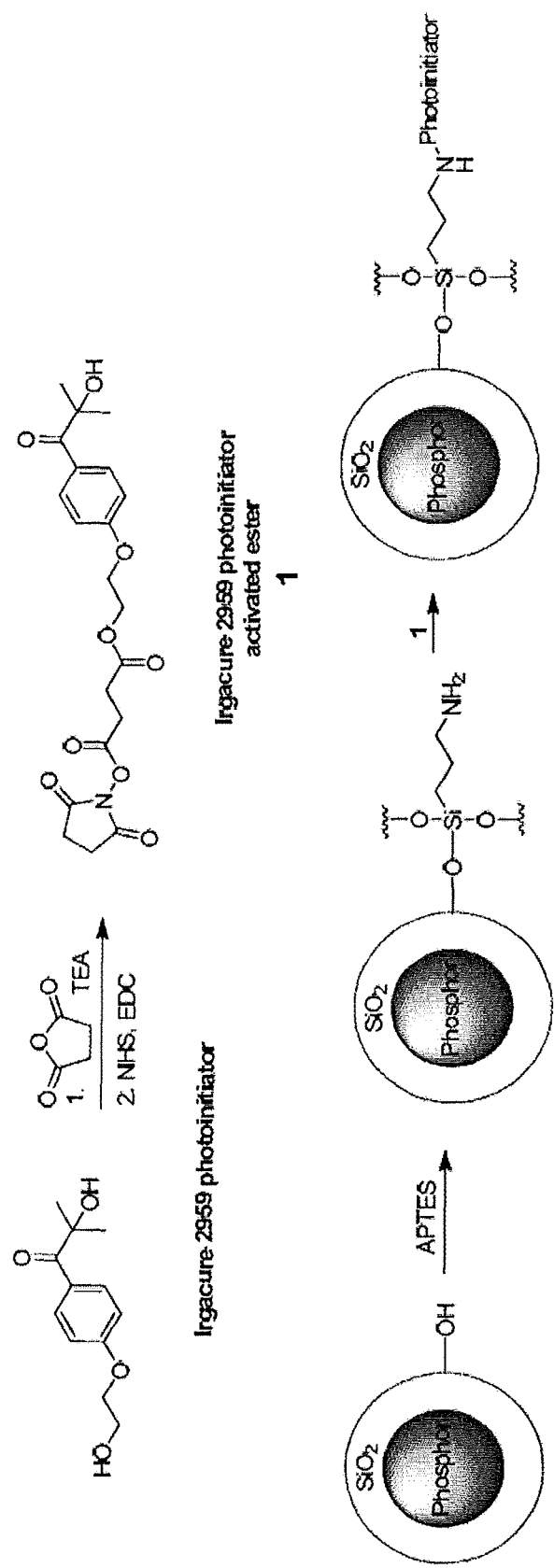
FIG. 93 depicts one suitable chemistry for tethering inorganic downconverter particles the photoinitiator whereby a silica coated phosphor is reacted with aminopropyltriethoxysilane (AVMS), then the modified photoinitiator is bound to the pendant aminopropyl group.

One suitable chemistry for tethering inorganic downconverter particles to the photoinitiator utilizes a silica coated phosphor is reacted with aminopropyltriethoxysilane (APTES), then the modified photoinitiator is bound to the pendant aminopropyl group, as shown in FIG. 93.

Other possible modifications include, but are not limited to, the modification of existing Adhesives by adding special downconverting particles from X-ray to UV in the range of susceptibility of a Photoinitiator Accordingly, in various embodiments of the present invention, the coated and/or tethered phosphors noted above activate the photo-initiators to affect curing of the adhesive medium between two or more substrates. In other embodiments, the coated and/or tethered phosphors promote curing or vulcanization of the natural or synthetic rubber compounds noted above.

Because the surface area (and hence the overall surface energy) of the nano-sized particles is very high, the viscosity rises quickly with the addition of a small amount of nano size powders. This limits the amount of filler that can be added. On one hand this limits the UV intensity that can be emitted by the phosphors under X-ray energy. On the other hand, the limited filler loading that can be achieved is not economically favorable since fillers are typically less expensive than the base resins and catalysts. Furthermore, the viscosity increase with the addition of nano-size particles becomes excessive which limits the use of the adhesive to certain application categories but not others. In most adhesive application it is favorable to use micron size particles when possible. Though as stated earlier, the best mode calls for a bi-modal particle size distribution consisting of mixture of nano and micron size particles.

In general, $SiO_2$ is more cost effective compared to phosphors. This is not always the case. One method by which enough UV light output is achieved while safeguarding a favorable economic phosphors-utilization is to build a composite particle based on $SiO_2$ as the core particle and decorated with the appropriate phosphors in terms of type and concentration necessary to achieve the targeted photocatalytic reactions (i.e.; the right wavelength output and luminosity or intensity output).

Building Composited Particles:

In applications that require the use of micron level particles that are cost effective down converters, the surface of a carrier particle made of silica can be decorated with desirable phosphors with nanometer particle size. The phosphors are chosen for the right emission UV wavelength and intensity under X-ray.

Figure 43:
FIGS. 43A and 43B show a representation of a bare silica carrier particle and a silica carrier particle decorated with nano-size phosphor particles, respectively.

The downconverting particle comprises a composite of nanoparticles and a silicate carrier particle. The silicate carrier particle has the same surface characteristics as a particle typically used as a filler (including silica). In this case the down converting particles are bonded to the surface of the base carrier particle followed by a coating as shown in FIGS. 43A and 43B.

By way of illustration the construction of such a composite particle is hereby provided. This description is non-inclusive of all the possibilities but provides one viable synthesis method.

The core or carrier particle can be made of glass, such as $SiO_2$ or alkali-lead-silicate and have a diameter of about 2 microns. Nanometer-scale downconverting particles are applied to the surface of the core particle, and subsequently made to adhere or bond to the surface of the core particle (see FIG. 43B). Some of the methods enabling this bonding process include precipitation techniques from a solution. Another method is based on condensation by heating the downconverting particles to much elevated temperatures compared to the core particles while maintaining the silicate based particles above their softening point. At the correct respective ranges of temperature, which are readily determined by one of ordinary skill in the art based on the compositions of the core particle and downconverting particle chosen, the downconverting particles and the carrier particles are forced into contact, leading to condensation, thus allowing surface deposition to take place. The downconverting particles can be any of the phosphors listed in Table 5 or elsewhere described herein.

Accordingly, in various embodiments of the present invention, the composite phosphor particles noted above activate the photoinitiators to affect curing of the adhesive medium between two or more substrates. In other embodiments, the composite phosphor particles (inorganic or organic) promote curing or vulcanization of the natural or synthetic rubber compounds noted above.

Figure 44:
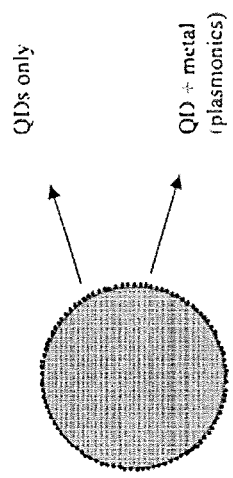
FIG. 44 provides a representation of a silica carrier particle coated with quantum dots or alloyed quantum dots or metal alloys exhibiting plasmonic behavior under X-ray.

The downconverting particles, for example, can be quantum dots with the suitable range of downconversion from X-ray to UV. The quantum dots and/or oxides used for the downconversion process can further comprise elements, or alloys of compounds or elements tuned for plasmonic activity (see FIG. 44).

In a preferred embodiment, the quantum dots preferably comprise a mixture of zinc sulfide and zinc selenide, more preferably in a ratio within a compositional window of 60% zinc sulfide, 40% o zinc selenide to 70% zinc sulfide, 30% zinc selenide. The metal alloys used for plasmonics comprise silver/gold mixtures, more preferably within the compositional window of 60% silver and 40% o gold, to 70% silver and 30% gold.

Figure 45:
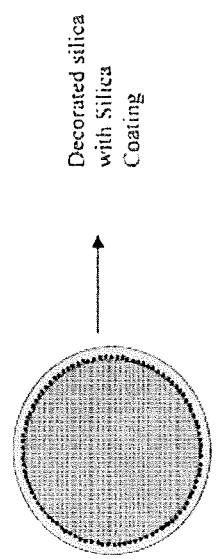
FIG. 45 provides a representation of a silica carrier particle decorated with nano-sized downconverters and then coated with silica.

After the carrier core particle is decorated with the down converting particles, coating the outer layer is desirable to encapsulate and protect the down converting particles as well as modify the surface. The outer layer coating can be accomplished using sol-gel processing followed by heat treatment. This leads to the formation of a composited particle consisting of a core particle with down-converting particles on the surface and the whole is coated with a silicate coating. (See FIG. 45). This special filler particle can be used to replace an existing filler material.

Figure 46:
FIG. 46 provides a representation of a photoinitiator tethered or adsorbed on the surface of a nano-sized phosphor particle.

Tethering to Composite Particles:

The present invention includes special provisions for a modified use of existing photoinitiators by tethering the photoinitiator to nanoparticles having downconverting properties. This close proximity of nanoparticle to photoinitiator maximizes the chance for photoinitiation or photo-catalysis, and can achieve improved cure efficiencies. (See FIG. 46)

Figure 47B:
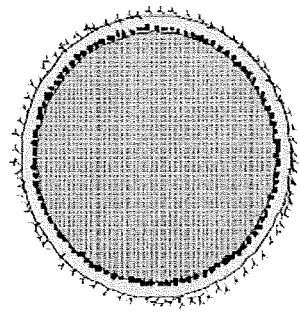
FIGS. 47A and 47B provide representations of a silica micro particle decorated with nano-size phosphor particles having photoinitiators tethered or adsorbed on the surfaces thereof and photoinitiators tethered directly on a silica coating around a particle that is decorated with nano-sized phosphors, respectively.
Figure 47A:
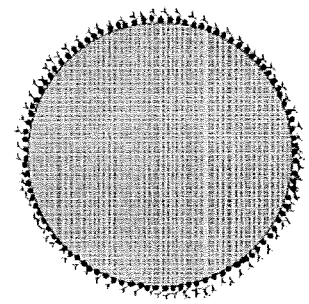

In the tethered case, the downconverting particles are added during mixing an adhesive preparation using tethered particles on a carrier particle and mixing into the adhesive. As an alternative embodiment, the tethered photoinitiator and downconverting particles can be positioned on the surfaces of micron level carrier particles. See FIGS. 47A and 47B. The carrier particles are then used as filler. This time no surface coating is necessary and the photoinitiator is in direct contact with the resin. See FIG. 47A. Alternatively, this arrangement can also use a coating of $SiO_2$, on which are tethered the photoinitiators. See FIG. 47B.

Since in this particular embodiment, micron size particles (large particles) are added to the mix, the impact on adhesive rheology is minimized compared to adding nano-size particles. This method can thus present added advantages, including the ability to use the micron size particles as a filler to otherwise alter the cured adhesive or polymer properties.

Figure 48B:
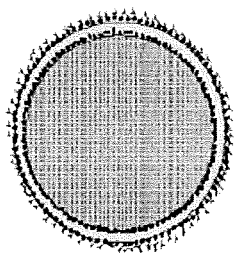
FIGS. 48A and 48B provide representations of a double layered decoration that is non-tethered with photoinitiators and a double layered decoration with tethered photoinitiators, respectively.
Figure 48A:
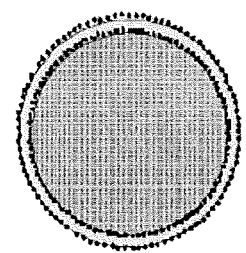

Composite Particles:

Achieving brighter particles can be done by having the carrier particle decorated with 2 layers of phosphors. First the carrier particle is decorated with nano-sized phosphors (FIG. 48A), then coated using sol gel derived silica and lastly decorated a second time with phosphors of the correct size (FIG. 48B). This technique can be repeated to obtain more phosphors or down conversion particles at the outerlayers of the carrier particles.

Accordingly, in various embodiments of the present invention, the composite phosphor structures noted above activate the photoinitiators to affect curing of the adhesive medium between two or more substrates. In other embodiments, the composite phosphor structures promote curing or vulcanization of the natural or synthetic rubber compounds noted above.

Surface Preparation:

Adhesion develops through various factors including mechanical interlocking, adsorption, electrostatic, diffusion, weak boundary layer, acid base, chemical (covalent bonding), etc. In general, the greater the surface irregularities and porosity at a joint area, the greater the joint strength. The greater the compatibility of the size of the adhesives and the interstices in the adherend, the greater the bond strength can be. Roughness of the surfaces can increase or decrease the joint strength.

The factors affecting joint strength include: surface energetics (wetting), intrinsic stresses and stress concentrations, mechanical response of various bulk phases and inter-phases involved, geometrical considerations, mode of applying external stresses, mode of fracture or separation, viscoelastic behavior.

The wetting and the setting of the adhesive bead is important for a good bond formation. The spreading co-efficient of an adhesive depends on the various surfaces and associated surface tensions involved. The surface tensions are referred to here as the energetic requirements. The substrate (solid), the adhesive (liquid) and the vapor (open air in most cases) all play a role. Wetting of the surface depends on the surface energy between the solid and the liquid, the liquid to vapor surface tension and between solid to vapor surface tension. Substrates such as Teflon, PET, Nylon, PE, and PS have low energy. Substrates such as metals, metal oxides, and ceramics have high energy.

The adhesive chemistry (the liquid in this example) can be tailored to adjust the energetic requirements at the various surfaces. But that is not sufficient. For example, most RTV silicone resins fulfill the energetic requirements but give negligible adhesion unless primers are used. Adhesive joints can be made stronger by surface treatments of the surfaces to be joined. Also, inter-phases can be made between the adherend and the adhesive.

For the above considerations (surface energetic requirements and primers treatments), many surface modification techniques are used to achieve the goal of strong and durable adhesion at joints. The treatment of polymer surfaces is used for various reasons including one or more of the following list extending to making the polymers more favorable to adhesion, increase their printability, make them more wettable, provide an enclosing layer, improve tribological behavior, potentially prepare them for metal plating, improve their flame resistance, provide antistatic properties, control permeation.

Dry surface modification includes, but is not limited to, a surface plasma ionized through RF or microwave, flame, UV, UV sensitized, ozone, UV/ozone, X-ray, LASER, electron beam, ion bombardment, and friction against other materials.

Wet surface modification encompasses chemical reactions such as oxidation, sulfonation, ozonation, phosphatization, chromate conversion, amination, grafting, selective etching, deposition of coupling layers (silanes), surfactant adsorption, photochemical compounds, solvent (surface swelling), prevention of diffusion of low molecular weight materials to the surface, and others.

Method of Use

Figure 94:
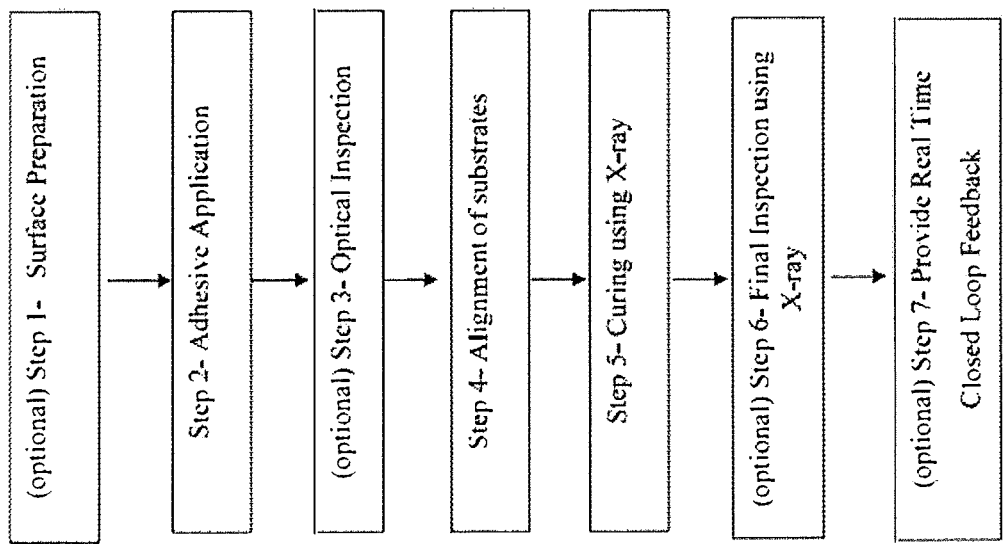
FIG. 94 depicts in a flow chart depicting illustrative method of the present invention FIGS. 95A-B provide representations of stages in the production of an embodiment of the present invention for forming various semiconductor IC devices with electrically conductive contacts and metallic heat sinks.

One embodiment of a typical method of use in the present invention can be summarized in the following steps shown also in FIG. 94.

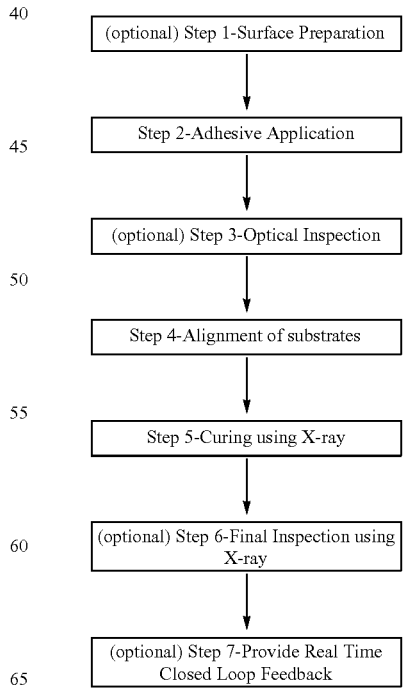

Below is a list of numbered items pertaining to FIGS. 49-90:
- 10: Anisotropic Conductive Polymer Sphere
- 10': Anisotropic Conductive Polymer Sphere—Partially Flattened
- 11: Anisotropic Conductive, UV or Visible Light Emitting, Polymer Sphere
- 11': Anisotropic Conductive, UV or Visible Light Emitting, Polymer Sphere—Partially Flattened
- 20: Polymer Core
- 20': Polymer Core—Partially Flattened
- 22: Nickel Plating
- 22': Nickel Plating—Partially Flattened
- 24: Gold Plating
- 24': Gold Plating—Partially Flattened
- 26: Down-Converting Photon Emitter Coating
- 26': Fractured Down-Converting Photon Emitter Coating
- 28: Flip Chip Device
- 30: Substrate
- 32: Flip Chip Device Bumps
- 32': Substrate Solder Bumps
- 34: Matrix Epoxy Resin
- 35: X-ray activated, UV or Visible Light curable, Anisotropic Conductive Adhesive (ACA) epoxy
- 36: Polymer Coating
- 36': Fractured Polymer Coating
- 38: Down-Converting Photon Emitters
- 39: Wafer Aligner and Bonder
- 40: Top Integrated Circuit (IC) Wafer
- 41: Bottom Integrated Circuit (IC) Wafer
- 42: Thru Silicon Via (TSV) Contacts
- 44: Vacuum Plate
- 46: Split field prism and lens device
- 47: Fixed lens-pair
- 48: Applied Force
- 49: Top wafer alignment fiducial
- 49': Bottom wafer alignment fiducial
- 50: X-ray Exposure Device
- 51: Superimposed alignment fiducials
- 52: X-ray Imaging Detector
- 60 Adhesive material
- 60-1 Liquid Encapsulant (Underfill)
- 60-2 Liquid Encapsulant (No Flow Underfill)
- 60-3 Liquid Encapsulant (Glob Top)
- 60-4 Liquid Encapsulant (Dam)
- 60-5 Liquid Encapsulant (Molding)
- 60-6 Thermally conductive Adhesive
- 60-7 film adhesive with proper resin and the proper phosphors and photo-initiators
- 60' adhesive bead with modified rheology for screen printing
- 60" adhesive fillet
- 70 adhesive dispenser
- 72 Substrate
- 72' PCB
- 72" High Density Circuit
- 73 UV source
- 74 Spacer element
- 75 Computer Control
- 76 Mechanical Drive
- 77 Mechanical arm
- 78 Mechanical Coupling
- 79 Platen
- 79' Vacuum ports
- 79" Thermode
- 80 Composite substrate
- 81 PET component
- 82 X-ray source
- 130 Pick & Place
- 131 Vacuum
- 132 contact pads
- 132' Wire Bond
- 133 metallic lid
- 133' glass lid
- 134 Flexible Circuit
- 140a plastic with injection molded features
- 140b plastic with mirror image injection molded features
- 140c bonded plastics
- 150 PET plastic with well
- 150' Liquid Crystal Polymer
- 100 Well joint features
- 101 protrusion piece
- 102 fluidic channels in PET
- 102' fluidic channel in LCP An example of an application and how these steps are used is provided in the following paragraphs. One preferred embodiment involves the bonding of a silicon integrated circuit, either to a substrate or to another integrated circuit (to make a multilayer stack). The penetrating power of X-rays will be such that the X-rays can pass through the uppermost layer of silicon and reach the bond layer, in which the downconverting particles will become stimulated and emit the desired wavelength of light (which may be UV or visible, depending on the particular photoinitiator being used).

Optional steps may include, without limitation: dispensing the adhesive in a pattern that will allow the adhesive to flow under a component through capillary action (e.g., "die underfill" processes); photo-patterning the adhesive; and applying pressure to the adhesive bond before and/or during the curing process.

Other applications will involve the following steps:
1. (optional) surface prep—the surface must be placed in a state in which the adhesive to be formed can bond to the surface. This prep can include a variety of different methods, including but not limited to, alcohol swabbing, plasma treatment, acid or base treatment, physical abrasion or roughening, a detailed overview of surface preparation was provided.
2. applying adhesive to the substrate—the adhesive can be applied using any desired method, depending on the viscosity of the pre-cured adhesive composition.
3. (optional) optically inspecting the applied adhesive for dispensing quality—this is to ensure that the adhesive has been applied properly, whether evenly coated, applied in drops or lines, etc. This step preferably requires that there be a visual contrast between the adhesive and the substrate to which it is applied. Such a contrast can be provided through the addition of one or more conventional coloring agents to the adhesive, or through the use of color-changing adhesives that change color upon curing.
4. placement of the substrate for cure—this ensures that the pieces to be adhered together are in proper alignment; and, applying pressure as needed.
5. curing using x-rays and performing final inspection
6. (optional) providing real-time closed loop feedback in an automation line (via reel to reel or islands of automation) This permits defects to be detected much earlier in mass production, thus minimizing waste due to misalignment of pieces or incomplete cure Conductive Fillers Optional components may include various organic or inorganic materials and additives to perform desired functions, such as modifying the electrical conductivity and dielectric properties of the cured polymer. Many of these components are well known to those skilled in the art.

Conductive fillers may include finely divided particles of metals including gold, silver, nickel, copper, and alloys such as Au—Pd, Ag—Pd, etc. Other conductive phases that may be used with the invention include $LaB_6$ as well as various conductive oxides and carbon. The conductive filler particles may alternatively be made from small polymer beads or spheres having a conductive coating thereon, such as a thin gold film. The polymer particles may be fairly rigid or they may have some degree of flexibility or compressibility in order to make the final bond more compliant. Plasticizers and flexibilizers can be added Isotropic conductivity may be achieved by using small particles ("small" meaning particles with an average diameter much less than the final bond or film thickness) loaded to a volume fraction that exceeds the percolation threshold so that the resulting polymer composite material exhibits substantial electrical conductivity in every direction. Conversely, the invention may also be used for anisotropic conductive materials, in which a film or sheet contains a monolayer of large individual spherical conductor particles ("large" meaning particles whose diameter is comparable to the final bond or film thickness) loaded to a volume fraction below the percolation threshold so that the resulting material is substantially conductive through the film thickness but is not conductive parallel to the plane of the film.

Other suitable filler materials include various dielectric materials such as metal titanates and zirconates, titanium oxide, etc., that may be added to tailor the dielectric properties of the film. Other inorganic additives may include boron nitride for applications where it is desired to have a bond that is electrically insulating yet thermally conductive.

Organic additives may include several classes of agents familiar in the art. These include, without limitation: plasticizers to modify the mechanical properties of the cured polymer; surfactants and dispersants to modify the rheology of the uncured material to make it easier to dispense as well as to allow any particulate fillers to be adequately dispersed; and solvents and comonomers.

Figure 49:
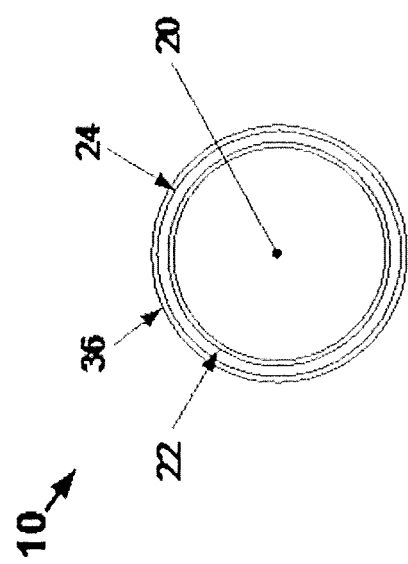
FIG. 49 provides a representation of an embodiment of an anisotropic conductive polymer sphere of the present invention.

Conductive Polymer Spheres:

One example of an anisotropic conductive polymer sphere is generally represented by 10 of FIG. 49. In this example, the sphere consists of an elastic polymer core 20 that is surrounded with a thin layer of plated nickel 22 under plated gold 24 and an outer layer of another, more brittle, thin polymer coating 36. As is well known within the art, anisotropic conductive adhesives (ACA) can be manufactured from rapid (snap-cure) thermosetting epoxy resins filled with approximately 4% of conductive polymer spheres which have a nominal diameter of 5-microns. The polymer spheres are designed to deform elastically when compressed, exposing the outer gold plated surface, which is then able to establish electrical continuity across the narrow gap between aligned contact pads of stacked IC chips, wafers or other substrates.

Figure 50:
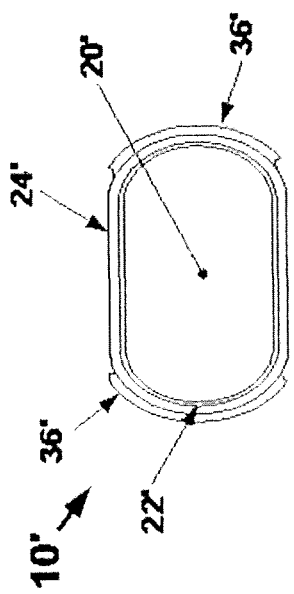
FIG. 50 provides a representation of an embodiment of an anisotropic conductive polymer sphere of the present invention after compression and flattening.
Figure 51:
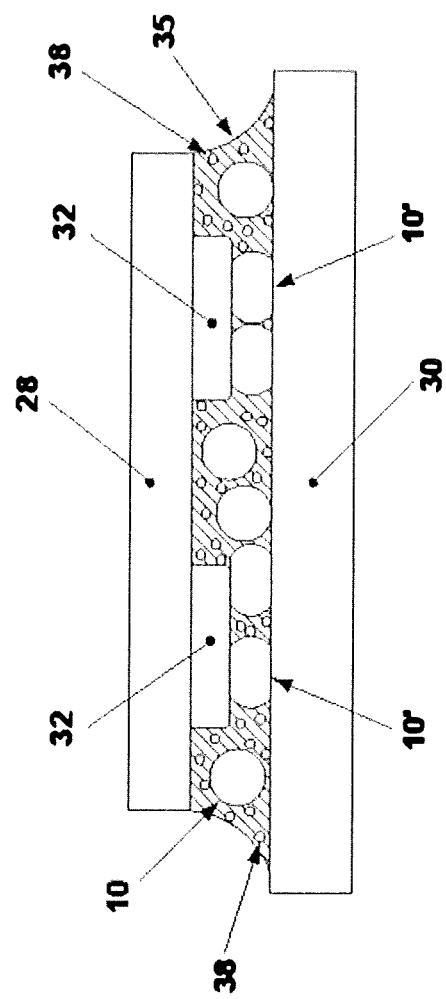
FIG. 51 provides a representation of an embodiment of the present invention using anisotropic conductive polymer spheres in an integrated circuit application, wherein the representation has features exaggerated for emphasis.

When compressed and deformed the polymer sphere 20' becomes partially flattened, as generally illustrated at 10' of FIG. 50.

As the diameter expands under compression the brittle outer polymer coating becomes fractured 36' at the top and bottom contact surfaces and exposes the malleable and partially flattened gold plating 24'. The gold plating still adheres to the partially flattened polymer sphere 20' by means of the plated nickel layer 22', which is also malleable and becomes partially flattened. As the plated gold metal becomes exposed under compression it establishes a metal-to-metal electrical contact with the metal pads disposed directly above and below the partially flattened polymer sphere. Electrical continuity is then achieved across the gap between top and bottom pads around the circumference of each polymer sphere thru the plated nickel and gold layers. This process is further described and illustrated in FIG. 51.

The first step of the inventive method is to place a polymerizable adhesive composition, including a photoinitiator and downconverting phosphor, in contact with two or more components to be bonded to form an assembly. As noted above, the viscosity of the adhesive may be varied over a significant range by the choice of monomer(s), the possible use of solvents, the loading of filler particles, etc., as is well understood by skilled artisans.

Many of the inventive compositions will be thixotropic, enabling them to be conveniently dispensed using standard processes familiar in the field of adhesives. In particular, for microelectronics assembly, the compositions may be applied to selected areas using automated needle-type applicators in conjunction with pick-and-place methods. Alternatively, they may be applied in various patterns using printing through screens or masks. Low-viscosity systems, which would typically contain solvents and a minimal amount of inorganic fillers, may be distributed in selected patterns by ink jet printing.

In order to form an aniostropically conductive bond, the inventive material may be formed into a sheet having conductive balls of the appropriate diameter, cut or diced to a desired size, and placed between the two components to be bonded. It will be understood that in some cases, this process may be repeated in order to make a multilayer stack of any desired number of components.

The second essential step of the inventive method is to irradiate the assembly with radiation at a first wavelength, capable of downconversion by the downconverter to a second wavelength capable of activating the photoinitiator, thus initiating the polymerization of the adhesive.

Applicants contemplate that in a most preferred embodiment, the radiation applied to the assembly after the bond material has been placed will be X-rays. Many industrial X-ray generators are available commercially from a number of suppliers, and the skilled artisan may easily select an appropriate X-ray source based upon routine engineering considerations.

Thermo-Set Adhesive:

With the surfaces held in compression, using an externally applied force, the thermo-set epoxy is rapidly cured in order to maintain the conductive polymer spheres in a state of compression after the external force is removed. A thermo-set epoxy may be rapidly cured by means of an appropriate heat source such as a cartridge heater, microwave or ultrasonic generator, IR heat lamp, laser beam, or various other means to apply heat to the surfaces being bonded. However, in general, the heat must generally be fairly high (>250° C.) in order to achieve rapid curing of the epoxy, and often requires that the heat be conducted through the surfaces used for achieving the applied force as well as the chip and/or substrate being bonded together. If the materials being electrically and mechanically bonded exhibit a significant difference in their characteristic coefficient of thermal expansion (CTE), a high state of shear stress may exist between these surfaces after the epoxy is cured and the materials return to room temperature. This shear stress is undesirable, as it may lead to a premature failure of electrical continuity between the aligned contact pads. This problem is more pronounced when there is a large difference in relative size between the materials being bonded.

Several significant advantages may therefore be realized if the epoxy can be cured without the necessity for using high heat. For example, if the epoxy can be cured at room temperature the materials may be joined without any residual shear stress thereby improving reliability. Moreover, if the fixtures used for aligning the parts and applying a compressive force between surfaces remain at room temperature, the time required for assembly may be substantially reduced.

UV or Light-Cured Adhesive:

One possible solution for rapid adhesive curing at room temperature is the substitution of an ultraviolet (UV) curable or visible light curable adhesive for manufacturing the ACA adhesives described above. A fundamental problem arises when attempting to expose the adhesive to sufficient (curing) UV or light energy through optically opaque surfaces that are commonly encountered in microelectronic assembly. Without adequate UV or visible light illumination the epoxy may not fully polymerize. Some manufacturers attempt to remedy this situation by combining properties within the epoxy that allow it to be partially cured with UV-energy followed by a final thermal cure. However, an ideal UV or light-curable epoxy for ACA applications would be realized if it can be fully cured without necessity of an external UV or visible light source or additional thermal-cure steps.

As noted above, according to the invention, various photoinitiator compounds and downconverting materials exist that can convert absorbed higher-energy (X-ray) photons to lower-energy photons (UV or visible light). If an adhesive epoxy is custom engineered to be sensitive (i.e. polymerize) when exposed to the spectral wavelength and energy level of one or more types of these "down-converting" lower-energy photon emitters, included as a "filler" within the epoxy, and can be used with or without energy augmentators, then the epoxy can be fully cured, even through optically opaque materials, by exposing it to an X-ray source. An added benefit is that the same X-ray energy may simultaneously be detected and converted into an image for quality control purposes.

An example of an X-ray activated, UV or visible light curable, anisotropic conductive adhesive (ACA) (35) is shown (as noted above) in FIG. 51. This anisotropic conductive adhesive (35) can be used with or without energy augmentators. Features of the figure are exaggerate to illustrate how an integrated chip (IC) can be assembled as a flip chip device (28) and electrically interconnected to a substrate (30). The bumps (32) on the bottom surface of the flip chip device are raised above the otherwise planar surface of the IC chip. The raised bumps are typically fashioned using either electro-plated or electro-less plating methods and may consist of metals such as nickel-gold, copper-nickel-gold, titanium-tungsten/copper/nickel/gold and other various metals and/or alloy combinations. The raised bumps typically range in height from 5-10 microns above the planar surface of the IC. The raised bumps are typically formed on the chips while they are still part of the whole wafer. However, the substrate will typically not include raised bumps. When assembled in a face down (flip chip) configuration, the raised bumps on the IC form a difference in thickness of the gap between the surfaces. And when properly filled with a sufficient amount and diameter of ACA polymer spheres (approximately 4% o of 5 micron diameter spheres) there is a high probability that one or more spheres will be captured between the flip chip device bumps and the substrate pads (not shown) and partially flattened (10') when a proper amount of external normal force is applied. The "proper" amount of force required is determined experimentally depending on the variable geometries and materials that are being assembled. The remaining AC polymer spheres (10) that fall between adjacent bumps will remain un compressed and will not generally conduct electricity, since the brittle polymer coating (36) is unbroken.

In the example illustrated above in FIG. 51, the X-ray activated adhesive (35) without energy augmentators is also filled with small down-converting photon emitters (38) which are engineered to emit lower-energy photons in the UV or visible light spectrum. The amount and size of these down-converting photon emitters would also be experimentally determined, depending on the material properties. In practice, the down-converting photon emitter particles would be smaller than the AC polymer spheres (10 or 10') and would be evenly distributed within the epoxy resin (35).

Figure 52:
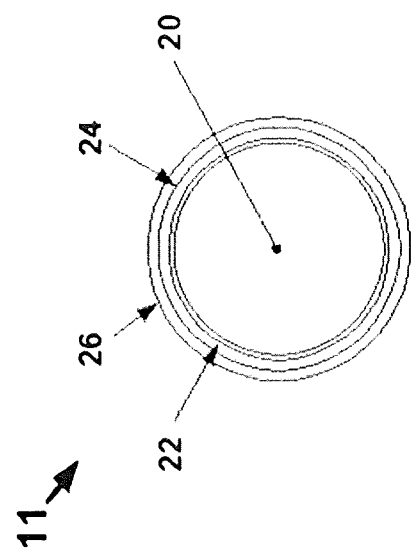
FIG. 52 provides a representation of a further embodiment of an anisotropic conductive UV emitting polymer sphere of the present invention.
Figure 53:
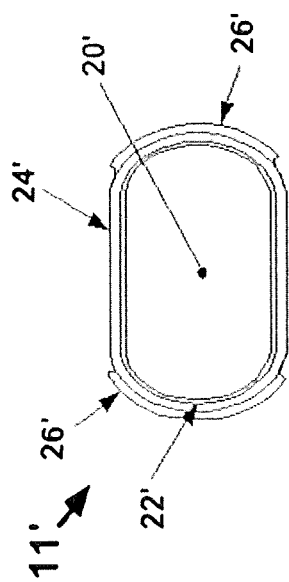
FIG. 53 provides a representation of an embodiment of the anisotropic conductive UV emitting polymer sphere of FIG. 52 after compression and flattening.

Adding the down-converting photon emitters as separate "filler" may adversely affect the viscosity and thixotropic characteristics of the UV adhesive. Therefore, an alternative and better practice would be to substitute the polymer coating (36) of the ACA polymer spheres (10) with a coating (26) consisting of the down-converting photon emitter material(s), with or without energy augmentators, to form a new type of anisotropic conductive, UV emitting, polymer sphere (11) as illustrated in FIG. 52. In this example the down-converting photon emitter coating is both electrically non-conductive and brittle in nature, so as to fracture when partially flattened (26') and thereby expose the gold coating (24') underneath, as illustrated in FIG. 53.

Figure 54:
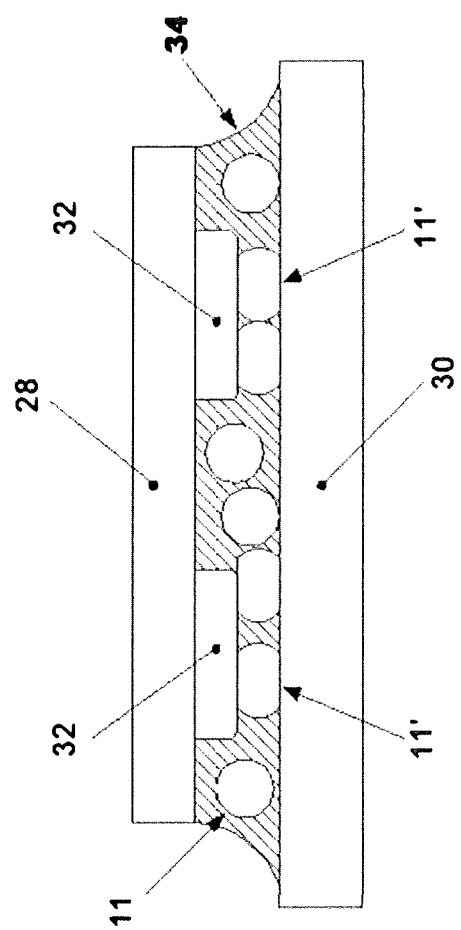
FIG. 54 provides a representation of an embodiment of the present invention using anisotropic conductive UV emitting polymer spheres in an integrated circuit application, wherein the representation has features exaggerated for emphasis.

FIG. 54 is similar to FIG. 52, but illustrates the absence of the down-converting photon emitter "filler" particles (38) and substitution of anisotropic conductive, UV emitting, polymer spheres (11 and 11'), as previously described, but without energy augmentators in this example. These polymer spheres would be similar in size and volume to existing ACA adhesive formulations and therefore would be expected to perform in a similar manner.

Figure 55:
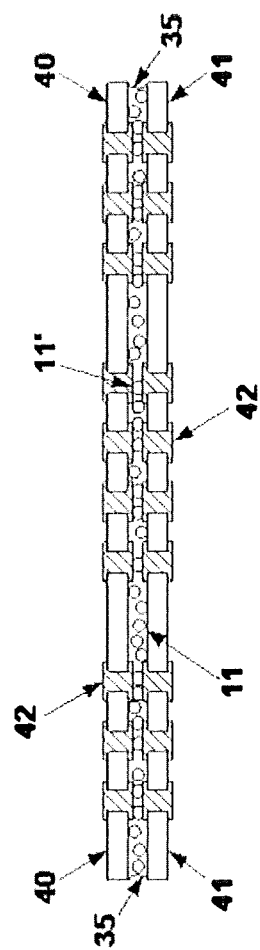
FIG. 55 provides a representation of a further embodiment of the present invention using anisotropic conductive UV emitting polymer spheres.

Another example of an assembly using anisotropic conductive, UV emitting, polymer spheres (11 and 11') is shown in FIG. 55. This illustration shows two similar IC wafers, such as memory chip wafers, stacked one above the other and electrically and mechanically joined together. Both the top IC wafer (40) and bottom IC wafer (41) include "Through Silicon Via" (TSV) contacts (42) that provide a means for routing circuit interconnections from the top (active) surface of the wafer to pads arrayed across the bottom surface of the wafer. In this manner, electrical functions that are present at a pad on the top (active) side of the wafer may also be present on the opposite or bottom (non-active) surface of the wafer; much like a thru-hole connection enables signals to be routed through a printed wiring board (PWB). The TSV contacts include small, raised, annular or square pads on the top and bottom surfaces that form contact surfaces for electrical connection through the partially flattened polymer spheres (11'). When the wafers are properly aligned and compressed the X-ray activated, UV or visible light curable, ACA epoxy (35) with or without energy augmentators is cured by exposing the assembly to an X-ray source.

X-Ray Alignment and Bonding:

To commercially implement the UV adhesive bonding technology described above, it is desirable to have equipment engineered to provide the correct X-ray exposure dosage in order to activate (in situ) the UV or visible light curable adhesive, and to simultaneously image and record the resulting cured bondline using the same X-ray energy. Some examples of suitable X-ray aligner and bonders are partially illustrated in FIGS. 56A-C, 57A-C and 58A-C.

Figure 56C:
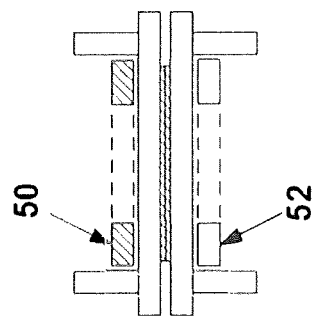
FIGS. 56A-C provide representations of an embodiment of an X-ray aligner and bonder according to the present invention.
Figure 56B:
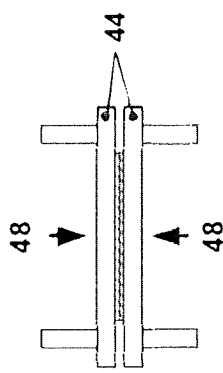
Figure 56A:
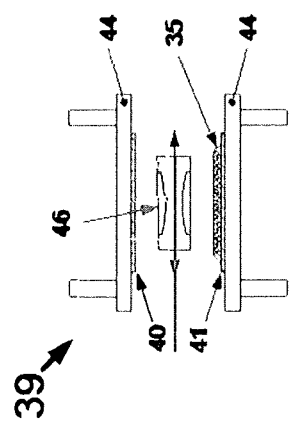

An X-ray wafer aligner and bonder (39) of FIG. 56A is designed to enable wafer-to-wafer alignment and bonding using an X-ray activated, UV or visible light curable, ACA epoxy (35), which is used in this embodiment with or without energy augmentators and without need for applying external heat to the wafer surfaces being joined. The bonder includes two vacuum plates (44), of sufficient size to hold a top IC wafer (40) and bottom IC-wafer (41), that are spaced apart sufficient to enable a split field prism and lens device (46) to be temporarily inserted and scanned between the surfaces, as shown. The prism device is used to precisely align the wafer surfaces with respect to one another, either manually or by automated means, prior to the wafer surfaces being compressed together. The prism device provides a means to view and superimpose fiducial images from multiple locations on the bottom surface of the upper wafer with similar fiducial images on a top view of the lower wafer. Once these fiducial images are superimposed and accurately aligned, the split field prism and lens device are removed and the wafers are brought together under an applied force (48) as shown in FIG. 56B. The applied force compresses and partially flattens the anisotropic conductive polymer spheres (10' or 11') trapped between the aligned flip chip device bumps (32) and/or Thru Silicon Via (TSV) contacts (42) of each IC on the two wafers, as previously described and shown in FIGS. 51, 54 and 55. Once the wafers are under an applied force, sufficient to enable the ACA polymer spheres to partially flatten and establish electrical conductivity across the juxtaposed bumps or contacts, an X-ray Exposure Device (50) and X-ray imaging device (52) are brought into position, as shown in FIG. 56C. X-ray exposure device (50) is used to generate a field of high energy photons that stimulate the fluorescent coating of the down-converting spheres which then spontaneously emit UV light of the correct wavelength and luminosity to cause the UV resin to rapidly cure by photo initiation. As the high energy photons pass through the materials they may also advantageously be detected on the surface of an X-ray imaging detector (52), positioned directly across from the X-ray exposure device and on the opposite side of the wafer vacuum plates. The X-ray imaging detector is designed to produce high resolution X-ray images of the bonded surfaces using analog and/or digital circuitry that is immune to damage from the X-ray source. Data from the X-ray imaging detector is collected and processed into high-resolution digital images, as either individual photos and/or continuous video, for data (archival) storage and/or image processing to provide a means for process and quality control.

Figure 57B:
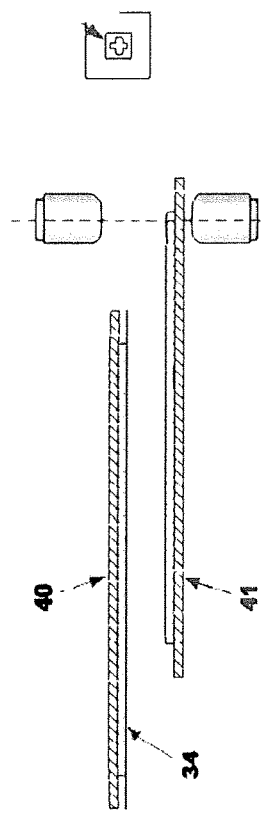
FIGS. 57A-C provide representations of a further embodiment of an X-ray aligner and bonder according to the present invention.
Figure 57A:
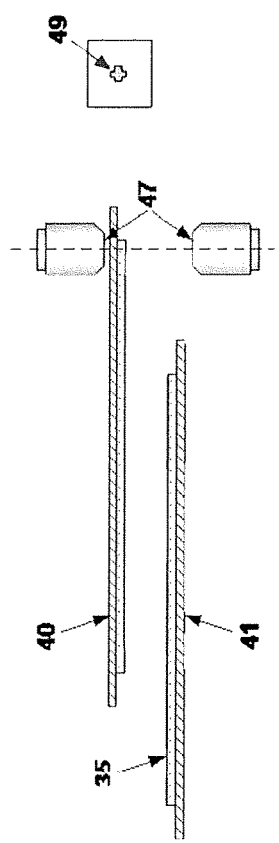
Figure 57C:
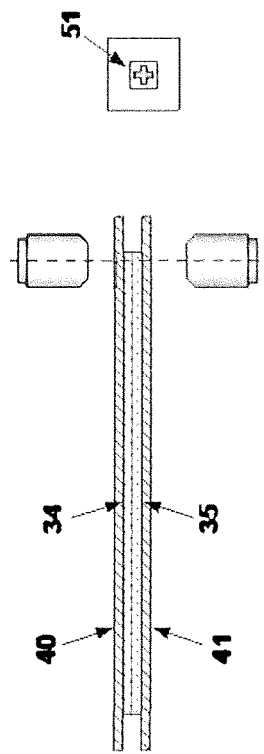

An alternative technique to achieve wafer-to-wafer alignment is illustrated in FIGS. 57A-C. In these illustrations, the movable split field prism and lens devices (46) are replaced by a pair of fixed lens (47) that remain stationary as the wafers are individually moved over or under the field of view of the lens-pair to locate alignment fiducials (49 and 49') disposed at multiple locations near the edges of both top and bottom IC-wafers. Alignment fiducials for the top IC-wafer (49) differ from the bottom IC-wafer (49') and are designed to be superimposed over each other to provide an optical reference for precise alignment in the x-axis, y-axis and theta-angle. When properly aligned, the fiducial images (49 and 49') as shown in FIGS. 57A and 57B would be superimposed, as illustrated at 51 of FIG. 57C.

Disposed on the top and/or bottom IC-wafers (40 and 41) are coatings of a UV-curable, ACA filled epoxy (35) and/or compatible matrix epoxy resin (34), which can be used with or without energy augmentators. In some applications it may be desirable to apply epoxy coatings on both top and bottom IC-wafers with differing compositions and viscosities to enhance the bonding process. For instance, the bottom epoxy coating may include ACA conductive spheres (10 or 11) within a high-viscosity resin matrix, whereas the top IC-wafer may be coated with a compatible resin that has a lower viscosity and does not contain any ACA conductive spheres. The differing compositions and viscosities of the coatings allow for a reduction in the amount of ACA spheres required to achieve reliable interconnect between stacked chips or wafers, enables better retention of individual ACA spheres where required on the bumped pads during application of the compressive force during bonding, and helps to reduce formation of voids within the cured epoxy.

As described earlier, once the top and bottom wafers are optically aligned with respect to one another, the surfaces are brought together and compressed under an applied force to enable the ACA polymer spheres to deform and establish electrical continuity between juxtaposed pads of the individuals IC devices on the wafers; thereby establishing a 3-D interconnect between surfaces. Since the pads that are to be joined may not have identical coefficient of thermal expansion (CTE) values, the polymer spheres provide a compliant interface that helps to absorb expansion mismatch during thermal cycling, thereby maintaining proper electrical continuity.

The resin and the photo-initiator materials were obtained from BASF. The materials were weighted in the proper ratios using a balance having +/0.1 grams measurement accuracy.

The materials were mixed in a laboratory environment with DCA (a class 10,000 clean room). All materials handling was done in a fume-hood. The laboratory had a fluorescent light source to light the room while the fume hood had a controlled light (no UV component to it).

The substrates used to demonstrate bonding included glass, polycarbonates, poly ethylene terephthalate, polyimides, cellulose (or paper), cross-ply carbon-prepreg composites, PEC, ABS, Mylar, intrinsic silicon, doped silicon, silicon based integrated circuits.

In some cases, the materials were mixed in the proper ratios, and then the mixed materials were transferred to syringes and subsequently centrifuged to remove air-bubbles. In other cases, the materials were placed in syringes but not centrifuged. Yet in another case the materials were enclosed inside of the mixing cups. Depending on the specific density of the materials, a high level or a low level of sedimentation was observed.

The materials preparation further included the addition of dispersants in an attempt to control sedimentation. In these cases, the surface of the phosphors was modified to enable the attachment of dispersants. The materials were then mixed inside resin materials and photo-initiators under heat. The materials were hand mixed using a stainless steel spatula that did not react or contaminate the raw materials. No materials contaminations were at play for the most part. The temperature used for mixing varied from room temperature to 80° C. The mixing was better when conducted at elevated temperatures.

Raw Materials Sources:

The sequence of mixing was investigated. Various mixing sequences may work. However, a preferred embodiment of preparation is obtained by heating the resin materials to 80° C. followed by adding the photo-initiators and mixing. The mixing and heating of the resin and photo-initiators is continued until a clear (air bubble free) solution is obtained. Mixing is done gently to avoid shearing the resins and the photo-initiators. Heating was found to have a significant impact in this step. The phosphors are added third followed by mixing. In this case the mixing is continued until the phosphors are well dispersed inside the solution before adding a filler material. Phosphor materials having particle size distributions in the micron scale are best. The filler materials are added last. In the best mode the filler material is $Y_2O_3$:Gd nano-particles and a fractional amount of Aerosil (or active silica). Filler materials in the nanoscale particle size worked best. It is of interest to note that in this case the $Y^2O_3$:Gd consists of 5 to 60 nm particles and that the Aerosil material has fibrous like morphology. It is also of interest to note that the $Y_2O_3$:Gd particles can agglomerate and could form micron level aggregates.

The mixing of raw materials was performed with the fluorescent room light on, although ideally it would be in the dark. Yet, the elapsed time under room fluorescent light did influence the outcome of the cure extent. In essence, the UV light from the room assisted in photo-initiating the chemical reaction. The longer the elapsed time for mixing under uncontrolled light, the more cure extent was achieved under X-ray energy. A controlled photo-catalysis initiation was performed to take advantage of this discovery. This was called "flashing" the material with a UV light prior to curing under X-ray.

The initiation of the photo-catalytic reactions in adhesive materials was achieved through UV-flashing by the following sequence in the preparation. The raw materials were prepared under controlled light only. The photo-catalysis initiation was performed using a set time exposure to UV light soon after the dispensing/application of the adhesive or during the dispensing/application of the adhesive prior to the placement of the top substrate. The sandwiched part was then placed under X-ray energy and cured farther. The materials that were subjected to flashing cured faster than those that were not subjected to flashing. Based on cure hardness, the flashing of select chemistries was done in less than (7.5 min) while the same select chemistries took longer (12.5 minutes) when no flashing was applied.

Figure 58C:
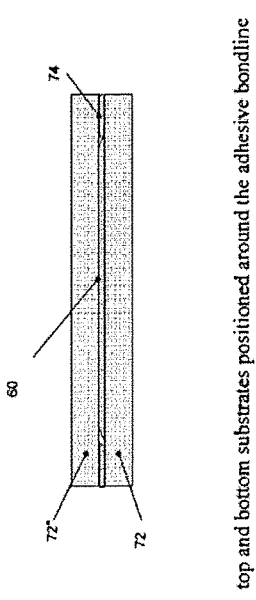
FIGS. 58A-C provide representations of another embodiment of an X-ray aligner and bonder according to the present invention.
Figure 58B:
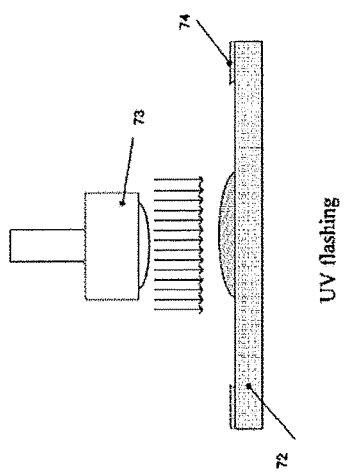
Figure 58A:
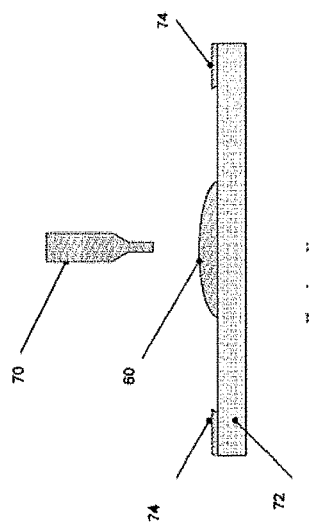
Figure 59:
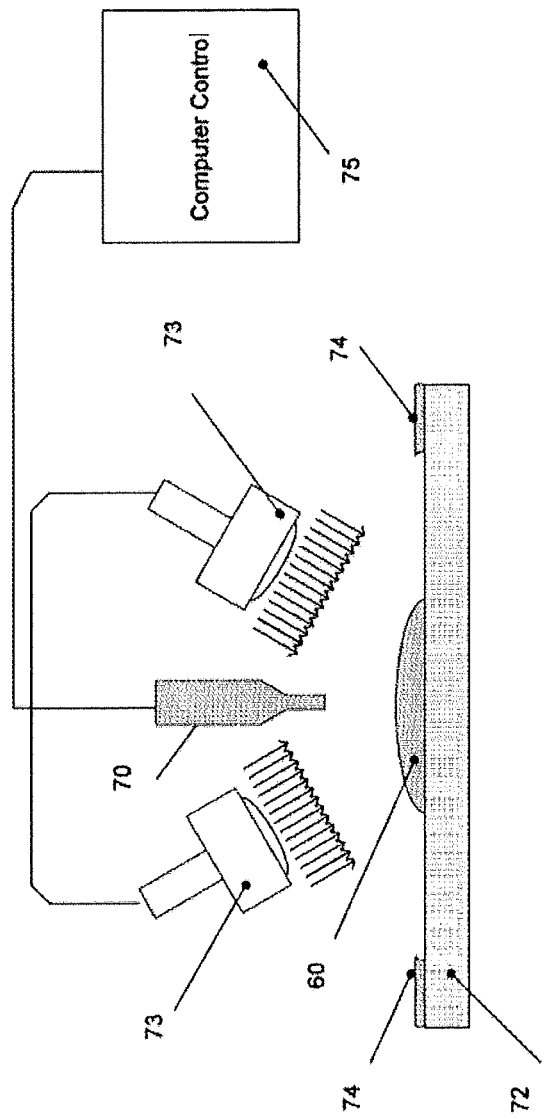
FIG. 59 provides a representation of an embodiment of a stationary dispense system having computer control and the ability to program LTV intensity and UV source with ON/OFF time.

The flashing is further exemplified in the following FIGS. 58A-C. A hand held or automatic piston pump dispenser 70 was used in this case. The adhesive bead 60 was dispensed on substrate element 72 illustrated in FIG. 58A. The substrate in this case was polycarbonate. However, it can be appreciated that the inventive method is applicable to other substrate materials including composites and PET among others. The dispenser applied the bead using a needle gauge 22. No phosphor segregation was observable using a piston pump of the appropriate gauge. In FIG. 58B the bottom substrate 72 had a spacer element 74 made of Kapton and having a thickness of 90 microns.

A UV source 73 can be used to apply energy from within UVA range centered around 365 nm. See FIG. 59. After 15 seconds to 25 seconds of UVA exposure another substrate element 72" was applied on top. The assembly hence formed was taken to the X-ray system for curing. It is recognized that the UV flashing can be done for longer times as needed; however, there a practical limitation to UV flashing.

Figure 60:
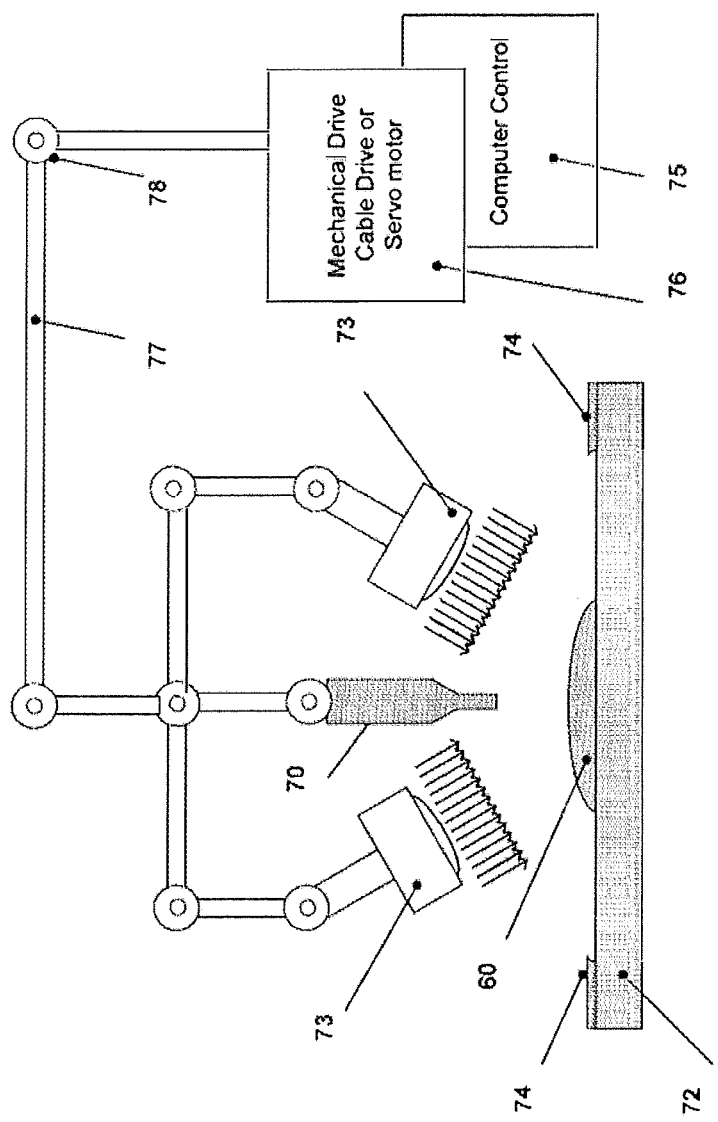
FIG. 60 provides a representation of a further embodiment of an automatic dispenser having a mechanical drive system and computer control, particularly useful for UV flashing.

Combining a UV light with the dispensing step is possible (FIG. 60). By adding at least one UV light source to an automatic dispenser and by adding the necessary control logic 75 to turn on the UV light in a controlled manner (UV intensity and UV elapsed time) at the end-of or during the adhesive dispense, this UV flashing can be easily be scaled to high volume manufacturing.

The UV flashing is an effective method that allows the reaction to be boosted from a cost effective source. Subsequently to the flashing and almost immediately, the substrates to be joined are preferably placed against one another. The adhesive bead is then placed inside an X-ray system. The X-ray energy can effectively complete the reaction of an adhesive bead that is inside a no line of sight region of an assembly.

The ability to dispense and flash the adhesive can be done with a high degree of repeatability using an automatic dispenser having a mechanical drive consisting of a servo motor or a cable drive. In this case, the robotic system in FIG. 60 is equipped with mechanical coupling mechanisms (or articulations) 78 and a mechanical arm 77 to enable the placement of the adhesive dispense needle in a precise manner over a large area. The mechanical system further comprises a drive system 76 based on a servo motor or simply a cable drive.

Figure 61:
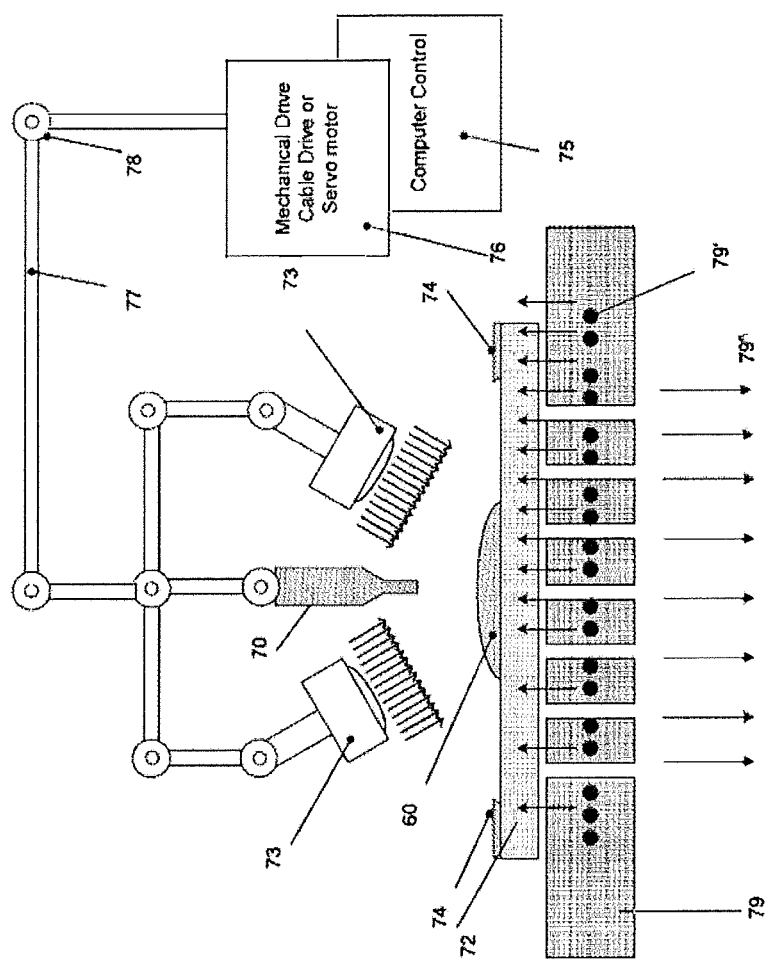
FIG. 61 provides a representation of another embodiment of an automatic dispenser having a mechanical drive system with computer control and a heated platen with vacuum apertures.
Figure 62A:
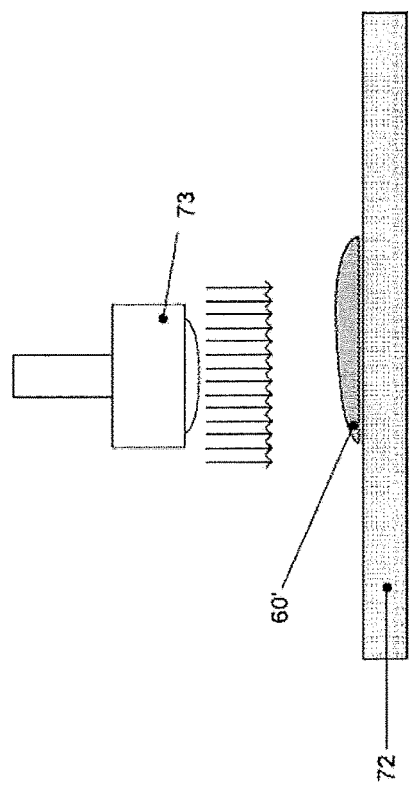
FIGS. 62A-D provide representations of an embodiment of the present invention whereby a screen printer is used for application of the adhesive composition and UV flashing is used to effect a partial cure prior to application of the second substrate and irradiation with X-rays.
Figure 62C:
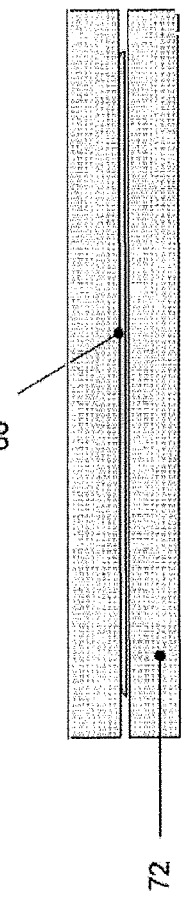
Figure 62B:
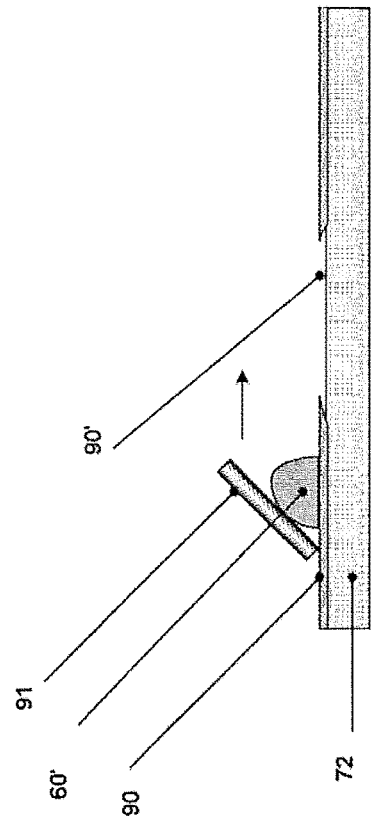
Figure 62D:
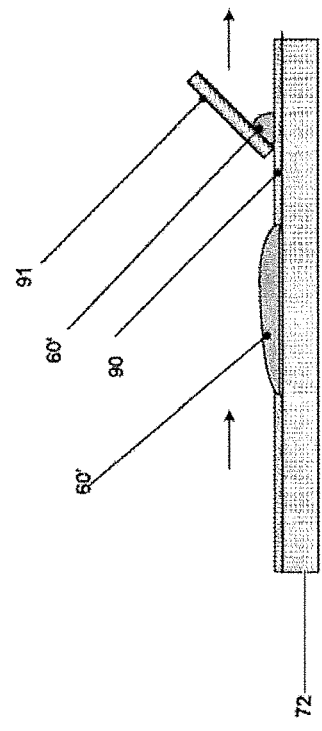

The system can further comprise a platen 79 that is equipped with vacuum ports 79' and a source of heat 79" such as a "thermode" (refer to FIG. 61). The vacuum helps secure the substrates in place. The thermode increases temperature of the substrate. Adhesives at slightly elevated temperature can flow much more readily than at room temperature. The viscosity of adhesives is typically lowered at elevated temperatures until curing starts taking place in which case the viscosity starts increasing. This is beneficial in specific applications but not others. Some applications require the wicking of adhesives through capillary forces underneath substrates or into porous materials.

In most applications, the adhesion curing is promoted by elevating the temperature. To avoid running into the coefficient of thermal expansion mismatch between two substrates, the upper most temperature to which the substrate can be heated should be below its glass transition temperature (Tg). Below Tg the substrate expands at one coefficient of thermal expansion and above its Tg the substrate's at a higher coefficient of thermal expansion. As long as the temperature remains below Tg, the adhesion could be promoted.

The UV flashing is accompanied by the curing of the outer layer (or the formation of a skin). This outer layer or skin reaches higher cure extent than the inside portion of the bead. Upon the formation of this skin, the bead becomes unpractical because of the hardened outer layer becomes an impediment to the controlled placement of the top substrate. The formation of an adhesive bond line through the juxtaposition of 2 substrates becomes hard to do.

In other examples, the steps described above were repeated without any UV flashing. So that the adhesive bead was prepared under controlled light inside the fume-hood and kept shielded from light exposure until it was exposed to the adhesive bead to X-ray energy. In this case, the adhesive curing was conducted for 12.5 minutes, a time found to be adequate for mechanical bonding in this example.

The flashing can be beneficial for other applications described in the following example and illustrated in FIGS. 62A-D. 30 A screen printer can be used instead of an adhesive dispenser. The substrate element 72 is positioned under the screen 90. A screen aperture 90' can be positioned above the substrate 72 but not contacting it. A blade 91 is passed with an adequate pressure to force the adhesive through the screen aperture. The screen is subsequently removed. The dispensed adhesive 60' is exposed to UV energy for a controlled time (between 15 and 25 seconds). The top substrate is then positioned on top of the adhesive. The sandwiched bead can be cured in X-ray for 7.5 min and successfully bond the two substrates.

Figure 63B:
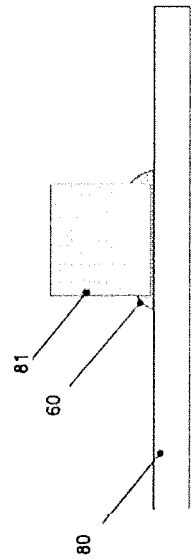
FIGS. 63A-C provide representations of an embodiment of the present invention bonding a PET component to a cross-ply carbon composite component.
Figure 63C:
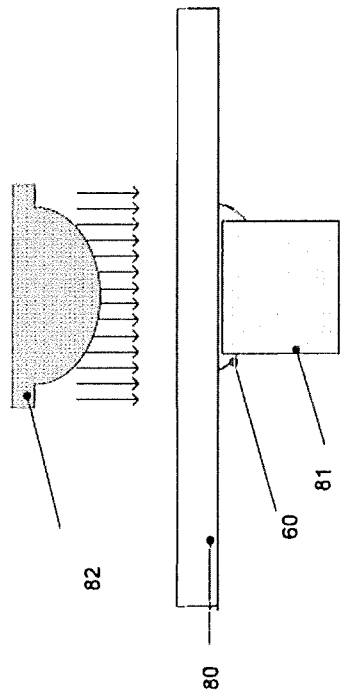
Figure 63A:
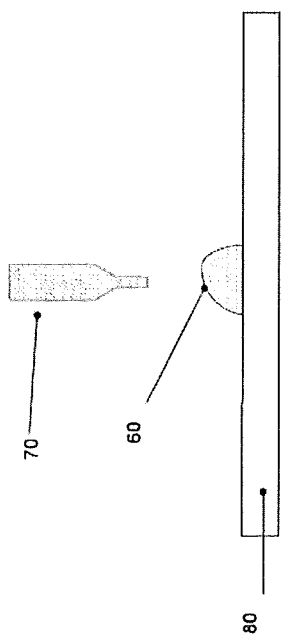
Figure 64:
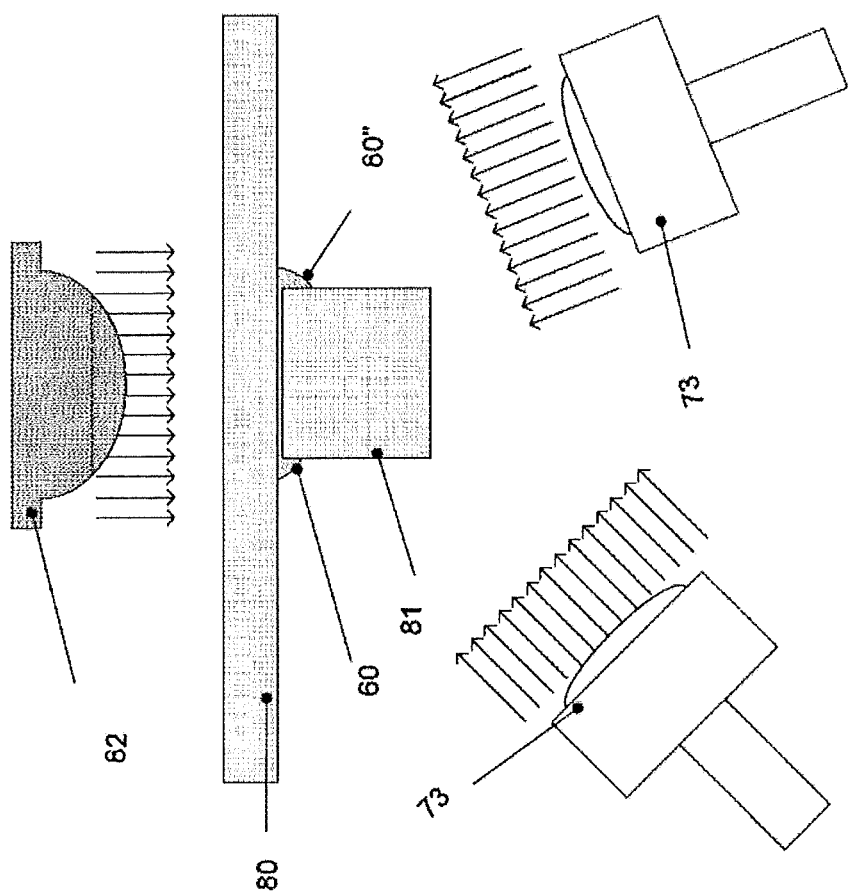
FIG. 64 provides a representation of an embodiment of the present invention whereby fillets having direct line-of-sight are further cured by direct application of UV energy.

In one case, the substrate was cross-ply carbon composite 80 in FIG. 63A-C. The adhesive 60 was applied to the adhesive. Subsequently, a component made of PET 81 was placed on the uncured adhesive bead. The assembly hence formed was turned around and placed under an X-ray source for curing. No flashing was used in this case. The adhesive bead cured in 15 minutes.

Accordingly, in one embodiment of this invention, the X-ray curing system can have an additional source of radiation, namely a UV radiation source. UV radiation from the UV source 73 can be used in conjunction with the X-ray radiation from X-ray source 82. This enables the cure of adhesive beads that have a portion that is exposed to the outside world and a portion that has no line of sight. An example is described in FIG. 64 where a fillet 60" has direct line of sight and can be cured using radiation.

The fillet 60" plays in an important role in flip chip applications where stresses are maximal at the corner of the IC chips. The curing of the fillet 60" can be done using an adequate recipe to minimize stresses. This would imply that the curing using UV radiation can be done simultaneously, before or after the x-ray radiation whichever minimizes the inherent stresses.

Figure 65C:
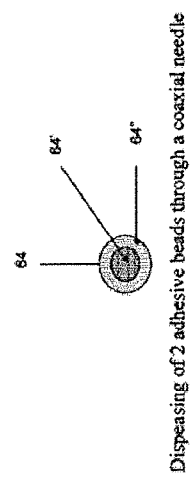
FIGS. 65A-C provide representations of an embodiment of the present invention whereby the 2 adhesives are administered either through separate dispensers (FIG. 65A) or to through 2 coaxial dispensers (FIGS. 65B-C).
Figure 65B:
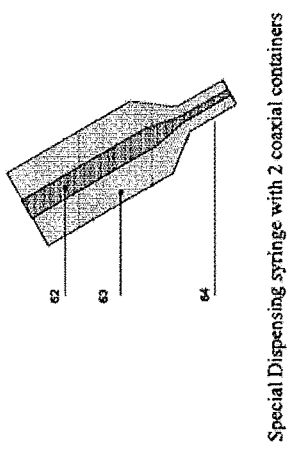
Figure 65A:
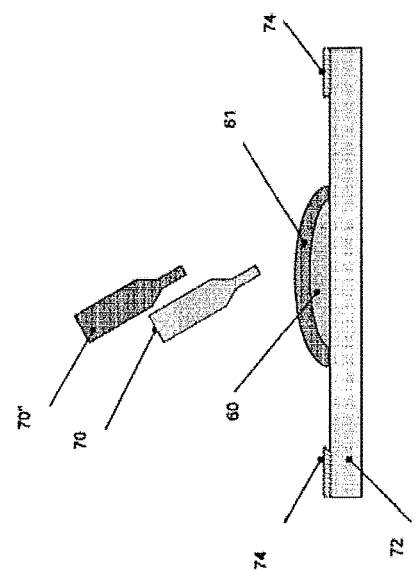

In some cases, dispensing two (2) adhesive beads can be desirable. A dispenser 70 contains adhesive 60 while dispenser 70" contains adhesive 61. The two (2) beads are dispensed in one embodiment sequentially. The dispenser 64 has 2 chambers and 2 coaxial needles as illustrated in FIG. 65A-C. The inside container 62 contains adhesive 61 while the external container 63 contains adhesive 63. Furthermore, the dispenser 64 has a coaxial needle containing needle 64' and 64" through which adhesives 61 and 60 with or without energy augmentators flow respectively.

The adhesives were applied to the substrates using various methods from simple to more complex. In the simplest form, the adhesive formulations were scooped from the mixing cup using a spatula and deposited on the top surface of one substrate. In other cases, the adhesives were placed in syringes and hand pressed through a needle with an 18 to 22 gauge. In other cases, the materials were dispensed through the needle of EDF air piston pump (also using 18 to 22 gauge needles). In some cases, the substrates had a spacer element sandwiched between the substrates to keep the materials from being squeezed out from between the substrates. The adhesive cure was demonstrated for adhesive bead thicknesses from 60 microns to 1000 microns.

These thicknesses represent adhesive beads that would be compatible with applications such as hermetic sealing applications.

In some cases, the adhesive bead was applied between two (2) polycarbonate substrates and kept in this configuration for 24 hours. No-flow or displacement was observable. The adhesive bead was therefore made to provide the end-user with enough work and pot life, after dispensing, to tolerate interruptions of the work in process during manufacturing. This is significant because no scarping of the work in process after dispensing is required.

| Formulations | 1 | 2 | 3 | 4 | 5 | 6 |
|---|---|---|---|---|---|---|
| Resin | 5 | 5 | 5 | 5 | — | — |
| Resin (shadow cure) | — | — | — | — | 5 | 5 |
| PI (369) | 1.3 | 1.3 | 1.3 | 1.3 | — | — |
| PI (2959) | — | — | — | — | 0.5 | 0.5 |
| LaOB:Tm | 1.5 | 2.5 | 3.5 | 2.5 | 2.5 | 2.5 |
| $Y_2O_3$ | — | — | — | 0.3 | — | — |
| AEROSIL | 0.2 | 0.2 | 0.2 | 0.2 | 0.2 | 0.2 |
| CABOSIL | — | — | — | — | — | — |
| MEKP | — | — | — | 0 | 0.1 | — |

It was found that recipe numbers 2, 3 and 4 cured faster than other formulations. However, adhesion was compromised when excess photo-initiator was used. For this reason, recipe 4 worked best. It cured faster that recipe 2, and had better adhesion than recipe 3.

The more uniform the dispersion the better results in terms of adhesion. When clusters of phosphor rich and or phosphor poor areas were noticeable, the cure was localized and the overall adhesion over a surface area was not good. When the photo-initiator saturates the mix (excessive amount of photoinitiator), the adhesion at surfaces is compromised as there is a migration of un-reacted photo-initiator at the surfaces.

Materials Information:

The first substrate is positioned in place. The location of the substrate and the mechanical registration is recorded. The adhesive is then applied to the first substrate. The adhesive may contain a contrast agent to resolute a bead pattern on top of the first substrate. In such case a first substrate that is black should not have an adhesive color that is black. A white or off-white colored bead would be more suitable. A whitening agent like $TiO_2$ can be used as the

| | Resin percent in Adhesive | 2100 percent in adhesive | 184 Weight percent in adhesive | Ratio of Adhesive % | Phosphor % by Weight | Phosphor Type | Cure Hardness |
|---|---|---|---|---|---|---|---|
| Around 100 microns | 0.94 | 0.02 | 0.04 | 0.75 | 0.25 | $CaWO_4$ | Yes |
| Between Glass Slides | 0.94 | 0.02 | 0.04 | 0.6 | 0.4 | $CaWO_4$ | Yes |
| | 0.88 | 0.04 | 0.08 | 0.75 | 0.25 | $CaWO_4$ | Yes |
| Around 250 microns | 0.94 | 0.02 | 0.04 | 0.75 | 0.25 | $CaWO_4$ | No |
| Between Glass Slides | 0.94 | 0.02 | 0.04 | 0.6 | 0.4 | $CaWO_4$ | No |
| | 0.88 | 0.04 | 0.08 | 0.75 | 0.25 | $CaWO_4$ | Yes |

In some cases, bonding was achieved using a polyimide film, while in other cases the spacer elements were glass beads. The curing of the adhesive thickness of the adhesive beads was successfully demonstrated at 60 microns to 250 microns. These thicknesses represent adhesive beads that would be compatible with applications such as B-staged films and chip on board applications. In other cases, the adhesive bead was between 500 microns to 1000 microns.

contrasting agent. In this case the color of the substrate is irrelevant, since the inspection can be performed using X-ray radiation, the inspection of the bead can simply be done regardless of the visible color contrast.

Figure 66:
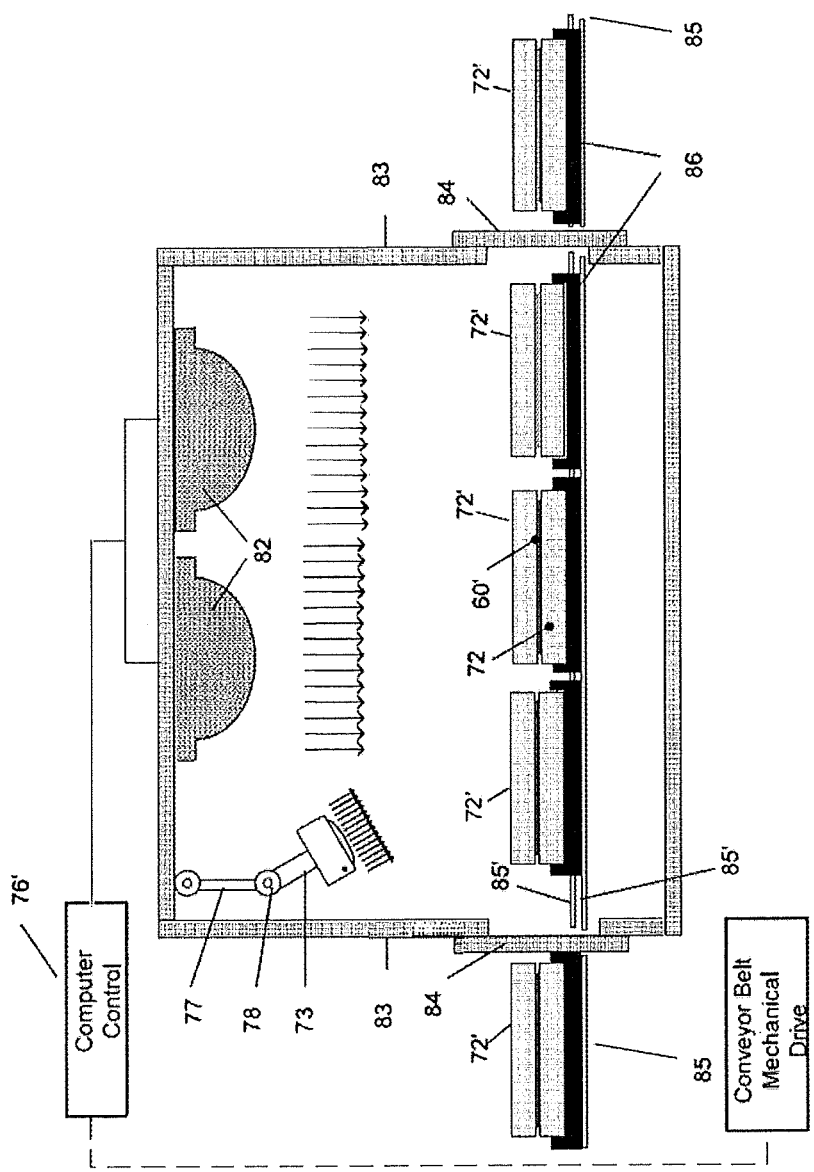
FIG. 66 provides a representation of one embodiment of X-ray system for use in the present invention having automated doors and an internal UV lamp.

The second substrate is then positioned in place on top of the adhesive bead and the first substrate. The assembly is transported under the X-ray system that would perform a combination of X-ray based steps namely inspection and cure or one step consisting of curing. The X-ray system comprises various elements that can be automated to satisfy manufacturing requirements. FIG. 66 illustrates some of these elements that form the X-ray curing system intended by the invention.

The step of X-ray radiation is preferably done in an enclosure 83 that stops the radiation from leaking to the outside world. The enclosure 83 can be made of various materials that include heavy metals such as lead. A single assembly 72' can be held static or can be moved during cure inside the enclosure. Such movement could include a rotation movement that can be achieved using a turn table. Such movement could also include a translational movement that can be achieved using an external conveyor belt 85 and an internal conveyor 85'. Both the internal and the external conveyor belts work in synch to shuttle parts in and out of the X-ray enclosure. The door 84 can open up and close down to shuttle assemblies 72' in and out of the X-ray radiation chamber. When the door is open (or up position) the X-ray energy is off to adhere to safety measures. The X-ray enclosure can have automated doors with sensors linked to a controller 76'. The enclosure can have doors that open up and down to shuttle at least one assembly in and out of the X-ray enclosure for irradiation leading to curing. Furthermore, the assembly to be cured can be positioned inside a process fixture 86. The process fixture carries with it the assemblies 72'.

Figure 67B:
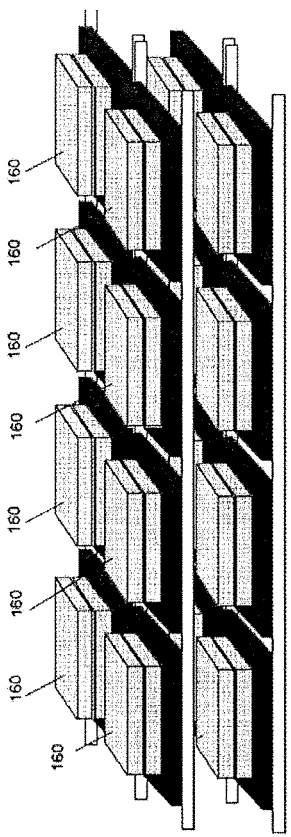
FIGS. 67A and 67B provide representations of embodiments of conveyor systems for use in the present invention.
Figure 67A:
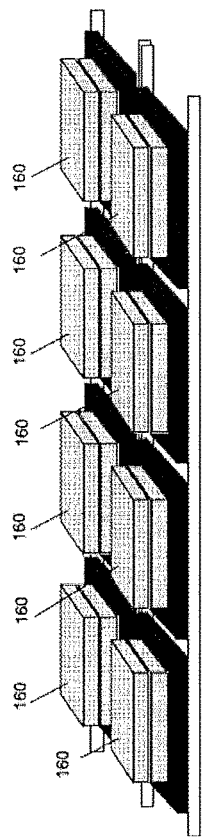
Figure 68:
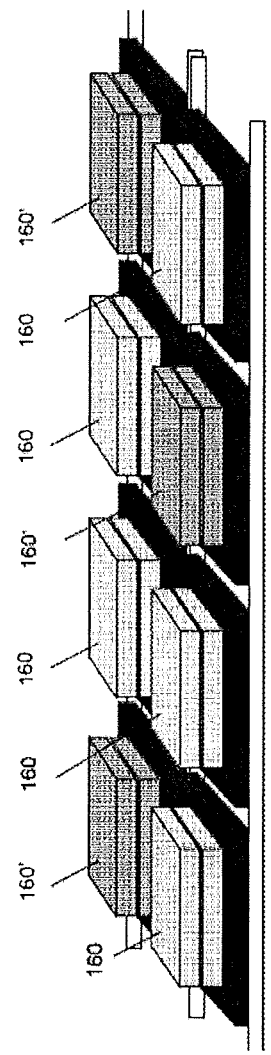
FIG. 68 provides a representation of an embodiment of the present invention using more than one X-ray source for curing of different assemblies at the same time.

More than one assembly can be placed inside the X-ray machine. The configuration having multiple assemblies can vary to maximize the loading of parts inside the X-ray curing system. As illustrated in FIGS. 67A and 67B, two (2) conveyors are juxtaposed one next to the other to increase the packing factor (number of assemblies) inside the X-ray system within plane. Because of the depth of penetration at the correct levels, conveyors can be disposed within planes (FIG. 67A) and across planes (FIG. 67B) inside the X-ray curing system.

An additional advantage of X-ray curing resides in its ability to cure various size adhesive beads residing within different products using the same curing parameters. As an alternative embodiment, the X-ray machine can have more than one source, permitting curing of different assemblies at the same time (see FIG. 68). This presents an advantage and enables the manufacturer to cure a different product mix inside the X-ray curing system. Assemblies 160 and 160' can be cured at the same time. This means that a product changeover is easier and means that the system is flexible in meeting cure requirements.

X-ray systems with the capability of programming recipes including pulsing up to 30 times per sec can be done. A level of control over the kVp as well as amperage can be done to exert control over output power as well as photon energy which in turns means control over depth of penetration.

Additionally, curing time and efficiency can be adjusted as desired by adjustment of various parameters, including, but not limited to, temperature, radiation source intensity, distance of the radiation source from the adhesive composition to be cured, and photon flux generated by the radiation source.

An X-ray delivery head is on one side of the assembly, either above the adhesive bead or below the adhesive bead which can be described (though not exact) that the adhesive bead is generally perpendicular to the direction of propagation. In some cases, the adhesive bead is generally parallel to the X-ray radiation path. It is recognized however that the X-ray radiation is emitted in a flood beam have multiple directions around one predominant direction of propagation.

Figure 69C:
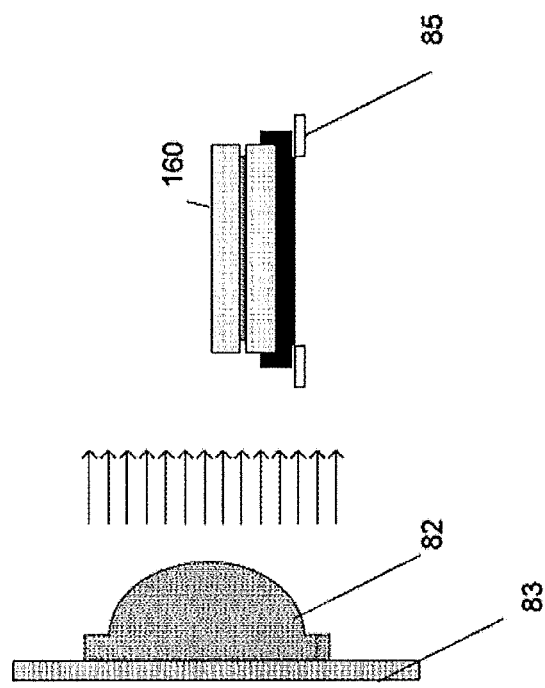

Metals and metallic coatings limit the penetration of X-ray radiation. For this reason, X-rays need to be oriented appropriately when curing integrated circuits having metallic traces and coatings. In these case scenarios the preferred orientation of the bead is parallel to the X-ray direction of propagation. As illustrated in FIGS. 69A-B, two configurations are possible. In one case FIG. 69A, the assemblies are oriented vertically to achieve the preferred orientation, while in the other case FIG. 69B, the X-ray source(s) is mounted in the appropriated orientation to achieve the desirable alignment between bead and direction of propagation. FIG. 69C provides a different view of the alignment between assembly 160 and the X-ray.

Wafer Bonding

Figure 70B:
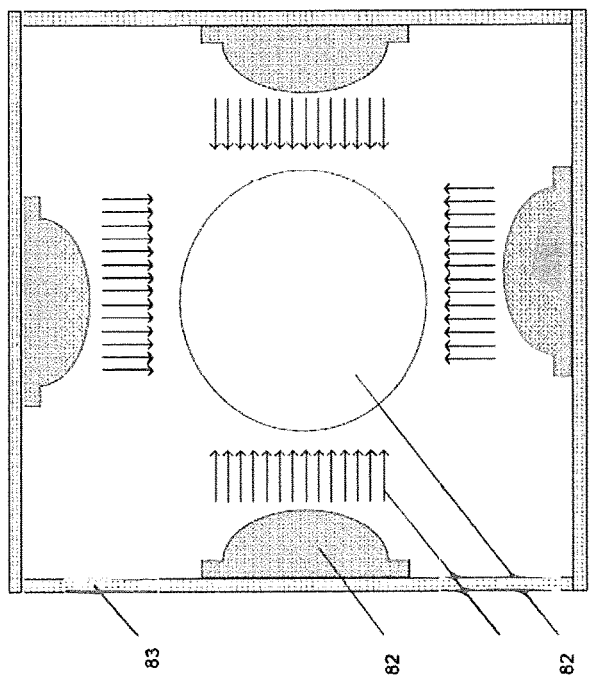
FIGS. 70A and 70B provide representations of an embodiment of the present invention of a wafer bonding tool having a rotating table and rotating arm, FIG. 71 provides a representation of an embodiment of a die to wafer bonding tool that can be used in the present invention.
Figure 70A:
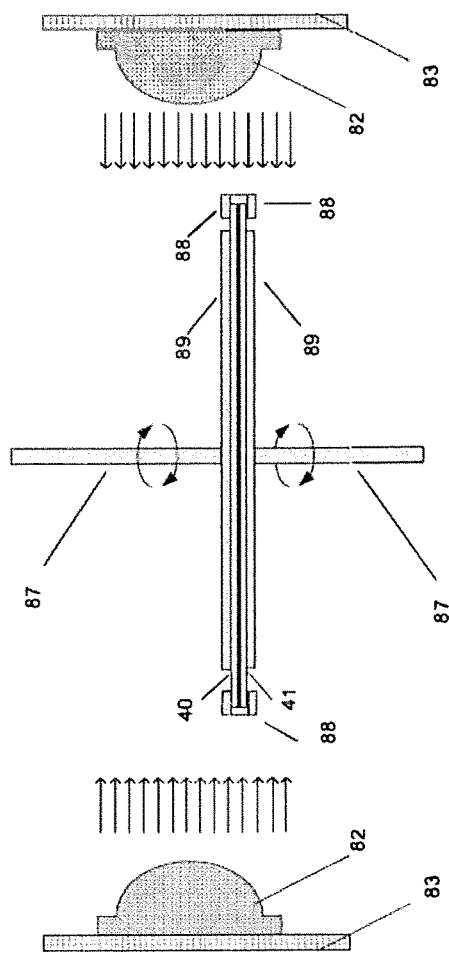

After the wafer alignment is completed (using the method described in FIGS. 56A and 56B), the wafers are clamped together using a clamping fixture 88. The clamping fixture allows the wafers to remain aligned during transport. The clamping fixture contacts the wafers on the wafer back side with a depth typically within the exclusion zone of the wafers. The wafers can be placed on a rotating table 89 with a rotating arm 87 as illustrated in FIG. 70A and FIG. 70B. The rotating table is capable of taking withstanding pressure up to 40 kN. The pressure can be applied using 2 mirror image rotating tables. The clamping fixture 88 can be removed once the 2 rotating table have been engaged.

Since X-ray curing is done at room temperature or done at below the glass transition of the polymers used for bonding, not much pressure is required after the placement of the wafers on top of one another. Similarly, when a die is placed on a wafer surface, not much pressure is required.

Figure 71:
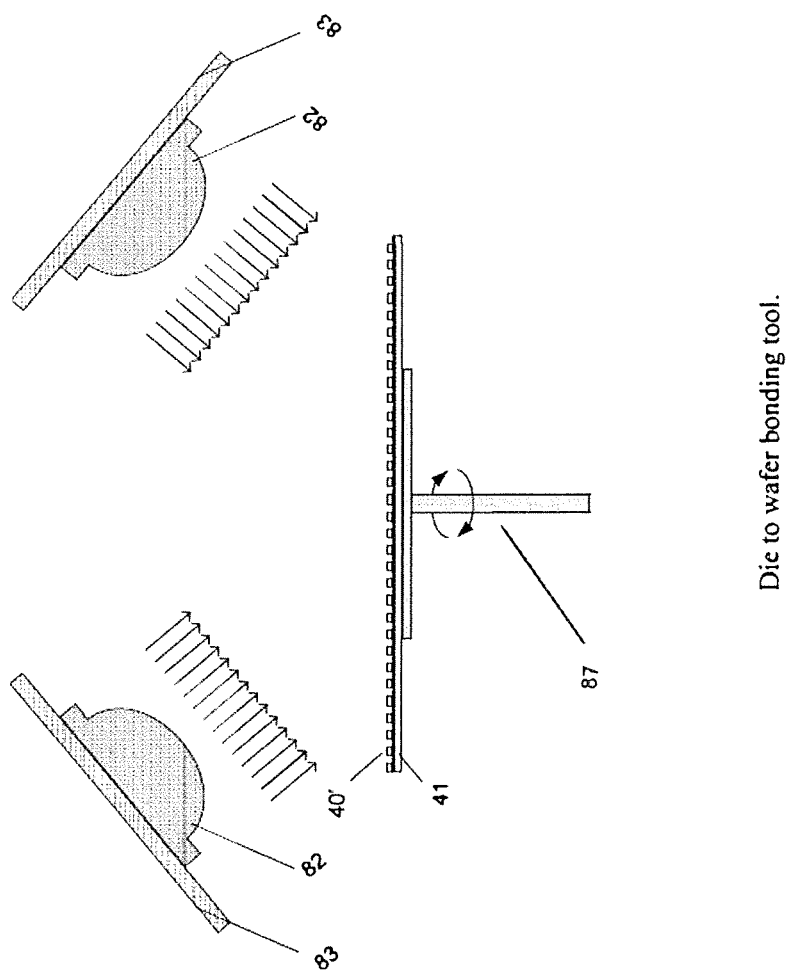

The die on wafer application could use the same wafer set up described in FIG. 71. However in the die on wafer bonding application the X-ray is aligned at an angle which leads to more depth of penetration over the area array of the ICs 40' disposed on top of the bottom wafer 41. The plane of the bond line in this case is at 45 degrees vis-á-vis the direction of propagation of the X-ray.

Designs of X-Ray Systems

Figure 72B:
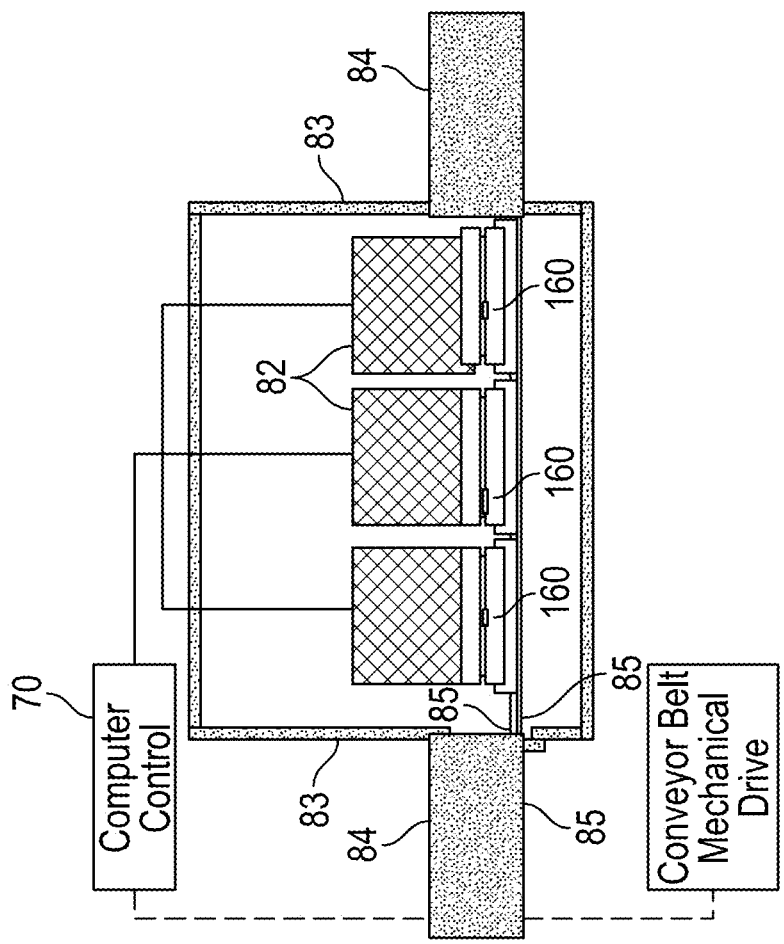
FIGS. 72A-C provide representations of different embodiments of X-ray systems and conveyor systems useful in the present invention.
Figure 72A:
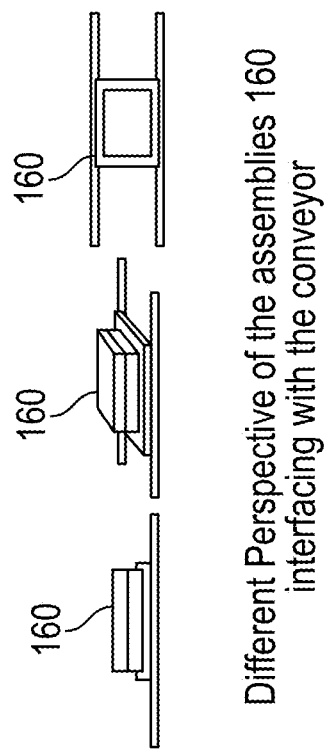
Figure 72C:
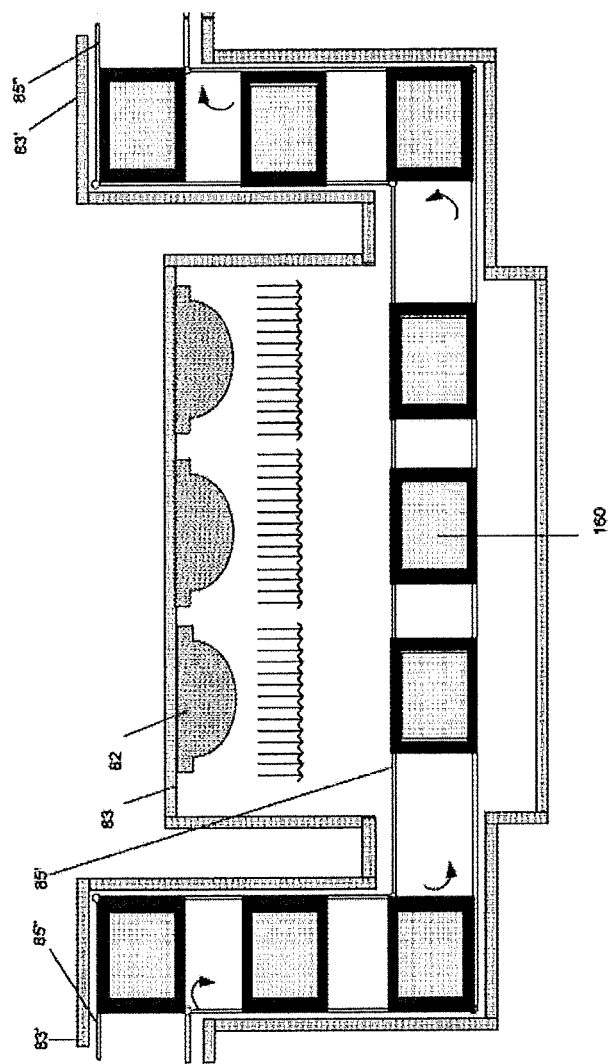

Designs of x-ray systems are shown in FIGS. 72A-C.

A. Contactless Design for Clean Rooms

Figure 73:
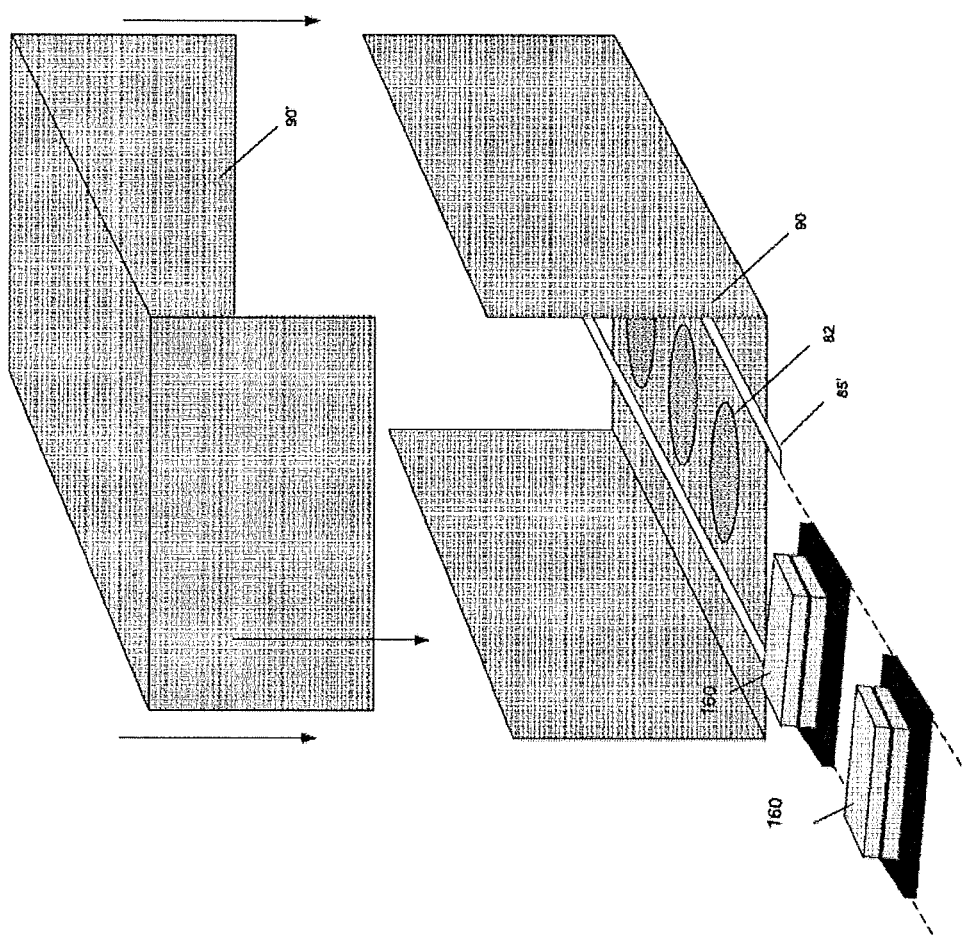
FIG. 73 provides a representation of an embodiment of a contactless chamber design useful in the present invention.
Figure 74:
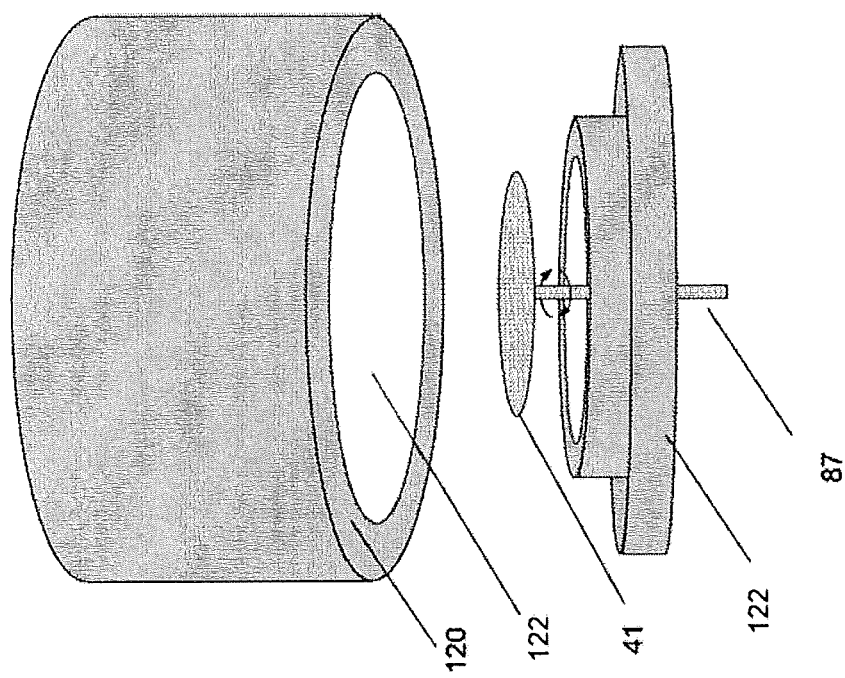
FIG. 74 provides a representation of a further embodiment of a contactless chamber design useful in the present invention.

FIGS. 73 and 74 illustrate an embodiment where containers that can be raised up and down to gate the assemblies 160 enter a processing chamber. Part of the cavity 90' can be raised to enable batching of assemblies 160.

Chamber 120 is fixed in place. The bottom of the cavity of chamber 122 can be raised up and down to enable positioning wafers 41 that enter the processing station. The movable bottom does not touch the upper processing chamber (no contact between 120 and 122.

Bonding Fasteners on Composites

Figure 75B:
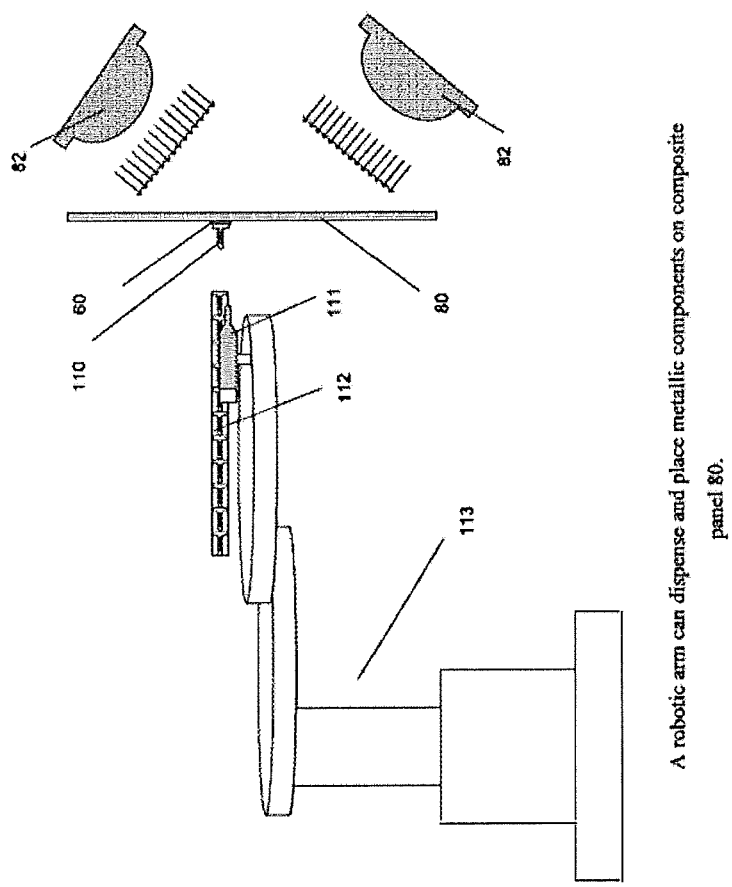
FIGS. 75A-B provide representations of embodiments of the present invention for bonding fasteners to a composite panel.
Figure 75A:
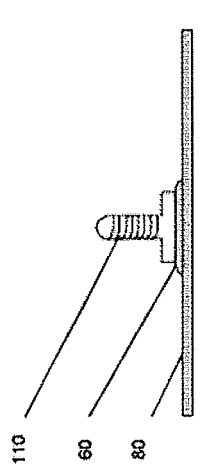

FIGS. 75A and 75B illustrate a process of bonding fasteners on composites. A composite panel 80 is dispensed with adhesive 60. The metallic fastener 110 is placed on top of the substrate 80 using a pick and place system that is pneumatically driven (112). Both the pick and place 112 and the adhesive dispenser 111 are mounted on KUKA robot 113. The X-ray sources 82 are placed at a slight angle to couple to the bottom of the bolt 110.

The following figures show various applications in semiconductors pertaining to packaging and encapsulation. These include: glob top, dam and fill, molding (PMC, insertion molding) and flip chip underfill.

Figure 76:
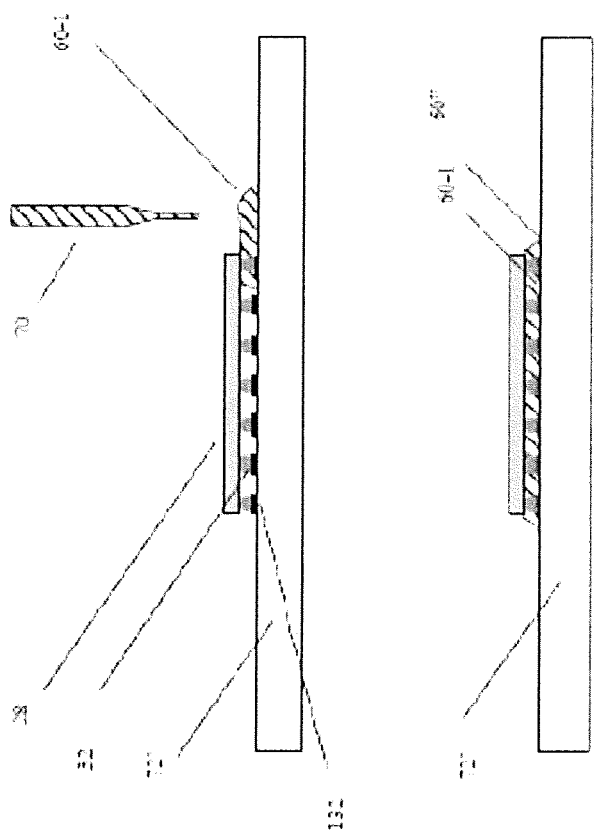
FIG. 76 provides a representation of use of an embodiment of the present invention for production of an underfill assembly.

As shown in FIG. 76, an IC 28 is soldered in place in such manner that bumps 32 enter into electrical contacts with electrical pads 132. A desirable adhesive 60-1 is applied by dispensing system 70. If the substrate is heated to 20° C.

above room temperature the adhesive wicks under the chip by virtue of the capillary forces set between the chip and the substrate 72. Once the adhesive is dispensed and wicked under the IC, the adhesive is ready for curing and optionally an inspection is performed prior to curing. The standard method is to inspect the adhesive using optical means. However, since the adhesive 60-1 is loaded with phosphors that have absorption characteristics in the X-ray regime, the inspection can be performed using X-ray radiation. The inspection using X-ray can reveal any striations that may exist under the IC 28. The uniformity of the adhesive can be determined to see if the adhesive has separated into resin rich or resin poor regions. The adhesive can be subsequently cured with X-ray.

The curing in this case can be done at room temperature and using an x-ray that is best coupled from the lateral side of the IC. In this case the direction of propagation is parallel to the plane of the adhesive bead.

Figure 77:
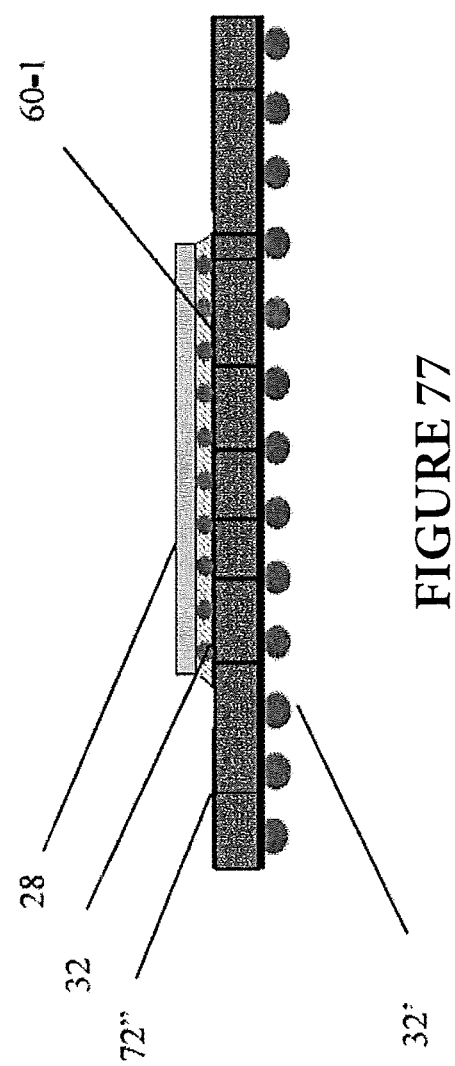
FIG. 77 provides a representation of use of an embodiment of the present invention for production of an underfill on a high density circuit.
Figure 78:
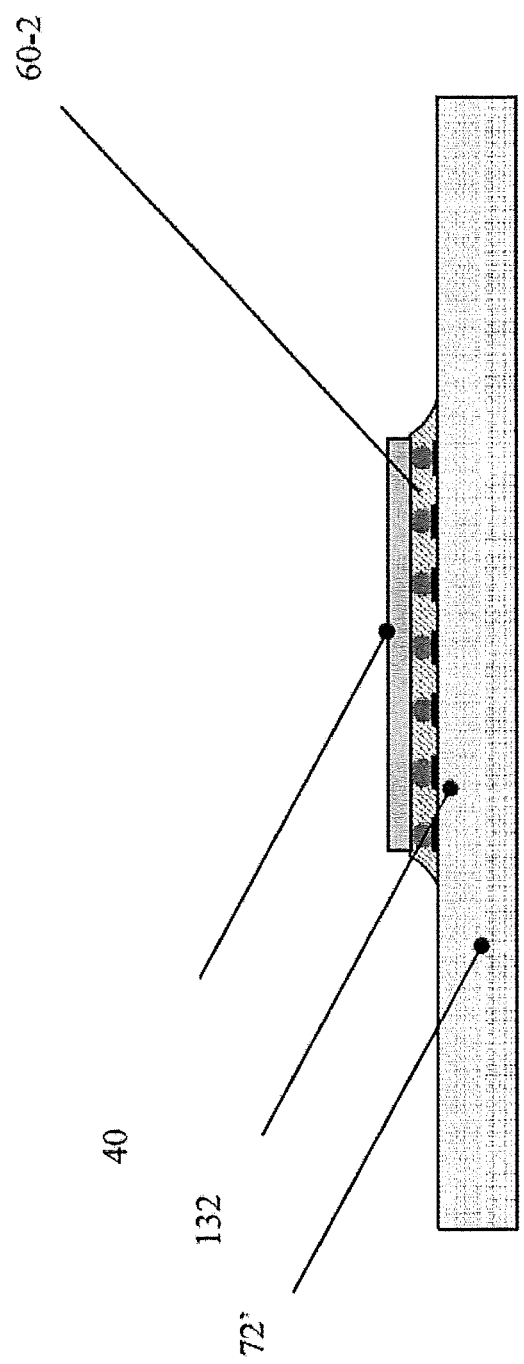
FIG. 78 provides a representation of use of an embodiment of present invention for production of a no-flow underfill assembly.
Figure 79:
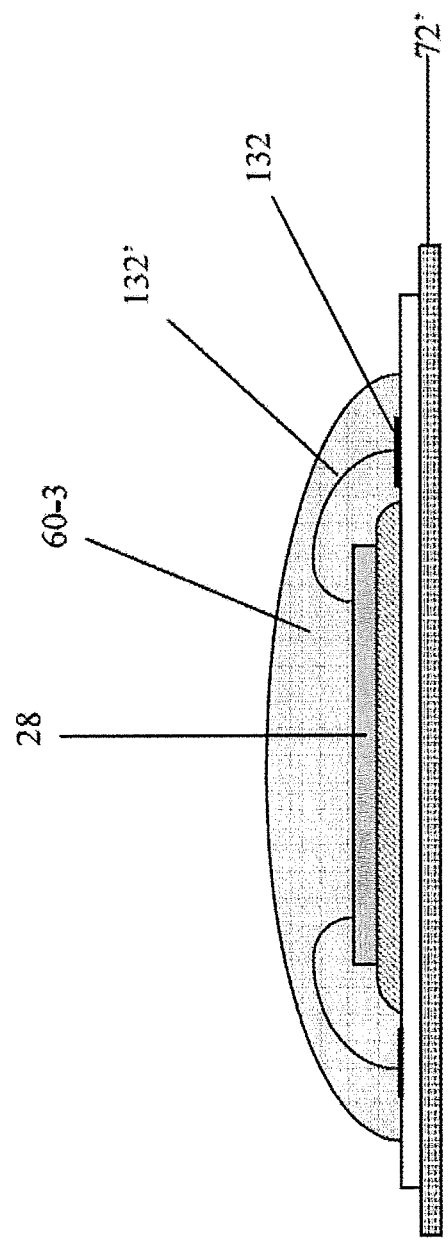
FIG. 79 provides a representation of use of an embodiment of the present invention for glob top encapsulation.
Figure 80:
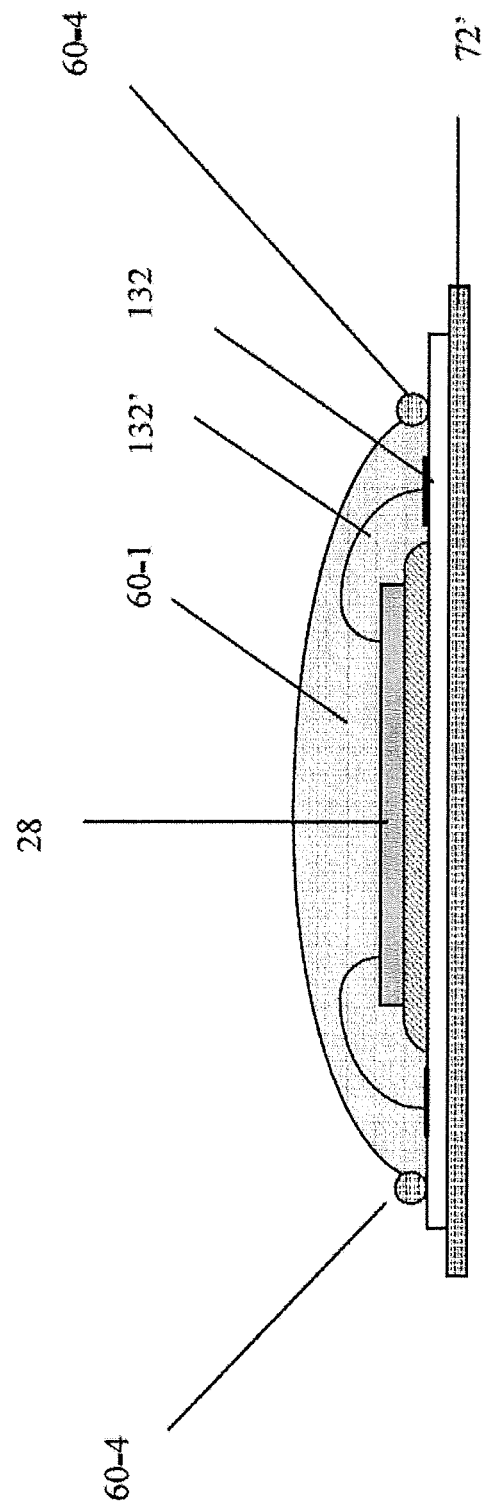
FIG. 80 provides a representation of use of an embodiment of the present invention as a dam-and-fill adhesive.
Figure 81:
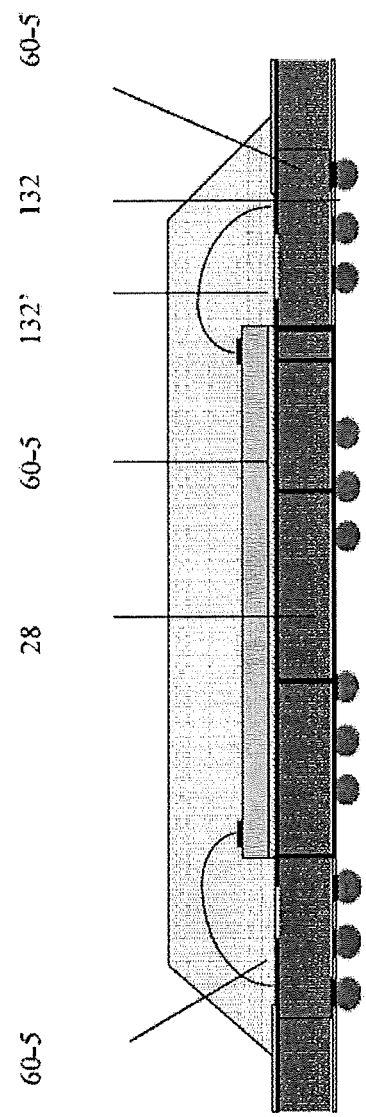
FIG. 81 provides a representation of use of an embodiment of the present invention in encapsulation through molding.

Underfill for a High Density Circuit:

FIG. 77 illustrates a similar process can be applied if the substrate is a high density circuit (72"). Once the assembly is formed, the assembly can be placed on the mother board of a PC or a server using solder bumps (32'). This process is similar to the one used for mounting logic assemblies (e.g.; micro-processors and high density interconnect devices).

No Flow Underfill:

To avoid the combination of time delay that takes place during adhesive wicking and the soldering process to connect the IC (28) onto substrate (72'), an encapsulant (60-2) can be dispensed on top of a substrate (72') above the area array of contact pads (132). See FIG. 78. An optical inspection is performed. A chip is picked using a programmable "Pick & Place" (130) having provisions for vacuum (131). An active alignment is performed before the chip is placed onto a PCB (72') in such manner that the IC bumps (32) enter into electrical contacts with PCB electrical pads (132). The no-flow adhesive can be inspected and cured using X-ray.

Glob Top Application:

Glob top applications comprise dispensing an electronic polymer on top of an IC (28) that has been die attached onto a PCB (72') and wire bonded to establish electrical contacts between the active area of IC (28) and the electrical pads (132) disposed on the PCB board (72'). See FIG. 79. The special adhesive (60-3) containing the appropriate phosphors and photo-initiators can be applied to the IC (28) and enough time is allowed for the electronic polymer to flow and to cover the IC (28) and wire bonds (132'). The assembly is then inspected using X-ray radiation and cured using an X-ray radiation treatment or recipe. The X-ray treatment can consist of pulses of controllable duration appropriate to harden the adhesive without inducing any damage to the assembly.

Dam and Fill Technique:

In some applications it is advantageous to apply a dam (60-4) or the first adhesive bead and subsequently cure the first bead prior to dispensing an encapsulant (60-1) containing the appropriate phosphors and photo-initiators required for X-ray curing. The current technology allows co-curing of both 60-1 and 60-4 using X-ray radiation. See FIG. 80. The amount of phosphors loaded in formulation 60-4 can be deliberately high to cure faster than 60-1.

Molding/Post Mold Curing

Another standardized way of applying the encapsulation is through injection molding. The resin is applied at the mold level. In this case the IC (28) is attached to the substrate (72") and then inserted into a mold. The mold is then clamped at high pressure and a liquid resin at high temperature is injected at high pressures to fill the spaces between the wire bonds (132') and the IC (28). See FIG. 89. The injection molding step is then accompanied by an elongated heat treatment. The present invention is enabled through the use of a low-viscosity resin (60-5) that contains the appropriate phosphors and photo-initiators. After the injection molding at low temperature is performed, the X-ray inspection and X-ray curing can take place. The benefits of using the present invention are various but the most pronounced benefit to release all the stresses that can be established post molding. This eliminates most thermal annealing steps required for stress release. These stress release steps can take up to 4 hours which increases the Work-In-Process and does not lead to favorable economics.

Lid Sealing for MEMS and Miroprocessors

Figure 82A:
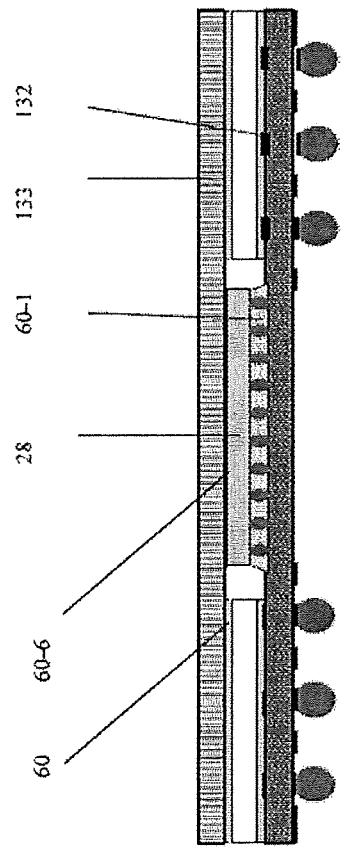
FIGS. 82A and 82B provide representations of use of embodiments of the present invention for lid sealing of logic devices and MEMS devices, respectively.
Figure 82B:
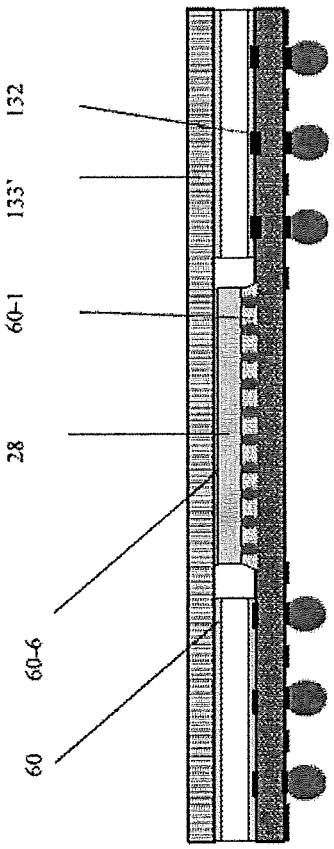
Figure 83:
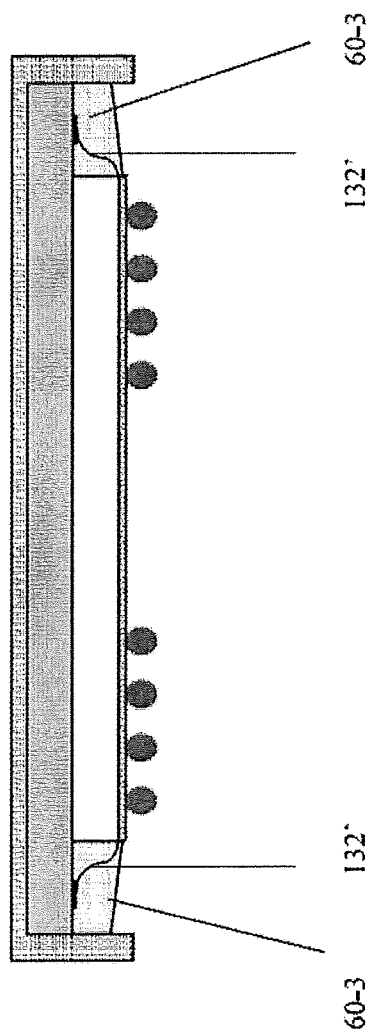
FIG. 83 provides a representation of use of an embodiment of the present invention in glob top encapsulation of a micro ball grid array.
Figure 84:
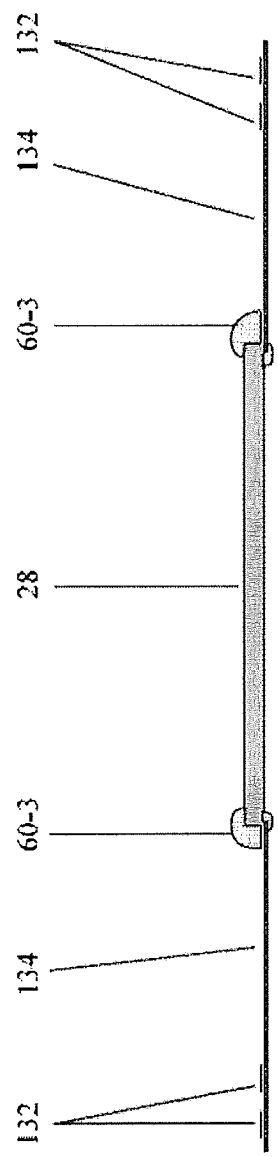
FIG. 84 provides a representation of use of an embodiment of the present invention in encapsulation of TAB bond areas between a flex circuit and an integrated circuit (IC).
Figure 85:
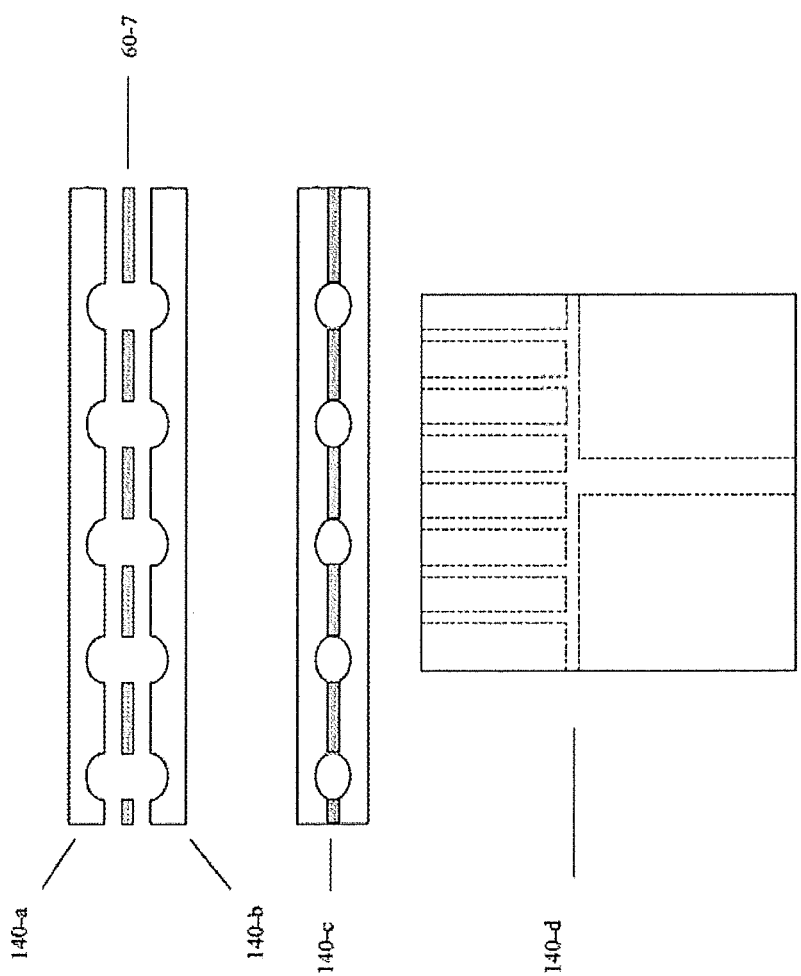
FIG. 85 provides a representation of use of an embodiment of the present invention in bonding of plastic devices having mirror image features using a film adhesive.
Figure 86A:
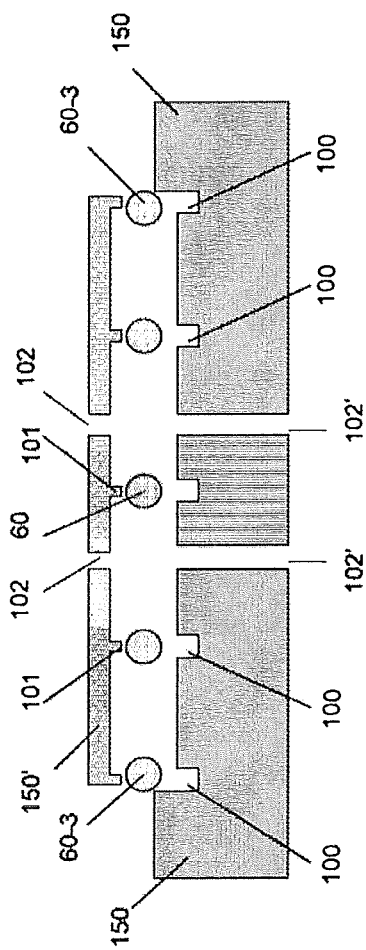
FIGS. 86A and 86B provide representations of use of an embodiment of the present invention in formation of sub-assemblies having fluidic channels.
Figure 86B:
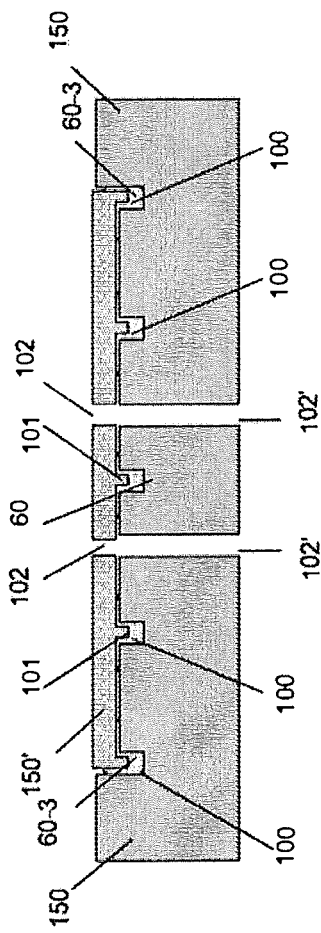

Another application that pertains to semiconductors and MEMS is lid sealing See FIGS. 82A and 82B. In this application three different adhesives can be used. The combination of 3 different adhesives can be used: 1—An adhesive bead (60), 2—an underfill adhesive (60-1), and 3—thermal conductive adhesive (60-6) that connects IC 28 with a lid 133. For semiconductors the lid 133 is typically metallic. For MEMS applications the lid 133' could be glass.

Micro-BGA Fill Encapsulation

A micro-ball-grid-array can be encapsulated in much the same way that was described for the glob top encapsulation. The configuration of the assembly is different than a chip on board application but the encapsulation of the wire bonds 132' remains the same. See FIG. 83. An appropriate encapsulation 60-3 with the proper viscosity is prepared to contain the amount of photo-initiators and phosphors to cure under X-ray.

Tab Bonding:

Tape automatic bonding (TAB) technique can be enhanced by the current application. TAB is used to electrically connect a flexible circuit 134 with a semiconductor IC (28). See FIG. 84. The flexible circuit contains electrical pads 132. The encapsulant 60-3 can be disposed on the TAB area. The application of the encapsulant is then followed by X-ray inspection and cure.

MicroFluidics:

The joining of plastic 140-*a* to plastic parts 140-*b* that has mirror image features can be used to build functional plastic containers that house fluids and that have usable fluidic channels that can channel fluids from one side of the container to the other. The 2 pieces of plastics having mate-able features are joined together using a film adhesive 60-7 to form piece 140*c*. (illustrating a cross sectional view). The film 60-7 has the proper resin and the proper phosphors and photo-initiators. The plastic housing formed is illustrated as part 140*d* (top view). See FIG. 85.

The fluidic channels can be formed using multiple pieces of plastics. The cross section of a PET plastic is shown in 150. The PET has well joints as shown by groves 100. The fluidic channels 102' are aligned with the fluidic channels 102 present on another plastic such as Liquid Crystal Polymer 150'. In turn the sub-assemblies hence formed can be used to form fluidic devices. An example of such subassemblies is provided. Each part of the subassembly can have conduits and interlocking features to allow apertures to be aligned. The adhesive bead 60-3 is dispensed and allowed to cure using X-ray. See FIGS. 86A and 86B.

The subassemblies can be collapsed controllably. The protruding features 101 enter into the well joint 100. These features enable the obtainment of a hermetic seal since a fluid (liquid of gas) has to travel through the split well that is formed when the protruding feature 101 is engaged inside the well joint 100. The travel distance increases and the hermetic seal is enhanced.

Yet another example includes when a flexible circuit 134 having contact pads 132. The flex 134 is TAB bonded to IC 150 using adhesive 60-3. The IC 150 has a resistive heating network that can increase the temperature around fluidic channels or apertures 102. The fluidic channels 102 are aligned with apertures or fluidic channels 102' that exist on plastic parts 145-d. The IC 150 is bonded using adhesive 60. The fluidic channels 102' connect with fluidic reservoirs 152. These reservoirs can contain Ink or insulin. See FIGS. 87A and 87B. When the flex assembly is wrapped around the housing 145-d the adhesive film 60-7 is activated to bond the outer walls of 145d with the flex 134.

The plastic joining does not have to use mirror image plastics nor does it have to use similar materials. In fact, dissimilar materials can be used to form plastic housing for insulin pumps or inkjet containers.

Formation of Ink Jet Cartridges;

Ink jet cartridges are typically made of a plastic housing made of a thermoplastic moldable resin, such as polyethylene terephthalate (PET), polyethylene, or polysulfone for example, as the base material. Polysulfone describes a family of thermoplastic polymers that have toughness, mechanical stability and ink resistance.

Typically, a print head made of silicon, has numerous nozzles that are used as ink outlets. The nozzle array on the silicon and the ink reservoirs are connected through a manifold structure having fluidic channels. The fluidic channels are employed to direct the inks of different colors from the primary reservoirs to appropriate printhead nozzle arrays.

Multicolor cartridges have a plurality of ink reservoirs, often three ink reservoirs. In such three ink cartridges, each of the reservoirs contains a primary color. These reservoirs need to be isolated from one another. The separation between the compartments has to be hermetic to avoid ink mixing between the various compartments. A plastic piece is adhesively bonded to seal the separate reservoirs.

The joint(s) of interest that seals or separates the various reservoirs must be made to withstand the prolonged contact with inks. Inks happen to be aggressive from a chemical stand point. Furthermore, the sealing joint needs to be able to overcome the mechanical stresses that may exist over the product's functional life and the pressure differential that needs to be regulated between atmospheric pressure and the internal pressure in the reservoir.

The ink reservoirs and the ink channels, the plastic structures and manifolds necessary to form the multicolor cartridge can be assembled from multiple injection molded plastic parts. The most economical way is to injection mold as one part all of these parts. However, the lid seal and the tri-chamber separation cannot be injection molded as a unitary body, since it is required to have accessibility to the reservoirs. Regardless, whether the cartridge is formed from three pieces, or more than three pieces, two process methods are typically used to bond plastics: ultrasonic energy welding and thermally curable adhesives.

The problem with ultrasonic welding is that it does not work with dissimilar materials. The other method consists of using adhesive materials to bond the various parts together. The various plastics parts in this case can be of similar or dissimilar materials provided the adhesive is subjected to enough thermal energy.

The application of thermal energy necessary to cure the adhesives leads to thermal expansion of the plastic parts. The thermal expansion mismatch between different materials results in thermally induced stresses locked at the interface of the various materials.

The print head is connected to a flexible circuit using a TAB bonding method. The print head rests on an adhesive bead that bonds the print head to the manifold containing fluidic channels. The print head contains nozzles that can be fired by the electrical signal that feed a resistive network built on the silicon. The electrical signals that are selectively applied to specific nozzles results in the heating of the select nozzles and therefore leads to the controllable ejection or squirting of ink droplets. The ink droplets are directed to the print media like paper to form patterns leading to words, images and the like.

The present invention adhesive composition can be used in the formation of inkjet cartridges, such as those described above or in formation of inkjet cartridges according to the conventional art, such as U.S. Pat. Nos. 7,832,839; 7,547,098; or U.S. Pat. No. 7,815,300, for example, the contents of each of which are hereby incorporated by reference.

Leaky Optical Fiber Element:

Fiber element 91 can be straight or can be flexible to adopt various shapes. The fiber element leaks UV energy around its core and along the direction of propagation of the UV light. When light is coupled from its ends the light propagates along the fiber and leaks UV lights to its environment. See FIGS. 88A and 88B.

The fiber element is inserted in a joint between two plastics. An adhesive is dispensed around the fiber and the assemblies are collapsed together. The curing can therefore be achieved by coupling UV to the external sides of the fiber element to distribute UV light to the inside of the assembly. See FIGS. 89A and 89B.

UV Ink for Digital Printing Presses

The $CaWO_4$ phosphors and $CaWO_4$:Pb emits in the visible and UVA under x-ray energy. Both these phosphors have a notoriously slow decay time. This phosphor keeps on emitting visible and UV light even after the initiating energy has stopped. The emission remains strong for 60 to 100 seconds after x-ray energy irradiation has stopped.

For this reason, the $CaWO_4$ as well as the $CaWO_4$:Pb can be applied for a delayed curing application such as UV inks. The UV ink offers the possibility of rapid cure under UV light. The inclusion of nano-particle size phosphors that have light modulating capability from x-ray and extreme UV to a desirable UVA and visible range are particularly preferred. The initiating radiation can flash (short burst exposure) the ink and the included phosphors with delay decay time can keep on emitting UV radiation that can cure the ink.

These special inks can be used in digital presses equipped with EUV or x-ray sources to flash activate the phosphors with slow decay times. The web-speed can therefore be accelerated from 400 feet per minute to over 900 feet per minute by virtue of the sustainable UV emissions that can keep on curing the inks from within the thickness of the ink itself.

This is especially useful when using glossy paper. The glossy paper offers limited porosity if any. For this reason, inks wetting the surface remain in wet form and do not dry quickly. Thermal energy can be imparted to the surface of the web to assist in removing the solvents used in the inks. The solvents have a slow drying rates and cannot be easily removed which slows down the web speed.

The combination of thermal energy and an initiation radiation can be used in the present invention.

Figure 90:
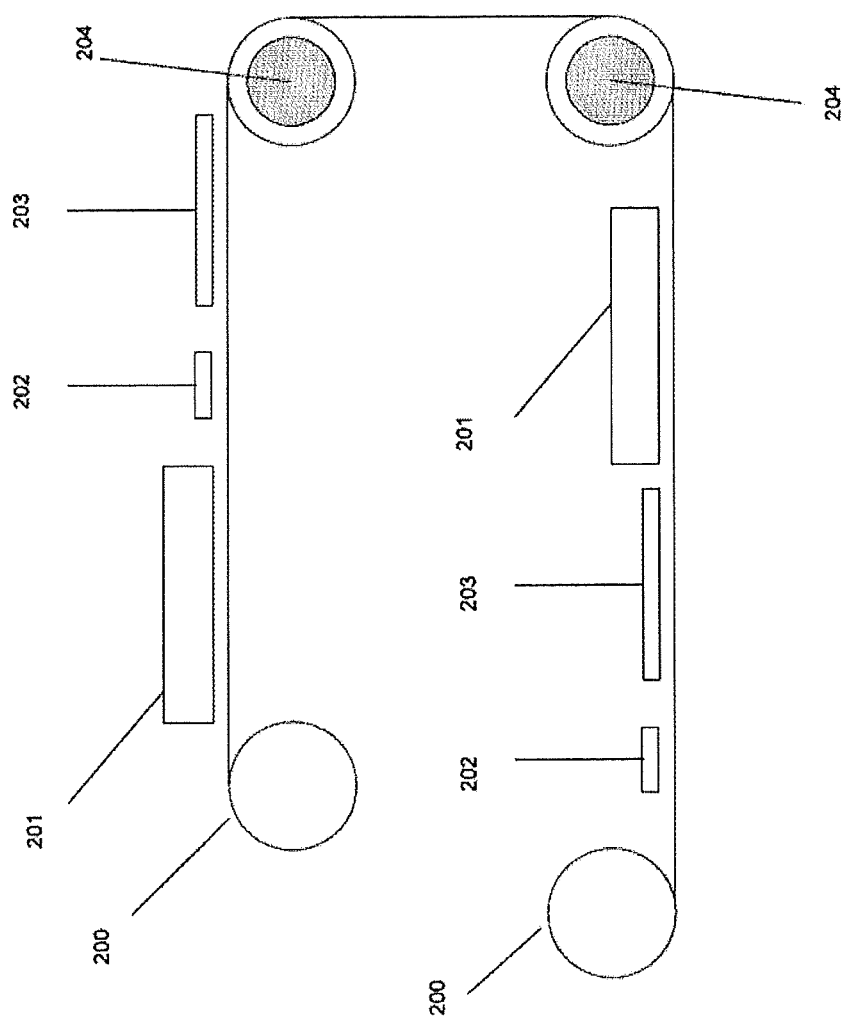
FIG. 90 provides a schematic representation of a digital printing press.

A reel of glossy paper (200) feeds a portion of the digital printing press described in FIG. 90. The paper is imparted with ink though an ink dispensing station (201). The source of an initiation radiation (202) flashes the ink with x-ray or EUV. The phosphors embedded within the ink and having a slow decay time are activated with the x-ray or EUV. The paper moves to the thermal station (203). The paper is then turned around a first pulley (204) and a second pulley (204). The back side of the paper is now ready for printing using an ink dispensing station (201). The thermal treatment as well as the UV flashing is imparted on the ink using station 203 and 202. The paper is then moved to another portion of the digital printing press.

Various other embodiments are possible.

Figure 91A:
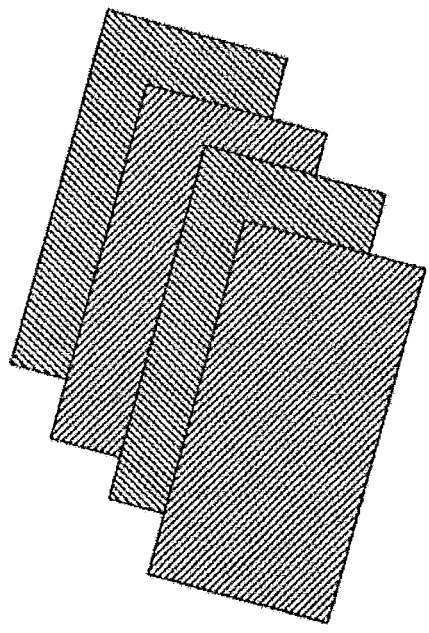
FIGS. 91A and 91B provide representations of an embodiment of the present invention for forming −45+45 composite ply assemblies.
Figure 91B:
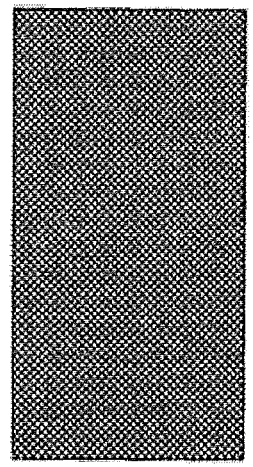
Figure 92A:
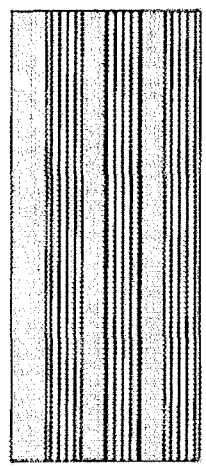
FIGS. 92A and 92B provide representations of an embodiment of the present invention for forming 0+90 composite ply assemblies.
Figure 92B:
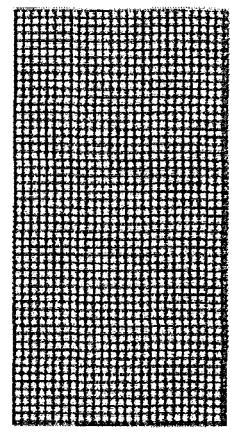

Composites:

The present invention adhesives can also be used in the formation of composites, by the adhesion of two or more plies, which are the fundamental building blocks of layered composites. The composites can be built by layering the plies, with the plies adhered one to the other using the adhesive composition of the present invention. Any conventional ply can be prepared, such as −45+45 assemblies (See FIGS. 91A and 91B), 0+90 composites (see FIGS. 92A and 92B).

The composite is preferably formed by preparation of a prepreg material formed of the plurality of plies, with each ply placed in the desired configuration with respect to the other plies, and having the curable adhesive composition of the present invention between respective layers of the plies. Once the prepreg is assembled, and the layers aligned as desired, the curable adhesive can be cured by application of the desired ionizing radiation, such as X-rays, thereby adhering the plies together to form the composite.

Front End Semiconductor PhotoLithography:

The adhesive composition of the present invention can alternatively be used in photolithography as a curable resin to accomplish either negative or positive photoresist development. By the use of heavy metal masking elements, it is possible to get selective curing of the present invention composition to form desired patterns or semiconductor elements. If the element is desired to be electrically conductive, the adhesive composition can be doped with electroconductive fillers, as desired.

Figure 95A:
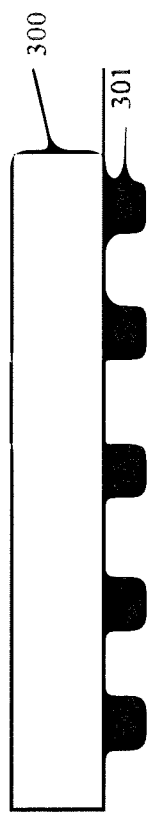
Figure 95B:
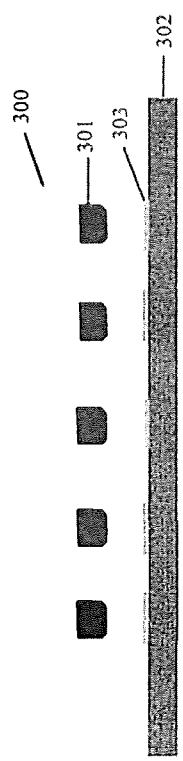
Figure 96A:
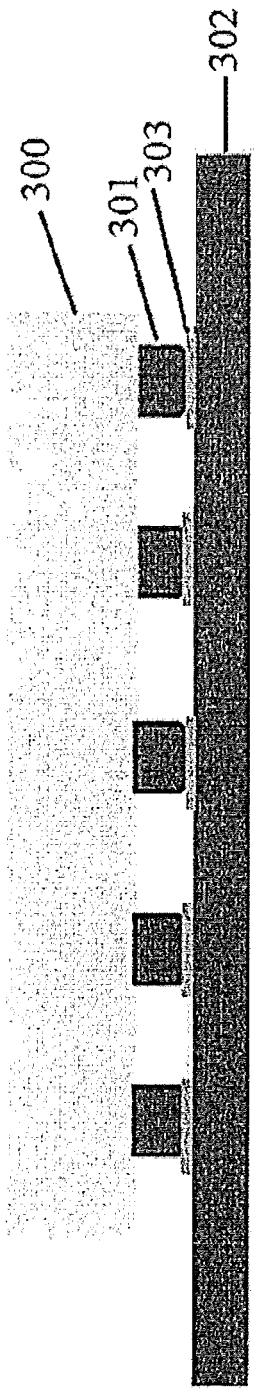
FIGS. 96A-B provide more representations of the stages in the production of various semiconductor IC devices with electrically conductive contacts and metallic heat sinks.
Figure 96B:
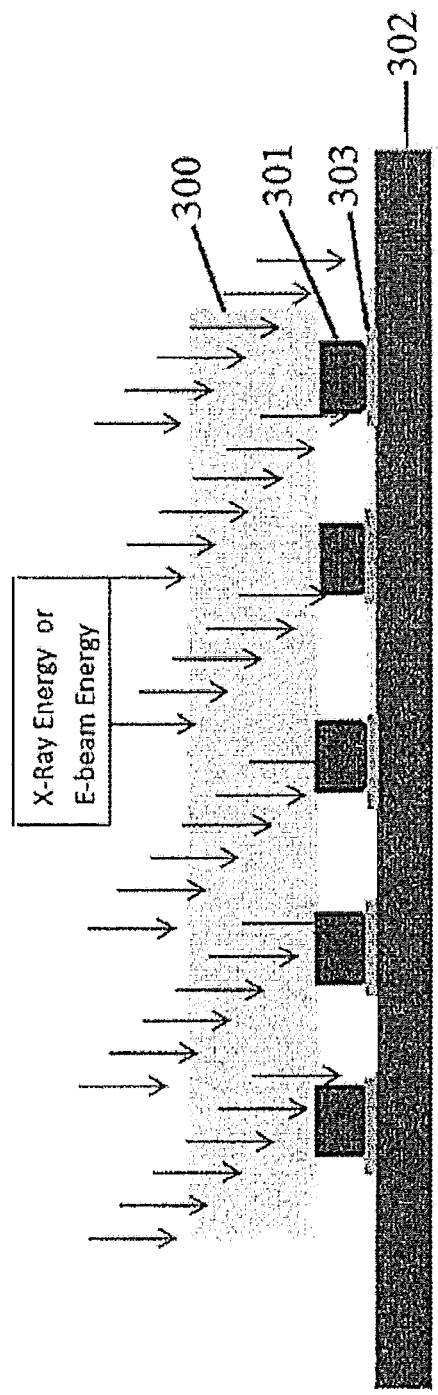

Semiconductor Integrated Circuits (IC):

In the production of semiconductor integrated circuit (IC) devices, an IC device is often conductively attached to a substrate by the use of solder balls attached to the IC device, then the solder balls are placed on conductive electrical pads attached to the substrate. FIGS. 95A, 95B, 96A, 96B, 97A, 97B, 98, and 99 provide a representation of one use of the adhesive and conductive resin compositions of the present invention in a manner to replace the use of such solder balls and solder masks while maintaining high electrical conductivity between the IC device and the electrical pads. In FIG. 95A, a semiconductor IC (300), such as those present in logic or memory devices, system on chip or optoelectronic devices, particularly devices based on GaInNAs or GaAs, has a plurality of "bumps", "pins" or "feet" otherwise referred to a protrusions (301) attached to one side of the semiconductor IC (300), wherein the protrusions (301) are formed of an electrically conductive curable resin, preferably an electrically conductive curable resin containing metallic silver flakes and energy converters of the present invention, most preferably an electrically conductive curable epoxy containing metallic silver flakes and energy converters of the present invention. The term protrusion in item (301) includes, but is not limited to, the above noted items 32: Flip Chip Device Bumps, and 32': Substrate Solder Bumps. The plurality of protrusions (301) can be applied to the semiconductor IC (300) through any desired method. Preferably, the protrusions (301) can be applied by jetting, screen printing, electroplating or another means of dispensing, in order to place the protrusions (301) at the desired locations for the particular device. The protrusions (301) can follow a desirable pattern such as an area array or a perimeter array configuration to mention two examples.

The semiconductor IC (300) having the protrusions (301) is then aligned (FIG. 95B) and placed (FIG. 96A) on a substrate (302) having a plurality of conductive electrical pads (303) in a pattern corresponding to the location of the protrusions (301) on the semiconductor IC (300).

Once the placement has been completed, the conductive resin protrusions (301) are cured in place by the application of X-ray or e-beam energy through the semiconductor IC device (300) (FIG. 96B) (or alternatively through the substrate (302) (not shown), whereby the energy converters in the conductive resin protrusions (301) convert the x-ray or e-beam energy into the initiation energy causing the conductive resin to cure and harden.

In this construction, the substrate (302) may contain traces that are conductive in order to provide desired electrical connection through the electrical pads (303), or the substrate (302) may be non-conductive. The 302 substrate can be a flexible or a rigid circuit board. Furthermore, the rigid circuit board can be organic such as FR4 and BT, or can be ceramic such as alumina ($Al_2O_3$) or doped alumina. The circuit board can be a multilayered circuit board containing at least two layered with via to interconnect internal planes such as a power plane or a ground plane. If the substrate (302) is non-conductive, the electrical pads (303) may be connected through patterned electrical connections from electrical pad (303) to electrical pad (303), if desired. This will be determined by the particular semiconductor IC assembly being prepared and is readily determined by one of ordinary skill in the art. One advantage provided by use of the present invention curable resin/adhesive compositions is the ability to generate finely controlled and intricate patterning for electrical conductivity by the use of conventional photolithography and similar techniques, while not requiring line-of-sight access for curing of the resins involved. Alternatively, the protrusions (301) can be placed on the substrate (302) and subsequently an IC (300) is aligned and placed on top of the substrate (302). Yet another alternative is that the protrusions (301) may be disposed on both the IC (300) and the substrate (302), and then joined during curing of the protrusions after the IC (300) and substrate (302) are aligned and placed together.

Figure 97A:
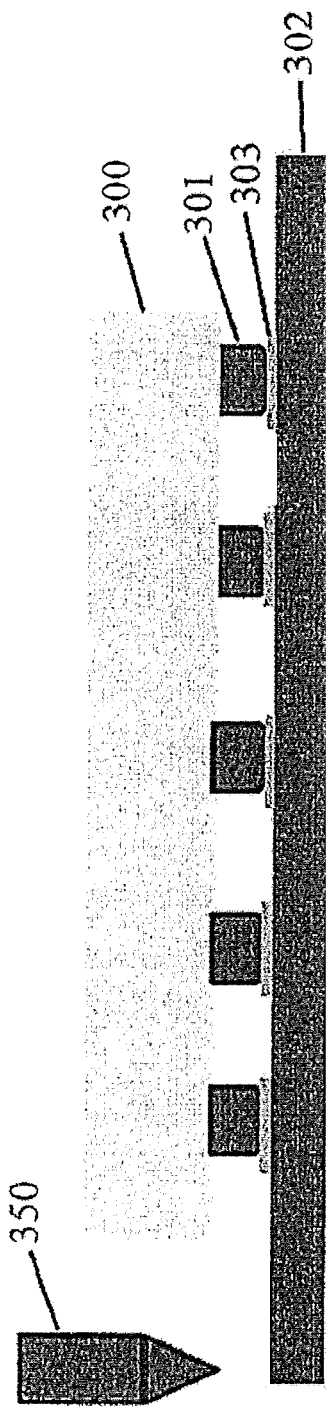
FIGS. 97A-B provide more representations of the stages in the production of various semiconductor IC devices with electrically conductive contacts and metallic heat sinks.
Figure 97B:
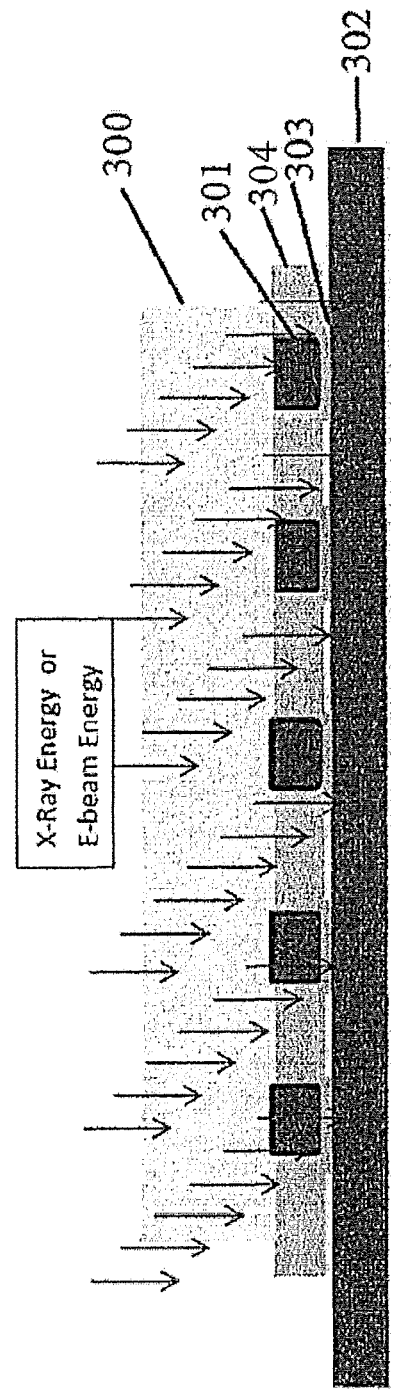

Once the conductive resin has been cured, a curable underfill adhesive (304) is applied via a dispenser (350), wherein the curable underfill adhesive (304) is an adhesive according to the present invention, containing one or more energy converters (see FIG. 97A).

Preferably, the underfill adhesive composition is a non-electrically conductive (or electrically insulating composition) to isolate the conductive paths formed by the protrusions (301) and electrical pads (303). Once dispensed, the curable underfill adhesive (304) is cured by application of x-ray or e-beam energy through the semiconductor IC device (300) (FIG. 97B) (or alternatively through the substrate (302), not shown).

Figure 98:
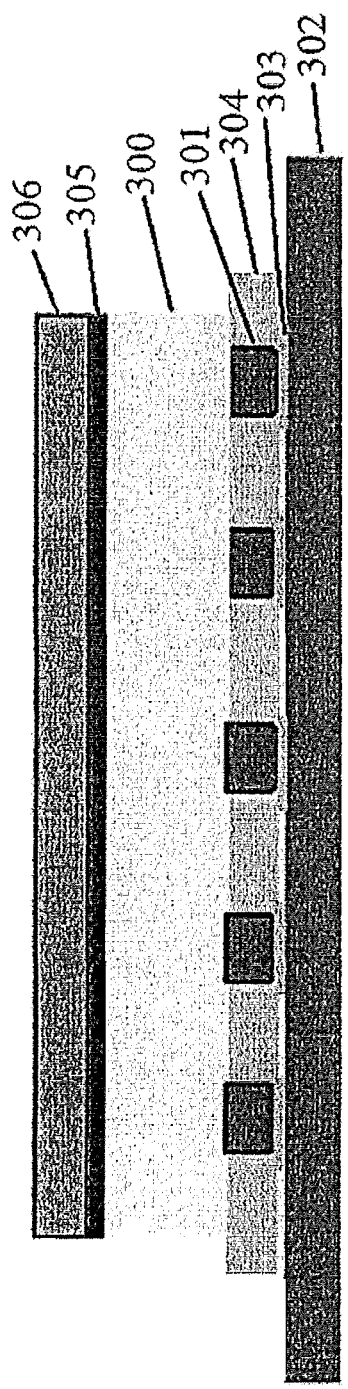
FIG. 98 is a schematic of a bonded assembly according to various embodiments of the invention.

When a metallic heat sink is desired, the metallic heat sink layer (306) is applied to a side of the semiconductor IC device (300) opposite to the protrusions (301), electrical pads (303), underfill layer (304) and substrate (302). Preferably, as shown in FIG. 98, the metallic heat sink layer (306) is attached to the semiconductor IC device (300) by way of an intermediate curable thermally conductive adhesive layer (305).

Once the metallic heat sink layer (306) is aligned and placed on the curable thermally conductive adhesive layer (305), the curable thermally conductive adhesive layer (305) is cured by application of x-ray or e-beam energy, through the metallic heat sink layer (306) or through the underlying semiconductor (300)-protrusion (301)-substrate (302) assembly. Alternatively, the X-Ray energy (or E-beam energy) can be applied from the sides of the device (as is shown in FIGS. 69C, 70A and 70B). A combination approach whereby the device is irradiated from all sides can also be envisaged.

The thermal conductivity of a curable adhesive or resin of the present invention can be enhanced by loading the resin with metallic particles (that are inherently thermally and electrically conductive). Alternatively, the resin can be doped with a metal nitride, such as AlN (aluminum nitride) and BN (boron nitride), for increasing thermal conductivity without necessarily increasing electrical conductivity.

Furthermore, the electrical conductivity of the resin can be increased much more than thermal conductivity through the use of materials such as graphene or other conductive carbon materials.

By way of example, a curable resin of the present invention containing x-ray to UV energy converting particles can be doped with silver, copper or graphene (as the electrically conductive material) and cured using X-Ray energy. The metallic particles generate significant secondary electrons which can also assist in the cure cycle of the resin. This is counter intuitive since UV resins normally need to be UV-transparent/clear to be cured by UV light. This is not the case for the present invention curable resins, which merely need to be penetrable by X-Ray energy. The UV light is generated deep inside the bead of adhesives and the metallic (or carbon) particles generate secondary electrons to enable/enhance free radical curing mechanisms to take place.

The thermal conductivity and the electrical conductivity of the present invention resins or adhesives can also be improved by doping them with metallic particles and flakes (especially for Ag). Similarly, the thermal conductivity can be improved through the use of high thermal conductivity dopants in particle or platelet forms such as for metal nitrides such as AlN or BN.

As an alternative to the standalone metallic heat sink (306) of FIG. 98, it is also possible to have the semiconductor (300)-protrusion (301)-substrate (302) assembly hermetically sealed inside a cavity formed by the metallic heat sink layer (307), having support sides (308) (see FIG. 99), wherein the metallic heat sink layer (307) is attached by way of the same type thermally conductive adhesive resin (305), but in this embodiment, the metallic heat sink layer (307) extends beyond the edges of the semiconductor (300)-protrusion (301)-substrate (302) assembly, and is supported at its ends by support sides (308). When these support sides (308) completely surround the semiconductor (300)-protrusion (301)-substrate (302) assembly, the semiconductor (300)-protrusion (301)-substrate (302) assembly is hermetically sealed, and has a cavity between its edges and the inner surface of the support sides (308).

As in the standalone metallic heat sink (306), the metallic heat sink layer (307) of this embodiment is connected to the semiconductor (300)-protrusion (301)-substrate (302) assembly via the thermally conductive adhesive resin (305), which is cured after the metallic heat sink layer (307) is aligned and put in place, by application of x-ray or e-beam energy through the metallic heat sink layer (307). The resulting assembly is a packaged IC product or device.

Figure 99:
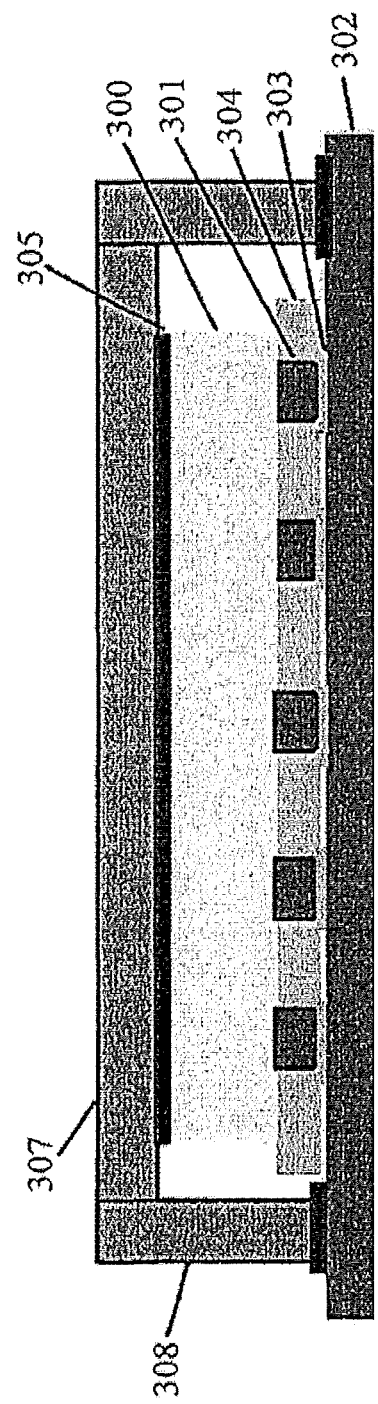
FIG. 99 is a schematic of a bonded assembly according to various embodiments of the invention.
Figure 100:
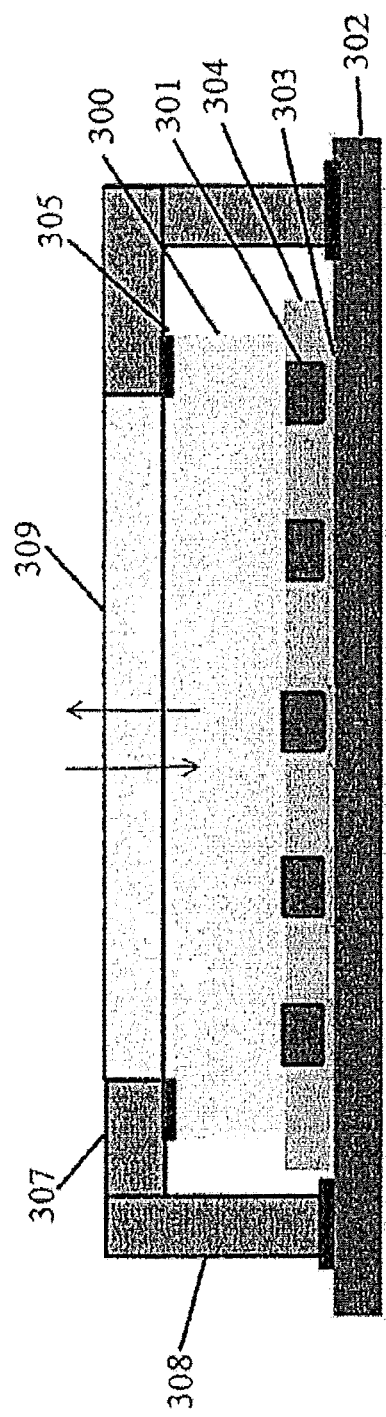
FIG. 100 is a schematic of a bonded assembly according to various embodiments of the invention.

In a further embodiment of the hermetically sealed assembly of FIG. 99, FIG. 100 shows a similar construction, except where the metallic heat sink layer (307) has had a section directly over the semiconductor (300)-protrusion (301)-substrate (302) assembly replaced with a window (309) that is transparent to a given wavelength of light, to enable the IC within the semiconductor (300)-protrusion (301)-substrate (302) assembly to receive and/or transmit the desired wavelengths.

Figure 101A:
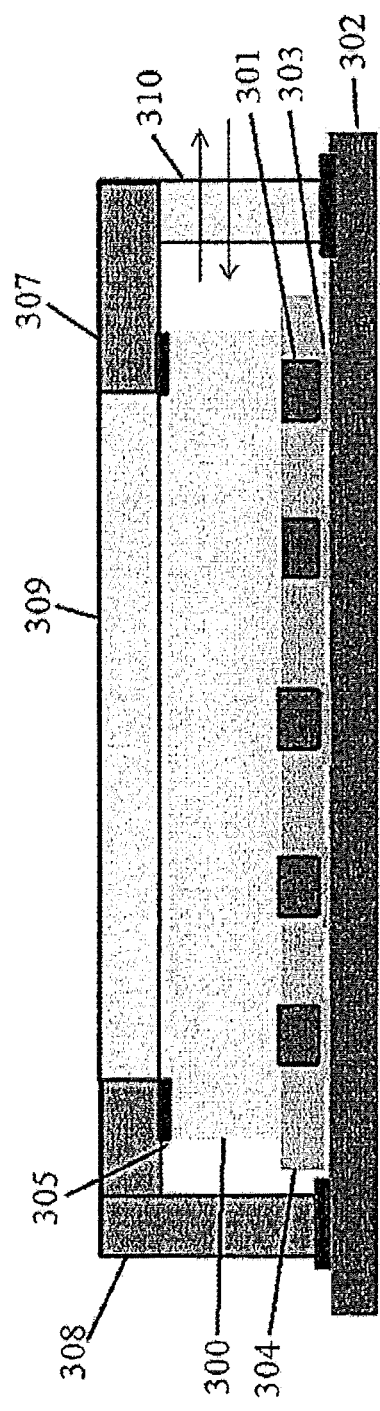
FIGS. 101A-B are schematics of bonded assemblies according to various embodiments of the invention.

Such IC's can be light emitting diodes, vertical-cavity surface-emitting lasers (VCSELs) or edge-emitting semiconductor lasers. In the case of the latter, one or more of the support sides (308) can be replaced by a suitable window (310) (rather than having a window (309) in the metallic heat sink layer (307) (not shown), or in addition to the window (309) in the metallic heat sink layer (307) (shown in FIG. 101A)) that is transparent to the desired wavelengths emitted or received by the edge-emitting semiconductor laser.

Figure 101B:
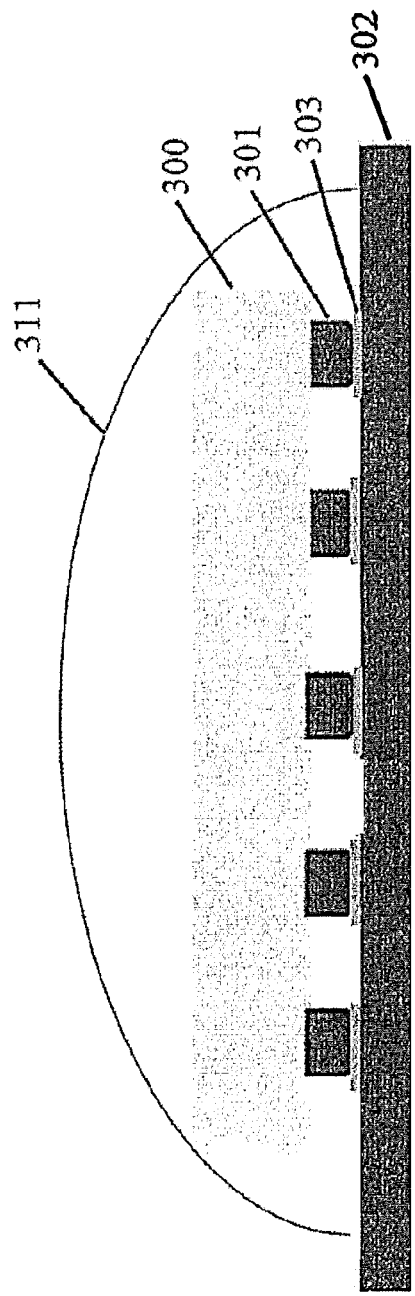

Alternatively, the semiconductor (300)-protrusion (301)-substrate (302) assembly (with or without the underfill layer (304)) can be encapsulated within a glob top (311), preferably one that has high optical transmissivity, as shown in FIG. 101B.

The glob top (311) can be formed from a direct UV cured adhesive or resin composition, a thermally cured adhesive or resin composition, or from an adhesive or resin composition of the present invention having one or more energy converting materials contained therein to permit x-ray or e-beam cure of the glob top (311). In the case of use of the adhesive or resin composition of the present invention in such configurations, since the glob top (311) desirably has high optical transmissivity, it is preferable to have the energy converting materials contained within the curable adhesive or resin be of a particle size that is below the optical wavelengths that are desired to be transmitted through the resin. Most preferably, these energy converting materials would have a particle size of 400 nm or less, in order to retain the desired optical transmissivity of the glob top (311). The glob top resin is X-Ray absorptive and can be made optically transparent by a careful selection of the size of the energy converters.

In addition to the device embodiments described above, methods of making these devices as described above are also included within the present invention. Of particular advantage in these methods is that the x-ray or e-beam curing of the various types of curable resin/adhesive compositions can be performed at room temperature in order to avoid problems associated with different coefficients of thermal expansion of the materials forming the various components, and avoidance of the potential heat damage of the often delicate and intricate circuitry present in the semiconductor ICs involved if thermal curing was used.

One of ordinary skill will readily understand that any of these embodiments described herein can be combined in various permutations as desired. Each of such permutations is likewise included within the scope of the present invention.

While many of the above described embodiments use downconverting particles that are dispersed throughout the curable adhesive composition, many other configurations are available for use with the present invention. For example, the downconverting particles can be adhered to a thin film (preferably to both sides of the thin film) which can be placed between two surfaces, each of which is coated with the curable adhesive monomer and photoinitiator formulation. Upon irradiation, the downconverting particles emit energy at the desired wavelength, activating the photoinitiator, and initiating curing of both layers of adhesive, thus bonding each of the surfaces to an opposite side of the thin film having the downconverting particles. One of ordinary skill, upon reviewing the present invention, would readily understand a wide variety of configurations that could be used to create novel adhered structures.

EXAMPLES

Having generally described this invention, a further understanding can be obtained by reference to certain specific examples which are provided herein for purposes of illustration only and are not intended to be limiting unless otherwise specified.

The materials chemistries were prepared by first weighing the key chemical ingredients and mixing these chemical ingredients under heat. A functionalized Acrylate resin was obtained from BASF. The resin was made from a mixture of 4 commercially available products including Laromer LR 9023, Laromer PO 94F, Laromer TPGDA, and Laromer LR 9004.

The photoinitiators were also obtained from BASF and consisted of IRGACURE 369 and IRGACURE 2529. The phosphors were obtained from Phosphor Technologies. The LaOBr:Tb$^{3+}$ phosphor as well as the YTaO$_4$ were used in the preparation of the curing formulations. The third phosphor was Y$_2$O$_3$ doped with Gadolinium (Y$_2$O$_3$:Gd). This third phosphor was synthesized in nano-particle size. It was used both as a phosphor and as a thickening agent.

The temperature that was used during all the mixing steps was 80° C. The sequence of adding the various chemicals was as follows: 1—resin, 2—photoinitiator, 3—phosphor and 4-thickening agent. In one case the thickening agent was the Y$_2$O$_3$:Gd. The mixtures stirred every 10 minutes for one hour to two hours. This ensured the obtainment of a homogenous mixture.

In one case MEKP was added to an adhesive formulation to assess the effectiveness of X-Ray curing on coupling energy to MEKP and enhancing the cure kinetics. It was found that recipe or formulation number 2, 3 and 4 cured faster than other formulations. However adhesion was compromised when excess photo-initiator was used. For this reason recipe 4 worked best. It cured faster that recipe 2 and had better adhesion than recipe 3.

The more uniform the dispersion the better results in terms of adhesion. When clusters of phosphor rich and or phosphor poor areas were noticeable, the cure was localized and the overall adhesion over a surface area was not good. When the photo-initiator is saturating the mix (excessive amount of photoinitiator), the adhesion at surfaces is compromised as there was a migration of un-reacted photo-initiator at the surfaces.

Curing of the various formulations was done on PET, glass, polycarbonate, polyimide, polysulfone, a carbon prepreg, a FR4 PCB. The adhesive bead was sandwiched between two similar substrates and cured while in between the substrates. No temperature was increased while in the x-ray. The temperature was measured using a hand-held IR thermometer. The only time a noticeable temperature increase of up to 10° C. was observed is in the case of the formulation containing MEKP.

| Formulations | 1 | 2 | 3 | 4 | 5 | 6 |
|---|---|---|---|---|---|---|
| Resin | 5 | 5 | 5 | 5 | — | — |
| Resin (shadow cure) | — | — | — | — | 5 | 5 |
| IRGACURE (369) | 1.3 | 1.3 | 1.3 | 1.3 | — | — |
| IRGACURE (2959) | — | — | — | — | 0.5 | 0.5 |
| LaOBr:Tb | 1.5 | 2.5 | 3.5 | 2.5 | 2.5 | 2.5 |
| Y$_2$O$_3$ | — | — | — | 0.3 | — | — |
| AEROSIL | 0.2 | 0.2 | 0.2 | 0.2 | 0.2 | 0.2 |
| CABOSIL | — | — | — | — | — | — |
| MEKP | — | — | — | 0 | 0.1 | — |

Additional formulations were cured. The elapsed time under X-Ray was 10 min, 12.5 min, 15 min, 17.5 min and 20 min. The formulations that were made using the LaOBr:Tb$^{3+}$ phosphor cured between 10 min and 12.5 min. The formulations that were made using the phosphor YTaO$_4$ cured between 12.5 min and 15 min. The formulations using the third phosphor was Y$_2$O$_3$ doped with Gadolinium (Y$_2$O$_3$:Gd) cured in 17.5 minutes. However when the LaOBr:Tb$^{3+}$ mixed with Y$_2$O$_3$:Gd were added to the adhesive formulations, the cure was accomplished in 10 min.

| Formulations | 1 | 2 | 3 | 4 | 5 | 6 |
|---|---|---|---|---|---|---|
| Resin 1 | 6 | 6 | 6 | 6 | 6 | 6 |
| Resin 2 (shadow Cure) | 0 | 0 | 0 | 0 | 0 | 0 |
| PI (369) | 0.6 | 0.6 | 0.6 | 0.6 | 0.6 | 0.6 |
| LaOBr:Tb | 1.5 | | | 1.5 | | |
| Y$_2$O$_3$ - Ian | | 1.5 | | | 1.5 | |
| YTaO$_4$ | | | 1.5 | | | 1.5 |
| AEROSIL | 0.3 | 0.3 | 0.3 | 0.3 | 0.3 | 0.3 |

The present invention reactive chemistries located across an interface between two substrates preferably are complimentary and reactive to one another. In one preferred embodiment, the reactive chemistries of the present invention can form the surface of one or both substrates, an adherent structure which can result in bonding one layer to the other across the interface. In an alternate embodiment, an adherent structure can be used which reacts with each substrate surface independently to affect the bond between the layers. In a further embodiment, the substrate surfaces are coated with reactive chemistry such as the natural and/or synthetic rubber compounds noted above, which results in reactive moiety formation, and the creation of chemical bonds (an adherent structure) to the surface, and between the coatings on each surface. In the present invention, the application of X-ray radiation to the novel chemistry causes the formation and/or release of a catalyst at the bonding interface.

The present invention relates to reactive chemistries and associated methods of use to bond two substrates across their interface under X-Ray, e-beam and UV radiation, wherein the reactive chemistries react by way of a mechanism including, but not limited to, radical formation (which can be by hydrogen or other atom or group abstraction, chain scission, or any other mechanism forming radicals), cation or anion formation, photo-initiation, and a combination of two or more of the above in the absence of line-of-sight. These mechanisms form an adherent structure to which a curable resin can adhere, thereby providing a mechanism to bond even low energy surfaces together.

The present invention methods are used for bonding two or more substrates together wherein the bond formation at the interface between two substrates is achieved without the requirement of UV activation or thermal heating. However, in an alternate embodiment, either or both of UV activation and thermal heating can be used in some cases to assist in the achievement of better bonding properties, as desired.

Within the context of the present invention, the term "substrate" or "substrates" is used merely to refer to an object being acted upon in the present invention method, such that the bonding of two substrates causes at least one surface of a first substrate to bond to at least one surface of a second substrate. While the method is described with respect to bonding two substrates to one another, it is possible to use the present invention method to simultaneously, or sequentially, bond multiple substrates to one another, depending on the final structure desired.

In this invention, substrates are caused to form a bond either directly or indirectly under the application of X-Ray energy, e-beam or a combination of UV and X-Ray and e-beam energy. In the present invention, these sources of energy can operate interchangeably, depending on the chemistry used.

In the case of the direct bond formation between two substrates, the chemistries of the two substrates is modified and made to include the novel reactive chemistries at their interfaces (such as the natural and/or synthetic rubber compounds noted above with or without energy converters) to form an adherent structure. The novel reactive chemistries can be disposed at the interface of the two substrates by virtue of being interwoven (or blended) in the composition of the objects or can be applied as a surface modification or coating on the surface of the substrate to be bonded (an adherent structure). In the case where one substrate is made of a polymer material, the reactive chemistry may be blended in as a co-polymer. The substrates can be made of any material, including, but not limited to, polymers and plastics, glass, ceramics, metals, metal oxides, etc.

In the case of indirect bond formation between two substrates, a layer of the present invention chemistry is applied either to one or both substrate surfaces to be bonded, or as a separate layer in the interface formed between the two substrate surfaces to be bonded, followed by pressing the objects together and exposing the thus formed assembly to X-Ray energy or other high energy penetrating radiation. The layer of the present invention chemistry is preferably applied as a conformable coating or as a conformable film.

In a preferred embodiment of the present invention, the generation of the reactive moiety, and formation of the bonds between substrates is performed at ambient temperature. This is particularly important in the case where the two substrates to be bonded are made of materials having differing coefficients of thermal expansion.

Another object of the present invention is to provide a film composition containing a polymer that undergoes reactive moiety formation under exposure to ionizing radiation, and that contains a down-converting energy converter, preferably a phosphor or scintillator material.

The reactive moieties of the present invention can be any reactive moiety that can be formed by reaction of the reactive composition with ionizing radiation, either by direct interaction with the ionizing radiation, or indirectly through energy conversion by an energy modulating agent to generate UV or another energy that generates the reactive moiety. The reactive moieties include, but are not limited to, free radicals, cations, anions, carbenes, nitrenes, etc. For ease of discussion, the following discussion is drawn to generation of free radicals. However, one of ordinary skill would understand that the same procedures can be used to generate the other forms of reactive moieties, which can then interact with compositions to form bonds, thus resulting in bonding of two substrates.

In one embodiment of the invention, peroxides and more suitably organic peroxides (used commercially) can also be used to initiate and create free-radical polymerization. Some peroxides are initiated by ionizing radiation and others are thermally activated. Examples of suitable peroxides of interest in the present invention include, but are not limited to:

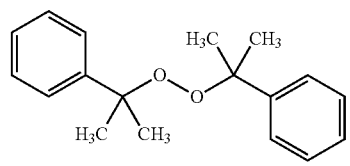

Dicumyl peroxide

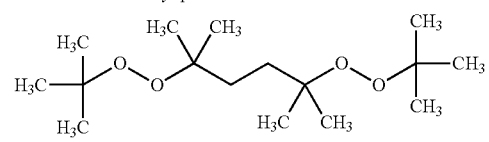

2,5-Bis(tert-butylperoxy)-2,5-dimethylhexane, (preferably blended with calcium carbonate and silica)

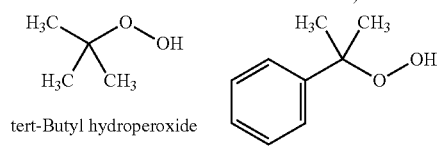

tert-Butyl hydroperoxide

Cumene hydroperoxide

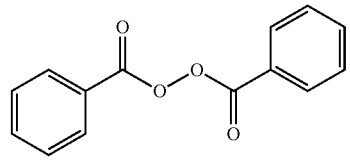

Benzoyl peroxide

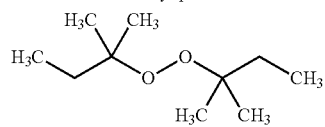

Di-tert-amyl peroxide

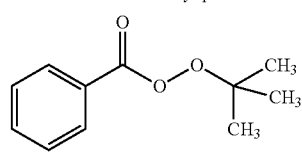

tert-Butyl peroxybenzoate

Once a free-radical initiation takes place, the polymerization of various chemistries can take place. However, in such free radical initiated reactions, oxygen inhibition can take place, resulting in incomplete polymerization, and incomplete reaction between chains. The oxygen dissolved in a given polymeric substance can play the role of a chain terminator in a free-radical curing reaction, by way of the formation of a peroxy radical, as shown in the scheme below. Oxygen inhibition is particularly pronounced in systems lacking active hydrogen.

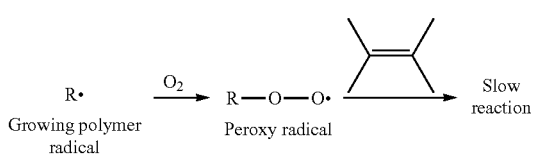

Active hydrogen containing compounds are able to counteract the peroxy radical which leads to further reaction. In various embodiments of this invention, oxygen inhibition can be circumvented using various techniques. Some active systems to counteract oxygen inhibition include the presence of hindered/secondary amines (—NH) and allylic (C═C—CH$_2$—) moieties. Methacrylates contain such allylic hydrogen moieties and are less susceptible than acrylates to oxygen inhibition.

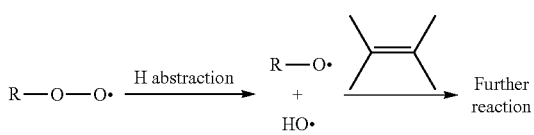

Another strategy for counteracting oxygen inhibition is by the inclusion of compounds having multiple active hydrogens. This can particularly be improved by increasing the functionality from di- to tri- and tetra-functionality. Tetra-functional alcohols provide monomers with six and eight functionalities.

The compositions of the present invention can be fine-tuned to include the appropriate concentration of these monomers along with systems with active hydrogen as well as photo and/or heat active peroxides. Iron, and more generally, catalytic transition metals result in the formation of hydroxyl radicals (HO.) superoxide generating systems. Those of ordinary skill in the art understand that superoxide can reduce ADP-Fe(III) to ADP-Fe(II) and, this iron facilitates the apparent production of (HO.). Chelating agents (in the proper proportions) can also alter the reactivity of iron in superoxide-generating systems. It has been shown that EDTA3 enhances the reactivity of iron toward O$_2$.—while DETAPAC4 drastically slows the O$_2$.— reaction with iron. The use of catalysts and chelating agents is beneficial to optimizing the desirable free radical generation that leads to the desirable reactions.

In a further preferred embodiment, catalysts can be added for increasing free radical formation. Suitable catalysts include, but are not limited to, manganese naphthenate, cobalt naphthenate, and vanadium pentoxide quaternary ammonium salt can be used.

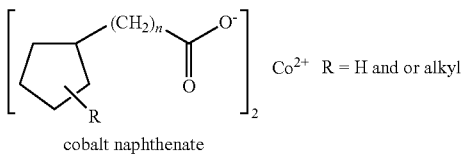

cobalt naphthenate

In the case where there is a combination of a UV and a heat activated peroxide, an initial UV activation can subsequently engender an exothermic reaction which in turn engenders the activation of a thermal peroxide. Another simple method of minimizing oxygen inhibition is to carry out the reaction using an inert atmosphere. The flow of nitrogen and argon on the surface of the materials can be used to limit the oxygen exposure and minimize oxygen induced cure inhibition.

The present invention in various embodiments can utilize a widely variety of resins to join to the adherent structures noted above. The examples provided here are illustrative of examples rather than inclusive of the possibilities.

In one embodiment of the present invention, an example of an "X-Ray susceptible polymer" can include, but is not limited to, aliphatic polymers. Aliphatic polymers can include alicyclic (no-aromatic rings), alkanes (single bonds), alkenes (unsaturated with double bonds), alkynes (triple bonds) of carbon and hydrogen atoms. One example of an aliphatic polymer would be polyethylene, or a polyethylene-polypropylene copolymer.

Peroxides are widely used commercially to initiate and create free-radical initiation. The reactive free radical species generated then reacts with its environment to form chemical bonds. Such methods are used, for example, to graft maleic anhydride to polyolefins. In general chain scission can outpace competing reactions. For example, in the particular case of propylene, chain scission and grafting are competitive reactions. However, chain scission outpaces grafting which curbs the achievable molecular weight of the grafted resin.

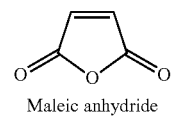

Maleic anhydride

Suitable polyolefins include, but are not limited to polyethylene (PE), polypropylene (PP) and ethyl vinyl acetate (EVA). Polyethylene is conventionally classified according to its density as Very Low Density Polyethylene (VLDPE), Low Density Polyethylene (LDPE), Linear Low Density Polyethylene (LLDPE), Medium Density Polyethylene (MDPE), and High Density Polyethylene (HDPE).

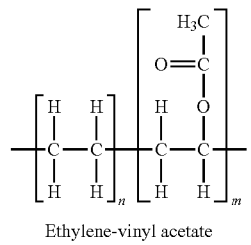

Ethylene-vinyl acetate

Examples of propylene polymers include propylene homopolymers and copolymers of propylene with ethylene or another unsaturated co-monomer. Copolymers also include terpolymers, tetrapolymers, etc. Typically, the units originating from propylene monomer comprise at least about 70 weight percent of the copolymer.

The mechanical and chemical properties of these resins can be tailored to become suitable for the desired application. The resin type, the catalyst, molecular weight, molecular weight distribution (MWD), crystallinity, branching and density all play a role in the microstructure and the behavior of the resin and its performance in the end use application. The choice of these characteristics depending on end use is well within the skill of one of ordinary skill in the art.

As a free radical inducing species for use in the present composition, suitable compounds include, but are not limited to, organic peroxides, azo free-radical initiators, and bicumene. Preferably, the free-radical inducing species is an organic peroxide. The organic peroxide can be added via direct injection or via blending with the chemistry of the polymer. The addition of the organic peroxide is in an amount sufficient to provide a concentration of free radicals sufficient for initiating reaction at enough sites to effect bonding, preferably from about 0.005 weight percent to about 20 weight percent, more preferably from about 0.25 weight percent to about 10 weight percent, most preferably from about 0.5 weight percent to about 5 weight percent.

In a similar fashion to the technical strategies employed to prohibit oxygen inhibition, the present invention methods can optionally employ one or more co-grafting reagents in order to minimize (or curb) chain scission. For this reason reagents containing two or more terminal carbon-carbon double bonds or triple bonds can be combined with free-radical generation to mitigate the loss in melt viscosity of polypropylene by coupling of polymer chains.

The present invention compositions can optionally further contain various conventional components that are suitable for the desired application. These can include, but are not limited to, the following agents: fillers, clays, fire retardant, scorch inhibitors, and blowing agents such as azodicarbonamide.

Activation with X-Ray and UV:

A preferred method of generating free-radicals in the present invention include the use of X-rays, electron-beam and gamma radiation. The present invention can use either X-ray or e-beam both as a source of free radical generation instead of, or in addition to UV light. UV generation is performed via the use of energy converters, preferably in the form of particles that absorb X-ray and convert it to UV. These particles are disposed at the interface where bonding is targeted to take place. The UV light (regardless of its generation) can in turn engender additional free radical generation.

Functional Energy Converters:

In one aspect of the invention, an energy converter is added to the chemistry where the energy converter is combined with an organic peroxide and an organic vehicle. Examples of the energy converter include, but are not limited to: $BaFCl:Eu^{2+}$, $BaSO_4^-:Eu^{2+}$, $LaOBr:Tm^{3+}$, $YTaO_4$, $YTaO_4:Nb(*)$, $CaWO_4$, $LaOBr:Tb^{3+}$, $Y_2O_2S:Tb^{3+}$, $ZnS:Ag$, $(Zn,Cd)S:Ag$, $Gd_2O_2S:Tb^{3+}$, $La_2O_2S:Tb^{3+}$. A more comprehensive list is provided in the following table.

Surface Preparation:

Adhesion develops through various factors including mechanical interlocking, adsorption, electrostatic, diffusion, weak boundary layer, acid base, chemical (covalent bonding), etc. In general, the greater the surface irregularities and porosity at a joint area, the greater the joint strength. The greater the compatibility of the size of the adhesives and the interstices in the adherend, the greater the bond strength can be. Roughness of the surfaces can increase or decrease the joint strength.

The factors affecting joint strength include: surface energetics (wetting), intrinsic stresses and stress concentrations, mechanical response of various bulk phases and inter-phases involved, geometrical considerations, mode of applying external stresses, and mode of fracture or separation, viscoelastic behavior.

The wetting and the setting of the adhesive bead is important for a good bond formation. The spreading coefficient of an adhesive depends on the various surfaces and associated surface tensions involved. The surface tensions are referred to here as the energetic requirements. The substrate (solid), the adhesive (liquid) and the vapor (open air in most cases) all play a role. Wetting of the surface depends on the surface energy between the solid and the liquid, the liquid to vapor surface tension and between solid to vapor surface tension. Substrates such as Teflon, PET, Nylon, PE, and PS have low energy. Substrates such as metals, metal oxides, and ceramics have high energy.

The adhesive chemistry (the liquid in this example) can be tailored to adjust the energetic requirements at the various surfaces. But that is not sufficient. For example, most RTV silicone resins fulfill the energetic requirements but give negligible adhesion unless primers are used. Adhesive joints can be made stronger by surface treatments of the surfaces to be joined. Also inter-phases can be made between the adherend and the adhesive.

For the above considerations (surface energetic requirements and primers treatments) many surface modification techniques are used to achieve the goal of strong and durable adhesion at joints, including but not limited to dry surface modification techniques, wet surface modification techniques, chemical vapor deposition (CVD) and physical vapor deposition (PVD). The treatment of polymer surfaces is used for various reasons including one or more of the following list extending to making the polymers more adhesionable, increase their printability, make them more wettable, provide an enclosing layer, improve tribological behavior, potentially prepare them for metal plating, improve their flame resistance, provide antistatic properties, control permeation. Such surface modification treatments can be especially useful for improving the ability to bond to a surface of a substrate such as rubber or fabric.

Dry surface modifications include, but are not limited to, a surface plasma ionized through RF or microwave, flame, UV, UV sensitized, ozone, UV/ozone, X-ray, LASER, electron beam, ion bombardment, and friction against other materials.

Wet surface modification encompasses chemical reactions such as oxidation, sulfonation, ozonation, phosphatization, chromate conversion, amination, grafting, selective etching, deposition of coupling layers (silanes), surfactant adsorption, photochemical compounds, solvent (surface swelling), prevention of diffusion of low molecular weight materials to the surface, and others.

In various embodiments of the present simplest form invention, the adhesives can be applied to the substrates using a variety of methods. In the, the adhesive formulations were scooped from the mixing cup using a spatula and deposited on the top surface of one substrate. In other cases the adhesives were placed in syringes and hand pressed through a needle with an 18 to 22 gauge. In other cases the materials were dispensed through the needle of EDF air piston pump (also using 18 to 22 gauge needles). In some cases the substrates had a spacer element sandwiched between the substrates to keep the materials from being squeezed out from between the substrates. The adhesive cure has been demonstrated for adhesive bead thicknesses from 60 microns to 1000 microns.

|  | Resin percent in Adhesive | 2100 percent in adhesive | 184 Weight percent in adhesive | Ratio of Adhesive % | Phosphor % by Weight | Phosphor Type | Cure Hardness |
|---|---|---|---|---|---|---|---|
| Around 100 microns | 0.94 | 0.02 | 0.04 | 0.75 | 0.25 | CaWO$_4$ | Yes |
| Between Glass Slides | 0.94 | 0.02 | 0.04 | 0.6 | 0.4 | CaWO$_4$ | Yes |
|  | 0.88 | 0.04 | 0.08 | 0.75 | 0.25 | CaWO$_4$ | Yes |
| Around 250 microns | 0.94 | 0.02 | 0.04 | 0.75 | 0.25 | CaWO$_4$ | No |
| Between Glass Slides | 0.94 | 0.02 | 0.04 | 0.6 | 0.4 | CaWO$_4$ | No |
|  | 0.88 | 0.04 | 0.08 | 0.75 | 0.25 | CaWO$_4$ | Yes |

The control over the rheology and thickness of the adhesive beads was achieved using filler elements such as AEROSIL and nanoparticles of doped $Y_2O_3$. Gadolinium was found to be the preferred doping elements in these cases. In order to achieve thicknesses of 500 microns and above the adhesive formulations had between 0.5% and 5% of filler. In some cases, the adhesive bead was applied between 2 polycarbonate substrates and kept in this configuration for 24 hours. No-flow or displacement was observable. The adhesive bead was therefore made to provide the end-user with enough work and pot life after dispensing and to tolerate interruptions of the work in process during manufacturing. This is significant because no scarping of the work in process after dispensing is required.

Ink Jet Cartridges

As noted above, ink jet cartridges are typically made of a plastic housing made of a thermoplastic moldable resin, such as polyethylene terephthalate (PET), polyethylene, or polysulfone for example, as the base material. Polysulfone describes a family of thermoplastic polymers that have toughness, mechanical stability and ink resistance.

Typically, a print head made of silicon, has numerous nozzles that are used as ink outlets. The nozzle array on the silicon and the ink reservoirs are connected through a manifold structure having fluidic channels. The fluidic channels are employed to direct the inks of different colors from the primary reservoirs to appropriate printhead nozzle arrays.

Multicolor cartridges have a plurality of ink reservoirs, often three ink reservoirs. In such three ink cartridges, each of the reservoirs contains a primary color. These reservoirs need to be isolated from one another. The separation between the compartments has to be hermetic to avoid ink mixing between the various compartments. A plastic piece is adhesively bonded to seal the separate reservoirs.

The joint of interest that seals or separates the various reservoirs must be made to withstand the prolonged contact with inks. Inks happen to be aggressive from a chemical stand point. Furthermore, the sealing joint needs to be able to overcome the mechanical stresses that may exist over the product's functional life and the pressure differential that needs to be regulated between atmospheric pressure and the internal pressure in the reservoir.

The present invention's polymerizable adhesive compositions including the adherent surface structures can be used in the formation of inkjet cartridges.

Besides the objects noted above, the bonding and curing and cross-linking processes described herein can be applied in the production of a variety of products adhering pieces together (having similar or dissimilar properties) to form final or intermediate products in a production process. Such products include, but are not limited to, athletic equipment, sporting equipment, industrial equipment, construction equipment, office equipment, baseballs, basketballs, volleyballs, golf balls, footballs, soccer balls, bowling pins, bowling balls, golf clubs, laminated furniture items, car panels, car interior products, tires, plastic covers, plastic containers, consumer and food packaging products, medical packaging products, etc.

Molecular Welding

The present invention in another embodiment relates to novel material chemistries which have the ability to form one or more reactive moieties, including but not limited to free radicals, cations, anions, carbenes, nitrenes, etc., under X-Ray or e-beam energy, alone or in combination with UV radiation and/or heat for further enhancement of reactive moiety formation, which upon the formation of such reactive moieties, can be used to effect bonding (i.e., molecular welding) of two adjacent substrates.

These materials and methods can be used with or without the energy augmentators described herein. With the energy augmentators present, this invention can generate local regions of intense electric fields to enhance light emission from the energy converters in proximity to those local regions generating the light or heat internally within the medium to be cured. The internally generated light would enhance/activate the molecular welding.

The present invention in one embodiment provides a reactive polymer composition comprising:
  a (co)polymer that forms one or more reactive moieties, either directly or indirectly, upon application of an ionizing radiation; and
  a curing coagent.

The present invention can further provide a system for bonding, comprising:
  a first substrate having at least one surface containing a first reactive polymer composition;
  a second substrate, optionally having at least one surface containing a second reactive polymer composition;
  wherein the first reactive polymer composition and the second reactive polymer composition may be the same or different, and each comprises a (co)polymer that forms one or more reactive moieties, either directly or indirectly, upon application of an ionizing radiation and a curing coagent; and
  a source of ionizing radiation.

The present invention additionally can provide a method for bonding, comprising:
  providing a first substrate and a second substrate to be bonded together, wherein the first and second substrates may be the same or different;
  providing a first reactive polymer composition comprising a (co)polymer that forms one or more reactive moieties, either directly or indirectly, upon application of an ionizing radiation and a curing coagent, wherein the first reactive polymer composition is in contact with at least one of the first and second substrates;

placing the first and second substrates in close proximity to one another; and applying the ionizing radiation, thus forming the one or more reactive moieties in the first reactive polymer composition which react to form a bond between the first and second substrates.

In a further embodiment, the present invention can provide a method for bonding, comprising:

providing a first substrate and a second substrate to be bonded together, wherein the first and second substrates may be the same or different;

providing a first reactive polymer composition comprising a (co)polymer that forms one or more reactive moieties, either directly or indirectly, upon application of an ionizing radiation and a curing coagent, wherein the first reactive polymer composition is in the form of a conformable film or coating;

placing the first and second substrates in close proximity to one another and having the first reactive polymer composition therebetween; and applying the ionizing radiation, thus forming the one or more reactive moieties in the first reactive polymer composition which react to form a bond between the first and second substrates.

The present invention can provide reactive chemistries located across an interface between two substrates are complimentary and reactive to one another. In one embodiment, the reactive chemistries of the present invention can form the surface of one or both substrates, which upon activation using the high energy radiation, undergo reaction to form the one or more reactive moieties, preferably free radicals, which result in bonding one layer to the other across the interface. In an alternate embodiment, a compatibilizing intermediary layer can be used which reacts with each substrate surface independently, while using the intermediary layer to effect the bond between the layers. In a further embodiment, the substrate surfaces are coated with the reactive chemistry, which results in reactive moiety formation, and the creation of chemical bonds between components of the coating on the surface, and between the coatings on each surface. In the present invention, the application of X-ray radiation to the novel chemistry causes the formation and/or release of a catalyst at the bonding interface.

The present invention in this embodiment relates to reactive chemistries and associated methods of use to bond two substrates across their interface under X-Ray, e-beam and UV radiation, wherein the reactive chemistries react by way of a mechanism including, but not limited to, radical formation (which can be by hydrogen or other atom or group abstraction, chain scission, or any other mechanism forming radicals), cation or anion formation, photo-initiation, and a combination of two or more of the above in the absence of line-of-sight.

The present invention methods can be used for bonding two or more substrates together wherein the bond formation at the interface between two substrates is achieved without the requirement of UV activation or thermal heating. However, in an alternate embodiment, either or both of UV activation and thermal heating can be used in some cases to assist in the achievement of better bonding properties, as desired.

Here, the term "substrate" or "substrates" is used merely to refer to an object being acted upon in the present invention method, such that the bonding of two substrates causes at least one surface of a first substrate to bond to at least one surface of a second substrate. While the method is described with respect to bonding two substrates to one another, it is possible to use the present invention method to simultaneously, or sequentially, bond multiple substrates to one another, depending on the final structure desired.

In this embodiment, substrates are caused to form a bond either directly or indirectly under the application of X-Ray energy, e-beam or a combination of UV and X-Ray and e-beam energy. In the present invention, these sources of energy can operate interchangeably, depending on the chemistry used.

In the case of the direct bond formation between two substrates, the chemistries of the two substrates is modified and made to include the novel reactive chemistries at their interfaces. The novel reactive chemistries can be disposed at the interface of the two substrates by virtue of being interwoven (or blended) in the composition of the objects or can be applied as a surface modification or coating on the surface of the substrate to be bonded. In the case where one substrate is made of a polymer material, the reactive chemistry may be blended in as a co-polymer. The substrates can be made of any material, including, but not limited to, polymers and plastics, glass, ceramics, metals, metal oxides, etc.

In the case of indirect bond formation between two substrates, a layer of the present invention chemistry is applied either to one or both substrate surfaces to be bonded, or as a separate layer in the interface formed between the two substrate surfaces to be bonded, followed by pressing the objects together and exposing the thus formed assembly to X-Ray energy. The layer of the present invention chemistry is preferably applied as a conformable coating or as a conformable film.

In one embodiment of the present invention, reactive chemistries are activated by X-Ray energy and or the combination of X-Ray and UV radiation. In embodiments that use UV radiation, when line-of-sight is not possible, or when the substrate material is not UV transmissive, the UV radiation at the interface of the two substrates in the present invention is generated through the down conversion of X-Ray energy into UV energy enabled by energy modulating agents, preferably in particle form. Suitable energy converters and particles for molecular welding are disclosed in U.S. application Ser. No. 12/764,184, filed Apr. 21, 2010; U.S. application Ser. No. 12/763,404, filed Apr. 20, 2010; U.S. application Ser. No. 12/843,188, filed Jul. 26, 2010; U.S. application Ser. No. 12/891,466, filed Sep. 27, 2010; U.S. application Ser. No. 12/943,787, filed Nov. 10, 2010; U.S. application Ser. No. 13/054,279, filed Jul. 13, 2011; U.S. application Ser. No. 13/102,277, filed May 6, 2011; U.S. application Ser. No. 13/204,355, filed Aug. 5, 2011; U.S. application Ser. No. 12/725,108, filed Mar. 16, 2010; U.S. application Ser. No. 12/059,484, filed Mar. 31, 2008; U.S. application Ser. No. 11/935,655, filed Nov. 6, 2007; U.S. application Ser. No. 12/401,478 filed Mar. 10, 2009; U.S. application Ser. No. 11/935,655, filed Nov. 6, 2007; and Ser. No. 12/059,484, filed Mar. 31, 2008; U.S. application Ser. No. 12/389,946, filed Feb. 20, 2009; and U.S. application Ser. No. 12/417,779, filed Apr. 3, 2009, the entire disclosures of each of which are hereby incorporated by reference Suitable energy converters for molecular welding are also described in the section of this application entitled B. ENERGY CONVERTERS. Moreover, the plasma capsules described elsewhere can be used as energy converters and light emitters. Of particular note also are the persistent x-ray induced phosphors, the mechano-luminescent devices, and the piezoluminescent materials Furthermore, adhesive processing may occur by exposure of the molecular weldable medium directly to x-rays or via an x-ray fluorescent material emitting lower energy x-rays after being exposed to higher energy x-rays.

In one embodiment of the present invention, the generation of the reactive moiety, and formation of the bonds between substrates is performed at ambient temperature. This is particularly important in the case where the two substrates to be bonded are made of materials having differing coefficients of thermal expansion.

Accordingly, one object of the present invention is to provide a film composition with or without energy augmentators containing a polymer that undergoes reactive moiety formation under exposure to ionizing radiation, and that contains a down-converting energy converter, preferably a phosphor or scintillator material.

The reactive moieties of the present invention can be any reactive moiety that can be formed by reaction of the reactive composition with ionizing radiation, either by direct interaction with the ionizing radiation, or indirectly through energy conversion by an energy modulating agent to generate UV or another energy that generates the reactive moiety. The reactive moieties include, but are not limited to, free radicals, cations, anions, carbenes, nitrenes, etc. For ease of discussion, the following discussion is drawn to generation of free radicals. However, one of ordinary skill would understand that the same procedures can be used to generate the other forms of reactive moieties, which can then interact with compositions to form bonds, thus resulting in bonding of two substrates.

Organic Peroxides for Molecular Welding with or without Energy Augmentators:

Peroxides and more suitably organic peroxides are widely used commercially to initiate and create free-radical polymerization. Some peroxides are initiated by ionizing radiation and others are thermally activated. Examples of suitable peroxides of interest in the present invention include, but are not limited to:

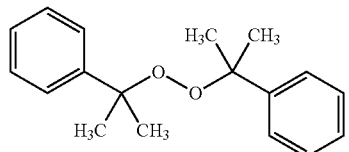

Dicumyl peroxide

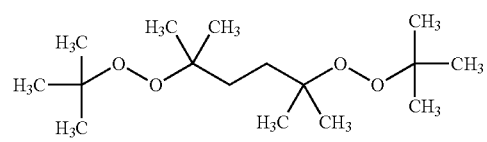

2,5-Bis(tert-butylperoxy)-2,5-dimethylhexane, (preferably blended with calcium carbonate and silica)

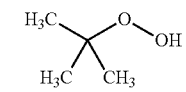

tert-Butyl hydroperoxide

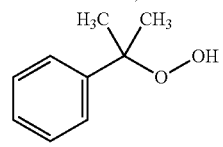

Cumene hydroperoxide

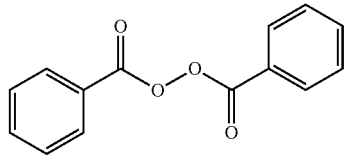

Benzoyl peroxide

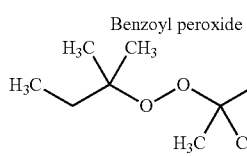

Di-tert-amyl peroxide

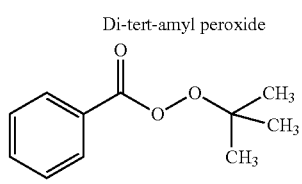

tert-Butyl peroxybenzoate

Oxygen Inhibition for Molecular Welding with or without Energy Augmentators:

Once a free-radical initiation takes place, the polymerization of various chemistries can take place. However, in such free radical initiated reactions, oxygen inhibition can take place, resulting in incomplete polymerization, and incomplete reaction between chains. The oxygen dissolved in a given polymeric substance can play the role of a chain terminator in a free-radical curing reaction, by way of the formation of a peroxy radical, as shown in the scheme below. Oxygen inhibition is particularly pronounced in systems lacking active hydrogen. The curing coagent of the present invention compositions can be any desired mono- or multifunctional curing coagent, which functions to assist the curing process by preventing or lessening reaction pathways such as chain termination, oxygen inhibition, unwanted chain transfer, etc. Various suitable curing coagents are listed and described herein and can be chosen by one of ordinary skill based upon skill in the art and the teachings herein.

In general the use of nitrogen environments sealed from oxygen by virtue of purging if the reaction is conducted in a vessel with environmental control capability is widely used in industry and is the most cost effective.

From a chemistry standpoint one embodiment of curing coagent includes one or more "anti-oxidant" agents including ascorbic acid

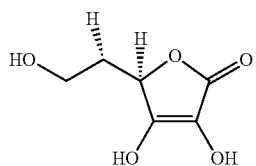

Conversely, the curing coagent can also include a variety of reducing agents such as, for example, earth metals, sodium borohydride NaBH4, sulfite compounds, formic acid, and oxalic acid.

One embodiment includes, especially for the case with 2 part adhesive systems and possibly across 2 surfaces that would mate to form a bond, chemistry categorizations such as:

It is noted that 2 component adhesive systems typically have a Part A (or resin) and a Part B (a curative, curing agent or catalyst). The Part B chemistry is dependent on the part A system:
In acrylic and methacrylayte resin systems, the Part B is usually a free radical cure and that cure can include the following:
UV radicals that are initiated when a UV light source decomposes a photo-initiating catalyst
Peroxide radicals that are initiated by a chemical reduction of the peroxide; typically by an amine initiator
Anaerobic cure by the decomposition on an inhibitor by the elimination of oxygen
In an epoxy resin system, the Part B is usually a system with an active nitrogen or other heteroatom including amine, imidazole, urea, mercaptan, alcohol, etc.
In addition, an epoxy resin can be cured via homopolymerization by an acid and heat that is either catalyzed by heat or via the decomposition of a photo-initiator by UV free radicals.
In a polyurethane resin system:
The resin is multi-functional alcohol and the curative is an isocyanate and there are cure catalysts that initiate cure; this is a 2 component system
Or the resin is isocyanate terminated and cure via catalyst by atmospheric moisture
In silicone resin systems; cure is usually completed via 2 component systems via free radical cure initiated by heat decomposition of sulfur, or via free radical cure initiated by UV photoinitiation or by atmospheric moisture.

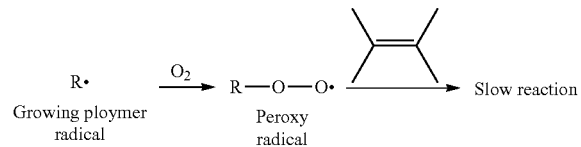

Other curing coagents include active hydrogen containing compounds which are able to counteract the peroxy radical which leads to further reaction. Oxygen inhibition can be circumvented using various techniques. Some active systems to counteract oxygen inhibition include the presence of hindered/secondary amines (—NH) and allylic (C=C—CH$_2$—) moieties. Methacrylates contain such allylic hydrogen moieties and are less susceptible than acrylates to oxygen inhibition.

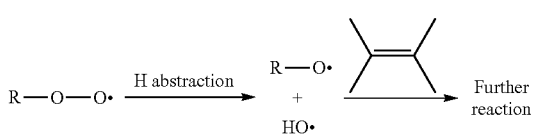

Another strategy for counteracting oxygen inhibition is by the inclusion of compounds having multiple active hydrogens. This can particularly be improved by increasing the functionality from di- to tri- and tetra-functionality. Tetrafunctional alcohols provide monomers with six and eight functionalities.

Catalyst for Molecular Welding with or without Energy Augmentators:
The compositions of the present invention in various embodiments with or without energy augmentators can be fine-tuned to include the appropriate concentration of these monomers along with systems with active hydrogen as well as photo and/or heat active peroxides. Iron, and more generally, catalytic transition metals result in the formation of hydroxyl radicals (HO.) superoxide generating systems. Those of ordinary skill in the art understand that superoxide can reduce ADP-Fe(III) to ADP-Fe(II) and, this iron facilitates the apparent production of (HO.). Chelating agents (in the proper proportions) can also alter the reactivity of iron in superoxide-generating systems. It has been shown that EDTA3 enhances the reactivity of iron toward O$_2$. — while DETAPAC4 drastically slows the O$_2$.— reaction with iron. The use of catalysts and chelating agents is beneficial to optimizing the desirable free radical generation that leads to the desirable reactions.

In a further preferred embodiment, catalysts can be added for increasing free radical formation. Suitable catalysts include, but are not limited to, manganese naphthenate, cobalt naphthenate, and vanadium pentoxide quaternary ammonium salt can be used.

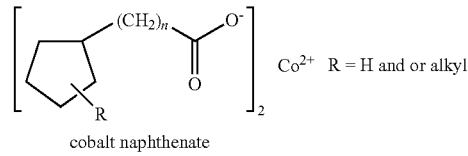

cobalt naphthenate

In the case where there is a combination of a UV and a heat activated peroxide, an initial UV activation can subsequently engender an exothermic reaction which in turn engenders the activation of a thermal peroxide. Another simple method of minimizing oxygen inhibition is to carry out the reaction using an inert atmosphere. The flow of nitrogen and argon on the surface of the materials can be used to limit the oxygen exposure and minimize oxygen induced cure inhibition.

Resins for Molecular Welding With or Without Energy Augmentators:

As used in this embodiment of the present invention, the term polymer includes both homopolymers and copolymers, which collectively can be referred to as (co)polymers. Polymers are molecules with many repetitive units (monomers). The units can be the same (identical) in which case this would be a homopolymer. On the other hand, the polymer can be made of dissimilar units (monomers) in which case the polymer would be a copolymer. Covalent bonding is prevalent but there are cases where ionic bonds and hydrogen bonding is present, depending on the particular monomers present. Examples of monomeric species include, but are not limited to, acrylates, methacrylates, olefins (such as ethylene, propylene, butylene and mixtures thereof), ethers, styrenes, fluoroolefins (such as fluoroethylenes, tetrafluoroethylenes, etc.), esters, carbonates, urethanes, vinyl chlorides, vinyl chloride acetates, amides, imides, acetals, methylpentenes, sulfones, acrylics, styrene acrylics, acrylonitrile, etc. Examples of a co-polymer would include, for example, a polymer made from two or more of these species. Furthermore, the definition extends to more than two monomeric species including terpolymers, and a variety of side groups of different structures than the blended monomeric species. The term polymer is inclusive of any of these variations. Within the present invention, when the present invention composition contains a polymer, it is important that the polymer be able to generate a free radical species by any free radical generation mechanism available to the polymer, including, but not limited to, hydrogen, atom or group abstraction, chain scission, radical addition to unsaturation points in the polymer, etc.

Activation with X-Ray for Molecular Welding with or without Energy Augmentators:

In one embodiment of the present invention, it is desired to initiate a chemical reaction using a deeply penetrating and ionizing form of energy such as X-Ray or e-beam (the initiation energy). The term "X-Ray susceptible polymer" refers to a polymer chemistry that undergoes free radical formation, such as by atom/group abstraction, chain scission, or other mechanism, under X-Ray; and, as a result will have various characteristics (at least one) changing post exposure to the initiation energy. The molecular weight of the polymer can be reduced or a side group can be cleaved. Either one of these characteristics is desirable in the present invention. Extended exposure to the initiation energy could result in degradation and therefore there is a low threshold of energy (Lower dose for initiation) required to initiate the reaction and an upper energy dose which represents a damage threshold (upper dose control limit).

In one embodiment of the present invention, an example of an "X-Ray susceptible polymer" can include, but is not limited to, aliphatic polymers with or without energy augmentators. Aliphatic polymers can include alicyclic (no-aromatic rings), alkanes (single bonds), alkenes (unsaturated with double bonds), allynes (triple bonds) of carbon and hydrogen atoms. One example of an aliphatic polymer would be polyethylene, or a polyethylene-polypropylene copolymer.

Peroxides are widely used commercially to initiate and create free-radical initiation. The reactive free radical species generated then reacts with its environment to form chemical bonds. Such methods are used, for example, to graft maleic anhydride to polyolefins. In general, chain scission can outpace competing reactions. For example, in the particular case of propylene, chain scission and grafting are competitive reactions. However, chain scission outpaces grafting which curbs the achievable molecular weight of the grafted resin.

Maleic anhydride

Suitable polyolefins with or without energy augmentators include, but are not limited to polyethylene (PE), polypropylene (PP) and ethyl vinyl acetate (EVA). Polyethylene is conventionally classified according to its density as Very Low Density Polyethylene (VLDPE), Low Density Polyethylene (LDPE), Linear Low Density Polyethylene (LLDPE), Medium Density Polyethylene (MDPE), and High Density Polyethylene (HDPE).

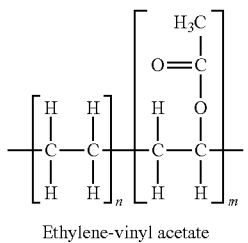

Ethylene-vinyl acetate

Examples of propylene polymers with or without energy augmentators include propylene homopolymers and copolymers of propylene with ethylene or another unsaturated co-monomer. Copolymers also include terpolymers, tetrapolymers, etc. Typically, the units originating from propylene monomer comprise at least about 70 weight percent of the copolymer.

The mechanical and chemical properties of these resins can be tailored to become suitable for the desired application. The resin type, the catalyst, molecular weight, molecular weight distribution (MWD), crystallinity, branching and density all play a role in the microstructure and the behavior of the resin and its performance in the end use application. The choice of these characteristics depending on end use is well within the skill of one of ordinary skill in the art.

As a free radical inducing species for use in the present composition, suitable compounds include, but are not limited to, organic peroxides, azo free-radical initiators, and bicumene. These can be used with or without energy augmentators. Preferably, the free-radical inducing species is an organic peroxide. The organic peroxide can be added via direct injection or via blending with the chemistry of the polymer. The addition of the organic peroxide is in an amount sufficient to provide a concentration of free radicals sufficient for initiating reaction at enough sites to effect bonding, preferably from about 0.005 weight percent to about 20 weight percent, more preferably from about 0.25 weight percent to about 10 weight percent, most preferably from about 0.5 weight percent to about 5 weight percent.

In a similar fashion to the technical strategies employed to prohibit oxygen inhibition, the present invention methods can optionally employ one or more co-grafting reagents in order to minimize (or curb) chain scission. For this reason reagents containing two or more terminal carbon-carbon double bonds or triple bonds can be combined with free-radical generation to mitigate the loss in melt viscosity of polypropylene by coupling of polymer chains.

Optional Additives for Molecular Welding with or without Energy Augmentators:

The present invention compositions in various embodiments can optionally further contain various conventional components that are suitable for the desired application. These can include, but are not limited to, the following agents: fillers, clays, fire retardant, scorch inhibitors, and blowing agents such as azodicarbonamide.

Activation with X-Ray and UV for Molecular Welding with or without Energy Augmentators:

A preferred method of generating free-radicals in the present invention include the use of X-rays, electron-beam and gamma radiation. The present invention can use either X-ray or e-beam both as a source of free radical generation instead of, or in addition to UV light. UV generation is performed via the use of energy converters, preferably in the form of particles that absorb X-ray and convert it to UV. These particles are disposed at the interface where bonding is targeted to take place with or without energy augmentators at the interface. The UV light (regardless of its generation) can in turn engender additional free radical generation.

In one aspect of the invention, an energy converter is added to the chemistry where the energy converter is combined with an organic peroxide and an organic vehicle with or without energy augmentators. Examples of the energy converter include, but are not limited to: $BaFCl:Eu^{2+}$, $BaSO_4^-:Eu^{2+}$, $LaOBr:Tm^{3+}$, $YTaO_4$, $YTaO_4:Nb(*)$, $CaWO_4$, $LaOBr:Tb^{3+}$, $Y_2O_2S:Tb^{3+}$, $ZnS:Ag$, $(Zn,Cd)S:Ag$, $Gd_2O_2S:Tb^3$, $La_2O_2S:Tb^3$. A more comprehensive list is provided in the following table.

| Phosphor | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|
| Zn3(PO4)2:T1+ | 310 | | | | | | N |
| BaF2 | 310 | | | | | | Slightly |
| CsI | 315 | | | | | | N |
| Ca3(PO4)2:T1+ | 330 | | | | | | N |
| YTaO4 | 337 | | 59.8 | 67.42 | 7.5 | Monolithic | N |
| CsI:Na | 338 | | | | | | Y |
| BaSi2O5:Pb2+ | 350 | | | | | | N |
| Borosilicate | 350 | | | | | | N |
| LaCl3(Ce) | 350 | | | | | | Y |
| SrB4O7F:Eu2+ | 360 | | | | | | N |
| RbBr:T1+ | 360 | | | | | | ? |
| (Ba,Sr,Mg)3Si2O7:Pb2+ | 370 | | | | | | N |
| YAlO3:Ce3+ | 370 | | | | | | N |
| BC-422 | 370 | | | | | Organic | ? |
| BaFCl:Eu2+ | 380 | 13 | 49.3 | 37.38 | 4.7 | Tetragonal | N |
| BaSO4—:Eu2+ | 390 | 6 | 45.5 | 37.38 | 4.5 | Rhombic | N |
| BaFBr:Eu2+ | 390 | | | | | | ? |
| BC-420 | 391 | | | | | Organic | ? |
| BC-414 | 392 | | | | | Organic | ? |
| SrMgP2O7:Eu2+ | 394 | | | | | | N |
| BaBr2:Eu2+ | 400 | | | | | | N |
| (Sr,Ba)Al2Si2O8:Eu2+ | 400 | | | | | | N |
| YTaO4:Nb (*) | 410 | 11 | 59.8 | 67.42 | 7.5 | Monolithic | N |
| Y2SiO5:Ce3+ | 410 | | | | | | N |
| CaWO4 | 420 | 5 | 61.8 | 69.48 | 6.1 | Tetragonal | N |
| LaOBr:Tb3+ | 420 | 20 | 49.3 | 38.92 | 6.3 | Tetragonal | N |
| Y2O2S:Tb3+ | 420 | 18 | 34.9 | 17.04 | 4.9 | Hexgonal | N |
| Ls2SiO5:Ce3+ | 420 | | | | | | N |
| La1.8Y0.2SiO5:Ce | 420 | | | | | | N |
| ZnS:Ag | 450 | 17 | 26.7 | 9.66 | 3.9 | Hexgonal | N |
| CdWO4 | 475 | | | | | | Slightly |
| Bi4Ge3O12 (BGO) | 480 | | | | | | N |
| (Zn,Cd)S:Ag | 530 | 19 | 38.4 | 9.66/26.7 | 4.8 | Hexgonal | N |
| Gd2O2S:Tb3+ | 545 | 13 | 59.5 | 50.22 | 7.3 | Hexgonal | N |
| La2O2S:Tb3+ | 545 | 12.5 | 52.6 | 38.92 | 6.5 | Hexgonal | N |
| Y3Al5O12 (Ce) | 550 | | | | | | N |
| LaOBr:Tm3+ | 360, 460 | 14 | 49.3 | 38.92 | 6.3 | Tetragonal | N |
| CaF2(Eu) | 435/300 | | | | | | N |

Figure 102A:
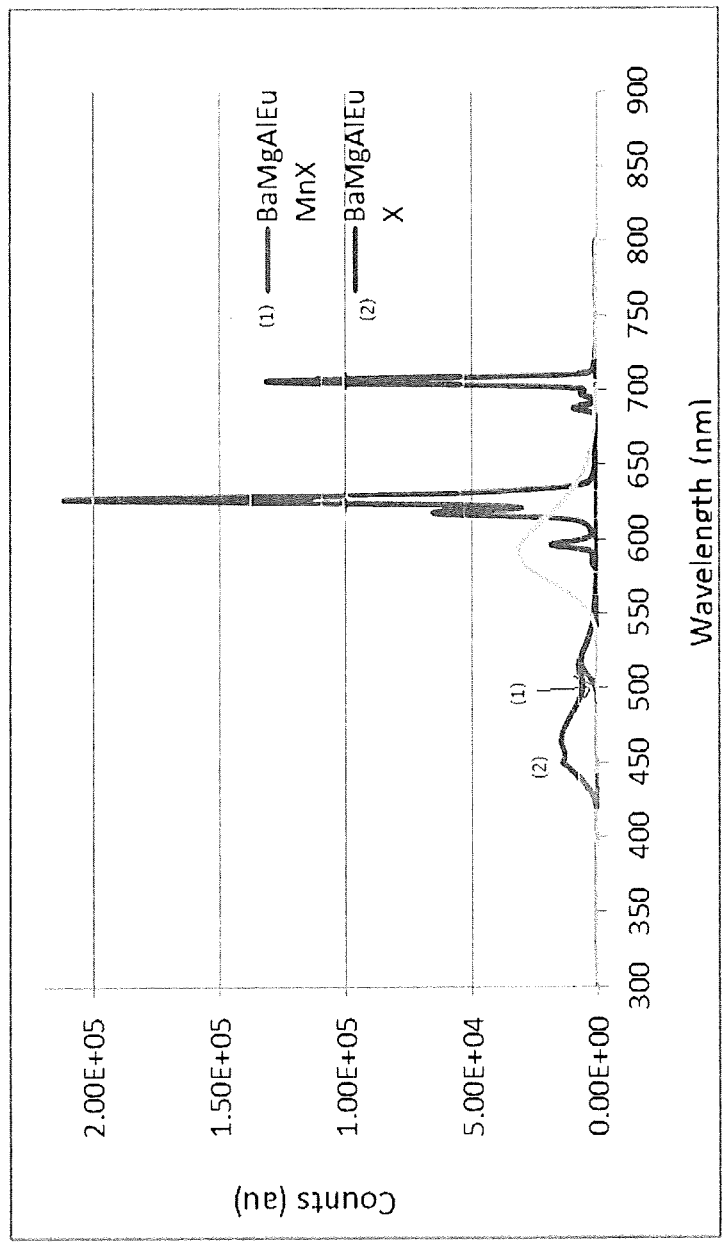
FIG. 102A is an emission spectrum for phosphors emitting light suitable for molecular welding across a spectrum of energies.

Visible phosphors in one embodiment of the present invention have the capability to generate radical oxygen species under X-Ray. The emission under X-Ray is shown in FIG. 102A.

Figure 102B:
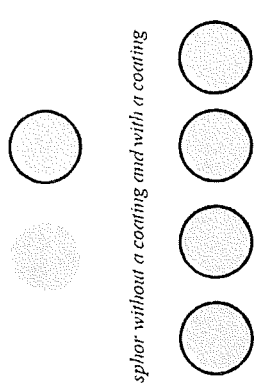
FIG. 102B is a schematic depicting phosphor particles with and without coating.

The various energy converter (such as phosphor) particles with or without energy augmentators can be preferably coated using poly(methyl)methacrylate (PMMA). The process was performed by first dissolving PMMA into acetone and then rolling the phosphors with the solution in a ball mill using 5 mm zirconia as the grinding and mixing balls. The solution is then recovered and then dried. Upon acetone evaporation the particles were left with a surface coating of PMMA. Alternatively, the energy converter can be incorporated directly into a polymer contained in the reactive chemistry of the present invention (either in the surface of the substrate, or in a coating applied to the substrate, or in an intermediary layer) by using the phosphor as a particulate filler, which is blended into the composition using any conventional mixing method. The energy converter/phosphor be used with or without a coating, and when a ball mill is used, a number of powders can be individually coated (see FIG. 102B).

The thickness of the coating can be estimated from the following calculations:

| PMMA Coating | |
|---|---|
| target thickness (nano meters) | 50 |
| Phosphor Density (g/cc) | 7.5 |
| Calculations | |
| Particle Size (m) | 1.00E−06 |
| Density (g/m$^3$) | 7.50E+06 |
| Volume (m$^3$) | 5.23E−19 |
| Surface Area (m$^2$) | 7.85E−13 |
| Weight per particle (g) | 3.93E−12 |
| Number of particles per gram | 2.55E+11 |
| Desirable Coating Thickness (m) | 5E−08 |
| Volume of the coating per gram | 1.00E−08 |
| Density of PMMA (g/cc) | 1.4 |
| Density of PMMA (g/m3) | 1.40E+06 |
| Weight of PMMA preferred per gram of phosphor | 1.40E−02 |
| Slurry Composition (per gram of phosphor) | |
| Phosphor (g) | 1 |
| PMMA (g) | 1.40E−02 |
| Acetone (cc) | 12.5 |
| Zirconia (g) | 125 |
| Jar Volume (cc) | 50 |

Furthermore, the PMMA coating can include some of the desirable organic peroxide chemistries. These chemistries can be added in liquid form and can be rolled in a jar in the ball mill in acetone. Upon drying the solvent, the PMMA coating is doped with the organic peroxide chemistry. As an example, dicumyl peroxide can be added at 1% by weight in the previous table.

Figure 102C:
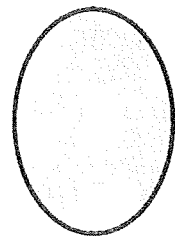
FIG. 102C is a schematic depicting a phosphor particle composite useful in the present invention.

If the particles are not completely dispersed, then an aggregate of the phosphors can be coated with the PMMA resin (See FIG. 102C).

Furthermore, if a combination of different phosphors is used then as an aggregate of the plurality of different phosphors can be coated using PMMA, which may optionally contain a peroxide chemistry (see FIG. 102D). The molecular weight of the PMMA can vary as needed to form a coating.

Figure 102E:
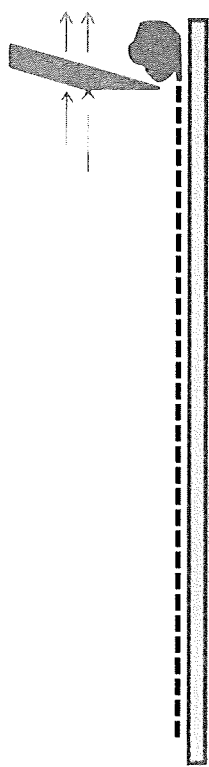
FIG. 102E is a schematic depicting a transfer method for depositing a phosphor mixture onto a substrate.

By adding the weight percent in the mix to high enough levels, such as above 0.03 g per 1 g of phosphors, the coating no longer forms a discontinuous phase where individual particles are coated; but, rather, the particles start to neck and to connect laterally which culminates in the formation of a film. At a ratio of 5 weight percent of higher, the necking of particles enables the formation of a film. The film can be preferably obtained by taking the slurry and using a drawing knife (FIG. 102E). The conformable film can be drawn using a 1 mil to 8 mil knife.

Figure 102F:
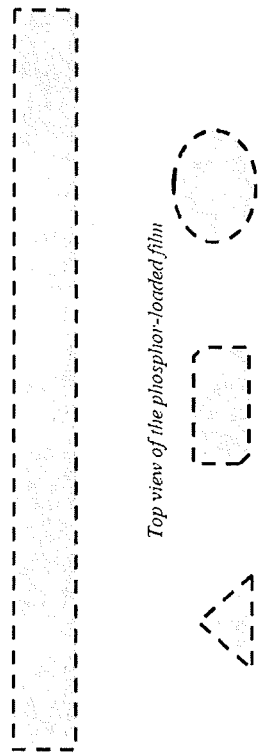
FIG. 102F is a schematic depicting differently shaped phosphor loaded conformable films.

A die cutter can punch a cut out from the phosphor loaded conformable film as shown in FIG. 102F. Various geometries can be formed in this manner.

Figure 102G:
FIG. 102G is a schematic depicting a conformal film conforming to the shape of both planar and complex interfaces.

The conformable film that is phosphor loaded (shown by dashed line) can accommodate stretching and maintaining its shape across complex interfaces (see FIG. 102G).

Furthermore, the preparation of the film can be done using plasticizers in the mix prior to casting. About 2% to 5% by weight is a preferable range of such plasticizers. Plasticizers with boiling point temperatures above room temperature remain embedded in the film and make the film's surface sticky. This is desirable in case the film is to be used between two substrates to be adhered. Examples of suitable plasticizers include, but are not limited to, tripropylene glycol. The addition of a small amount of tripropylene glycol in the film (around 2% by weight of solids) and the placement of the film at the interface of two substrates allows a good material transport between the substrates and promotes bonding. Excessive tripropylene glycol would prohibit adhesion.

$$H[OC_2H_3(CH_3)]_3OH$$

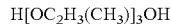
Tripropylene glycol

Accordingly, the energy augmentation structures of the present invention can be used in conjunction with the energy converters described herein in a wide variety of applications. The use of energy converters in such applications has been described in the following: US Published Application No. 2008/0248001; US Published Application No. 2009/0104212; US Published Application No. 2009/0294692; US Published Application No. 2010/0003316; US Published Application No. 2010/0016783; US Published Application No. 2010/0261263; US Published Application No. 2010/0266621; US Published Application No. 2011/0021970; US Published Application No. 2011/0117202; US Published Application No. 2011/0126889; US Published Application No. 2011/0129537; US Published Application No. 2011/0263920; US Published Application No. 2012/0064134; US Published Application No. 2012/0089180; US Published Application No. 2013/0102054; US Published Application No. 2013/0129757; US Published Application No. 2013/0131429; US Published Application No. 2013/0156905; US Published Application No. 2013/0171060; US Published Application No. 2013/0240758; US Published Application No. 2014/0134307; US Published Application No. 2014/0163303; US Published Application No. 2014/0166202; US Published Application No. 2014/0222117; US Published Application No. 2014/0242035; US Published Application No. 2014/0243934; US Published Application No. 2014/0272030; US Published Application No. 2014/0323946; US Published Application No. 2014/0341845; US Published Application No. 2014/0343479; US Published Application No. 2015/0182934; US Published Application No. 2015/0202294; US Published Application No. 2015/0246521; US Published Application No. 2015/0251016; US Published Application No. 2015/0265706; US Published Application No. 2015/0283392; US Published Application No. 2015/0290614; US Published Application No. 2016/0005503; US Published Application No. 2016/0067524; US Published Application No. 2016/0159065; US Published Application No. 2016/0243235; US Published Application No. 2016/0263393; US Published Application No. 2016/0325111; US Published Application No. 2016/0331731; US Published Application No. 2016/0354467; US Published Application No. 2016/0362534; US Published Application No. 2017/0027197; US Published Application No. 2017/0043178; US Published Application No. 2017/0050046; US Published Application No. 2017/0096585; US Published Application No. 2017/0113061; US Published Application No. 2017/0121472; US Published Application No. 2017/0154866; US Published Application No. 2017/0157418; US Published Application No. 2017/0162537; US Published Application No. 2017/0173350; US Published Application No. 2017/0186720; US Published Application No. 2017/0190166; US Published Application No. 2017/0196977; US Published Application No. 2017/0239489; US Published Application No. 2017/0239637; US Published Application No. 2017/0240717; US Published Application No. 2017/0258908; US Published Application No. 2017/0319868; US Published Application No. 2017/0319869; US Published Application No. 2018/0036408; US Published Application No. 2018/0154171; US Published Application No. 2018/0154178; US Published Application No. 2018/0169433; US Published Application No. 2018/0170028; US Published Application No. 2018/0269174; US Published Application No. 2018/0271121; US Published Application No. 2018/0304225; US Published Application No. 2018/0311355; US Published Application No. 2018/0317307; US Published Application No. 2018/0344850; US Published Application No. 2018/0358327; US Published Application No. 2019/0016869; US Published Application No. 2019/0022221; US Published Application No. 2019/0100680; US Published Application No. 2019/0134419; US Published Application No. 2019/0134595; US Published Application No. 2019/0134596; US Published Application No. 2019/0157234; US Published Application No. 2019/0168015; US Published Application No. 2019/0184190; US Published Application No. 2019/308030; US Published Application No. 2019/0336605; US Published Application No. 2019/0336785; US Published Application No. 2019/0336786; US Published Application No. 2019/0341364; U.S. application Ser. No. 16/074,707, filed Aug. 1, 2018; U.S. application Ser. No. 16/516,463, filed Jul. 19, 2019; U.S. application Ser. No. 16/554,831, filed Aug. 29, 2019 U.S. application Ser. No. 16/599,732, filed Oct. 11, 2019; U.S. application Ser. No. 16/674,435, filed Nov. 5, 2019; and U.S. application Ser. No. 16/728,803, filed Dec. 27, 2019; the contents of each of which are hereby incorporated by reference in their entireties. The energy augmentation structures and/or energy converters described herein have uses with the subject matter in the above noted published and unpublished US patent applications.

The following are exemplary embodiments of the present invention:

Embodiment 1

An energy emitter comprising:
at least one energy augmentation structure; and
an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present.

Embodiment 2

The emitter of Embodiment 1, wherein the at least one energy augmentation structure comprises a structure in which a locally intensified electric field exists in one part of the structure when the structure receives electromagnetic energy.

Embodiment 3

The emitter of Embodiment 1 or 2, wherein the at least one energy augmentation structure comprises at least one resonator dimensioned to be resonant with the applied electromagnetic energy.

Embodiment 4

The emitter of any one of Embodiments 1-3, wherein the resonator comprises a folded resonator.

Embodiment 5

The emitter of Embodiment 4, wherein the folded resonator comprises electrical conductors configured as a fractal pattern.

Embodiment 6

The emitter of Embodiment 4, wherein the folded resonator comprises a ¾ wavelength resonator having opposing ends folded inwards from a center of the folded resonator with a gap in between the opposing ends.

Embodiment 7

The emitter of Embodiment 6, wherein the locally intensified electric field exists in a vicinity of the opposing ends.

Embodiment 8

The emitter of Embodiment 4, wherein the folded resonator comprises a ¾ wavelength resonator having opposing ends folded outwards from a center of the folded resonator with a gap in between the opposing ends.

Embodiment 9

The emitter of Embodiment 8, wherein the locally intensified electric field exists in a vicinity of the opposing ends.

Embodiment 10

The emitter of Embodiment 4, wherein the resonator comprises a fractal pattern.

Embodiment 11

The emitter of Embodiment 10, wherein the fractal pattern comprises a three-dimensional fractal pattern.

Embodiment 12

The emitter of Embodiment 4, wherein the at least one resonator comprises a plurality of resonators.

Embodiment 13

The emitter of Embodiment 12, wherein the resonators are disposed on a sheet.

Embodiment 14

The emitter of Embodiment 13, wherein the sheet comprises a sheet for disposal within a medium to be treated.

Embodiment 15

The emitter of Embodiment 13, wherein the sheet comprises a flexible sheet for disposal within a medium to be treated.

Embodiment 16

The emitter of Embodiment 13, wherein the sheet comprises a rigid sheet for disposal within a medium to be treated.

Embodiment 17

The emitter of Embodiment 13, wherein the plurality of resonators comprises an array of the resonators disposed on a sheet.

Embodiment 18

The emitter of Embodiment 12, wherein each of the resonators comprises a free-standing resonator.

Embodiment 19

The emitter of Embodiment 18, wherein the free-standing resonator is disposed within a medium to be treated.

Embodiment 20

The emitter of any one of Embodiments 1 to 19, wherein the at least one energy augmentation structure comprises a first level of metallic patterns and a second level of metallic patterns offset in in at least one of a lateral or axial direction from the first level of metallic patterns.

Embodiment 21

The emitter of Embodiment 20, wherein at least one of the metallic patterns comprises a first resonator dimensioned to be resonant with an applied electromagnetic energy.

Embodiment 22

The emitter of Embodiment 21, wherein the at least one of the metallic patterns comprises a folded resonator having opposing electrodes with electric fields directed in between, and the energy converter is positioned between the opposing electrodes or within fringing electric field of the opposing electrodes.

Embodiment 23

The emitter of Embodiment 22, wherein the opposing electrodes are directed external to the folded resonator and parallel to one another.

Embodiment 24

The emitter of Embodiment 22, wherein the opposing electrodes are directed internal to the folded resonator and parallel to one another.

Embodiment 25

The emitter of any one of Embodiments 22-24, wherein the folded resonator comprises a ¾ folded resonator.

Embodiment 26

The emitter of Embodiment 20, wherein the at least one of the metallic patterns comprises a plurality of the folded resonators concentrically arranged and optionally co-planar to one another, such that the external opposing electrodes of each folded resonator do not overlap spatially with the external opposing electrodes of the other of the plurality of folded resonators.

Embodiment 27

The emitter of Embodiment 20, wherein the at least one of the metallic patterns comprises a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 28

The emitter of any one of Embodiments 1 to 27, wherein the at least one energy augmentation structure comprises at least one of Au, Ag, Cu, Al, transparent metal oxides or refractory metals.

Embodiment 29

The emitter of any one of Embodiments 1 to 28, further comprising an antireflection film disposed on the at least one energy augmentation structure or the energy converter.

Embodiment 30

The emitter of any one of Embodiments 1 to 29, wherein the at least one energy augmentation structure is disposed in vicinity of a down conversion material comprising the energy converter.

Embodiment 31

The emitter of any one of Embodiments 1 to 29, wherein the at least one energy augmentation structure is disposed in vicinity of an up-conversion material comprising the energy converter.

Embodiment 32

The emitter of any one of Embodiments 1 to 29, wherein the at least one energy augmentation structure is disposed in vicinity of a phosphor comprising the energy converter.

Embodiment 33

The emitter of any one of Embodiments 1 to 29, wherein the at least one energy augmentation structure is disposed in vicinity of a piezoelectric device comprising the energy converter.

Embodiment 34

The emitter of Embodiment 33, wherein the piezoelectric device is configured to receive sonic or acoustic energy and emit at least one of ultraviolet or visible light in response to absorbing the sonic or acoustic energy.

Embodiment 35

The emitter of any one of Embodiments 1 to 29, wherein the at least one energy augmentation structure is disposed in vicinity of a mechanoluminescent device comprising the energy converter.

Embodiment 36

The emitter of Embodiment 35, wherein the mechanoluminescent device is configured to receive sonic or acoustic energy and emit at least one of ultraviolet or visible light in response to absorbing the sonic or acoustic energy.

Embodiment 37

The emitter of any one of Embodiments 1 to 36, wherein the at least one energy augmentation structure is disposed inside a plasma capsule device comprising the energy converter.

Embodiment 38

The emitter of Embodiment 37, wherein the plasma capsule device is configured to receive radio frequency or microwave energy and emit at least one of ultraviolet or visible light in response to absorbing the radio frequency or microwave energy.

Embodiment 39

The emitter of any one of Embodiments 1 to 29, wherein the at least one energy augmentation structure is disposed in vicinity of an x-ray stimulated phosphor comprising the energy converter.

Embodiment 40

The emitter of Embodiment 39, wherein the x-ray stimulated phosphor emits one of ultraviolet or visible light in response to absorbing x-rays.

Embodiment 41

The emitter of Embodiment 40, wherein the x-ray stimulated phosphor emits the one of ultraviolet or visible light for at least a time of 1 minute after x-ray stimulation.

Embodiment 42

The emitter of Embodiment 40, wherein the x-ray stimulated phosphor emits the one of ultraviolet or visible light for at least a time of 10 minutes after x-ray stimulation.

Embodiment 43

The emitter of Embodiment 40, wherein the x-ray stimulated phosphor emits the one of ultraviolet or visible light for at least a time of 60 minutes after x-ray stimulation.

Embodiment 44

The emitter of Embodiment 39, wherein the x-ray stimulated phosphor emits lower energy x-rays in response to absorbing higher energy x-rays.

Embodiment 45

The emitter of any one of Embodiments 1 to 44, wherein the energy received from the energy source is one or more selected from acoustic waves, sound waves, radio waves, microwaves, far infrared, near infrared, visible light, UV, x-rays, gamma rays, electron beams, and proton beams.

Embodiment 46

The emitter of any one of Embodiments 1 to 45, wherein the energy converter being disposed in a vicinity of the at least one energy augmentation structure comprises a conductive coupling of the energy converter to the at least one energy augmentation structure.

Embodiment 47

The emitter of Embodiment 46, wherein the conductive coupling comprises a physical conductive connection between the energy converter and the at least one energy augmentation structure.

Embodiment 48

The emitter of any one of Embodiments 1 to 29, wherein the energy converter comprises either one or both of (i) a down converter converting ultraviolet or blue light into red, yellow, or green light, or (ii) an up converter converting infrared or red light into yellow, green light, or blue light.

Embodiment 49

The emitter of any one of Embodiments 1 to 29, wherein the at least one energy augmentation structure comprises a plurality of energy collectors.

Embodiment 50

The emitter of Embodiment 49, wherein the energy converters are positioned to convert energy being internally scattered within the energy collectors.

Embodiment 51

The emitter of Embodiment 49, wherein the energy collectors comprise a metal core cladded with a high-K dielectric and a subsequent cladding of a low-K dielectric.

Embodiment 52

The emitter of Embodiment 49, wherein the energy collectors comprise a radial pattern of collectors.

Embodiment 53

The emitter of Embodiment 7, wherein the energy collectors comprise a fractal pattern.

Embodiment 54

The emitter of Embodiment 53, wherein the fractal pattern is embedded within a dielectric material.

Embodiment 55

The emitter of any one of Embodiments 1 to 54, wherein the at least one energy augmentator comprises metallic conductors including at least one of Au, Ag, Cu, Ni, Pt, Pd, Co, Ru, Rh, Al, Ga, or a combination or alloys or layers thereof.

Embodiment 56

The emitter of any one of Embodiments 1 to 54, wherein the energy converter comprises at least one of Y2O3, $Y_2O_2S$, NaYF4, NaYbF4, YAG, YAP, Nd2O3, LaF3, LaCl3, $La_2O_3$, $TiO_2$, LuPO4, YVO4, YbF3, YF3, Na-doped YbF3, or $SiO_2$ or alloys or layers thereof.

Embodiment 57

The emitter of Embodiment 56, wherein the energy converter further comprises a dopant including at least one of Er, Eu, Yb, Tm, Nd, Tb, Ce, Y, U, Pr, La, Gd and other rare-earth species or a combination thereof.

Embodiment 58

The emitter of Embodiment 57, wherein the dopant is included at a concentration of 0.01%-50% o by mol concentration.

Embodiment 59

The emitter of any one of Embodiments 1 to 54, wherein the energy converter comprises a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe;

Mn,Yb MgS; Mn, Yb CaS; Mn,Yb ZnS:Tb3+, Er3+; ZnS: Tb3+; $Y_2O_3$:Tb3+; $Y_2O_3$:Tb3+, Er3+; ZnS:Mn2+; ZnS:Mn, Er3+.

Embodiment 60

The emitter of any one of Embodiments 1 to 54, wherein the energy converter comprises an up converter including at least one of Y2O3, $Y_2O_2S$, NaYF4, NaYbF4, YAG, YAP, Nd2O3, LaF3, LaCl3, $La_2O_3$, $TiO_2$, LuPO4, YVO4, YbF3, YF3, Na-doped YbF3, or $SiO_2$ or alloys or layers thereof.

Embodiment 61

The emitter of any one of Embodiments 1 to 54, wherein the energy converter comprises an up converter including at least one of Tm3+ doped flourozirconate glasses, LuPO4: Yb3+, Tm3+, and YbPO4:Er3+ nanocrystals, tellurium and germanium oxides, tellurium and germanium oxides doped with at least one Tm, Yb, Ho, Er, or Pr, Yb3+ doped BaZrO3, Nd3+:Cs2NaGdCl6, Nd3+, Yb3+:Cs2NaGdCl6, Nd3+ and Ho3+ co-doped-based ZrF4 fluoride glasses, Tm3+/Yb3+-codoped TeO2-Ga2O3-R2O (R═Li, Na, K) glasses, and metal-to-ligand charge transfer (MLCT) transition materials, and MLCT transition materials including [Ru(dmb)3]2+ (dmb=4,4-dimethyl-2,2-bipyridine).

Embodiment 62

An energy augmentation structure capable of capturing one or more wavelengths of electromagnetic energy, and augmenting the one or more wavelengths of electromagnetic energy in at least one property.

Embodiment 63

The energy augmentation emitter of Embodiment 62, wherein the energy augmentation structure is at least one non-plasmonic member selected from the group consisting of resonators, fractal antennas, electrical grid patterns, antennas, cavities, etalons, nanoparticles, microparticles, nanostructures, and microstructures.

Embodiment 64

The energy augmentation structure of Embodiment 62, comprising a folded resonator having opposing electrodes with electric fields directed in between.

Embodiment 65

The energy augmentation structure of Embodiment 64, wherein the opposing electrodes are directed external to the folded resonator and parallel to one another.

Embodiment 66

The energy augmentation structure of Embodiment 64, wherein the opposing electrodes are directed internal to the folded resonator and parallel to one another.

Embodiment 67

The energy augmentation structure of any one of Embodiments 64 to 66, wherein the folded resonator comprises a ¾ λ folded resonator.

Embodiment 68

The energy augmentation structure of Embodiment 64, wherein the folded resonator is a plurality of the folded resonators concentrically arranged and optionally co-planar to one another, such that the external opposing electrodes of each folded resonator do not overlap spatially with the external opposing electrodes of the other of the plurality of folded resonators.

Embodiment 69

The energy augmentation structure of Embodiment 64, wherein the folded resonator is a plurality of the folded resonators concentrically arranged and optionally co-planar to one another, such that the external opposing electrodes of each folded resonator overlap spatially with the external opposing electrodes of one or more of the other of the plurality of folded resonators.

Embodiment 70

An energy collector comprising at least one energy augmentation structure; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

Embodiment 71

The energy collector of Embodiment 70, wherein the at least one energy converter is at least one member selected from the group consisting of phosphors, lumiphors, electroluminescent particles, up-converters, down-converters, and scintillators.

Embodiment 72

The energy collector of Embodiment 70 or 71, wherein the energy augmentation structure is at least one non-plasmonic member selected from the group consisting of resonators, fractal antennas, electrical grid patterns, antennas, cavities, etalons, nanoparticles, microparticles, nanostructures, and microstructures.

Embodiment 73

The energy collector of any one of Embodiments 70 to 72, wherein having the energy converter disposed in a vicinity of the at least one energy augmentation structure comprises conductively coupling the at least one energy converter to the at least one energy augmentation structure.

Embodiment 74

The energy collector of Embodiment 73, wherein conductively coupling comprises having the at least one energy converter be proximate the at least one energy augmentation structure, physically located within the at least one energy augmentation structure, or located within a generated electric field of the at least one energy augmentation structure.

Embodiment 75

The energy collector of Embodiment 73, wherein conductively coupling comprises a physical conductive connection between the at least one energy converter and the at least one energy augmentation structure.

Embodiment 76

The energy collector of Embodiment 70, wherein the applied electromagnetic energy is selected from radio waves, microwaves, far infrared, near infrared, visible light, UV, x-rays, gamma rays, electron beams, and proton beams.

Embodiment 77

The energy collector of Embodiment 70, wherein the at least one energy augmentation structure comprises a first resonator dimensioned to be resonant with the applied electromagnetic energy, said first resonator optionally comprising a fractal pattern.

Embodiment 78

The energy collector of Embodiment 70, wherein the energy augmentation structure comprises a folded resonator having opposing electrodes with electric fields directed in between.

Embodiment 79

The energy collector of Embodiment 76, wherein the opposing electrodes are directed external to the folded resonator and parallel to one another.

Embodiment 80

The energy collector of Embodiment 76, wherein the opposing electrodes are directed internal to the folded resonator and parallel to one another.

Embodiment 81

The energy collector of any one of Embodiments 78-80, wherein the folded resonator comprises a ¾ folded resonator.

Embodiment 82

The energy collector of Embodiment 78, wherein the folded resonator is a plurality of the folded resonators concentrically arranged and optionally co planar to one another, such that the external opposing electrodes of each folded resonator do not overlap spatially with the external opposing electrodes of the other of the plurality of folded resonators.

Embodiment 83

The energy collector of Embodiment 78, wherein the folded resonator is a plurality of the folded resonators concentrically arranged and optionally co planar to one another, such that the external opposing electrodes of each folded resonator overlap spatially with the external opposing electrodes of one or more of the other of the plurality of folded resonators.

Embodiment 84

A wafer to wafer bonded assembly, comprising a plurality of semiconductor wafers bonded together by a cured adhesive composition obtained by curing of a curable adhesive composition, wherein the curable adhesive composition comprises an organic vehicle comprising at least one polymerizable monomer; at least one photo-initiator responsive to a selected wavelength of light; and at least one energy emitter of any one of Embodiments 1-61, or at least one energy augmentation structure of any one of Embodiments 62-69, or at least one energy collector of any one of Embodiments 70-83.

Embodiment 85

The assembly of Embodiment 84, wherein said at least one energy emitter or said at least one energy collector is present, and wherein said at least one energy converter contained therein is selected to emit said selected wavelength of light when exposed to an imparted radiation.

Embodiment 86

The assembly of Embodiment 85, wherein the at least one energy converter is an upconverting material.

Embodiment 87

The assembly of Embodiment 86, wherein the imparted radiation is near infrared.

Embodiment 88

The assembly of Embodiment 85, wherein the at least one energy converter is a downconverting material.

Embodiment 89

The assembly of Embodiment 88, wherein the imparted radiation is an ionizing radiation.

Embodiment 90

The assembly of Embodiment 89, wherein the ionizing radiation is X-rays.

Embodiment 91

An encapsulated semiconductor component, comprising a semiconductor assembly having thereon a covering of a cured adhesive composition, wherein the cured adhesive composition is formed by curing a curable adhesive composition comprising an organic vehicle comprising at least one polymerizable monomer; at least one photo-initiator responsive to a selected wavelength of light; and at least one energy emitter of any one of Embodiments 1-61, or at least one energy augmentation structure of any one of Embodiments 62-69, or at least one energy collector of any one of Embodiments 70-83.

Embodiment 92

The encapsulated semiconductor component of Embodiment 91, wherein said at least one energy emitter or said at least one energy collector is present, and wherein said at least one energy converter contained therein is selected to emit said selected wavelength of light when exposed to an imparted radiation.

Embodiment 93

The encapsulated semiconductor component of Embodiment 92, wherein the at least one energy converter is an upconverting material.

Embodiment 94

The encapsulated semiconductor component of Embodiment 93, wherein the imparted radiation is near infrared.

Embodiment 95

The encapsulated semiconductor component of Embodiment 92, wherein the at least one energy converter is a downconverting material.

Embodiment 96

The encapsulated semiconductor component of Embodiment 95, wherein the imparted radiation is an ionizing radiation.

Embodiment 97

The encapsulated semiconductor component of Embodiment 96, wherein the ionizing radiation is X-rays.

Embodiment 98

The encapsulated semiconductor component of any one of Embodiments 91-97, wherein the cured adhesive composition is in a form selected from the group consisting of underfill, glob top, dam and fill, and molded.

Embodiment 99

An integrated circuit assembly comprising a plurality of electrically connected material layers, wherein the plurality of electrically connected material layers are held together by a cured adhesive composition obtained by curing a curable adhesive composition comprising an organic vehicle comprising at least one polymerizable monomer; at least one photo-initiator responsive to a selected wavelength of light; and at least one energy emitter of any one of Embodiments 1-61, or at least one energy augmentation structure of any one of Embodiments 62-69, or at least one energy collector of any one of Embodiments 70-83, and wherein the integrated circuit has no external conductive connections between layers.

Embodiment 100

The assembly of Embodiment 99, wherein said at least one energy emitter or said at least one energy collector is present and wherein said at least one energy converter contained therein is selected to emit said selected wavelength of light when exposed to an imparted radiation.

Embodiment 101

The assembly of Embodiment 100, wherein the at least one energy converter is an upconverting material.

Embodiment 102

The assembly of Embodiment 101, wherein the imparted radiation is near infrared.

Embodiment 103

The assembly of Embodiment 100, wherein the at least one energy converter is a downconverting material.

Embodiment 104

The assembly of Embodiment 103, wherein the imparted radiation is an ionizing radiation.

Embodiment 105

The assembly of Embodiment 104, wherein the ionizing radiation is X-rays.

Embodiment 106

An encapsulated semiconductor component, comprising a semiconductor assembly having a substrate containing an insertion molded portion, wherein the insertion molded portion comprises a molding resin and has at least one energy emitter of any one of Embodiments 1-61, or at least one energy augmentation structure of any one of Embodiments 62-69, or at least one energy collector of any one of Embodiments 70-83 on a surface thereof, wherein the substrate has formed thereon at least one semiconductor component, and wherein the semiconductor component has thereon a covering of a cured adhesive composition, wherein the cured adhesive composition is formed by curing a curable adhesive composition comprising an organic vehicle comprising at least one polymerizable monomer; and at least one photo-initiator responsive to a selected wavelength of light.

Embodiment 107

The encapsulated semiconductor component of Embodiment 106, wherein said at least one energy emitter or said at least one energy collector is present and wherein the at least one energy converter contained therein is a first energy converter and is on the surface of the insertion molded portion and is selected to emit said selected wavelength of light when exposed to an imparted radiation.

Embodiment 108

The encapsulated semiconductor component of Embodiment 107, wherein the curable adhesive composition further comprises a second energy converter, which may be the same as or different from the first energy converter, wherein the second energy converter is selected to emit said selected wavelength of light when exposed to the imparted radiation.

Embodiment 109

The encapsulated semiconductor component of Embodiment 107 or 108, wherein the first energy converter is an upconverting material.

Embodiment 110

The encapsulated semiconductor component of Embodiment 109, wherein the imparted radiation is near infrared.

Embodiment 111

The encapsulated semiconductor component of Embodiment 107 or 108, wherein the first energy converter is a downconverting material.

Embodiment 112

The encapsulated semiconductor component of Embodiment 111, wherein the imparted radiation is an ionizing radiation.

Embodiment 113

The encapsulated semiconductor component of Embodiment 112, wherein the ionizing radiation is X-rays.

Embodiment 114

The encapsulated semiconductor component of Embodiment 108, wherein the second energy converter is an upconverting material.

Embodiment 115

The encapsulated semiconductor component of Embodiment 114, wherein the imparted radiation is near infrared.

Embodiment 116

The encapsulated semiconductor component of Embodiment 108, wherein the second energy converter is a downconverting material.

Embodiment 117

The encapsulated semiconductor component of Embodiment 116, wherein the imparted radiation is an ionizing radiation.

Embodiment 118

The encapsulated semiconductor component of Embodiment 117, wherein the ionizing radiation is X-rays.

Embodiment 119

A wafer to wafer bonded assembly, comprising a plurality of semiconductor wafers bonded together by a cured adhesive composition obtained by curing of a curable adhesive composition, wherein the curable adhesive composition comprises an organic vehicle comprising at least one polymerizable monomer; at least one photo-initiator responsive to a selected wavelength of light; and at least one energy emitter of any one of Embodiments 1-61, or at least one energy augmentation structure of any one of Embodiments 62-69, or at least one energy collector of any one of Embodiments 70-83, wherein (1) the viscosity of said organic vehicle is suitable for dispensing through an automated dispenser onto a selected substrate, (2) the viscosity of said organic vehicle is suitable for printing onto a selected substrate through a mask, or (3) wherein said adhesive is photo-patternable.

Embodiment 120

The assembly of Embodiment 119, wherein said at least one energy emitter or said at least one energy collector is present, and wherein said at least one energy converter contained therein is selected to emit said selected wavelength of light when exposed to an imparted radiation.

Embodiment 121

The assembly of Embodiment 120, wherein the at least one energy converter is an upconverting material.

Embodiment 122

The assembly of Embodiment 121, wherein the imparted radiation is near infrared.

Embodiment 123

The assembly of Embodiment 120, wherein the at least one energy converter is a downconverting material.

Embodiment 124

The assembly of Embodiment 123, wherein the imparted radiation is an ionizing radiation.

Embodiment 125

The assembly of Embodiment 124, wherein the ionizing radiation is X-rays.

Embodiment 126

The assembly of any one of Embodiments 119-125, wherein said organic vehicle comprises a monomer forming a thermoset resin.

Embodiment 127

The assembly of Embodiment 126, wherein said thermoset resin is selected from the group consisting of: acrylics, phenolics, urethanes, epoxies, styrenes, and silicones.

Embodiment 128

The assembly of any one of Embodiments 119-127, wherein said at least one photoinitiator is selected from the group consisting of: benzoin ethers, benzil ketals, α-dialkoxyacetophenones, α-aminoalkylphenones, acylphosphine oxides, benzophenones/amines, thioxanthones/amines, and titanocenes.

Embodiment 129

The assembly of any one of Embodiments 123-125, wherein said selected wavelength of light is in the UV range and said imparted radiation comprises X-rays.

Embodiment 130

The assembly of any one of Embodiments 123-125, wherein said downconverting material comprises dispersed inorganic particulates selected from the group consisting of: metal oxides; metal sulfides; doped metal oxides; and mixed metal chalcogenides.

Embodiment 131

The assembly of any one of Embodiments 119-130, wherein the viscosity of said organic vehicle is suitable for dispensing through an automated dispenser onto a selected substrate.

Embodiment 132

The assembly of any one of Embodiments 119-131, wherein the viscosity of said organic vehicle is suitable for printing onto a selected substrate through a mask.

Embodiment 133

The assembly of any one of Embodiments 119-132, wherein said adhesive is photo-patternable.

Embodiment 134

The assembly of any one of Embodiments 119-133, further comprising inorganic particulates selected from the group consisting of: metals and metal alloys, ceramics and dielectrics, and metal-coated polymers.

Embodiment 135

The assembly of any one of Embodiments 119-134, further comprising an organic component selected from the group consisting of: solvents, viscosity modifiers, surfactants, dispersants, and plasticizers.

Embodiment 136

The assembly of any one of Embodiments 119-135, further comprising a sheet containing a monolayer of conductive particles of a suitable size to render the resulting adhesive bond anisotropically conductive.

Embodiment 137

The assembly of any one of Embodiments 119-136, wherein the at least one photo-initiator and the at least one energy converter are chemically tethered to one another.

Embodiment 138

An electronic component, comprising: a substrate and one or more electronic elements, wherein the electronic component contains a cured adhesive formed from a curable adhesive composition,
  wherein the curable adhesive composition comprises:
  an organic vehicle comprising at least one polymerizable monomer,
  at least one photo-initiator responsive to a selected wavelength of light; and
  at least one energy emitter of any one of Embodiments 1-61, or at least one energy augmentation structure of any one of Embodiments 62-69, or at least one energy collector of any one of Embodiments 70-83
  wherein the electronic component is a semiconductor component.

Embodiment 139

The electronic component of Embodiment 138, wherein said at least one energy emitter or said at least one energy collector is present and wherein said at least one energy converter contained therein is selected to emit said selected wavelength of light when exposed to an imparted radiation.

Embodiment 140

The electronic component of Embodiment 139, wherein the at least one energy converter is a downconverting material.

Embodiment 141

The electronic component of any one of Embodiments 138-140, wherein the adhesive is an electrically conductive adhesive.

Embodiment 142

The electronic component of any one of Embodiments 138-140, wherein the adhesive is a thermally conductive adhesive.

Embodiment 143

The electronic component of Embodiment 141, wherein the adhesive is a thermally conductive adhesive.

Embodiment 144

The electronic component of Embodiment 142, wherein the thermally conductive adhesive is electrically insulating.

Embodiment 145

The electronic component of Embodiment 141, wherein the electrically conductive adhesive comprises an electrically conductive filler.

Embodiment 146

The electronic component of Embodiment 145, wherein the electrically conductive filler is an organic filler.

Embodiment 147

The electronic component of Embodiment 145, wherein the electrically conductive filler is an inorganic filler.

Embodiment 148

The electronic component of Embodiment 146, wherein the organic filler is carbon.

Embodiment 149

The electronic component of Embodiment 147, wherein the inorganic filler is finely divided metal particles.

Embodiment 150

The electronic component of Embodiment 149, wherein the finely divided metal particles are formed of a metal or a metal oxide.

Embodiment 151

The electronic component of Embodiment 150, wherein the finely divided metal particles are formed of a metal selected from the group consisting of gold, silver, nickel, copper, and alloys containing at least these metals.

Embodiment 152

The electronic component of Embodiment 146, wherein the organic filler comprises small polymer beads or spheres having a conductive coating thereon.

Embodiment 153

The electronic component of Embodiment 152, wherein the conductive coating is a thin gold film.

Embodiment 154

The electronic component of any one of Embodiments 138-153, wherein the curable adhesive composition further comprises a dielectric material.

Embodiment 155

The electronic component of Embodiment 154, wherein the dielectric material is a member selected from the group consisting of metal titanates and metal zirconates.

Embodiment 156

The electronic component of any one of Embodiments 138-155, wherein the cured adhesive is present in a form selected from the group consisting of glob-top structures, dam-and-fill structures, underfill structures, die-underfill structures, and lid sealing structures.

Embodiment 157

The electronic component of any one of Embodiments 138-155, wherein the semiconductor component contains a wafer bonding connection and the wafer bonding is provided by the cured adhesive.

Embodiment 158

The electronic component of any one of Embodiments 138-155, wherein the semiconductor component contains a die to wafer connection and the die to wafer bonding is provided by the cured adhesive.

Embodiment 159

The electronic component of any one of Embodiments 138-155, wherein the semiconductor component contains a die to die connection and the die to die bonding is provided by the cured adhesive.

Embodiment 160

The electronic component of any one of Embodiments 138-155, wherein the semiconductor component contains a package on package assembly and package on package assembly is bonded with the cured adhesive.

Embodiment 161

The electronic component of Embodiment 156, wherein the cured adhesive is an anisotropically conductive adhesive.

Embodiment 162

The electronic component of Embodiment 157, wherein the cured adhesive is an anisotropically conductive adhesive.

Embodiment 163

The electronic component of Embodiment 158, wherein the cured adhesive is an anisotropically conductive adhesive.

Embodiment 164

The electronic component of Embodiment 159, wherein the cured adhesive is an anisotropically conductive adhesive.

Embodiment 165

The electronic component of Embodiment 160, wherein the cured adhesive is an anisotropically conductive adhesive.

Embodiment 166

The electronic component of any one of Embodiments 138-155, wherein the semiconductor component is a front end semiconductor and the cured adhesive is present as a pattern gate structure.

Embodiment 167

The electronic component of any one of Embodiments 138-155, wherein the electronic component is an optoelectronic component.

Embodiment 168

The electronic component of any one of Embodiments 138-155, wherein the electronic component is a multichip module having a die on KOVAR substrate.

Embodiment 169

The electronic component of any one of Embodiments 138-155, wherein the electronic component is a multichip module, and the cured adhesive is present as a lid sealer on the multichip module.

Embodiment 170

The electronic component of any one of Embodiments 138-155, wherein the electronic component is an integrated circuit device.

Embodiment 171

The electronic component of Embodiment 170, wherein the integrated circuit device is an integrated circuit wafer stack.

Embodiment 172

The electronic component of Embodiment 171, wherein the integrated circuit wafer stack comprises at least two integrated circuit wafers which are electrically connected to one another, and having Through Silicon Via (TSV) contacts, and the cured adhesive is present between the integrated circuit wafers, adhering the integrated circuit wafers one to another.

Embodiment 173

The electronic component of Embodiment 172, wherein the cured adhesive provides the electrical connection between the integrated circuit wafers.

Embodiment 174

The electronic component of any one of Embodiments 138-155, wherein the electronic component is a high density circuit.

Embodiment 175

The electronic component of Embodiment 170, wherein the integrated circuit device is a flip chip.

Embodiment 176

The electronic component of Embodiment 175, wherein the cured adhesive is present as a flip chip underfill.

Embodiment 177

The electronic component of Embodiment 176, wherein said at least one energy emitter or said at least one energy collector is present and wherein the at least one energy converter is a phosphor having absorption characteristics in an X-ray regime, such that inspection of the resulting flip chip can be performed using X-rays.

Embodiment 178

The electronic component of any one of Embodiments 138-155, wherein the electronic component further comprises a micro-ball-grid-array encapsulated by the cured adhesive.

Embodiment 179

The electronic component of any one of Embodiments 138-155, wherein the electronic component comprises a flexible circuit electrically connected with a semiconductor integrated circuit by tape automatic bonding (TAB) technique, wherein the TAB area is encapsulated by the cured adhesive.

Embodiment 180

The electronic component of Embodiment 146, wherein the organic filler comprises anisotropic conductive polymer spheres.

Embodiment 181

The electronic component of Embodiment 170, wherein the cured adhesive further comprises anisotropic conductive polymer spheres.

Embodiment 182

The electronic component of any one of Embodiments 138-155, wherein the at least one energy converter comprises anisotropic conductive UV emitting polymer spheres.

Embodiment 183

The electronic component of Embodiment 170, wherein the at least one energy converter comprises anisotropic conductive UV emitting polymer spheres.

Embodiment 184

The electronic component of any one of Embodiments 138-183, wherein the imparted radiation is an ionizing radiation.

Embodiment 185

The electronic component of Embodiment 184, wherein the ionizing radiation is X-rays.

Embodiment 186

The electronic component of any one of Embodiments 138-185, wherein said organic vehicle comprises a monomer forming a thermoset resin.

Embodiment 187

The electronic component of Embodiment 186, wherein said thermoset resin is selected from the group consisting of: acrylics, phenolics, urethanes, epoxies, styrenes, and silicones.

Embodiment 188

The electronic component of any one of Embodiments 138-187, wherein said at least one photoinitiator is selected from the group consisting of: benzoin ethers, benzil ketals, α-dialkoxyacetophenones, α-aminoalkylphenones, acylphosphine oxides, benzophenones/amines, thioxanthones/amines, and titanocenes.

Embodiment 189

The electronic component of Embodiment 140, wherein said selected wavelength of light is in the UV range and said ionizing radiation comprises X-rays.

Embodiment 190

The electronic component of Embodiment 140, wherein said downconverting material comprises dispersed inorganic particulates selected from the group consisting of: metal oxides; metal sulfides; doped metal oxides; and mixed metal chalcogenides.

Embodiment 191

The electronic component of any one of Embodiments 138-190, wherein said organic vehicle has a viscosity that is suitable for printing onto a selected substrate through a mask.

Embodiment 192

The electronic component of any one of Embodiments 138-191, wherein said curable adhesive composition is photo-patternable.

Embodiment 193

The electronic component of any one of Embodiments 138-192, wherein said curable adhesive composition further comprises inorganic particulates selected from the group consisting of: metals and metal alloys, ceramics and dielectrics, and metal-coated polymers.

Embodiment 194

The electronic component of any one of Embodiments 138-193, wherein said curable adhesive composition further comprises an organic component selected from the group consisting of: solvents, viscosity modifiers, surfactants, dispersants, and plasticizers.

Embodiment 195

The electronic component of Embodiment 139, wherein the at least one photo-initiator and the at least one energy converter are chemically tethered to one another.

Embodiment 196

The electronic component of any one of Embodiments 138-195, wherein the cured adhesive is in the form of a film.

Embodiment 197

The electronic component of Embodiment 196, wherein the cured adhesive in the form of a film is partially cured.

Embodiment 198

The cured adhesive of Embodiment 196, wherein the film has anisotropic properties.

Embodiment 199

The electronic component of any one of Embodiments 138-155, wherein the cured adhesive is an isotropically conductive adhesive.

Embodiment 200

The electronic component of Embodiment 157, wherein the cured adhesive is an isotropically conductive adhesive.

Embodiment 201

The electronic component of Embodiment 158, wherein the cured adhesive is an isotropically conductive adhesive.

Embodiment 202

The electronic component of Embodiment 159, wherein the cured adhesive is an isotropically conductive adhesive.

Embodiment 203

The electronic component of Embodiment 160, wherein the cured adhesive is an isotropically conductive adhesive.

Embodiment 204

An electronic component, comprising: a substrate and one or more electronic elements, wherein the electronic component contains a cured adhesive formed from a curable adhesive composition,
wherein the curable adhesive composition comprises:
an organic vehicle comprising at least one polymerizable monomer,
at least one photo-initiator responsive to a selected wavelength of light; and
at least one energy emitter of any one of Embodiments 1-61, or at least one energy augmentation structure of any one of Embodiments 62-69, or at least one energy collector of any one of Embodiments 70-83;
wherein the cured adhesive is an electrically conductive adhesive;
wherein:
(i) the electronic component is at least one member selected from the group consisting of:
a semiconductor component, wherein the semiconductor component contains a wafer bonding connection and the wafer bonding is provided by the cured adhesive;
a semiconductor component, wherein the semiconductor component contains a die to wafer connection and the die to wafer bonding is provided by the cured adhesive;
a semiconductor component, wherein the semiconductor component contains a die to die connection and the die to die bonding is provided by the cured adhesive;
a semiconductor component, wherein the semiconductor component contains a package on package assembly and package on package assembly is bonded with the cured adhesive;
a semiconductor component, wherein the semiconductor component is a front end semiconductor and the cured adhesive is present as a pattern gate structure;
a multichip module having a die on KOVAR substrate;
a multichip module, and the cured adhesive is present as a lid sealer on the multichip module;
an integrated circuit device, wherein the integrated circuit device is an integrated circuit wafer stack;
an integrated circuit device, wherein the integrated circuit device is a flip chip; and
a high density circuit;
or
(ii) the electronic component further comprises a micro-ball-grid-array encapsulated by the cured adhesive;

or
(iii) the electrically conductive adhesive comprises an electrically conductive filler which is carbon;
or
(iv) the curable adhesive composition further comprises a dielectric material;
or
(v) the electrically conductive adhesive comprises an electrically conductive filler that is an organic filler comprising anisotropic conductive polymer spheres;
or
(vi) the at least one energy converter comprises anisotropic conductive UV emitting polymer spheres;
or
(vii) the at least one photo-initiator and the at least one energy converter are chemically tethered to one another;
or
(viii) the cured adhesive is in the form of a film that is partially cured;
or
(ix) the cured adhesive is an isotropically conductive adhesive.

Embodiment 205

The electronic component of Embodiment 204, wherein said at least one energy emitter or said at least one energy collector is present, and wherein said at least one energy converter contained therein is selected to emit said selected wavelength of light when exposed to an imparted radiation.

Embodiment 206

The electronic component of Embodiment 205, wherein the at least one energy converter is a downconverting material, Embodiment 207. The electronic component of any one of Embodiments 204-206, wherein the adhesive is a thermally conductive adhesive.

Embodiment 208

The electronic component of any one of Embodiments 204-207, wherein the electrically conductive adhesive comprises an electrically conductive filler.

Embodiment 209

The electronic component of Embodiment 208, wherein the electrically conductive filler is an organic filler.

Embodiment 210

The electronic component of Embodiment 208, wherein the electrically conductive filler is an inorganic filler.

Embodiment 211

The electronic component of Embodiment 208, wherein the electrically conductive filler is an organic filler which is carbon.

Embodiment 212

The electronic component of Embodiment 210, wherein the inorganic filler is finely divided metal particles.

Embodiment 213

The electronic component of Embodiment 212, wherein the finely divided metal particles are formed of a metal or a metal oxide.

Embodiment 214

The electronic component of Embodiment 213, wherein the finely divided metal particles are formed of a metal selected from the group consisting of gold, silver, nickel, copper, and alloys containing at least these metals.

Embodiment 215

The electronic component of Embodiment 209, wherein the organic filler comprises small polymer beads or spheres having a conductive coating thereon.

Embodiment 216

The electronic component of Embodiment 215, wherein therein the conductive coating is a thin gold film.

Embodiment 217

The electronic component of any one of Embodiments 204-216, wherein the curable adhesive composition further comprises the dielectric material.

Embodiment 218

The electronic component of Embodiment 217, wherein the dielectric material is a member selected from the group consisting of metal titanates and metal zirconates.

Embodiment 219

The electronic component of any one of Embodiments 204-218, wherein the electronic component is the semiconductor component, wherein the semiconductor component contains the wafer bonding connection and the wafer bonding is provided by the cured adhesive.

Embodiment 220

The electronic component of any one of Embodiments 204-218, wherein the electronic component is the semiconductor component, wherein the semiconductor component contains the die to wafer connection and the die to wafer bonding is provided by the cured adhesive.

Embodiment 221

The electronic component of any one of Embodiments 204-218, wherein the electronic component is the semiconductor component, wherein the semiconductor component contains the die to die connection and the die to die bonding is provided by the cured adhesive.

Embodiment 222

The electronic component of any one of Embodiments 204-218, wherein the electronic component is the semiconductor component, wherein the semiconductor component contains the package on package assembly and package on package assembly is bonded with the cured adhesive.

Embodiment 223

The electronic component of any one of Embodiments 204-218, wherein the cured adhesive is an anisotropically conductive adhesive.

Embodiment 224

The electronic component of Embodiment 219, wherein the cured adhesive is an anisotropically conductive adhesive.

Embodiment 225

The electronic component of Embodiment 220, wherein the cured adhesive is an anisotropically conductive adhesive.

Embodiment 226

The electronic component of Embodiment 221, wherein the cured adhesive is an anisotropically conductive adhesive.

Embodiment 227

The electronic component of Embodiment 222, wherein the cured adhesive is an anisotropically conductive adhesive.

Embodiment 228

The electronic component of any one of Embodiments 204-218, wherein the electronic component is the semiconductor component, wherein the semiconductor component is the front end semiconductor and the cured adhesive is present as a pattern gate structure.

Embodiment 229

The electronic component of any one of Embodiments 204-218, wherein the electronic component is an optoelectronic component.

Embodiment 230

The electronic component of any one of Embodiments 204-218, wherein the electronic component is the multichip module having the die on KOVAR substrate.

Embodiment 231

The electronic component of any one of Embodiments 204-218, wherein the electronic component is the multichip module, and the cured adhesive is present as the lid sealer on the multichip module.

Embodiment 232

The electronic component of any one of Embodiments 204-218, wherein the electronic component is the integrated circuit wafer stack.

Embodiment 233

The electronic component of Embodiment 232, wherein the integrated circuit wafer stack comprises at least two integrated circuit wafers which are electrically connected to one another, and having Through Silicon Via (TSV) contacts, and the cured adhesive is present between the integrated circuit wafers, adhering the integrated circuit wafers one to another.

Embodiment 234

The electronic component of Embodiment 233, wherein the cured adhesive provides the electrical connection between the integrated circuit wafers.

Embodiment 235

The electronic component of any one of Embodiments 204-218, wherein the electronic component is the high density circuit.

Embodiment 236

The electronic component of any one of Embodiments 204-218, wherein the electronic component is the integrated circuit device, wherein the integrated circuit device is the flip chip.

Embodiment 237

The electronic component of Embodiment 236, wherein the cured adhesive is present as a flip chip underfill.

Embodiment 238

The electronic component of Embodiment 236, wherein said at least one energy emitter or said at least one energy collector is present, and wherein the at least one energy converter contained therein is a phosphor having absorption characteristics in an X-ray regime, such that inspection of the resulting flip chip can be performed using X-rays.

Embodiment 239

The electronic component of any one of Embodiments 204-218, wherein the electronic component further comprises the micro-ball-grid-array encapsulated by the cured adhesive.

Embodiment 240

The electronic component of any one of Embodiments 204-218, wherein the electrically conductive adhesive comprises an electrically conductive filler that is the organic filler which comprises anisotropic conductive polymer spheres.

Embodiment 241

The electronic component of Embodiment 205, wherein the at least one energy converter comprises anisotropic conductive UV emitting polymer spheres.

Embodiment 242

The electronic component of Embodiment 205, wherein the imparted radiation is an ionizing radiation.

Embodiment 243

The electronic component of Embodiment 242, wherein the ionizing radiation is X-rays.

Embodiment 244

The electronic component of any one of Embodiments 204-243, wherein said organic vehicle comprises a monomer forming a thermoset resin.

Embodiment 245

The electronic component of Embodiment 244, wherein said thermoset resin is selected from the group consisting of: acrylics, phenolics, urethanes, epoxies, styrenes, and silicones.

Embodiment 246

The electronic component of any one of Embodiments 204-245, wherein said at least one photoinitiator is selected from the group consisting of: benzoin ethers, benzil ketals, α-dialkoxyacetophenones, α-aminoalkylphenones, acylphosphine oxides, benzophenones/amines, thioxanthones/amines, and titanocenes.

Embodiment 247

The electronic component of Embodiment 205, wherein said selected wavelength of light is in the UV range and said imparted radiation comprises X-rays.

Embodiment 248

The electronic component of Embodiment 205, wherein said downconverting material comprises dispersed inorganic particulates selected from the group consisting of: metal oxides; metal sulfides; doped metal oxides; and mixed metal chalcogenides.

Embodiment 249

The electronic component of any one of Embodiments 204-248, wherein said organic vehicle has a viscosity that is suitable for printing onto a selected substrate through a mask.

Embodiment 250

The electronic component of any one of Embodiments 204-249, wherein said curable adhesive composition is photo-patternable.

Embodiment 251

The electronic component of any one of Embodiments 204-250, wherein said curable adhesive composition further comprises inorganic particulates selected from the group consisting of: metals and metal alloys, ceramics and dielectrics, and metal-coated polymers.

Embodiment 252

The electronic component of any one of Embodiments 204-251, wherein said curable adhesive composition further comprises an organic component selected from the group consisting of: solvents, viscosity modifiers, surfactants, dispersants, and plasticizers.

Embodiment 253

The electronic component of Embodiment 205, wherein the at least one photo-initiator and the at least one energy converter are chemically tethered to one another.

Embodiment 254

The electronic component of any one of Embodiments 204-253, wherein the cured adhesive is in the form of a film.

Embodiment 255

The electronic component of any one of Embodiments 204-254, wherein the cured adhesive in the form of the film that is partially cured.

Embodiment 256

The cured adhesive of Embodiment 254, wherein the film has anisotropic properties.

Embodiment 257

The electronic component of any one of Embodiments 204-218, wherein the cured adhesive is the isotropically conductive adhesive.

Embodiment 258

The electronic component of Embodiment 219, wherein the cured adhesive is an isotropically conductive adhesive.

Embodiment 259

The electronic component of Embodiment 220, wherein the cured adhesive is an isotropically conductive adhesive.

Embodiment 260

The electronic component of Embodiment 221, wherein the cured adhesive is an isotropically conductive adhesive.

Embodiment 261

The electronic component of Embodiment 222, wherein the cured adhesive is an isotropically conductive adhesive.

Embodiment 262

An electronic component, comprising: a substrate and one or more electronic elements, wherein the electronic component contains a cured adhesive formed from a curable adhesive composition,
wherein the curable adhesive composition comprises:
an organic vehicle comprising at least one polymerizable monomer,
at least one photo-initiator responsive to a selected wavelength of light; and
at least one energy emitter of any one of Embodiments 1-61, or at least one energy augmentation structure of any one of Embodiments 62-69, or at least one energy collector of any one of Embodiments 70-83;
wherein the adhesive is a thermally conductive adhesive;

wherein:
(i) the electronic component is at least one member selected from the group consisting of:
a semiconductor component, wherein the semiconductor component contains a wafer bonding connection and the wafer bonding is provided by the cured adhesive;
a semiconductor component, wherein the semiconductor component contains a die to wafer connection and the die to wafer bonding is provided by the cured adhesive;
a semiconductor component, wherein the semiconductor component contains a die to die connection and the die to die bonding is provided by the cured adhesive;
a semiconductor component, wherein the semiconductor component contains a package on package assembly and package on package assembly is bonded with the cured adhesive;
a semiconductor component, wherein the semiconductor component is a front end semiconductor and the cured adhesive is present as a pattern gate structure;
a multichip module having a die on KOVAR substrate;
a multichip module, and the cured adhesive is present as a lid sealer on the multichip module;
an integrated circuit device, wherein the integrated circuit device is an integrated circuit wafer stack;
an integrated circuit device, wherein the integrated circuit device is a flip chip; and
a high density circuit;
or
(ii) the thermally conductive adhesive is electrically insulating;
or
(iii) the cured adhesive is present in a form selected from the group consisting of glob-top structures, dam-and-fill structures, underfill structures, die-underfill structures, and lid sealing structures;
or
(iv) the electronic component further comprises a micro-ball-grid-array encapsulated by the cured adhesive;
or
(v) the electronic component comprises a flexible circuit electrically connected with a semiconductor integrated circuit by tape automatic bonding (TAB) technique, wherein the TAB area is encapsulated by the cured adhesive;
or
(vi) the at least one photo-initiator and the at least one energy converter are chemically tethered to one another;
or
(vii) the cured adhesive is in the form of a film that is partially cured;
or
(viii) the curable adhesive composition further comprises a dielectric material.

Embodiment 263

The electronic component of Embodiment 262, wherein said at least one energy emitter or said at least one energy collector is present and wherein said at least one energy converter contained therein is selected to emit said selected wavelength of light when exposed to an imparted radiation.

Embodiment 264

The electronic component of Embodiment 263, wherein the at least one energy converter is a downconverting material, Embodiment 265. The electronic component of any one of Embodiments 262-264, wherein the thermally conductive adhesive is electrically insulating.

Embodiment 266

The electronic component of any one of Embodiments 262-264, wherein the curable adhesive composition further comprises the dielectric material.

Embodiment 267

The electronic component of Embodiment 266, wherein the dielectric material is a member selected from the group consisting of metal titanates and metal zirconates.

Embodiment 268

The electronic component of any one of Embodiments 262-267, wherein the cured adhesive is present in the form selected from the group consisting of glob-top structures, dam-and-fill structures, underfill structures, die-underfill structures, and lid sealing structures.

Embodiment 269

The electronic component of any one of Embodiments 262-267, wherein the electronic component is the semiconductor component, wherein the semiconductor component contains the wafer bonding connection and the wafer bonding is provided by the cured adhesive.

Embodiment 270

The electronic component of any one of Embodiments 262-267, wherein the electronic component is the semiconductor component, wherein the semiconductor component contains the die to wafer connection and the die to wafer bonding is provided by the cured adhesive.

Embodiment 271

The electronic component of any one of Embodiments 262-267, wherein the electronic component is the semiconductor component, wherein the semiconductor component contains the die to die connection and the die to die bonding is provided by the cured adhesive.

Embodiment 272

The electronic component of any one of Embodiments 262-267, wherein the electronic component is the semiconductor component, wherein the semiconductor component contains the package on package assembly and package on package assembly is bonded with the cured adhesive.

Embodiment 273

The electronic component of any one of Embodiments 262-267, wherein the electronic component is the semiconductor component, wherein the semiconductor component is the front end semiconductor and the cured adhesive is present as the pattern gate structure.

Embodiment 274

The electronic component of any one of Embodiments 262-267, wherein the electronic component is an optoelectronic component.

Embodiment 275

The electronic component of any one of Embodiments 262-267, wherein the electronic component is the multichip module having a die on KOVAR substrate.

Embodiment 276

The electronic component of any one of Embodiments 262-267, wherein the electronic component is the multichip module, and the cured adhesive is present as the lid sealer on the multichip module.

Embodiment 277

The electronic component of any one of Embodiments 262-267, wherein the electronic component is an integrated circuit device.

Embodiment 278

The electronic component of any one of Embodiments 262-267, wherein the electronic component is the integrated circuit device which is the integrated circuit wafer stack.

Embodiment 279

The electronic component of Embodiment 278, wherein the integrated circuit wafer stack comprises at least two integrated circuit wafers which are electrically connected to one another, and having Through Silicon Via (TSV) contacts, and the cured adhesive is present between the integrated circuit wafers, adhering the integrated circuit wafers one to another.

Embodiment 280

The electronic component of any one of Embodiments 262-267, wherein the electronic component is the high density circuit.

Embodiment 281

The electronic component of any one of Embodiments 262-267, wherein the electronic component is the integrated circuit device, wherein the integrated circuit device is the flip chip.

Embodiment 282

The electronic component of Embodiment 281, wherein the cured adhesive is present as a flip chip underfill.

Embodiment 283

The electronic component of Embodiment 282, wherein said at least one energy emitter or said at least one energy collector is present, and wherein the at least one energy converter contained therein is a phosphor having absorption characteristics in an X-ray regime, such that inspection of the resulting flip chip can be performed using X-rays.

Embodiment 284

The electronic component of any one of Embodiments 262-267, wherein the electronic component further comprises a micro-ball-grid-array encapsulated by the cured adhesive.

Embodiment 285

The electronic component of any one of Embodiments 262-267, wherein the electronic component comprises the flexible circuit electrically connected with the semiconductor integrated circuit by tape automatic bonding (TAB) technique, wherein the TAB area is encapsulated by the cured adhesive.

Embodiment 286

The electronic component of Embodiment 263, wherein the imparted radiation is an ionizing radiation.

Embodiment 287

The electronic component of Embodiment 286, wherein the ionizing radiation is X-rays.

Embodiment 288

The electronic component of any one of Embodiments 262-287, wherein said organic vehicle comprises a monomer forming a thermoset resin.

Embodiment 289

The electronic component of Embodiment 288, wherein said thermoset resin is selected from the group consisting of: acrylics, phenolics, urethanes, epoxies, styrenes, and silicones.

Embodiment 290

The electronic component of any one of Embodiments 262-289, wherein said at least one photoinitiator is selected from the group consisting of: benzoin ethers, benzil ketals, α-dial koxyacetophenones, α-aminoalkylphenones, acylphosphine oxides, benzophenones/amines, thioxanthones/amines, and titanocenes.

Embodiment 291

The electronic component of Embodiment 264, wherein said selected wavelength of light is in the UV range and said imparted radiation comprises X-rays.

Embodiment 292

The electronic component of Embodiment 264, wherein said downconverting material comprises dispersed inorganic particulates selected from the group consisting of: metal oxides; metal sulfides; doped metal oxides; and mixed metal chalcogenides.

Embodiment 293

The electronic component of any one of Embodiments 262-292, wherein said organic vehicle has a viscosity that is suitable for printing onto a selected substrate through a mask.

Embodiment 294

The electronic component of any one of Embodiments 262-293, wherein said curable adhesive composition is photo-patternable.

Embodiment 295

The electronic component of any one of Embodiments 262-294, wherein said curable adhesive composition further comprises inorganic particulates selected from the group consisting of: metals and metal alloys, ceramics and dielectrics, and metal-coated polymers.

Embodiment 296

The electronic component of any one of Embodiments 262-295, wherein said curable adhesive composition further comprises an organic component selected from the group consisting of: solvents, viscosity modifiers, surfactants, dispersants, and plasticizers.

Embodiment 297

The electronic component of Embodiment 263, wherein the at least one photo-initiator and the at least one energy converter are chemically tethered to one another.

Embodiment 298

The electronic component of any one of Embodiments 262-297, wherein the cured adhesive is in the form of a film.

Embodiment 299

The electronic component of any one of Embodiments 262-297, wherein the cured adhesive is in the form of the film that is partially cured.

Embodiment 300

The cured adhesive of Embodiment 298 or 299, wherein the film has anisotropic properties.

Embodiment 301

An electronic component, comprising:
a semiconductor device attached to a substrate,
wherein the semiconductor device is attached to the substrate through a plurality of rigid protrusions attached to one side of the semiconductor device, which are configured to be in electrical contact with a plurality of electrical pads situated on the substrate;
wherein the plurality of rigid protrusions are formed from a first curable resin or adhesive composition comprising:
 a first organic vehicle comprising at least one first polymerizable monomer;
 at least one first photo-initiator responsive to a first selected wavelength of light; and,
 at least one first energy emitter of any one of Embodiments 1-61, or at least one first energy augmentation structure of any one of Embodiments 62-69, or at least one first energy collector of any one of Embodiments 70-83;
 such that upon application of a first imparted radiation, the first curable resin or adhesive composition is cured to provide the rigid protrusions between the semiconductor device and the plurality of electrical pads on the substrate.

Embodiment 302

The electronic component of Embodiment 301, wherein said at least one first energy emitter or said at least one first energy collector is present, and wherein said at least one first energy converter contained therein is selected to emit said first selected wavelength of light when exposed to a first imparted radiation.

Embodiment 303

The electronic component of Embodiment 301 or 302, wherein the plurality of rigid protrusions are electrically conductive.

Embodiment 304

The electronic component of Embodiment 301 or 302, further comprising an underfill material forming a layer between the semiconductor device and substrate and between each of the plurality of protrusions and electrical pads, wherein the underfill material comprises a second cured resin formed from a second curable resin or adhesive composition comprising:
 a second organic vehicle comprising at least one second polymerizable monomer;
 at least one second photo-initiator responsive to a second selected wavelength of light; and,
 at least one second energy emitter of any one of Embodiments 1-61, or at least one second energy augmentation structure of any one of Embodiments 62-69, or at least one second energy collector of any one of Embodiments 70-83.

Embodiment 305

The electronic component of Embodiment 304, wherein said at least one second energy emitter or said at least one second energy collector is present, and wherein said at least one second energy converter contained therein is selected to emit said second selected wavelength of light when exposed to a second imparted radiation.

Embodiment 306

The electronic component of Embodiment 301, further comprising a metallic heat sink layer attached to a side of the semiconductor component opposite the side having the plurality of protrusions, wherein the metallic heat sink layer is attached to the semiconductor component using a third cured resin formed from a third curable resin or adhesive composition, comprising:

a third organic vehicle comprising at least one third polymerizable monomer;

at least one third photo-initiator responsive to a third selected wavelength of light; and, at least one third energy emitter of any one of Embodiments 1-61, or at least one third energy augmentation structure of any one of Embodiments 62-69, or at least one third energy collector of any one of Embodiments 70-83;

wherein the third cured resin is thermally conductive.

Embodiment 307

The electronic component of Embodiment 306, wherein said at least one third energy emitter or said at least one third energy collector is present, and wherein said at least one third energy converter contained therein is selected to emit said third selected wavelength of light when exposed to a third imparted radiation Embodiment 308

The electronic component of Embodiment 306, wherein the third cured resin is made thermally conductive by the inclusion of particles in the third cured resin, wherein the particles are selected from the group consisting of metal particles and metal nitride particles.

Embodiment 309

The electronic component of Embodiment 308, wherein particles are metal nitride particles.

Embodiment 310

The electronic component of Embodiment 309, wherein the metal nitride particles are a member selected from the group consisting of AlN and BN.

Embodiment 311

The electronic component of Embodiment 303, further comprising a metallic heat sink layer attached to a side of the semiconductor component opposite the side having the plurality of protrusions, wherein the metallic heat sink layer is attached to the semiconductor component using a third cured resin formed from a third curable resin or adhesive composition, comprising:

a third organic vehicle comprising at least one third polymerizable monomer;

at least one third photo-initiator responsive to a third selected wavelength of light; and, at least one third energy emitter of any one of Embodiments 1-61, or at least one third energy augmentation structure of any one of Embodiments 62-69, or at least one third energy collector of any one of Embodiments 70-83;

wherein the third cured resin is thermally conductive.

Embodiment 312

The electronic component of Embodiment 311, wherein said at least one third energy emitter or said at least one third energy collector is present, and wherein said at least one third energy converter contained therein is selected to emit said third selected wavelength of light when exposed to a third imparted radiation.

Embodiment 313

The electronic component of Embodiment 311 or 312, wherein the third cured resin is made thermally conductive by the inclusion of particles in the third cured resin, wherein the particles are selected from the group consisting of metal particles and metal nitride particles.

Embodiment 314

The electronic component of Embodiment 313, wherein particles are metal nitride particles.

Embodiment 315

The electronic component of Embodiment 314, wherein the metal nitride particles are a member selected from the group consisting of AlN and BN.

Embodiment 316

The electronic component of Embodiment 304, further comprising a metallic heat sink layer attached to a side of the semiconductor component opposite the side having the plurality of protrusions, wherein the metallic heat sink layer is attached to the semiconductor component using a third cured resin formed from a third curable resin or adhesive composition, comprising:

a third organic vehicle comprising at least one third polymerizable monomer;

at least one third photo-initiator responsive to a third selected wavelength of light; and, at least one third energy emitter of any one of Embodiments 1-61, or at least one third energy augmentation structure of any one of Embodiments 62-69, or at least one third energy collector of any one of Embodiments 70-83;

wherein the third cured resin is thermally conductive.

Embodiment 317

The electronic component of Embodiment 316, wherein said at least one third energy emitter or said at least one third energy collector is present, and wherein said at least one third energy converter contained therein is selected to emit said third selected wavelength of light when exposed to a third imparted radiation.

Embodiment 318

The electronic component of Embodiment 316, wherein the third cured resin is made thermally conductive by the inclusion of particles in the third cured resin, wherein the particles are selected from the group consisting of metal particles and metal nitride particles.

Embodiment 319

The electronic component of Embodiment 318, wherein particles are metal nitride particles.

Embodiment 320

The electronic component of Embodiment 319, wherein the metal nitride particles are a member selected from the group consisting of AlN and BN.

Embodiment 321

A packaged device, comprising the electric component according to any one of Embodiments 301-320, wherein the metallic heat sink layer extends beyond edges of the semiconductor device and is connected to support sides which support the metallic heat sink layer from the substrate to hermetically seal the semiconductor device.

Embodiment 322

The packaged device of Embodiment 321, wherein at least a portion of the metallic heat sink layer is replaced with a window which is transparent to one or more wavelengths of light received or transmitted by the semiconductor component.

Embodiment 323

The packaged device of Embodiment 322, wherein at least a portion of at least one support side is replaced with a window which is transparent to one or more wavelengths of light received or transmitted by the semiconductor component.

Embodiment 324

The packaged device of Embodiment 321, wherein at least a portion of at least one support side is replaced with a window which is transparent to one or more wavelengths of light received or transmitted by the semiconductor component.

Embodiment 325

An encapsulated semiconductor device, comprising an electronic component of Embodiment 301, having a glob top encapsulating at least the substrate, protrusions and electrical pads.

Embodiment 326

The encapsulated semiconductor device of Embodiment 325, wherein the glob top is formed from curing a second curable resin or adhesive composition, comprising:
  a second organic vehicle comprising at least one second polymerizable monomer;
  at least one second photo-initiator responsive to a second selected wavelength of light; and,
  at least one second energy emitter of any one of Embodiments 1-61, or at least one second energy augmentation structure of any one of Embodiments 62-69, or at least one second energy collector of any one of Embodiments 70-83.

Embodiment 327

The electronic component of Embodiment 326, wherein said at least one second energy emitter or said at least one second energy collector is present, and wherein said at least one second energy converter contained therein is selected to emit said second selected wavelength of light when exposed to a second imparted radiation

Embodiment 328

The encapsulated semiconductor device of any one of Embodiments 325-327, wherein the glob top has high optical transmissivity.

Embodiment 329

The encapsulated semiconductor device of Embodiment 327, wherein the at least one second energy converter has a particle size smaller than a desired wavelength of transmissivity of the cured resin or adhesive composition, in order to provide the glob top with a desired optical transmissivity.

Embodiment 330

The encapsulated semiconductor device of Embodiment 329, wherein the at least one second energy converter has a particle size of 400 nm or less.

Embodiment 331

An optically transparent resin or adhesive composition comprising:
  an organic vehicle comprising at least one polymerizable monomer which, upon polymerization, forms an optically transparent resin or adhesive;
  at least one photo-initiator responsive to a selected wavelength of light; and,
  at least one energy emitter of any one of Embodiments 1-61 or at least one energy collector of any one of Embodiments 70-83, wherein the at least one energy converter contained therein is selected to emit said selected wavelength of light when exposed to an imparted radiation, wherein the at least one energy converter has a particle size below a desired wavelength of transmissivity transmitted through the cured optically transparent resin or adhesive.

Embodiment 332

The optically transparent resin or adhesive composition of Embodiment 331, wherein the at least one energy converter has a particle size of 400 nm or less.

Embodiment 333

An electrically conductive resin or adhesive composition comprising:
  an organic vehicle comprising at least one polymerizable monomer;
  at least one photo-initiator responsive to a selected wavelength of light;
  at least one energy emitter of any one of Embodiments 1-61 or at least one energy collector of any one of Embodiments 70-83, wherein the at least one energy converter contained therein is selected to emit said selected wavelength of light when exposed to an imparted radiation,
  wherein the at least one energy converter comprises an isotropically or anisotropically conductive polymer particle, or the composition further comprises at least one electrically conductive additive, or both, and wherein (1) the viscosity of said organic vehicle is suitable for dispensing through an automated dispenser onto a selected substrate, (2) the viscosity of said organic vehicle is suitable for printing onto a selected substrate through a mask, or (3) wherein said adhesive is photo-patternable.

Embodiment 334

The electrically conductive resin or adhesive composition of Embodiment 333, further comprising wherein the composition comprises the at least one electrically conductive additive.

Embodiment 335

The electrically conductive resin or adhesive composition of Embodiment 334, wherein the at least one electrically conductive additive is an electrically conductive organic additive.

Embodiment 336

The electrically conductive resin or adhesive composition of Embodiment 334, wherein the at least one electrically conductive additive is an electrically conductive inorganic additive.

Embodiment 337

The electrically conductive resin or adhesive composition of Embodiment 334, wherein the at least one electrically conductive additive is an isotropically or anisotropically conductive polymer particle.

Embodiment 338

The electrically conductive resin or adhesive composition of Embodiment 337, wherein the at least one electrically conductive additive is an isotropically conductive polymer particle.

Embodiment 339

The electrically conductive resin or adhesive composition of Embodiment 337, wherein the at least one electrically conductive additive is an anisotropically conductive polymer particle.

Embodiment 340

The electrically conductive resin or adhesive composition of Embodiment 338, wherein the composition is isotropically conductive.

Embodiment 341

The electrically conductive resin or adhesive composition of Embodiment 339, wherein the composition is anisotropically conductive.

Embodiment 342

The electrically conductive resin or adhesive composition of Embodiment 335, wherein the electrically conductive organic additive is an electrically conductive form of carbon.

Embodiment 343

The electrically conductive resin or adhesive composition of Embodiment 336, wherein the electrically conductive inorganic additive is a member selected from the group consisting of metal particles and metal oxide particles.

Embodiment 344

The electrically conductive resin or adhesive composition of Embodiment 343, wherein the electrically conductive inorganic additive is finely divided metal particles.

Embodiment 345

The electrically conductive resin or adhesive composition of Embodiment 344, wherein the finely divided metal particles are a member selected from the group consisting of gold, silver, nickel, copper, and alloys thereof.

Embodiment 346

The electrically conductive resin or adhesive composition of Embodiment 333, wherein the at least one energy converter comprises an isotropically or anisotropically conductive polymer particle.

Embodiment 347

The electrically conductive resin or adhesive composition of Embodiment 346, wherein the at least one energy converter comprises an isotropically conductive polymer particle.

Embodiment 348

The electrically conductive resin or adhesive composition of Embodiment 346, wherein the at least one energy converter comprises an anisotropically conductive polymer particle.

Embodiment 349

The electrically conductive resin or adhesive composition of Embodiment 347, wherein the composition is isotropically conductive.

Embodiment 350

The electrically conductive resin or adhesive composition of Embodiment 348, wherein the composition is anisotropically conductive.

Embodiment 351

The electrically conductive resin or adhesive composition of any one of Embodiments 333-350, wherein the viscosity of said organic vehicle is suitable for dispensing through an automated dispenser onto a selected substrate.

Embodiment 352

The electrically conductive resin or adhesive composition of any one of Embodiments 333-351, wherein the viscosity of said organic vehicle is suitable for printing onto a selected substrate through a mask.

Embodiment 353

The electrically conductive resin or adhesive composition of any one of Embodiments 333-352, wherein said adhesive is photo-patternable.

Embodiment 354

An anisotropic conductive polymer sphere comprising a polymeric core having at least a portion of an outer surface of the sphere coated with at least one energy emitter of any one of Embodiments 1-61, or at least one energy augmentation structure of any one of Embodiments 62-69, or at least one energy collector of any one of Embodiments 70-83.

Embodiment 355

The anisotropic conductive polymer sphere of Embodiment 354, wherein said at least one energy emitter or said at least one energy collector is present and wherein said at least one energy converter contained therein is at least one down-converting material that responds to X-ray photons.

Embodiment 356

The anisotropic conductive polymer sphere of Embodiment 354 or 355, further comprising an outer coating of silica.

Embodiment 357

The anisotropic conductive polymer sphere of any one of Embodiments 354-356, wherein the at least one down-converting material is in a form of nanoparticles.

Embodiment 358

The anisotropic conductive polymer sphere of Embodiment 354, wherein said at least one energy emitter or said at least one energy collector is present, and wherein said at least one energy converter contained therein is at least one up-converting material that responds to near infrared photons.

Embodiment 359

The anisotropic conductive polymer sphere of Embodiment 358, further comprising an outer coating of silica.

Embodiment 360

The anisotropic conductive polymer sphere of Embodiment 358 or 359, wherein the at least one up-converting material is in a form of nanoparticles.

Embodiment 361

An electrically conductive resin or adhesive composition comprising:
  an organic vehicle comprising at least one polymerizable monomer which, upon polymerization, forms an electrically conductive resin or adhesive;
  at least one photo-initiator responsive to a selected wavelength of light; and,
  at least one energy emitter of any one of Embodiments 1-61, or at least one energy augmentation structure of any one of Embodiments 62-69, or at least one energy collector of any one of Embodiments 70-83;
  such that the resin or adhesive composition formed exhibits electrical conductivity or semiconductivity without the presence of an electrically conductive additive.

Embodiment 362

The electrically conductive resin or adhesive composition of Embodiment 361, wherein said at least one energy emitter or said at least one energy collector is present, and wherein said at least one energy converter contained therein is selected to emit said selected wavelength of light when exposed to an imparted radiation.

Having generally described this invention, a further understanding can be obtained by reference to certain specific examples which are provided herein for purposes of illustration only and are not intended to be limiting unless otherwise specified.

Numerous modifications and variations of the invention are possible in light of the above teachings. It is therefore to be understood that within the scope of the appended claims, the invention may be practiced otherwise than as specifically described herein.

The invention claimed is:

1. A wafer to wafer bonded assembly, comprising a plurality of semiconductor wafers bonded together by a cured adhesive composition obtained by curing of a curable adhesive composition, wherein the curable adhesive composition comprises an organic vehicle comprising at least one polymerizable monomer; at least one photo-initiator responsive to a selected wavelength of light; and at least one (i) energy emitter, (ii) energy augmentation structure, or (iii) energy collector, wherein:
  the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
  the at least one (ii) energy augmentation structure, when present, is capable of capturing one or more wavelengths of electromagnetic energy, and augmenting the one or more wavelengths of electromagnetic energy in at least one property;
  the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

2. An encapsulated semiconductor component, comprising a semiconductor assembly having thereon a covering of a cured adhesive composition, wherein the cured adhesive composition is formed by curing a curable adhesive composition comprising an organic vehicle comprising at least one polymerizable monomer; at least one photo-initiator responsive to a selected wavelength of light; and at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

3. An integrated circuit assembly comprising a plurality of electrically connected material layers, wherein the plurality of electrically connected material layers are held together by a cured adhesive composition obtained by curing a curable adhesive composition comprising an organic vehicle comprising at least one polymerizable monomer; at least one photo-initiator responsive to a selected wavelength of light; and at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

and wherein the integrated circuit has no external conductive connections between layers.

4. An encapsulated semiconductor component, comprising a semiconductor assembly having a substrate containing an insertion molded portion, wherein the insertion molded portion comprises a molding resin and has at least one (i) energy emitter, (ii) energy augmentation structure, or (iii) energy collector on a surface thereof, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

wherein the substrate has formed thereon at least one semiconductor component, and wherein the semiconductor component has thereon a covering of a cured adhesive composition, wherein the cured adhesive composition is formed by curing a curable adhesive composition comprising an organic vehicle comprising at least one polymerizable monomer; and at least one photo-initiator responsive to a selected wavelength of light.

5. A wafer to wafer bonded assembly, comprising a plurality of semiconductor wafers bonded together by a cured adhesive composition obtained by curing of a curable adhesive composition, wherein the curable adhesive composition comprises an organic vehicle comprising at least one polymerizable monomer; at least one photo-initiator responsive to a selected wavelength of light; and at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

wherein (1) the viscosity of said organic vehicle is suitable for dispensing through an automated dispenser onto a selected substrate, (2) the viscosity of said organic vehicle is suitable for printing onto a selected substrate through a mask, or (3) wherein said adhesive is photo-patternable.

6. An electronic component, comprising: a substrate and one or more electronic elements, wherein the electronic component contains a cured adhesive formed from a curable adhesive composition, wherein the curable adhesive composition comprises:
an organic vehicle comprising at least one polymerizable monomer,
at least one photo-initiator responsive to a selected wavelength of light; and
at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

wherein the electronic component is a semiconductor component.

7. An electronic component, comprising: a substrate and one or more electronic elements, wherein the electronic component contains a cured adhesive formed from a curable adhesive composition, wherein the curable adhesive composition comprises:
an organic vehicle comprising at least one polymerizable monomer,
at least one photo-initiator responsive to a selected wavelength of light; and
at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
the at least one (ii) energy augmentation structure, when present, is capable of capturing one or more wavelengths of electromagnetic energy, and augmenting the one or more wavelengths of electromagnetic energy in at least one property;
the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;
wherein the cured adhesive is an electrically conductive adhesive;
wherein:
(i) the electronic component is at least one member selected from the group consisting of:
 a semiconductor component, wherein the semiconductor component contains a wafer bonding connection and the wafer bonding is provided by the cured adhesive;
 a semiconductor component, wherein the semiconductor component contains a die to wafer connection and the die to wafer bonding is provided by the cured adhesive;
 a semiconductor component, wherein the semiconductor component contains a die to die connection and the die to die bonding is provided by the cured adhesive;
 a semiconductor component, wherein the semiconductor component contains a package on package assembly and package on package assembly is bonded with the cured adhesive;
 a semiconductor component, wherein the semiconductor component is a front end semiconductor and the cured adhesive is present as a pattern gate structure;
 a multichip module having a die on KOVAR substrate;
 a multichip module, and the cured adhesive is present as a lid sealer on the multichip module;
 an integrated circuit device, wherein the integrated circuit device is an integrated circuit wafer stack;
 an integrated circuit device, wherein the integrated circuit device is a flip chip; and
 a high density circuit;
or
(ii) the electronic component further comprises a micro-ball-grid-array encapsulated by the cured adhesive;
or
(iii) the electrically conductive adhesive comprises an electrically conductive filler which is carbon;
or
(iv) the curable adhesive composition further comprises a dielectric material;
or
(v) the electrically conductive adhesive comprises an electrically conductive filler that is an organic filler comprising anisotropic conductive polymer spheres;
or
(vi) the at least one energy converter comprises anisotropic conductive UV emitting polymer spheres;
or
(vii) the at least one photo-initiator and the at least one energy converter are chemically tethered to one another;
or
(viii) the cured adhesive is in the form of a film that is partially cured;
or
(ix) the cured adhesive is an isotropically conductive adhesive.

8. An electronic component, comprising: a substrate and one or more electronic elements, wherein the electronic component contains a cured adhesive formed from a curable adhesive composition,
wherein the curable adhesive composition comprises:
an organic vehicle comprising at least one polymerizable monomer,
at least one photo-initiator responsive to a selected wavelength of light; and
at least one (i) energy emitter, (ii) energy augmentation structure, or (iii) energy collector, wherein:
the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
the at least one (ii) energy augmentation structure, when present, is capable of capturing one or more wavelengths of electromagnetic energy, and augmenting the one or more wavelengths of electromagnetic energy in at least one property;
the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;
wherein the adhesive is a thermally conductive adhesive;

wherein:
(i) the electronic component is at least one member selected from the group consisting of:
a semiconductor component, wherein the semiconductor component contains a wafer bonding connection and the wafer bonding is provided by the cured adhesive;
a semiconductor component, wherein the semiconductor component contains a die to wafer connection and the die to wafer bonding is provided by the cured adhesive;
a semiconductor component, wherein the semiconductor component contains a die to die connection and the die to die bonding is provided by the cured adhesive;
a semiconductor component, wherein the semiconductor component contains a package on package assembly and package on package assembly is bonded with the cured adhesive;
a semiconductor component, wherein the semiconductor component is a front end semiconductor and the cured adhesive is present as a pattern gate structure;
a multichip module having a die on KOVAR substrate;
a multichip module, and the cured adhesive is present as a lid sealer on the multichip module;
an integrated circuit device, wherein the integrated circuit device is an integrated circuit wafer stack;
an integrated circuit device, wherein the integrated circuit device is a flip chip; and
a high density circuit;
or
(ii) the thermally conductive adhesive is electrically insulating;
or
(iii) the cured adhesive is present in a form selected from the group consisting of glob-top structures, dam-and-fill structures, underfill structures, die-underfill structures, and lid sealing structures;
or
(iv) the electronic component further comprises a micro-ball-grid-array encapsulated by the cured adhesive;
or
(v) the electronic component comprises a flexible cirduit electrically connected with a semiconductor integrated circuit by tape automatic bonding (TAB) technique, wherein the TAB area is encapsulated by the cured adhesive;
or
(vi) the at least one photo-initiator and the at least one energy converter are chemically tethered to one another;
or
(vii) the cured adhesive is in the form of a film that is partially cured;
or
(viii) the curable adhesive composition further comprises a dielectric material.

9. An electronic component, comprising:
a semiconductor device attached to a substrate,
wherein the semiconductor device is attached to the substrate through a plurality of rigid protrusions attached to one side of the semiconductor device, which are configured to be in electrical contact with a plurality of electrical pads situated on the substrate;
wherein the plurality of rigid protrusions are formed from a first curable resin or adhesive composition comprising:
a first organic vehicle comprising at least one first polymerizable monomer;
at least one first photo-initiator responsive to a first selected wavelength of light; and,
at least one (i) energy emitter, (ii) energy augmentation structure, or (iii) energy collector, wherein:
the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
the at least one (ii) energy augmentation structure, when present, is capable of capturing one or more wavelengths of electromagnetic energy, and augmenting the one or more wavelengths of electromagnetic energy in at least one property;
the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;
such that upon application of a first imparted radiation, the first curable resin or adhesive composition is cured to provide the rigid protrusions between the semiconductor device and the plurality of electrical pads on the substrate.

10. The electronic component of claim 9, further comprising an underfill material forming a layer between the semiconductor device and substrate and between each of the plurality of protrusions and electrical pads, wherein the underfill material comprises a second cured resin formed from a second curable resin or adhesive composition comprising:
a second organic vehicle comprising at least one second polymerizable monomer;
at least one second photo-initiator responsive to a second selected wavelength of light; and,
at least one (i) energy emitter, (ii) energy augmentation structure, or (iii) energy collector, wherein:
the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

11. The electronic component of claim 9, further comprising a metallic heat sink layer attached to a side of the semiconductor component opposite the side having the plurality of protrusions, wherein the metallic heat sink layer is attached to the semiconductor component using a third cured resin formed from a third curable resin or adhesive composition, comprising:

a third organic vehicle comprising at least one third polymerizable monomer;

at least one third photo-initiator responsive to a third selected wavelength of light; and, at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

wherein the third cured resin is thermally conductive.

12. The electronic component of claim 9, further comprising a metallic heat sink layer attached to a side of the semiconductor component opposite the side having the plurality of protrusions, wherein the metallic heat sink layer is attached to the semiconductor component using a third cured resin formed from a third curable resin or adhesive composition, comprising:

a third organic vehicle comprising at least one third polymerizable monomer;

at least one third photo-initiator responsive to a third selected wavelength of light; and, at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

wherein the third cured resin is thermally conductive.

13. The electronic component of claim 10, further comprising a metallic heat sink layer attached to a side of the semiconductor component opposite the side having the plurality of protrusions, wherein the metallic heat sink layer is attached to the semiconductor component using a third cured resin formed from a third curable resin or adhesive composition, comprising:
- a third organic vehicle comprising at least one third polymerizable monomer;
- at least one third photo-initiator responsive to a third selected wavelength of light; and,
- at least one (i) energy emitter, (ii) energy augmentation structure, or (iii) energy collector, wherein:
  - the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
  - the at least one (ii) energy augmentation structure, when present, is capable of capturing one or more wavelengths of electromagnetic energy, and augmenting the one or more wavelengths of electromagnetic energy in at least one property;
  - the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;
- wherein the third cured resin is thermally conductive.

14. A packaged device, comprising the electric component according to claim 9, wherein the metallic heat sink layer extends beyond edges of the semiconductor device and is connected to support sides which support the metallic heat sink layer from the substrate to hermetically seal the semiconductor device.

15. An encapsulated semiconductor device, comprising an electronic component of claim 9, having a glob top encapsulating at least the substrate, protrusions and electrical pads.

16. The encapsulated semiconductor device of claim 15, wherein the glob top is formed from curing a second curable resin or adhesive composition, comprising:
- a second organic vehicle comprising at least one second polymerizable monomer;
- at least one second photo-initiator responsive to a second selected wavelength of light; and,
- at least one (i) energy emitter, (ii) energy augmentation structure, or (iii) energy collector, wherein:
  - the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
  - the at least one (ii) energy augmentation structure, when present, is capable of capturing one or more wavelengths of electromagnetic energy, and augmenting the one or more wavelengths of electromagnetic energy in at least one property;
  - the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

17. An optically transparent resin or adhesive composition comprising:
- an organic vehicle comprising at least one polymerizable monomer which, upon polymerization, forms an optically transparent resin or adhesive;
- at least one photo-initiator responsive to a selected wavelength of light; and,
- at least one (i) energy emitter, (ii) energy augmentation structure, or (iii) energy collector, wherein:
  - the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;
  - the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

wherein the at least one energy converter contained therein is selected to emit said selected wavelength of light when exposed to an imparted radiation, wherein the at least one energy converter has a particle size below a desired wavelength of transmissivity transmitted through the cured optically transparent resin or adhesive.

18. An electrically conductive resin or adhesive composition comprising:

an organic vehicle comprising at least one polymerizable monomer;

at least one photo-initiator responsive to a selected wavelength of light;

at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

wherein the at least one energy converter contained therein is selected to emit said selected wavelength of light when exposed to an imparted radiation, wherein the at least one energy converter comprises an isotropically or anisotropically conductive polymer particle, or the composition further comprises at least one electrically conductive additive, or both, and wherein (1) the viscosity of said organic vehicle is suitable for dispensing through an automated dispenser onto a selected substrate, (2) the viscosity of said organic vehicle is suitable for printing onto a selected substrate through a mask, or (3) wherein said adhesive is photo-patternable.

19. An anisotropic conductive polymer sphere comprising a polymeric core having at least a portion of an outer surface of the sphere coated with at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure.

20. An electrically conductive resin or adhesive composition comprising:

an organic vehicle comprising at least one polymerizable monomer which, upon polymerization, forms an electrically conductive resin or adhesive;

at least one photo-initiator responsive to a selected wavelength of light; and, at least one (i) energy emitter, (ii) energy augmentation structure, or (iii) energy collector, wherein:

the at least one (i) energy emitter, when present, comprises at least one energy augmentation structure capable of capturing one or more wavelengths of electromagnetic energy, and augmenting the one or more wavelengths of electromagnetic energy in at least one property; and an energy converter capable of receiving energy from an energy source, converting the energy and emitting therefrom an emitted light of a higher or lower energy than the received energy, and the energy converter being disposed in a vicinity of the at least one energy augmentation structure such that the emitted light is emitted with an intensity larger than if the energy converter were remote from the at least one energy augmentation structure, or if the energy augmentation structure were not present;

the at least one (ii) energy augmentation structure, when present, is capable of capturing one or more wavelengths of electromagnetic energy, and augmenting the one or more wavelengths of electromagnetic energy in at least one property;

the at least one (iii) energy collector, when present, comprises at least one energy augmentation structure capable of capturing one or more wavelengths of electromagnetic energy, and augmenting the one or more wavelengths of electromagnetic energy in at least one property; and at least one energy converter capable of receiving an applied electromagnetic energy, converting the applied electromagnetic energy and emitting therefrom an emitted electromagnetic energy shifted in wavelength or energy from the applied electromagnetic energy and the energy converter being disposed in a vicinity of the at least one energy augmentation structure such that the emitted electromagnetic energy is emitted with at least one augmented property compared to if the energy converter were remote from the at least one energy augmentation structure;

such that the resin or adhesive composition formed exhibits electrical conductivity or semiconductivity without the presence of an electrically conductive additive.

21. The assembly of claim 1, wherein said at least one energy emitter or said at least one energy collector is present, and wherein said at least one energy converter contained therein is selected to emit said selected wavelength of light when exposed to an imparted radiation.

22. The assembly of claim 21, wherein the at least one energy converter is an upconverting material.

23. The assembly of claim 22, wherein the imparted radiation is near infrared.

24. The assembly of claim 21, wherein the at least one energy converter is a downconverting material.

25. The assembly of claim 24, wherein the imparted radiation is an ionizing radiation.

26. The assembly of claim 25, wherein the ionizing radiation is X-rays.

27. The encapsulated semiconductor component of claim 2, wherein said at least one energy emitter or said at least one energy collector is present, and wherein said at least one energy converter contained therein is selected to emit said selected wavelength of light when exposed to an imparted radiation.

28. The encapsulated semiconductor component of claim 27, wherein the at least one energy converter is an upconverting material.

29. The encapsulated semiconductor component of claim 28, wherein the imparted radiation is near infrared.

30. The encapsulated semiconductor component of claim 27, wherein the at least one energy converter is a downconverting material.

31. The encapsulated semiconductor component of claim 30, wherein the imparted radiation is an ionizing radiation.

32. The encapsulated semiconductor component of claim 31, wherein the ionizing radiation is X-rays.

33. The encapsulated semiconductor component of claim 2, wherein the cured adhesive composition is in a form selected from the group consisting of underfill, glob top, dam and fill, and molded.

34. The assembly of claim 3, wherein said at least one energy emitter or said at least one energy collector is present and wherein said at least one energy converter contained therein is selected to emit said selected wavelength of light when exposed to an imparted radiation.

35. The assembly of claim 34, wherein the at least one energy converter is an upconverting material.

36. The assembly of claim 35, wherein the imparted radiation is near infrared.

37. The assembly of claim 34, wherein the at least one energy converter is a downconverting material.

38. The assembly of claim 37, wherein the imparted radiation is an ionizing radiation.

39. The assembly of claim 38, wherein the ionizing radiation is X-rays.

40. The encapsulated semiconductor component of claim 4, wherein said at least one energy emitter or said at least one energy collector is present and wherein the at least one energy converter contained therein is a first energy converter and is on the surface of the insertion molded portion and is selected to emit said selected wavelength of light when exposed to an imparted radiation.

41. The encapsulated semiconductor component of claim 40, wherein the curable adhesive composition further comprises a second energy converter, which may be the same as or different from the first energy converter, wherein the second energy converter is selected to emit said selected wavelength of light when exposed to the imparted radiation.

42. The encapsulated semiconductor component of claim 40, wherein the first energy converter is an upconverting material.

43. The encapsulated semiconductor component of claim 42, wherein the imparted radiation is near infrared.

44. The encapsulated semiconductor component of claim 40, wherein the first energy converter is a downconverting material.

45. The encapsulated semiconductor component of claim 44, wherein the imparted radiation is an ionizing radiation.

46. The encapsulated semiconductor component of claim 45, wherein the ionizing radiation is X-rays.

47. The encapsulated semiconductor component of claim 41, wherein the second energy converter is an upconverting material.

48. The encapsulated semiconductor component of claim 47, wherein the imparted radiation is near infrared.

49. The encapsulated semiconductor component of claim 41, wherein the second energy converter is a downconverting material.

50. The encapsulated semiconductor component of claim 49, wherein the imparted radiation is an ionizing radiation.

51. The encapsulated semiconductor component of claim 50, wherein the ionizing radiation is X-rays.

52. The assembly of claim 5, wherein said at least one energy emitter or said at least one energy collector is present, and wherein said at least one energy converter contained therein is selected to emit said selected wavelength of light when exposed to an imparted radiation.

53. The assembly of claim 52, wherein the at least one energy converter is an upconverting material.

54. The assembly of claim 53, wherein the imparted radiation is near infrared.

55. The assembly of claim 52, wherein the at least one energy converter is a downconverting material.

56. The assembly of claim 55, wherein the imparted radiation is an ionizing radiation.

57. The assembly of claim 56, wherein the ionizing radiation is X-rays.

58. The assembly of claim 5, wherein said organic vehicle comprises a monomer forming a thermoset resin.

59. The assembly of claim 58, wherein said thermoset resin is selected from the group consisting of: acrylics, phenolics, urethanes, epoxies, styrenes, and silicones.

60. The assembly of claim 5, wherein said at least one photoinitiator is selected from the group consisting of: benzoin ethers, benzil ketals, α-dialkoxyacetophenones, α-aminoalkylphenones, acylphosphine oxides, benzophenones/amines, thioxanthones/amines, and titanocenes.

61. The assembly of claim 55, wherein said selected wavelength of light is in the UV range and said imparted radiation comprises X-rays.

62. The assembly of claim 55, wherein said downconverting material comprises dispersed inorganic particulates selected from the group consisting of: metal oxides; metal sulfides; doped metal oxides; and mixed metal chalcogenides.

63. The assembly of claim 5, wherein the viscosity of said organic vehicle is suitable for dispensing through an automated dispenser onto a selected substrate.

64. The assembly of claim 5, wherein the viscosity of said organic vehicle is suitable for printing onto a selected substrate through a mask.

65. The assembly of claim 5, wherein said adhesive is photo-patternable.

66. The assembly of claim 5, further comprising inorganic particulates selected from the group consisting of: metals and metal alloys, ceramics and dielectrics, and metal-coated polymers.

67. The assembly of claim 5, further comprising an organic component selected from the group consisting of: solvents, viscosity modifiers, surfactants, dispersants, and plasticizers.

68. The assembly of claim 5, further comprising a sheet containing a monolayer of conductive particles of a suitable size to render the resulting adhesive bond anisotropically conductive.

69. The assembly of claim 5, wherein the at least one photo-initiator and the at least one energy converter are chemically tethered to one another.

70. The electronic component of claim 6, wherein said at least one energy emitter or said at least one energy collector is present and wherein said at least one energy converter contained therein is selected to emit said selected wavelength of light when exposed to an imparted radiation.

71. The electronic component of claim 70, wherein the at least one energy converter is a downconverting material.

72. The electronic component of claim 6, wherein the adhesive is an electrically conductive adhesive.

73. The electronic component of claim 6, wherein the adhesive is a thermally conductive adhesive.

74. The electronic component of claim 72, wherein the adhesive is a thermally conductive adhesive.

75. The electronic component of claim 73, wherein the thermally conductive adhesive is electrically insulating.

76. The electronic component of claim 72, wherein the electrically conductive adhesive comprises an electrically conductive filler.

77. The electronic component of claim 76, wherein the electrically conductive filler is an organic filler.

78. The electronic component of claim 76, wherein the electrically conductive filler is an inorganic filler.

79. The electronic component of claim 77, wherein the organic filler is carbon.

80. The electronic component of claim 78, wherein the inorganic filler is finely divided metal particles.

81. The electronic component of claim 80, wherein the finely divided metal particles are formed of a metal or a metal oxide.

82. The electronic component of claim 81, wherein the finely divided metal particles are formed of a metal selected from the group consisting of gold, silver, nickel, copper, and alloys containing at least these metals.

83. The electronic component of claim 77, wherein the organic filler comprises small polymer beads or spheres having a conductive coating thereon.

84. The electronic component of claim 83, wherein therein the conductive coating is a thin gold film.

85. The electronic component of claim 6, wherein the curable adhesive composition further comprises a dielectric material.

86. The electronic component of claim 85, wherein the dielectric material is a member selected from the group consisting of metal titanates and metal zirconates.

87. The electronic component of claim 6, wherein the cured adhesive is present in a form selected from the group consisting of glob-top structures, dam-and-fill structures, underfill structures, die-underfill structures, and lid sealing structures.

88. The electronic component of claim 6, wherein the semiconductor component contains a wafer bonding connection and the wafer bonding is provided by the cured adhesive.

89. The electronic component of claim 6, wherein the semiconductor component contains a die to wafer connection and the die to wafer bonding is provided by the cured adhesive.

90. The electronic component of claim 6, wherein the semiconductor component contains a die to die connection and the die to die bonding is provided by the cured adhesive.

91. The electronic component of claim 6, wherein the semiconductor component contains a package on package assembly and package on package assembly is bonded with the cured adhesive.

92. The electronic component of claim 6, wherein the cured adhesive is an anisotropically conductive adhesive.

93. The electronic component of claim 88, wherein the cured adhesive is an anisotropically conductive adhesive.

94. The electronic component of claim 89, wherein the cured adhesive is an anisotropically conductive adhesive.

95. The electronic component of claim 90, wherein the cured adhesive is an anisotropically conductive adhesive.

96. The electronic component of claim 91, wherein the cured adhesive is an anisotropically conductive adhesive.

97. The electronic component of claim 6, wherein the semiconductor component is a front end semiconductor and the cured adhesive is present as a pattern gate structure.

98. The electronic component of claim 6, wherein the electronic component is an optoelectronic component.

99. The electronic component of claim 6, wherein the electronic component is a multichip module having a die on KOVAR substrate.

100. The electronic component of claim 6, wherein the electronic component is a multichip module, and the cured adhesive is present as a lid sealer on the multichip module.

101. The electronic component of claim 6, wherein the electronic component is an integrated circuit device.

102. The electronic component of claim 101, wherein the integrated circuit device is an integrated circuit wafer stack.

103. The electronic component of claim 102, wherein the integrated circuit wafer stack comprises at least two integrated circuit wafers which are electrically connected to one another, and having Through Silicon Via (TSV) contacts, and the cured adhesive is present between the integrated circuit wafers, adhering the integrated circuit wafers one to another.

104. The electronic component of claim 103, wherein the cured adhesive provides the electrical connection between the integrated circuit wafers.

105. The electronic component of claim 6, wherein the electronic component is a high density circuit.

106. The electronic component of claim 101, wherein the integrated circuit device is a flip chip.

107. The electronic component of claim 106, wherein the cured adhesive is present as a flip chip underfill.

108. The electronic component of claim 107, wherein said at least one energy emitter or said at least one energy collector is present and wherein the at least one energy converter is a phosphor having absorption characteristics in an X-ray regime, such that inspection of the resulting flip chip can be performed using X-rays.

109. The electronic component of claim 6, wherein the electronic component further comprises a micro-ball-grid-array encapsulated by the cured adhesive.

110. The electronic component of claim 6, wherein the electronic component comprises a flexible circuit electrically connected with a semiconductor integrated circuit by tape automatic bonding (TAB) technique, wherein the TAB area is encapsulated by the cured adhesive.

111. The electronic component of claim 77, wherein the organic filler comprises anisotropic conductive polymer spheres.

112. The electronic component of claim 101, wherein the cured adhesive further comprises anisotropic conductive polymer spheres.

113. The electronic component of claim 6, wherein the at least one energy converter comprises anisotropic conductive UV emitting polymer spheres.

114. The electronic component of claim 101, wherein the at least one energy converter comprises anisotropic conductive UV emitting polymer spheres.

115. The electronic component of claim 6, wherein the imparted radiation is an ionizing radiation.

116. The electronic component of claim 115, wherein the ionizing radiation is X-rays.

117. The electronic component of claim 6, wherein said organic vehicle comprises a monomer forming a thermoset resin.

118. The electronic component of claim 117, wherein said thermoset resin is selected from the group consisting of: acrylics, phenolics, urethanes, epoxies, styrenes, and silicones.

119. The electronic component of claim 6, wherein said at least one photoinitiator is selected from the group consisting of: benzoin ethers, benzil ketals, α-dialkoxyacetophenones, α-aminoalkylphenones, acylphosphine oxides, benzophenones/amines, thioxanthones/amines, and titanocenes.

120. The electronic component of claim 70, wherein said selected wavelength of light is in the UV range and said ionizing radiation comprises X-rays.

121. The electronic component of claim 70, wherein said downconverting material comprises dispersed inorganic particulates selected from the group consisting of: metal oxides; metal sulfides; doped metal oxides; and mixed metal chalcogenides.

122. The electronic component of claim 6, wherein said organic vehicle has a viscosity that is suitable for printing onto a selected substrate through a mask.

123. The electronic component of claim 6, wherein said curable adhesive composition is photo-patternable.

124. The electronic component of claim 6, wherein said curable adhesive composition further comprises inorganic particulates selected from the group consisting of: metals and metal alloys, ceramics and dielectrics, and metal-coated polymers.

125. The electronic component of claim 6, wherein said curable adhesive composition further comprises an organic component selected from the group consisting of: solvents, viscosity modifiers, surfactants, dispersants, and plasticizers.

126. The electronic component of claim 70, wherein the at least one photo-initiator and the at least one energy converter are chemically tethered to one another.

127. The electronic component of claim 6, wherein the cured adhesive is in the form of a film.

128. The electronic component of claim 127, wherein the cured adhesive in the form of a film is partially cured.

129. The cured adhesive of claim 127, wherein the film has anisotropic properties.

130. The electronic component of claim 6, wherein the cured adhesive is an isotropically conductive adhesive.

131. The electronic component of claim 88, wherein the cured adhesive is an isotropically conductive adhesive.

132. The electronic component of claim 89, wherein the cured adhesive is an isotropically conductive adhesive.

133. The electronic component of claim 90, wherein the cured adhesive is an isotropically conductive adhesive.

134. The electronic component of claim 91, wherein the cured adhesive is an isotropically conductive adhesive.

135. The electronic component of claim 7, wherein said at least one energy emitter or said at least one energy collector is present, and wherein said at least one energy converter contained therein is selected to emit said selected wavelength of light when exposed to an imparted radiation.

136. The electronic component of claim 135, wherein the at least one energy converter is a downconverting material.

137. The electronic component of claim 7, wherein the adhesive is a thermally conductive adhesive.

138. The electronic component of claim 7, wherein the electrically conductive adhesive comprises an electrically conductive filler.

139. The electronic component of claim 138, wherein the electrically conductive filler is an organic filler.

140. The electronic component of claim 138, wherein the electrically conductive filler is an inorganic filler.

141. The electronic component of claim 7, wherein the electrically conductive filler is an organic filler which is carbon.

142. The electronic component of claim 140, wherein the inorganic filler is finely divided metal particles.

143. The electronic component of claim 142, wherein the finely divided metal particles are formed of a metal or a metal oxide.

144. The electronic component of claim 143, wherein the finely divided metal particles are formed of a metal selected from the group consisting of gold, silver, nickel, copper, and alloys containing at least these metals.

145. The electronic component of claim 139, wherein the organic filler comprises small polymer beads or spheres having a conductive coating thereon.

146. The electronic component of claim 145, wherein therein the conductive coating is a thin gold film.

147. The electronic component of claim 7, wherein the curable adhesive composition further comprises the dielectric material.

148. The electronic component of claim 147, wherein the dielectric material is a member selected from the group consisting of metal titanates and metal zirconates.

149. The electronic component of claim 7, wherein the electronic component is the semiconductor component, wherein the semiconductor component contains the wafer bonding connection and the wafer bonding is provided by the cured adhesive.

150. The electronic component of claim 7, wherein the electronic component is the semiconductor component, wherein the semiconductor component contains the die to wafer connection and the die to wafer bonding is provided by the cured adhesive.

151. The electronic component of claim 7, wherein the electronic component is the semiconductor component, wherein the semiconductor component contains the die to die connection and the die to die bonding is provided by the cured adhesive.

152. The electronic component of claim 7, wherein the electronic component is the semiconductor component, wherein the semiconductor component contains the package on package assembly and package on package assembly is bonded with the cured adhesive.

153. The electronic component of claim 7, wherein the cured adhesive is an anisotropically conductive adhesive.

154. The electronic component of claim 149, wherein the cured adhesive is an anisotropically conductive adhesive.

155. The electronic component of claim 150, wherein the cured adhesive is an anisotropically conductive adhesive.

156. The electronic component of claim 151, wherein the cured adhesive is an anisotropically conductive adhesive.

157. The electronic component of claim 152, wherein the cured adhesive is an anisotropically conductive adhesive.

158. The electronic component of claim 7, wherein the electronic component is the semiconductor component, wherein the semiconductor component is the front end semiconductor and the cured adhesive is present as a pattern gate structure.

159. The electronic component of claim 7, wherein the electronic component is an optoelectronic component.

160. The electronic component of claim 7, wherein the electronic component is the multichip module having the die on KOVAR substrate.

161. The electronic component of claim 7, wherein the electronic component is the multichip module, and the cured adhesive is present as the lid sealer on the multichip module.

162. The electronic component of claim 7, wherein the electronic component is the integrated circuit wafer stack.

163. The electronic component of claim 162, wherein the integrated circuit wafer stack comprises at least two integrated circuit wafers which are electrically connected to one another, and having Through Silicon Via (TSV) contacts, and the cured adhesive is present between the integrated circuit wafers, adhering the integrated circuit wafers one to another.

164. The electronic component of claim 163, wherein the cured adhesive provides the electrical connection between the integrated circuit wafers.

165. The electronic component of claim 7, wherein the electronic component is the high density circuit.

166. The electronic component of claim 7, wherein the electronic component is the integrated circuit device, wherein the integrated circuit device is the flip chip.

167. The electronic component of claim 166, wherein the cured adhesive is present as a flip chip underfill.

168. The electronic component of claim 166, wherein said at least one energy emitter or said at least one energy collector is present, and wherein the at least one energy converter contained therein is a phosphor having absorption characteristics in an X-ray regime, such that inspection of the resulting flip chip can be performed using X-rays.

169. The electronic component of claim 7, wherein the electronic component further comprises the micro-ball-grid-array encapsulated by the cured adhesive.

170. The electronic component of claim 7, wherein the electrically conductive adhesive comprises an electrically conductive filler that is the organic filler which comprises anisotropic conductive polymer spheres.

171. The electronic component of claim 135, wherein the at least one energy converter comprises anisotropic conductive UV emitting polymer spheres.

172. The electronic component of claim 7, wherein the imparted radiation is an ionizing radiation.

173. The electronic component of claim 172, wherein the ionizing radiation is X-rays.

174. The electronic component of claim 7, wherein said organic vehicle comprises a monomer forming a thermoset resin.

175. The electronic component of claim 174, wherein said thermoset resin is selected from the group consisting of: acrylics, phenolics, urethanes, epoxies, styrenes, and silicones.

176. The electronic component of claim 7, wherein said at least one photoinitiator is selected from the group consisting of: benzoin ethers, benzil ketals, α-dialkoxyacetophenones, α-aminoalkylphenones, acylphosphine oxides, benzophenones/amines, thioxanthones/amines, and titanocenes.

177. The electronic component of claim 136, wherein said selected wavelength of light is in the UV range and said imparted radiation comprises X-rays.

178. The electronic component of claim 136, wherein said downconverting material comprises dispersed inorganic particulates selected from the group consisting of: metal oxides; metal sulfides; doped metal oxides; and mixed metal chalcogenides.

179. The electronic component of claim 7, wherein said organic vehicle has a viscosity that is suitable for printing onto a selected substrate through a mask.

180. The electronic component of claim 7, wherein said curable adhesive composition is photo-patternable.

181. The electronic component of claim 7, wherein said curable adhesive composition further comprises inorganic particulates selected from the group consisting of: metals and metal alloys, ceramics and dielectrics, and metal-coated polymers.

182. The electronic component of claim 7, wherein said curable adhesive composition further comprises an organic component selected from the group consisting of: solvents, viscosity modifiers, surfactants, dispersants, and plasticizers.

183. The electronic component of claim 135, wherein the at least one photo-initiator and the at least one energy converter are chemically tethered to one another.

184. The electronic component of claim 7, wherein the cured adhesive is in the form of a film.

185. The electronic component of claim 7, wherein the cured adhesive in the form of the film that is partially cured.

186. The cured adhesive of claim 184, wherein the film has anisotropic properties.

187. The electronic component of claim 7, wherein the cured adhesive is the isotropically conductive adhesive.

188. The electronic component of claim 149, wherein the cured adhesive is an isotropically conductive adhesive.

189. The electronic component of claim 150, wherein the cured adhesive is an isotropically conductive adhesive.

190. The electronic component of claim 151, wherein the cured adhesive is an isotropically conductive adhesive.

191. The electronic component of claim 152, wherein the cured adhesive is an isotropically conductive adhesive.

192. The electronic component of claim 8, wherein said at least one energy emitter or said at least one energy collector is present and wherein said at least one energy converter contained therein is selected to emit said selected wavelength of light when exposed to an imparted radiation.

193. The electronic component of claim 192, wherein the at least one energy converter is a downconverting material.

194. The electronic component of claim 8, wherein the thermally conductive adhesive is electrically insulating.

195. The electronic component of claim 8, wherein the curable adhesive composition further comprises the dielectric material.

196. The electronic component of claim 195, wherein the dielectric material is a member selected from the group consisting of metal titanates and metal zirconates.

197. The electronic component of claim 8, wherein the cured adhesive is present in the form selected from the group consisting of glob-top structures, dam-and-fill structures, underfill structures, die-underfill structures, and lid sealing structures.

198. The electronic component of claim 8, wherein the electronic component is the semiconductor component, wherein the semiconductor component contains the wafer bonding connection and the wafer bonding is provided by the cured adhesive.

199. The electronic component of claim 8, wherein the electronic component is the semiconductor component, wherein the semiconductor component contains the die to wafer connection and the die to wafer bonding is provided by the cured adhesive.

200. The electronic component of claim 8, wherein the electronic component is the semiconductor component, wherein the semiconductor component contains the die to die connection and the die to die bonding is provided by the cured adhesive.

201. The electronic component of claim 8, wherein the electronic component is the semiconductor component, wherein the semiconductor component contains the package on package assembly and package on package assembly is bonded with the cured adhesive.

202. The electronic component of claim 8, wherein the electronic component is the semiconductor component, wherein the semiconductor component is the front end semiconductor and the cured adhesive is present as the pattern gate structure.

203. The electronic component of claim 8, wherein the electronic component is an optoelectronic component.

204. The electronic component of claim 8, wherein the electronic component is the multichip module having a die on KOVAR substrate.

205. The electronic component of claim 8, wherein the electronic component is the multichip module, and the cured adhesive is present as the lid sealer on the multichip module.

206. The electronic component of claim 8, wherein the electronic component is an integrated circuit device.

207. The electronic component of claim 8, wherein the electronic component is the integrated circuit device which is the integrated circuit wafer stack.

208. The electronic component of claim 207, wherein the integrated circuit wafer stack comprises at least two integrated circuit wafers which are electrically connected to one another, and having Through Silicon Via (TSV) contacts, and the cured adhesive is present between the integrated circuit wafers, adhering the integrated circuit wafers one to another.

209. The electronic component of claim 8, wherein the electronic component is the high density circuit.

210. The electronic component of claim 8, wherein the electronic component is the integrated circuit device, wherein the integrated circuit device is the flip chip.

211. The electronic component of claim 210, wherein the cured adhesive is present as a flip chip underfill.

212. The electronic component of claim 211, wherein said at least one energy emitter or said at least one energy collector is present, and wherein the at least one energy converter contained therein is a phosphor having absorption characteristics in an X-ray regime, such that inspection of the resulting flip chip can be performed using X-rays.

213. The electronic component of claim 8, wherein the electronic component further comprises a micro-ball-grid-array encapsulated by the cured adhesive.

214. The electronic component of claim 8, wherein the electronic component comprises the flexible circuit electrically connected with the semiconductor integrated circuit by tape automatic bonding (TAB) technique, wherein the TAB area is encapsulated by the cured adhesive.

215. The electronic component of claim 8, wherein the imparted radiation is an ionizing radiation.

216. The electronic component of claim 215, wherein the ionizing radiation is X-rays.

217. The electronic component of claim 8, wherein said organic vehicle comprises a monomer forming a thermoset resin.

218. The electronic component of claim 217, wherein said thermoset resin is selected from the group consisting of: acrylics, phenolics, urethanes, epoxies, styrenes, and silicones.

219. The electronic component of claim 8, wherein said at least one photoinitiator is selected from the group consisting of: benzoin ethers, benzil ketals, α-dialkoxyacetophenones, α-aminoalkylphenones, acylphosphine oxides, benzophenones/amines, thioxanthones/amines, and titanocenes.

220. The electronic component of claim 193, wherein said selected wavelength of light is in the UV range and said imparted radiation comprises X-rays.

221. The electronic component of claim 193, wherein said downconverting material comprises dispersed inorganic particulates selected from the group consisting of: metal oxides; metal sulfides; doped metal oxides; and mixed metal chalcogenides.

222. The electronic component of claim 8, wherein said organic vehicle has a viscosity that is suitable for printing onto a selected substrate through a mask.

223. The electronic component of claim 8, wherein said curable adhesive composition is photo-patternable.

224. The electronic component of claim 8, wherein said curable adhesive composition further comprises inorganic particulates selected from the group consisting of: metals and metal alloys, ceramics and dielectrics, and metal-coated polymers.

225. The electronic component of claim 8, wherein said curable adhesive composition further comprises an organic component selected from the group consisting of: solvents, viscosity modifiers, surfactants, dispersants, and plasticizers.

226. The electronic component of claim 8, wherein the at least one photo-initiator and the at least one energy converter are chemically tethered to one another.

227. The electronic component of claim 8, wherein the cured adhesive is in the form of a film.

228. The electronic component of claim 8, wherein the cured adhesive is in the form of the film that is partially cured.

229. The electronic component of claim 227, wherein the film has anisotropic properties.

230. The electronic component of claim 9, wherein said at least one first energy emitter or said at least one first energy collector is present, and wherein said at least one first energy converter contained therein is selected to emit said first selected wavelength of light when exposed to a first imparted radiation.

231. The electronic component of claim 9, wherein the plurality of rigid protrusions are electrically conductive.

232. The electronic component of claim 10, wherein said at least one second energy emitter or said at least one second energy collector is present, and wherein said at least one second energy converter contained therein is selected to emit said second selected wavelength of light when exposed to a second imparted radiation.

233. The electronic component of claim 11, wherein said at least one third energy emitter or said at least one third energy collector is present, and wherein said at least one third energy converter contained therein is selected to emit said third selected wavelength of light when exposed to a third imparted radiation.

234. The electronic component of claim 11, wherein the third cured resin is made thermally conductive by the inclusion of particles in the third cured resin, wherein the particles are selected from the group consisting of metal particles and metal nitride particles.

235. The electronic component of claim 234, wherein particles are metal nitride particles.

236. The electronic component of claim 235, wherein the metal nitride particles are a member selected from the group consisting of AlN and BN.

237. The electronic component of claim 12, wherein said at least one third energy emitter or said at least one third energy collector is present, and wherein said at least one third energy converter contained therein is selected to emit said third selected wavelength of light when exposed to a third imparted radiation.

238. The electronic component of claim 12, wherein the third cured resin is made thermally conductive by the inclusion of particles in the third cured resin, wherein the particles are selected from the group consisting of metal particles and metal nitride particles.

239. The electronic component of claim 238, wherein particles are metal nitride particles.

240. The electronic component of claim 239, wherein the metal nitride particles are a member selected from the group consisting of AlN and BN.

241. The electronic component of claim 13, wherein said at least one third energy emitter or said at least one third energy collector is present, and wherein said at least one third energy converter contained therein is selected to emit said third selected wavelength of light when exposed to a third imparted radiation.

242. The electronic component of claim 13, wherein the third cured resin is made thermally conductive by the inclusion of particles in the third cured resin, wherein the particles are selected from the group consisting of metal particles and metal nitride particles.

243. The electronic component of claim 242, wherein particles are metal nitride particles.

244. The electronic component of claim 243, wherein the metal nitride particles are a member selected from the group consisting of AlN and BN.

245. The packaged device of claim 14, wherein at least a portion of the metallic heat sink layer is replaced with a window which is transparent to one or more wavelengths of light received or transmitted by the semiconductor component.

246. The packaged device of claim 245, wherein at least a portion of at least one support side is replaced with a window which is transparent to one or more wavelengths of light received or transmitted by the semiconductor component.

247. The packaged device of claim 14, wherein at least a portion of at least one support side is replaced with a window which is transparent to one or more wavelengths of light received or transmitted by the semiconductor component.

248. The electronic component of claim 16, wherein said at least one second energy emitter or said at least one second energy collector is present, and wherein said at least one second energy converter contained therein is selected to emit said second selected wavelength of light when exposed to a second imparted radiation.

249. The encapsulated semiconductor device of claim 15, wherein the glob top has high optical transmissivity.

250. The encapsulated semiconductor device of claim 248, wherein the at least one second energy converter has a particle size smaller than a desired wavelength of transmissivity of the cured resin or adhesive composition, in order to provide the glob top with a desired optical transmissivity.

251. The encapsulated semiconductor device of claim 250, wherein the at least one second energy converter has a particle size of 400 nm or less.

252. The optically transparent resin or adhesive composition of claim 17, wherein the at least one energy converter has a particle size of 400 nm or less.

253. The electrically conductive resin or adhesive composition of claim 18, further comprising wherein the composition comprises the at least one electrically conductive additive.

254. The electrically conductive resin or adhesive composition of claim 253, wherein the at least one electrically conductive additive is an electrically conductive organic additive.

255. The electrically conductive resin or adhesive composition of claim 18, wherein the at least one electrically conductive additive is an electrically conductive inorganic additive.

256. The electrically conductive resin or adhesive composition of claim 18, wherein the at least one electrically conductive additive is an isotropically or anisotropically conductive polymer particle.

257. The electrically conductive resin or adhesive composition of claim 18, wherein the at least one electrically conductive additive is an isotropically conductive polymer particle.

258. The electrically conductive resin or adhesive composition of claim 18, wherein the at least one electrically conductive additive is an anisotropically conductive polymer particle.

259. The electrically conductive resin or adhesive composition of claim 18, wherein the composition is isotropically conductive.

260. The electrically conductive resin or adhesive composition of claim 18, wherein the composition is anisotropically conductive.

261. The electrically conductive resin or adhesive composition of claim 253, wherein the electrically conductive organic additive is an electrically conductive form of carbon.

262. The electrically conductive resin or adhesive composition of claim 254, wherein the electrically conductive inorganic additive is a member selected from the group consisting of metal particles and metal oxide particles.

263. The electrically conductive resin or adhesive composition of claim 262, wherein the electrically conductive inorganic additive is finely divided metal particles.

264. The electrically conductive resin or adhesive composition of claim 263, wherein the finely divided metal particles are a member selected from the group consisting of gold, silver, nickel, copper, and alloys thereof.

265. The electrically conductive resin or adhesive composition of claim 18, wherein the at least one energy converter comprises an isotropically or anisotropically conductive polymer particle.

266. The electrically conductive resin or adhesive composition of claim 265, wherein the at least one energy converter comprises an isotropically conductive polymer particle.

267. The electrically conductive resin or adhesive composition of claim 265, wherein the at least one energy converter comprises an anisotropically conductive polymer particle.

268. The electrically conductive resin or adhesive composition of claim 266, wherein the composition is isotropically conductive.

269. The electrically conductive resin or adhesive composition of claim 267, wherein the composition is anisotropically conductive.

270. The electrically conductive resin or adhesive composition of claim 18, wherein the viscosity of said organic vehicle is suitable for dispensing through an automated dispenser onto a selected substrate.

271. The electrically conductive resin or adhesive composition of claim 18, wherein the viscosity of said organic vehicle is suitable for printing onto a selected substrate through a mask.

272. The electrically conductive resin or adhesive composition of claim 18, wherein said adhesive is photo-patternable.

273. The anisotropic conductive polymer sphere of claim 19, wherein said at least one energy emitter or said at least one energy collector is present and wherein said at least one energy converter contained therein is at least one down-converting material that responds to X-ray photons.

274. The anisotropic conductive polymer sphere of claim 273, further comprising an outer coating of silica.

275. The anisotropic conductive polymer sphere of claim 273, wherein the at least one down-converting material is in a form of nanoparticles.

276. The anisotropic conductive polymer sphere of claim 19, wherein said at least one energy emitter or said at least one energy collector is present, and wherein said at least one energy converter contained therein is at least one up-converting material that responds to near infrared photons.

277. The anisotropic conductive polymer sphere of claim 276, further comprising an outer coating of silica.

278. The anisotropic conductive polymer sphere of claim 276, wherein the at least one up-converting material is in a form of nanoparticles.

279. The electrically conductive resin or adhesive composition of claim 20, wherein said at least one energy emitter or said at least one energy collector is present, and wherein said at least one energy converter contained therein is selected to emit said selected wavelength of light when exposed to an imparted radiation.

\* \* \* \* \*